US009725590B2

(12) United States Patent
Chun et al.

(10) Patent No.: US 9,725,590 B2

(45) Date of Patent: Aug. 8, 2017

(54) EPOXY COMPOUND HAVING ALKOXYSILYL GROUP, METHOD FOR PREPARING THE SAME, COMPOSITION INCLUDING THE SAME, CURED PRODUCT MADE FROM THE COMPOSITION, AND USE OF THE COMPOSITION

(71) Applicant: KOREA INSTITUTE OF INDUSTRIAL TECHNOLOGY, Cheonan (KR)

(72) Inventors: Hyun-Aee Chun, Seongnam (KR); Yun-Ju Kim, Seoul (KR); Su-Jin Park, Ansan (KR); Sang-Yong Tak, Busan (KR); Sung-Hwan Park, Gunpo (KR); Kyung-Nam Kang, Ansan (KR); Sook-Yeon Park, Gunpo (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 44 days.

(21) Appl. No.: 14/427,990

(22) PCT Filed: Sep. 17, 2013

(86) PCT No.: PCT/KR2013/008439

§ 371 (c)(1),
(2) Date: Mar. 12, 2015

(87) PCT Pub. No.: WO2014/042491

PCT Pub. Date: Mar. 20, 2014

(65) Prior Publication Data

US 2015/0247033 A1 Sep. 3, 2015

(30) Foreign Application Priority Data

Sep. 17, 2012 (KR) ........................ 10-2012-0102932
Sep. 17, 2013 (KR) ........................ 10-2013-0111473

(51) Int. Cl.
*C07F 7/08* (2006.01)
*C07F 7/10* (2006.01)
(Continued)

(52) U.S. Cl.
CPC ............ *C08L 63/00* (2013.01); *C07F 7/1836* (2013.01); *C08G 59/306* (2013.01);
(Continued)

(58) Field of Classification Search
CPC ....... C08G 59/306; C08G 59/00–59/72; C08G 59/3281; C08L 63/00–63/10;
(Continued)

(56) References Cited

U.S. PATENT DOCUMENTS 2,864,804 A * 12/1958 Shokal ................. C07D 303/24
525/386
3,223,577 A * 12/1965 Plueddemann ......... B29C 70/12
428/428
(Continued)

FOREIGN PATENT DOCUMENTS

EP 0 022 073 A1 1/1981
EP 0 282 977 A2 9/1988
(Continued)

OTHER PUBLICATIONS

European Search Report for European Patent Application No. 13837901.1 dated Jan. 25, 2016.
(Continued)

*Primary Examiner* — Kregg Brooks

(57) ABSTRACT

Provided are an alkoxysilylated epoxy compound, a composite of which exhibits good heat resistance properties, particularly low CTE and increased glass transition temperature, and a cured product thereof exhibits good flame retardancy and composition of which does not require additional silane coupling agent, a method for preparing the
(Continued)

same and a composition and a cured product including the same. An alkoxysilylated epoxy compound including at least one alkoxysilyl group and at least two epoxy groups, a method for preparing the same by epoxide ring-opening reaction of starting material and alkoxysilylation, an epoxy composition including the epoxy compound, and a cured product and a use of the composition are provided. Since chemical bonds may be formed between alkoxysilyl group and filler and between alkoxysilyl groups, chemical bonding efficiency of the composite may be improved. Thus, the composite exhibits good heat resistance properties and the cured product exhibits good flame retardancy.

16 Claims, 3 Drawing Sheets

(51) Int. Cl.

| | |
|---|---|
| ***C07F 7/18*** | (2006.01) |
| ***C08L 63/00*** | (2006.01) |
| ***C09J 163/00*** | (2006.01) |
| ***C08G 59/20*** | (2006.01) |
| ***C08G 59/30*** | (2006.01) |
| ***C08K 5/50*** | (2006.01) |
| ***C08K 7/14*** | (2006.01) |
| ***C08G 59/32*** | (2006.01) |
| *H01L 33/52* | (2010.01) |
| *H05K 1/03* | (2006.01) |

(52) U.S. Cl.
CPC ............ *C08G 59/3281* (2013.01); *C08K 5/50* (2013.01); *C08K 7/14* (2013.01)

(58) Field of Classification Search
CPC .. C09D 163/00–163/10; C09J 163/00–163/10; C07F 7/1812–7/1844
See application file for complete search history.

(56) References Cited

U.S. PATENT DOCUMENTS

| | | | | |
|---|---|---|---|---|
| 4,859,722 | A * | 8/1989 | Shiobara | C08G 59/3218 523/427 |
| 5,300,588 | A * | 4/1994 | Shiobara | C08L 79/085 525/422 |
| 6,174,967 | B1 | 1/2001 | Soucek et al. | |
| 6,462,141 | B1 | 10/2002 | Kim et al. | |
| 7,223,821 | B2 | 5/2007 | Okuhira et al. | |
| 7,498,085 | B2 | 3/2009 | Kashiwagi et al. | |
| 8,062,468 | B2 | 11/2011 | Finter et al. | |
| 8,124,715 | B2 | 2/2012 | Tanaka et al. | |
| 2008/0221238 | A1 | 9/2008 | Su et al. | |
| 2011/0244326 | A1 | 10/2011 | Murase et al. | |

FOREIGN PATENT DOCUMENTS

| | | | |
|---|---|---|---|
| JP | 63-227621 | A | 9/1988 |
| JP | 2004-210977 | A | 7/2004 |
| JP | 2005-158766 | A | 6/2005 |
| JP | 2006-169368 | A | 6/2006 |
| JP | 2009-43678 | A | 2/2009 |
| JP | 2011-116745 | A | 6/2011 |
| KR | 10-2000-0061084 | A | 10/2000 |
| KR | 10-0587480 | B1 | 5/2006 |
| KR | 10-2010-0027245 | A | 3/2010 |

OTHER PUBLICATIONS

International Search Report for PCT/KR2013/008439 mailed on Jan. 28, 2014.

Extended European Search Report for European Application No. 13837901.1 dated Jun. 10, 2016.

* cited by examiner

EXAMPLE 1

COMPARATIVE EXAMPLE 1

EPOXY COMPOUND HAVING ALKOXYSILYL GROUP, METHOD FOR PREPARING THE SAME, COMPOSITION INCLUDING THE SAME, CURED PRODUCT MADE FROM THE COMPOSITION, AND USE OF THE COMPOSITION

TECHNICAL FIELD

The present invention relates to an epoxy compound having an alkoxysilyl group (hereinafter 'alkoxysilylated epoxy compound'), a composite thereof exhibiting good heat resistance properties and/or a cured product thereof exhibiting good flame retardancy, a method for preparing the same, a composition including the same, a cured product made therefrom, and a use thereof. More particularly, the present invention relates to an alkoxysilylated epoxy compound, a composite thereof exhibiting good heat resistance properties, in particular, exhibiting a low coefficient of thermal expansion (CTE) and a high glass transition temperature (including a glass transition temperature-less (Tg-less) state, which means that the composite does not have a glass transition temperature) and not requiring a separate silane coupling agent, a method for preparing the same, a composition including the same, a cured product made therefrom, and a use thereof. In addition, an epoxy compound having a hydroxyl group and an allyl group obtained during the preparation of the alkoxysilylated epoxy compound as an intermediate, is provided.

BACKGROUND ART

The coefficient of thermal expansion (CTE) of a polymer material—specifically, an epoxy resin—is about 50 to 80 ppm/° C., significantly higher several to tens of times than the CTE of a ceramic material such as inorganic particles or a metal material, (for example, the CTE of silicon is 3 to 5 ppm/° C., and the CTE of copper is 17 ppm/° C.). Thus, when a polymer material is used in conjunction with an inorganic material or a metal material in a semiconductor, a display, or the like, the properties and processability of the polymer material are significantly degraded due to the CTE-mismatch of the polymer material and the inorganic material or the metal material. In addition, during semiconductor packaging in which a silicon wafer and a polymer substrate are used in parallel, or during a coating in which a polymer film is coated with an inorganic barrier layer to impart gas barrier properties, product defects such as the generation of cracks in an inorganic layer, the warpage of a substrate, the peeling of a coating layer, the failure of a substrate, and the like, may be generated due to a high CTE-mismatch between constituent elements upon the changes in processing and/or applied temperature conditions.

Because of the high CTE of the polymer material and the resultant dimensional change of the polymer material, the development of technologies such as next generation semiconductor substrates, printed circuit boards (PCBs), packaging, organic thin film transistors (OTFTs), and flexible display substrates may be limited. Particularly, currently, in the semiconductor and PCB fields, designers are facing challenges in the design of next generation parts requiring high degrees of integration, miniaturization, flexibility, performance, and the like, in securing processability and reliability in parts due to polymer materials having significantly high CTEs as compared to metal/ceramic materials. In other words, due to the high thermal expansion properties of polymer materials at processing temperatures, defects may be generated, processability may be limited, and the design of parts and the securing of processability and reliability therein may be objects of concern. Accordingly, improved thermal expansion properties or dimensional stability of the polymer material are necessary in order to secure processability and reliability in electronic parts.

To date, in order to improve thermal expansion properties, i.e. to obtain a low CTE value in a polymer material such as an epoxy resin, (1) a method of producing a composite of an epoxy resin with inorganic particles (an inorganic filler) and/or fabrics and (2) a method of designing and synthesizing a novel epoxy resin having a decreased CTE have been used.

When the composite of the epoxy compound and the inorganic particles as the filler is formed in order to improve thermal expansion properties, a large amount of inorganic silica particles, having a diameter of about 2 to 30 μm is required in order to decrease the CTE sufficiently. However, due to the addition of the large amount of inorganic particles, the processability and performance of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to the miniaturization of semiconductor structures. When a filler having a particle size of 1 μm or less is used, a decrease in fluidity (increase in viscosity) may be intensified. When inorganic particles having a large average particle diameter are used, the frequency of insufficient filling in the case of a composition including a resin and the inorganic particles may increase. While the CTE of the composite may be decreased significantly when a composition including an organic resin and a fiber as the filler is used, the CTE of fiber composite is still high as compared to that of a silicon chip or the like.

As described above, the manufacturing of highly integrated and high performance electronic parts for next generation semiconductor substrates, PCBs, and the like, may be restricted due to limitations in the composite technology of epoxy resins. Thus, the development of an epoxy composite having improved heat resistance properties—namely, a low CTE and a high glass transition temperature—is required to overcome a lack of heat resistance properties due to a high CTE and poor processability of a common thermosetting polymer composite.

DISCLOSURE

Technical Problem

An aspect of the present invention provides an epoxy compound having an alkoxysilyl group, a composite thereof exhibiting improved heat resistance properties, particularly a low CTE and high Tg, and/or a cured product thereof exhibiting good flame retardancy.

Another aspect of the present invention provides a method for preparing an epoxy compound having an alkoxysilyl group, a composite thereof exhibiting improved heat resistance properties, particularly a low CTE and high Tg, and/or a cured product thereof exhibiting good flame retardancy.

Another aspect of the present invention provides an epoxy composition including an epoxy compound having an alkoxysilyl group, a composite thereof exhibiting improved heat resistance properties, particularly a low CTE and high Tg, and/or a cured product thereof exhibiting good flame retardancy.

Another aspect of the present invention provides a cured product of an epoxy composition according to an embodiment of the present invention, a composite thereof exhibiting improved heat resistance properties, particularly a low CTE and high Tg, and/or a cured product thereof exhibiting good flame retardancy.

In addition, another aspect of the present invention provides a use of an epoxy composition according to an embodiment of the present invention.

Another aspect of the present invention provides an epoxy compound having a hydroxyl group and an allyl group.

Technical Solution

According to an aspect of the present invention, there is provided an epoxy compound having an alkoxysilyl group, including at least one alkoxysilyl group in a core (1) independently selected from the group consisting of Formulae S11 to S16, (2) independently selected from the group consisting of Formulae S21 to S26, (3) independently selected from the group consisting of Formulae S11 to S16 and Formulae S31 to S38 or (4) independently selected from the group consisting of Formulae S21 to S26 and Formulae S31 to S38; and at least two epoxy groups in a core.

[Formula S1]

(S11)

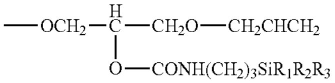

(S12)

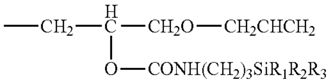

(S13)

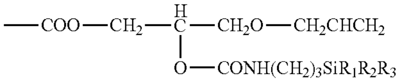

(S14)

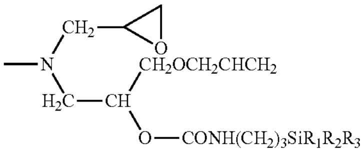

(S15)

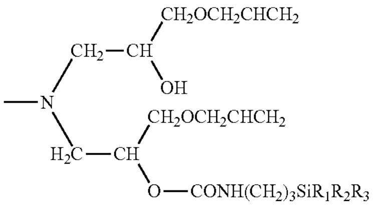

and (S16)

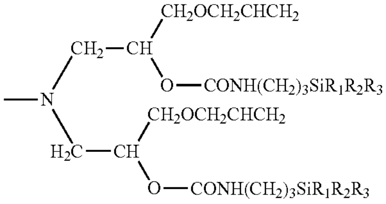

in Formulae S11 to S16, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched;

[Formula S2]

(S21)

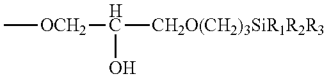

(S22)

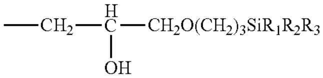

(S23)

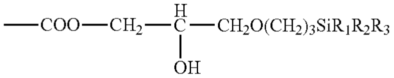

(S24)

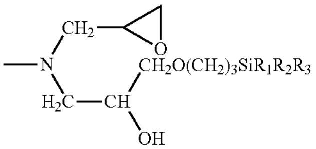

(S25)

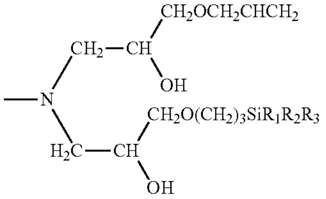

and (S26)

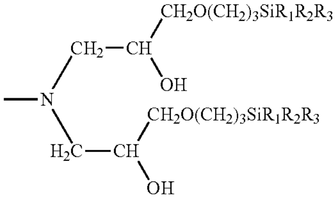

in Formulae S21 to S26, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched;

[Formula S3]

(S31)

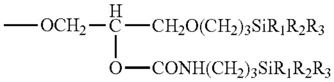

(S32)

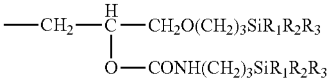

(S33)

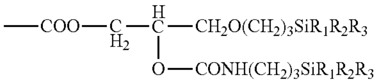

-continued (S34)

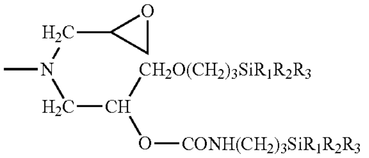

(S35)

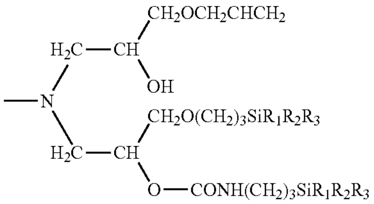

(S36)

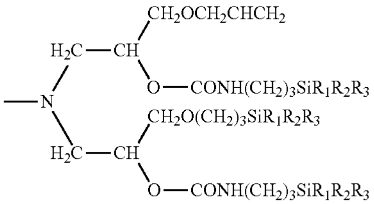

(S37)

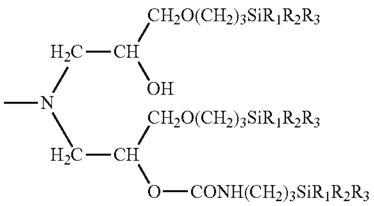

and (S38)

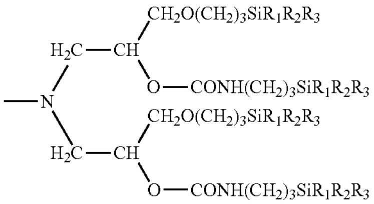

in Formulae S31 to S38, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to a second aspect of the present invention, there is provided an epoxy compound having an alkoxysilyl group wherein the epoxy group may be independently selected from the group consisting of Formulae S51 to S58 according to the first aspect.

[Formula S5(3)]

(S51)

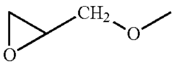

(S52)

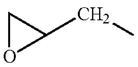

(S53)

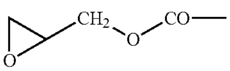

-continued (S54)

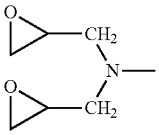

(S55)

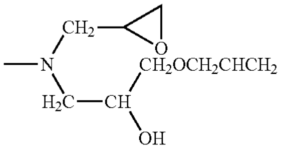

(S56)

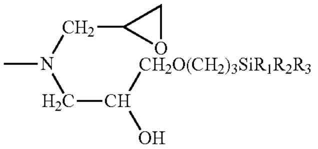

(S57)

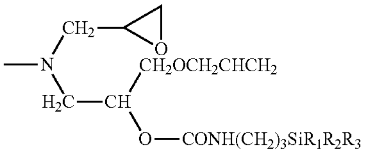

and (S58)

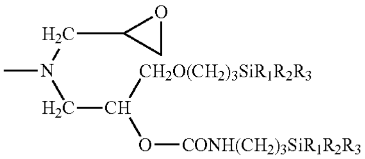

in Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to a third aspect of the present invention, the epoxy compound may include bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as the core according to the first or second aspect.

According to a fourth aspect of the present invention, the core may be one selected from the group consisting of Formulae A' to N' according to the third aspect.

(A')

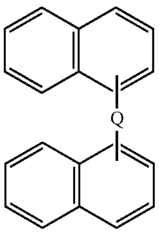

-continued
(B')
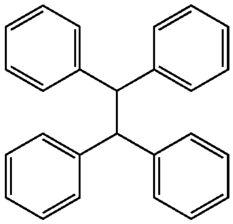
(C')
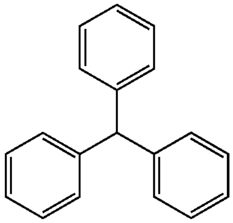
(D')
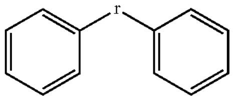
(E')
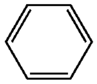
(F')
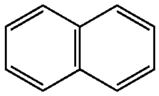
(G')
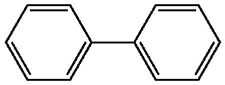
(H')
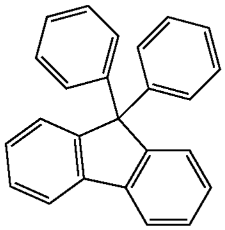
(I')
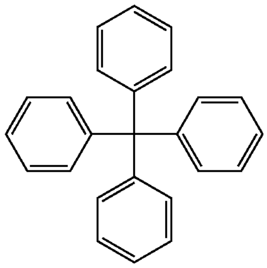
(J')
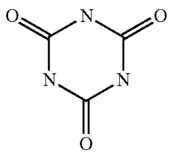
-continued
(K')
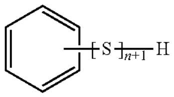
(L')
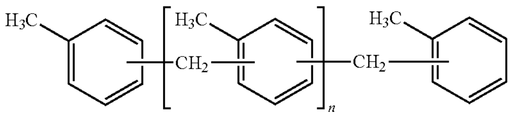
(M')
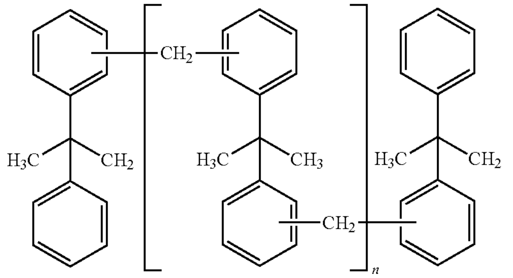
and
(N')
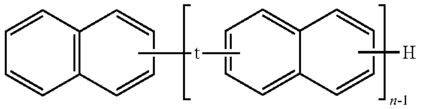
in Formula A', -q- is —$CH_2$— or a direct linkage, in Formula D', -r- is —$C(CH_3)_2$—, —$CH_2$—, —$C(CF_3)_2$—, —$SO_2$—, —S—,
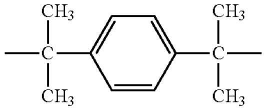
or
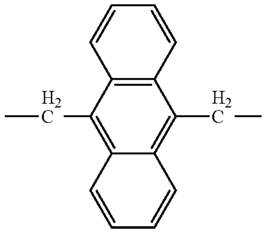
,
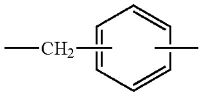
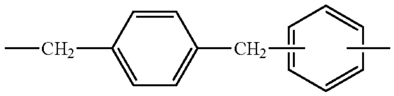
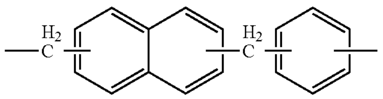
in Formula K', s is
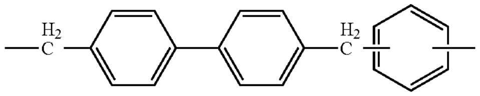

-continued

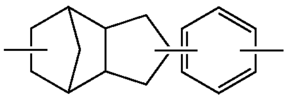

or

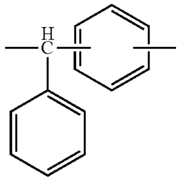

, in Formula N', t is $-CH_2-$ ,

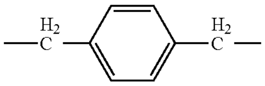

or

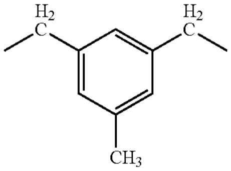

, and in Formulae K' to N', n is an integer equal to or greater than 1 and preferably an integer from 1 to 1,000.

According to a fifth aspect of the present invention, if the number of the cores selected from the group consisting of Formulae A' to J' is equal to or greater than two, the cores of Formulae A' to I' may be connected via a connecting group independently selected from the group consisting of Formulae LG1 to LG14, and the cores of the above Formula J' may be connected via a connecting group independently selected from the group consisting of Formulae LG2 and LG9 according to the fourth aspect.

[Formula 6(2)]

(LG1)

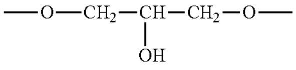

(LG2)

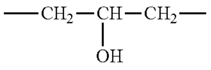

(LG3)

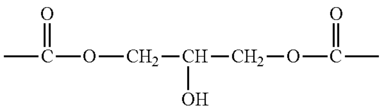

(LG4)

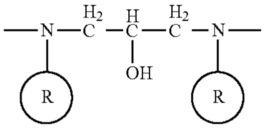

(LG5)

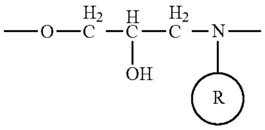

(LG6)

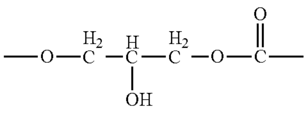

-continued (LG7)

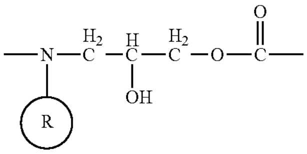

(LG8)

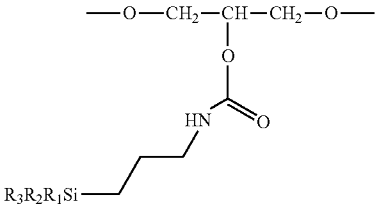

(LG9)

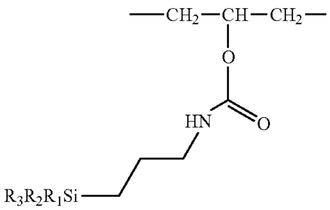

(LG10)

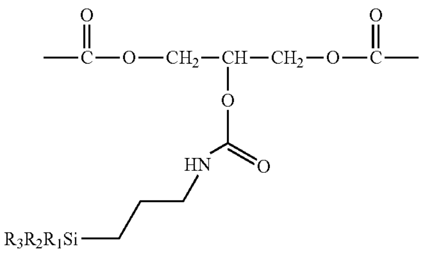

(LG11)

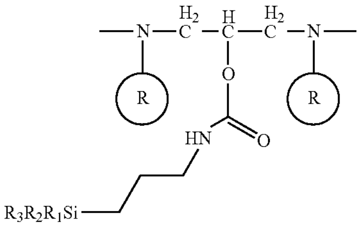

(LG12)

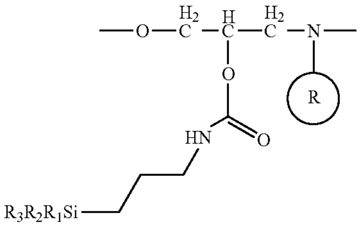

(LG13)

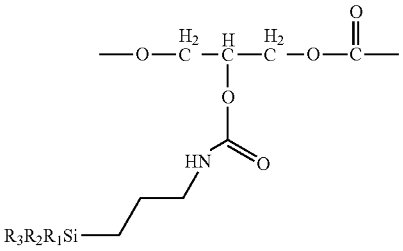

-continued (LG14)

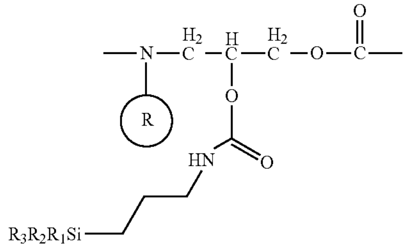

in Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen, a glycidyl group or

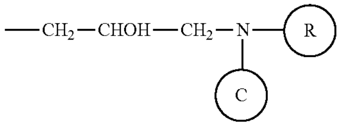

, where Ⓒ is a linking moiety to another core, Ⓡ is as defined hereinbefore, and Ⓡ is repeated according to the number of the cores.

According to a sixth aspect of the present invention, the epoxy compound having an alkoxysilyl group may further include a substituent of Formula S4 selected from the group consisting of Formulae S41 to S45 according to any one of the first to fifth aspects.

[Formula S4]

(S41)

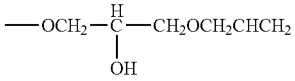

(S42)

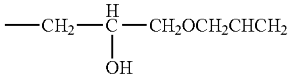

(S43)

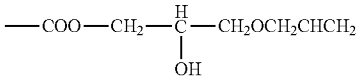

(S44)

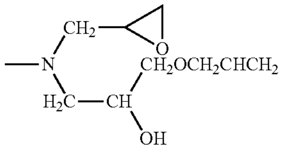

and (S45)

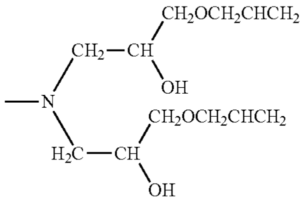

According to a seventh aspect of the present invention, there is provided an epoxy compound having a hydroxyl group and an alkyl group including a core selected from the group consisting of Formulae (A') to (N'), and at least one S4 substituent selected from the group consisting of Formulae S41 to S45 and at least two S5(1) epoxy groups selected from the group consisting of Formulae S51 to S55, wherein if the number of the cores of Formulae (A') to (J') is equal to or greater than two, the cores of Formulae (A') to (I') may be connected via a connecting group independently selected from the group consisting of Formulae LG1 to LG7, and the cores of the above Formula (J') may be connected via a connecting group of Formula LG2.

(A')

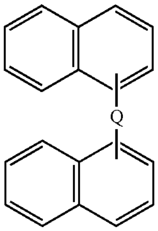

(B')

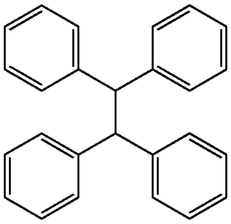

(C')

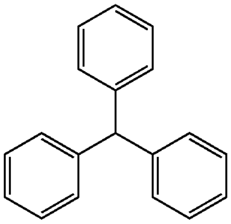

(D')

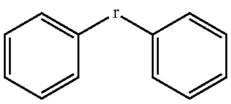

(E')

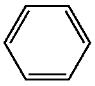

(F')

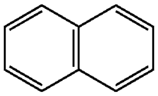

(G')

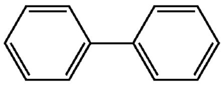

-continued
(H')
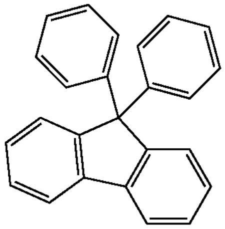
(I')
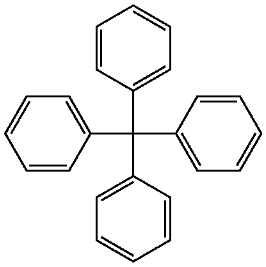
(J')
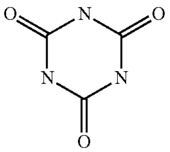
(K')
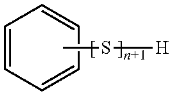
(L')
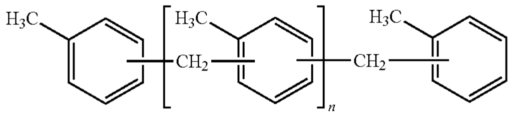
(M')
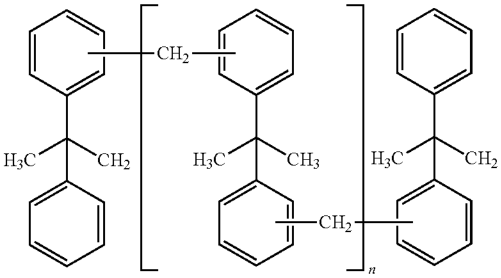
and
(N')
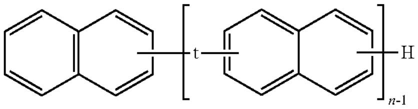
in Formula A', -q- is $—CH_2—$ or a direct linkage,
in Formula D', -r- is $—C(CH_3)_2—$, $—CH_2—$, $—C(CF_3)_2—$, $—SO_2—$, $—S—$,
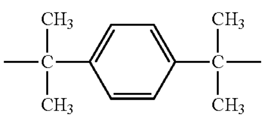
or
-continued
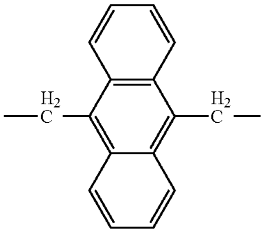
,
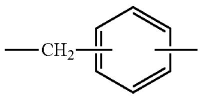
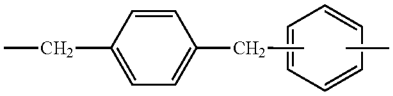
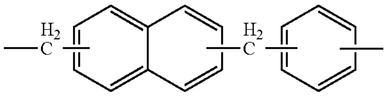
in Formula K', s is
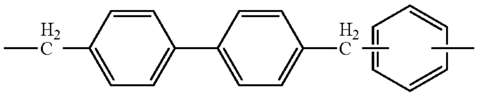
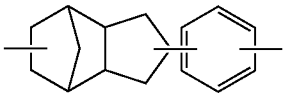
or
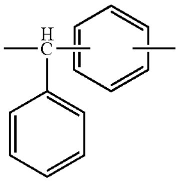
,
in Formula N', t is
$—CH_2—$ ,
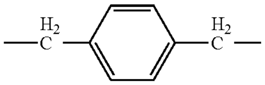
or
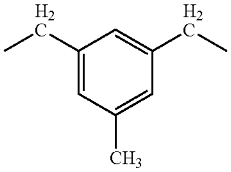
,
and
in Formulae K' to N', n is an integer equal to or greater than 1,
[Formula S4]
(S41)
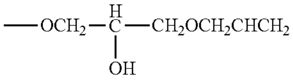
(S42)
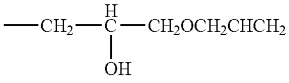
(S43)
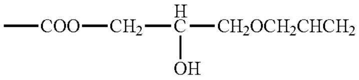

-continued (S44)

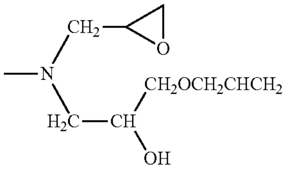

and (S45)

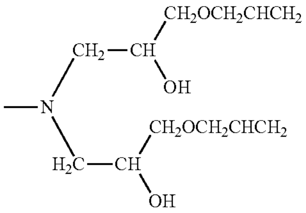

[Formula S5(1)]

(S51)

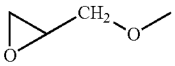

(S52)

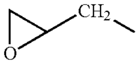

(S53)

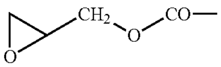

(S54)

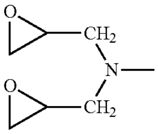

and (S55)

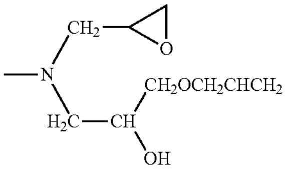

[Formula S6(1)]

(LG1)

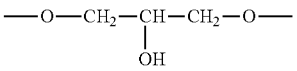

(LG2)

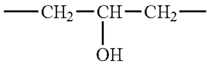

(LG3)

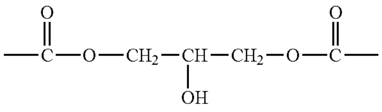

(LG4)

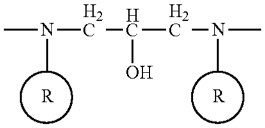

(LG5)

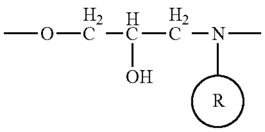

-continued (LG6)

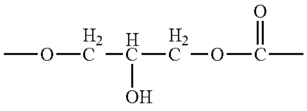

and (LG7)

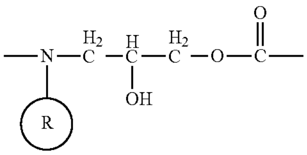

in Formulae LG4, LG5 and LG7, Ⓡ is hydrogen, a glycidyl group or

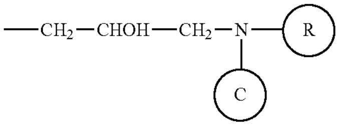

, where Ⓒ is a linking moiety to another core, and Ⓡ is as defined hereinbefore and is repeated according to the number of the cores.

According to an eighth aspect of the present invention, there is provided a method for preparing an epoxy compound including a first step of preparing an intermediate by reacting a starting material of an epoxy compound having at least three epoxy groups and allyl alcohol in the presence of a base and an optional solvent; and a second step of reacting the intermediate and a compound of the following Formula B1 in the presence of a base and an optional solvent to prepare an epoxy compound including at least one alkoxysilyl group in a core independently selected from the group consisting of Formulae S11 to S16 in a core; and at least two epoxy groups in a core.

$OCN(CH_2)_3SiR_1R_2R_3$ [Formula B1]

in Formula B1, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched,

[Formula S1]

(S11)

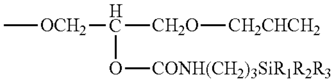

(S12)

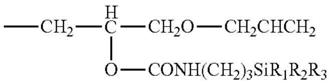

(S13)

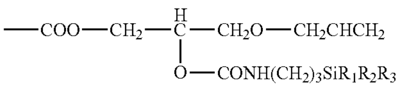

(S14)

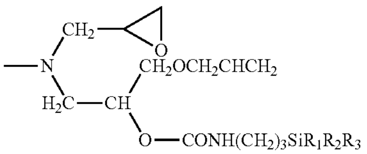

-continued (S15)

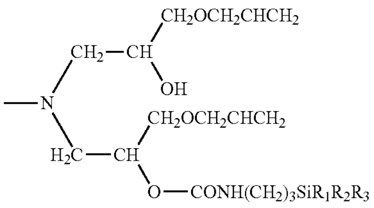

and (S16)

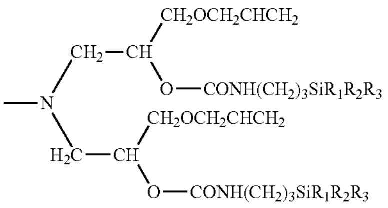

in Formulae S11 to S16, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to a ninth aspect of the present invention, an optional third step of reacting the epoxy compound prepared in the second step and a compound of the following Formula B2 in the presence of a metal catalyst and an optional solvent may be further included to prepare an epoxy compound having at least one alkoxysilyl group in a core independently selected from the group consisting of Formulae S11 to S16 and Formulae S31 to S38; and at least two epoxy groups in a core according to the eighth aspect.

$HSiR_1R_2R_3$ [Formula B2]

in Formulae B2, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched,

[Formula S3]

(S31)

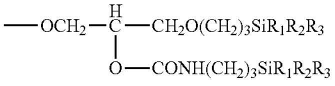

(S32)

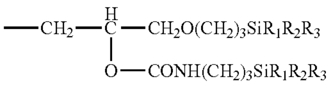

(S33)

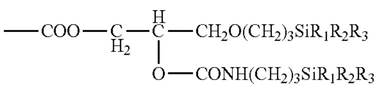

(S34)

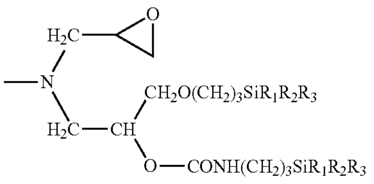

-continued (S35)

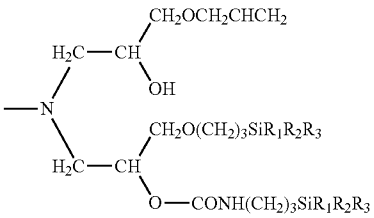

(S36)

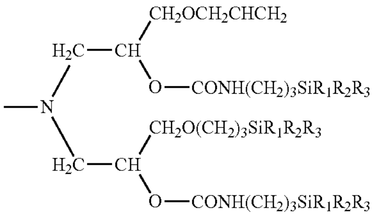

(S37)

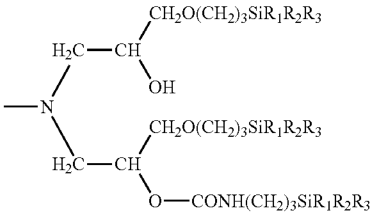

and (S38)

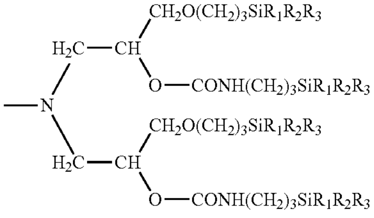

in Formulae S31 to S38, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to a tenth aspect of the present invention, there is provided a method for preparing an epoxy compound having an alkoxysilyl group including a first step of preparing an intermediate by reacting a starting material of an epoxy compound having at least three epoxy groups and allyl alcohol in the presence of a base and an optional solvent; and a second step of reacting the intermediate and a compound of the following Formula B2 in the presence of a metal catalyst and an optional solvent to prepare an epoxy compound including at least one alkoxysilyl group in a core independently selected from the group consisting of Formulae S21 to S26 in a core; and at least two epoxy groups in a core.

$HSiR_1R_2R_3$ [Formula B2]

in Formula B2, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched,

[Formula S2]

(S21)

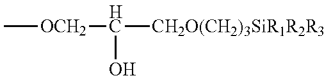

(S22)

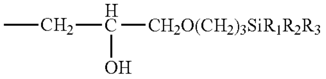

(S23)

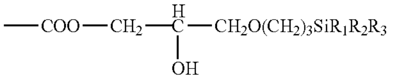

(S24)

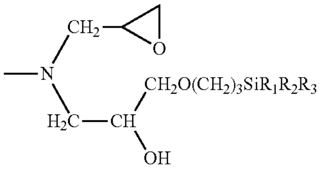

(S25)

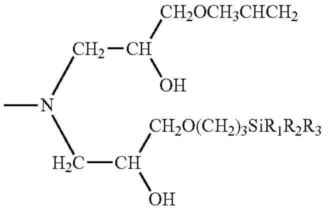

and (S26)

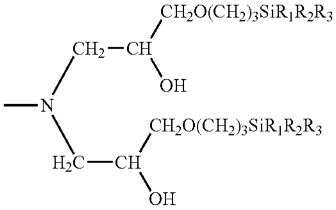

in Formulae S21 to S26, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to an eleventh aspect of the present invention, an optional third step of reacting the epoxy compound prepared in the second step and a compound of the following Formula B1 in the presence of a base and an optional solvent may be further included to prepare an epoxy compound having at least one alkoxysilyl group in the core independently selected from the group consisting of Formulae S21 to S26 and Formulae S31 to S38; and at least two epoxy groups in the core according to the tenth aspect.

$OCN(CH_2)_3SiR_1R_2R_3$ [Formula B1]

in Formula B1, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched,

[Formula S3]

(S31)

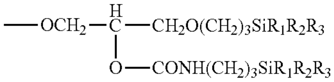

-continued (S32)

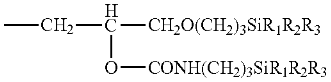

(S33)

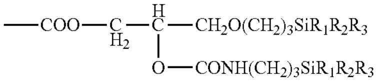

(S34)

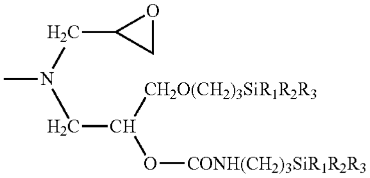

(S35)

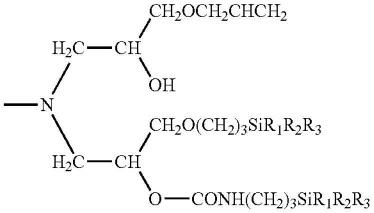

(S36)

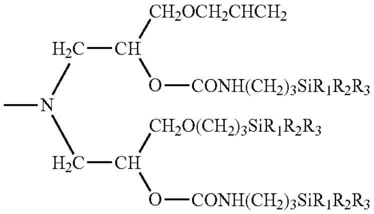

(S37)

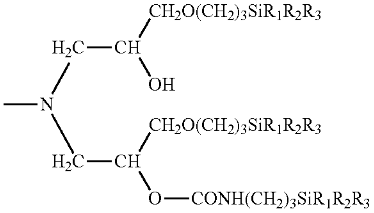

and (S38)

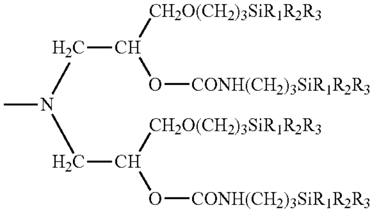

in Formulae S31 to S38, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

According to a twelfth aspect of the present invention, the staring material of the epoxy compound having at least three epoxy groups may include a core selected from the group consisting of Formulae (A') to (N') and at least three epoxy groups selected from the group consisting of Formulae S51 to S54, and if the number of the cores of Formulae (A') to (J') is equal to or greater than two, the cores of Formulae (A') to (I') may be connected via a connecting group independently selected from the group consisting of Formulae LG1 to LG7 and the core of Formula (J') may be connected via a connecting group of LG2 according to the eighth or tenth aspect.
(A')
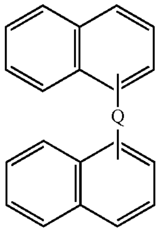
(B')
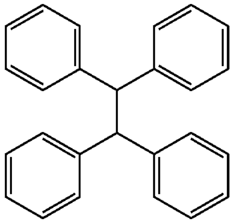
(C')
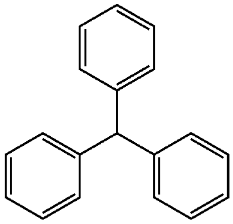
(D')
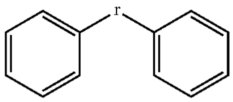
(E')
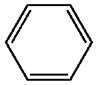
(F')
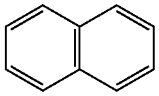
(G')
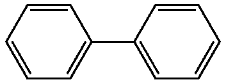
(H')
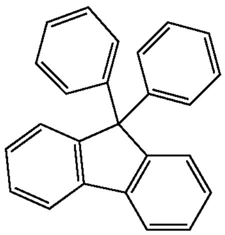
-continued
(I')
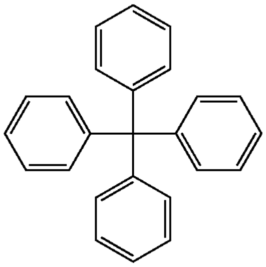
(J')
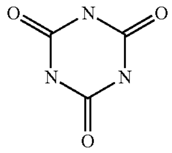
(K')
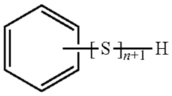
(L')
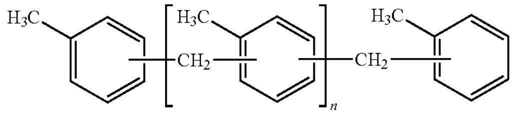
(M')
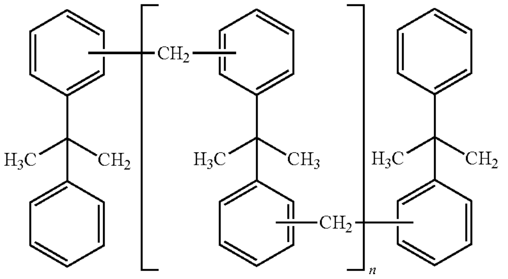
and
(N')
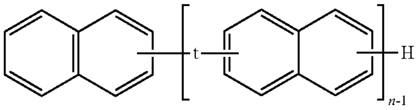
in Formula A', -q- is $—CH_2—$ or a direct linkage,
in Formula D', -r- is $—C(CH_3)_2—$, $—CH_2—$, $—C(CF_3)_2—$, $—SO_2—$, —S—,
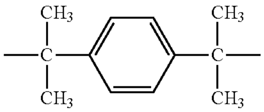
or
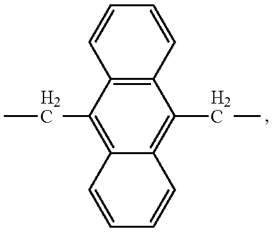
,
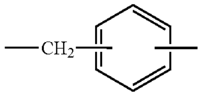

-continued

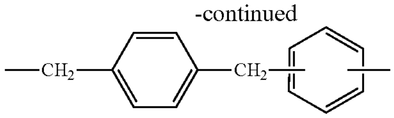

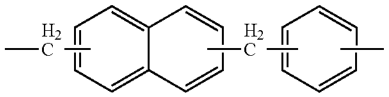

in Formula K', s is

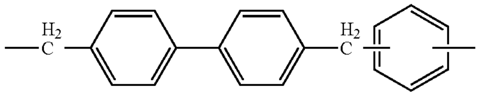

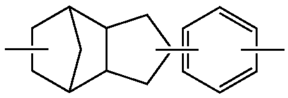 or 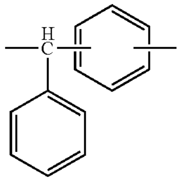, in Formula N', t is

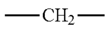, 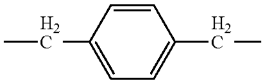 or

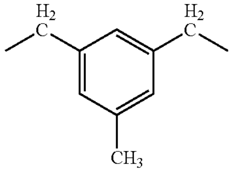, and in Formulae K' to N', n is an integer equal to or greater than 1.

[Formula S5(0)]

(S51)

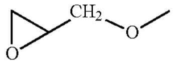

(S52)

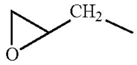

(S53)

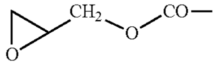

(S54)

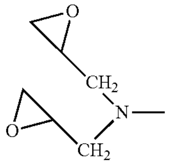

[Formula S6(1)]

(LG1)

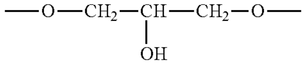

-continued (LG2)

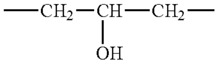

(LG3)

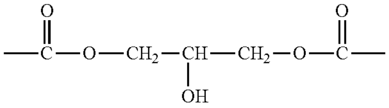

(LG4)

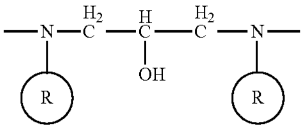

(LG5)

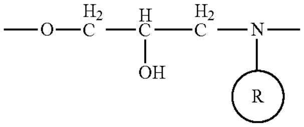

(LG6)

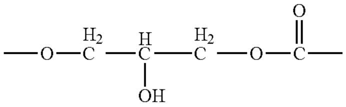 and (LG7)

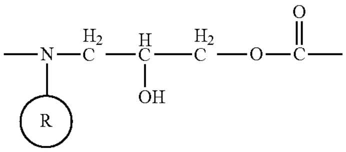

in Formulae LG4, LG5 and LG7, Ⓡ is hydrogen, a glycidyl group or

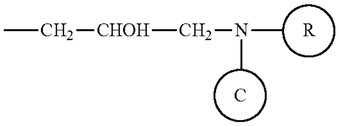, where Ⓒ is a linking moiety to another core, and Ⓡ is as defined hereinbefore and is repeated depending on the number of the cores.

According to a thirteenth aspect of the present invention, the intermediate prepared in the first step may include a core selected from the group consisting of Formulae (A') to (N'), at least one substituent selected from the group consisting of Formulae S41 to S45, and at least two epoxy groups selected from the group consisting of Formulae S51 to S55, and when the number of the cores of Formulae (A') to (N') is equal to or greater than two, the cores of Formulae (A') to (I') may be connected via a connecting group independently selected from the group consisting of Formulae LG1 to LG7 and the cores of Formula (J') may be connected via a connecting group of LG2 according to the eighth or tenth aspect.

(A')
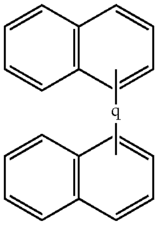
(B')
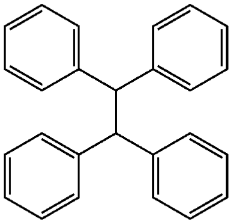
(C')
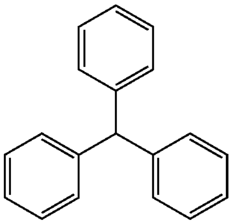
(D')
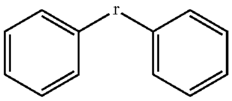
(E')
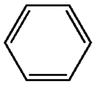
(F')
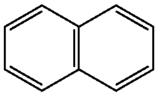
(G')
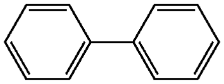
(H')
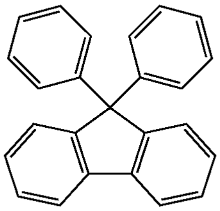
(I')
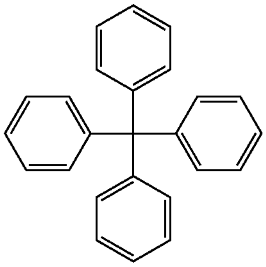
-continued
(J')
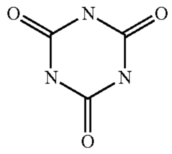
(K')
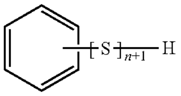
(L')
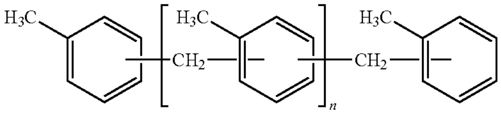
(M')
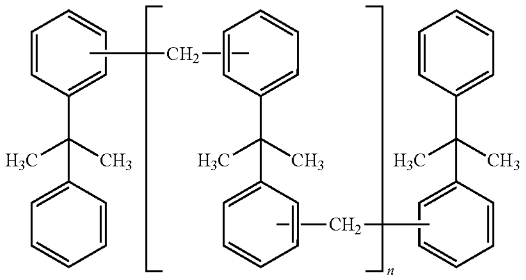
and
(N')
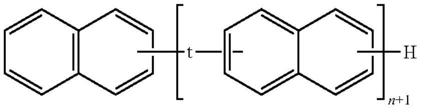
in Formula A', -q- is $—CH_2—$ or a direct linkage,
in Formula D', -r- is $—C(CH_3)_2—$, $—CH_2—$, $—C(CF_3)_2—$, $—SO_2—$, $—S—$,
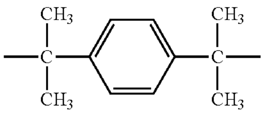
or
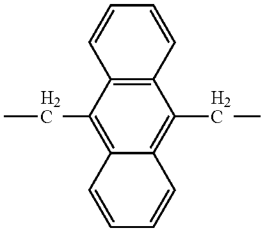
,
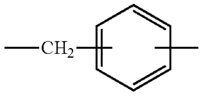
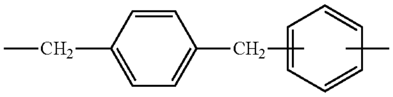
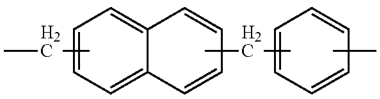

in Formula K', s is
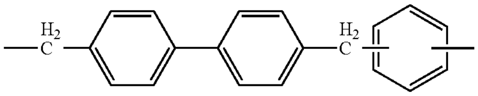
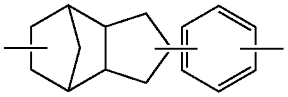
or
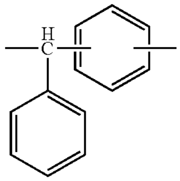
,
in Formula N', t is
—$CH_2$—, 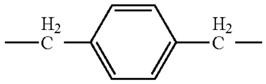 or
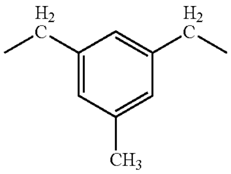
,
and
in Formulae K' to N', n is an integer equal to or greater than 1,
[Formula S4]
(S41)
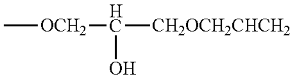
(S42)
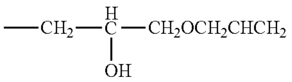
(S43)
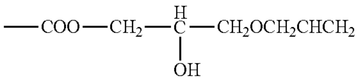
(S44)
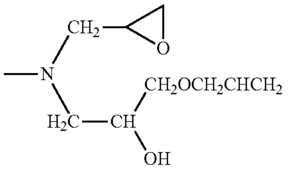
and
(S45)
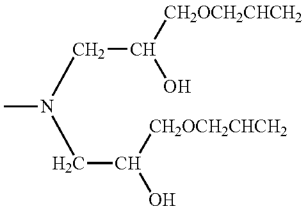
-continued
[Formula S5(1)]
(S51)
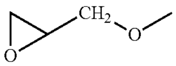
(S52)
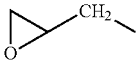
(S53)
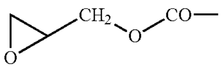
(S54)
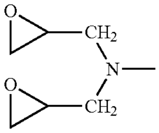
and
(S55)
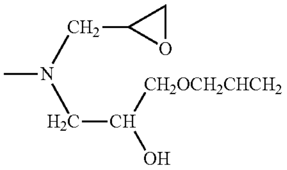
[Formula S6(1)]
(LG1)
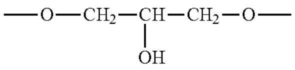
(LG2)
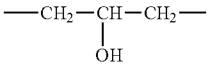
(LG3)
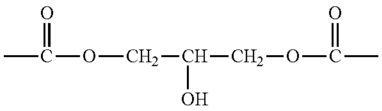
(LG4)
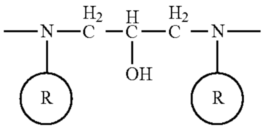
(LG5)
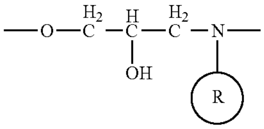
(LG6)
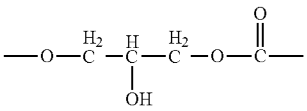
and
(LG7)
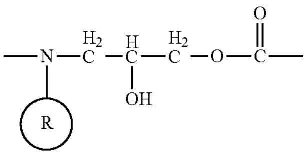
in Formulae LG4, LG5 and LG7, Ⓡ is hydrogen, a glycidyl group or

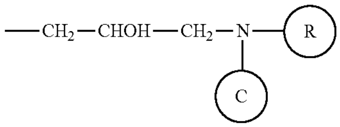
, where Ⓒ is a linking moiety to another core, and Ⓡ is as defined hereinbefore and is repeated according to the number of the cores.

According to a fourteenth aspect of the present invention, the epoxy compound having an alkoxysilyl group prepared in the second step may include a core selected from the group consisting of Formulae (A') to (N'), at least one alkoxysilyl group independently selected from the group consisting of Formulae S11 to S16, at least two epoxy groups selected from the group consisting of Formulae S51 to S55 and S57, and an optional substituent selected from the group consisting of Formulae S41 to S45, and when the number of the cores of Formulae (A') to (J') is equal to or greater than two, the cores of Formulae (A') to (I') may be connected via a connecting group independently selected from the group consisting of Formulae LG1 to LG14, and the cores of Formula (J') may be connected via a connecting group of LG2 and LG9 according to the eighth aspect.

(A')

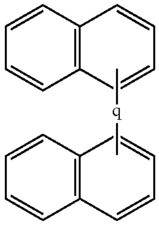

(B')

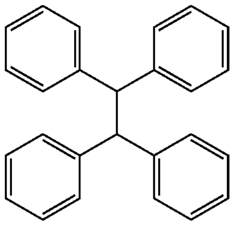

(C')

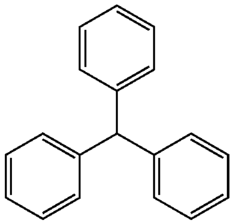

(D')

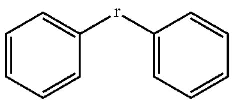

(E')

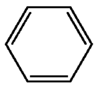

-continued (F')

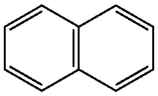

(G')

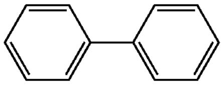

(H')

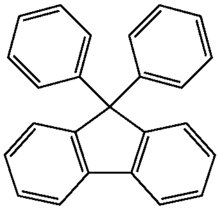

(I')

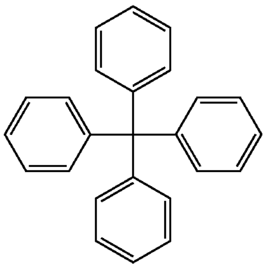

(J')

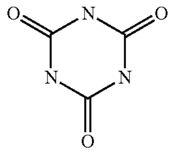

(K')

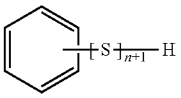

(L')

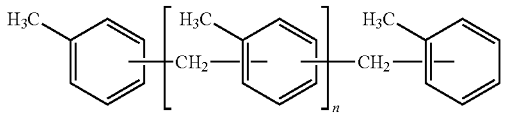

(M')

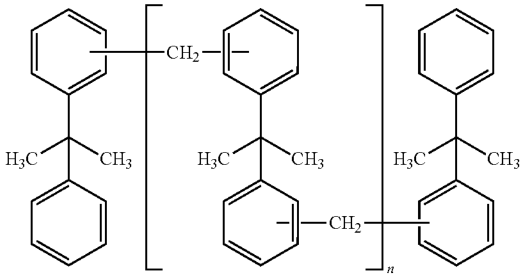

and (N')

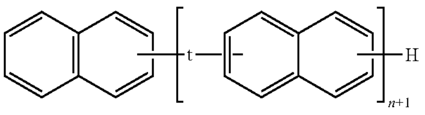

in Formula A', -q- is —$CH_2$— or a direct linkage, in Formula D', -r- is $-C(CH_3)_2-$, $-CH_2-$, $-C(CF_3)_2-$, $-SO_2-$, $-S-$,

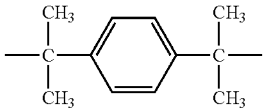
or

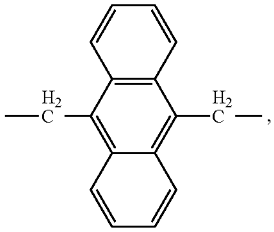
,
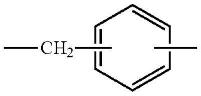

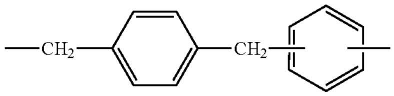

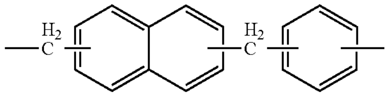

in Formula K', s is

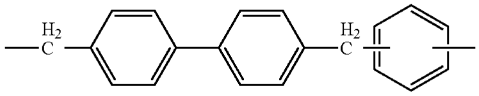

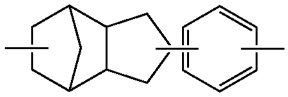
or
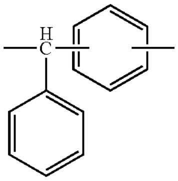
, in Formula N', t is $-CH_2-$ ,

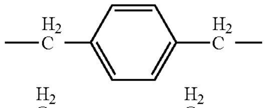
or

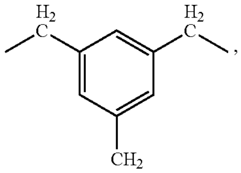
, and in Formulae K' to N', n is an integer equal to or greater than 1.

[Formula S4]

(S41)

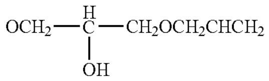

-continued (S42)

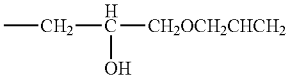

(S43)

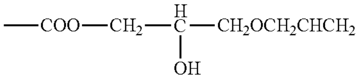

(S44)

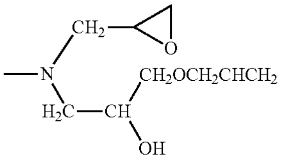
and (S45)

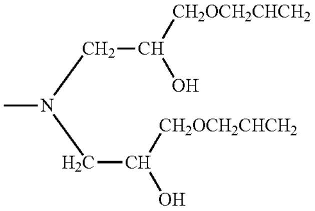

[Formula S5(2-1)]

(S51)

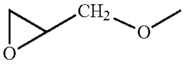

(S52)

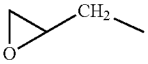

(S53)

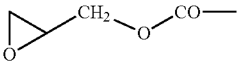

(S54)

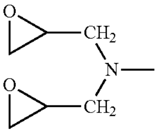

(S55)

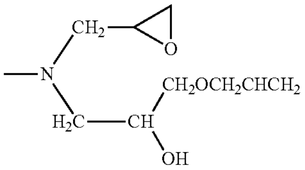
and (S57)

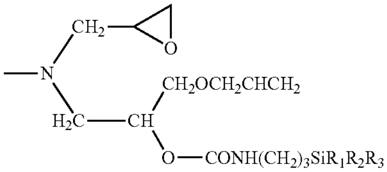

in Formula S57, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

[Formula 6(2)]

(LG1)

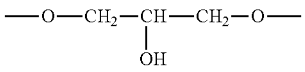

(LG2)

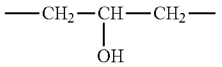

(LG3)

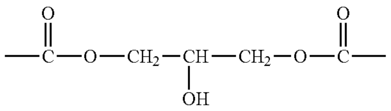

(LG4)

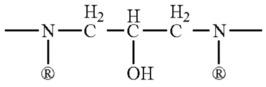

(LG5)

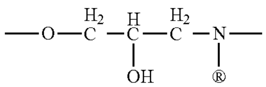

(LG6)

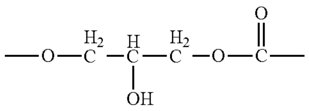

(LG7)

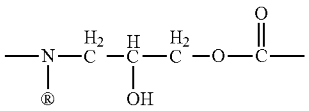

(LG8)

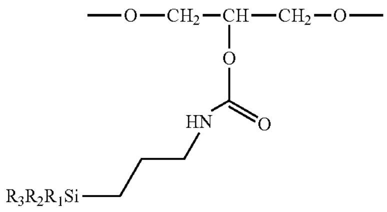

(LG9)

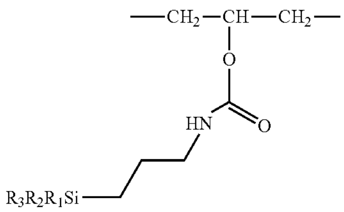

(LG10)

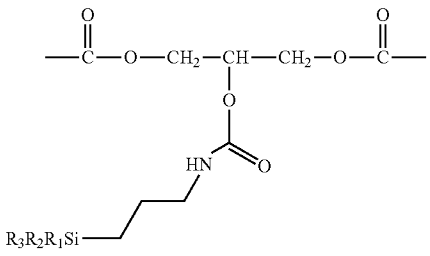

-continued (LG11)

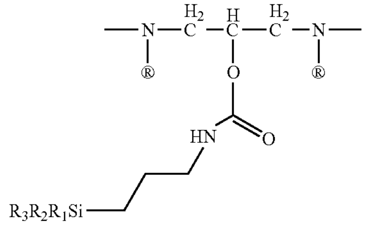

(LG12)

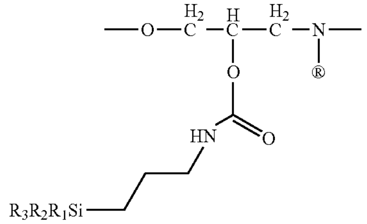

(LG13)

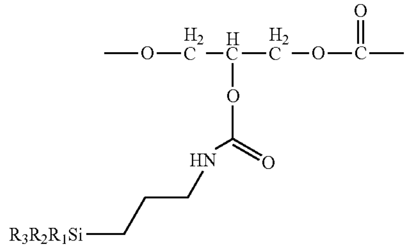

(LG14)

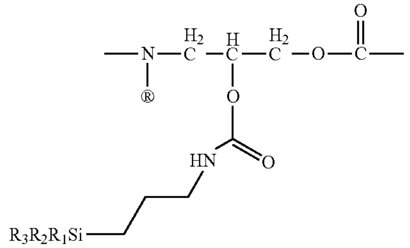

in Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen, a glycidyl group or

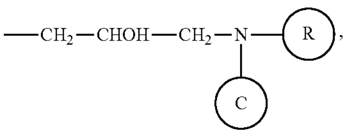

where Ⓒ is a linking moiety to another core, and Ⓡ is as defined hereinbefore and Ⓡ is repeated according to the number of the cores.

According to a fifteenth aspect of the present invention, the epoxy compound having an alkoxysilyl group prepared in the third step may include a core selected from the group consisting of the above following (A') to (N'), at least one alkoxysilyl group selected from the group consisting of Formulae S11 to S16 and Formulae S31 to S38, at least two epoxy groups selected from the group consisting of Formulae S51 to S58, and an optional substituent selected from the group consisting of Formulae S41 to S45, and when the number of the cores of Formulae (A') to (J') is equal to or greater than two, the cores of Formulae (A') to (I') may be connected via a connecting group independently selected from the group consisting of Formulae LG1 to LG14 and the cores of Formula (J') may be connected via a connecting group of LG2 and LG9 according to the ninth aspect.

(A')

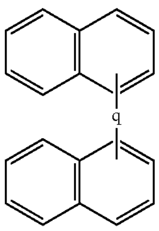

(B')

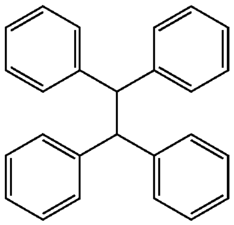

(C')

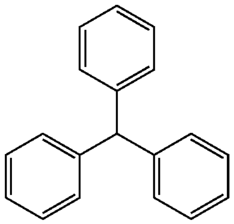

(D')

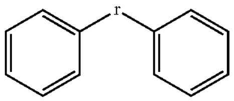

(E')

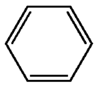

(F')

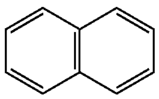

(G')

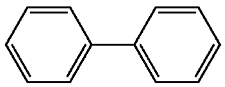

(H')

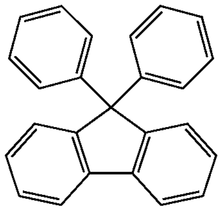

-continued (I')

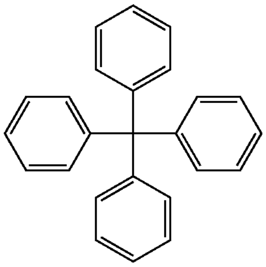

(J')

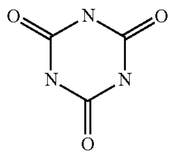

(K')

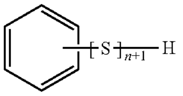

(L')

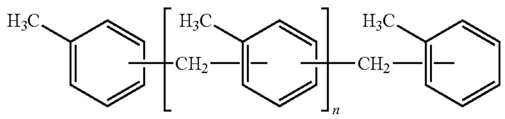

(M')

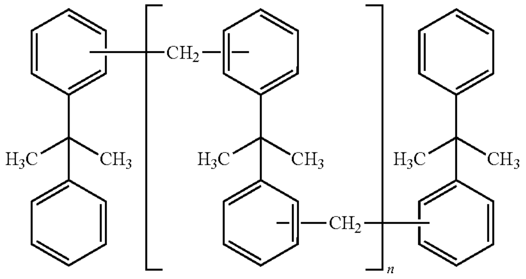

and (N')

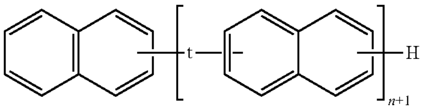

in Formula A', -q- is $—CH_2—$ or a direct linkage, in Formula D', -r- is $—C(CH_3)_2—$, $—CH_2—$, $—C(CF_3)_2—$, $—SO_2—$, —S—,

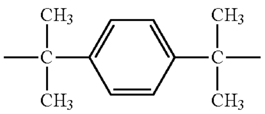

or

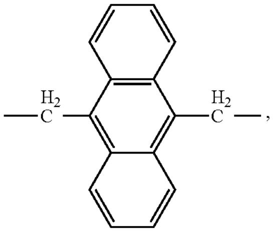

-continued
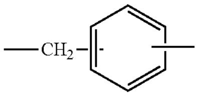
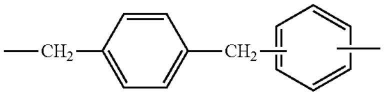
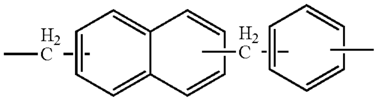
in Formula K', s is
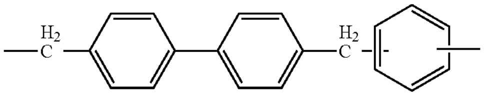
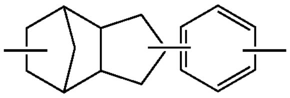
or
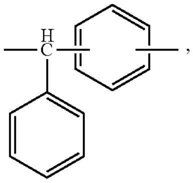
,
in Formula N', t is
$—CH_2—$,
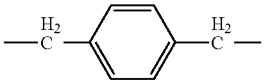
or
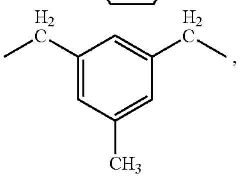
,
and
in Formulae K' to N', n is an integer equal to or greater than 1.
[Formula S4]
(S41)
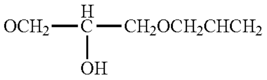
(S42)
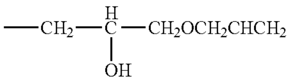
(S43)
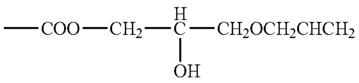
-continued
(S44)
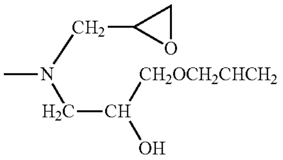
and
(S45)
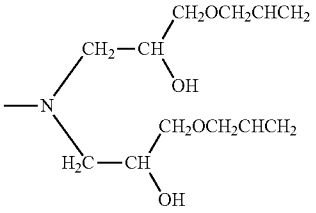
[Formula S5(3-1)]
(S51)
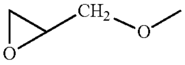
(S52)
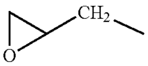
(S53)
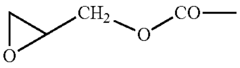
(S54)
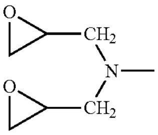
(S55)
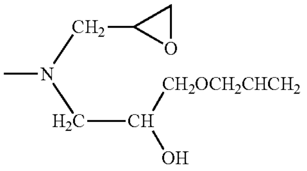
(S56)
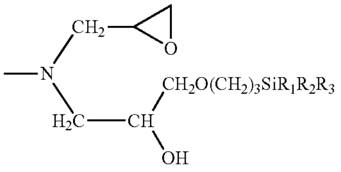
(S57)
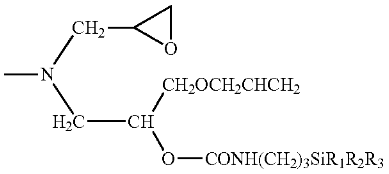
and
(S58)
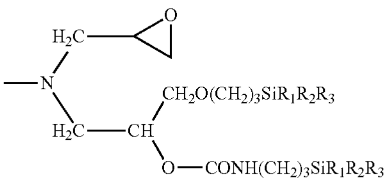
in Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

[Formula 6(2)]

(LG1)

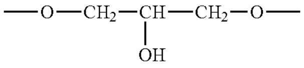

(LG2)

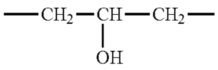

(LG3)

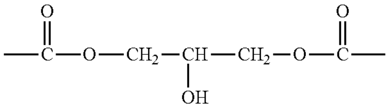

(LG4)

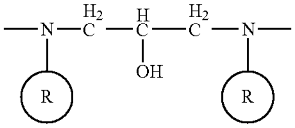

(LG5)

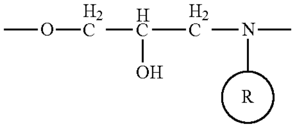

(LG6)

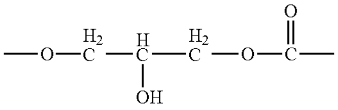

(LG7)

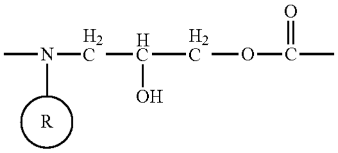

(LG8)

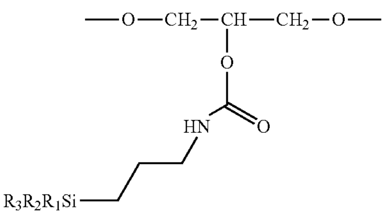

(LG9)

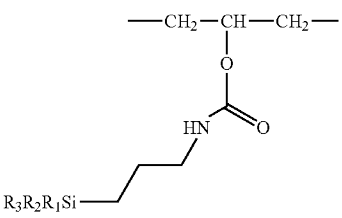

-continued (LG10)

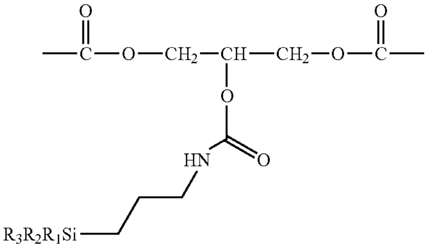

(LG11)

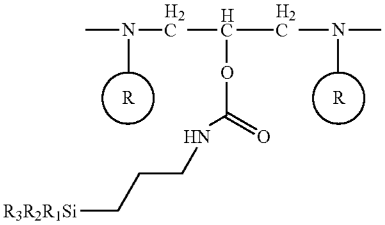

(LG12)

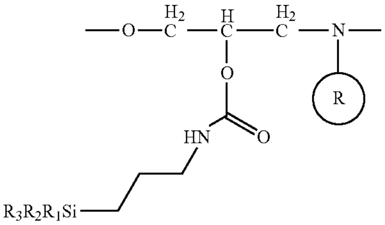

(LG13)

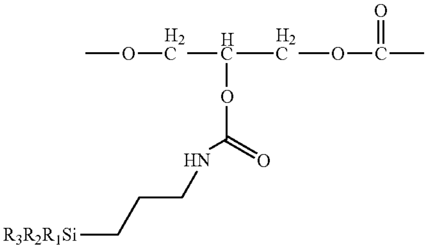

(LG14)

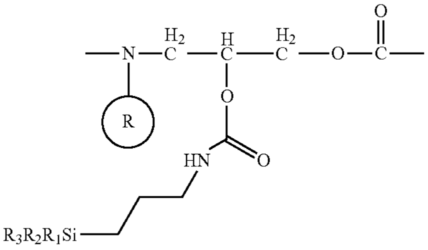

in Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen, a glycidyl group or

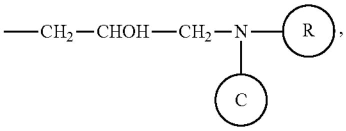, where Ⓒ is a linking moiety to another core, Ⓡ is as defined hereinbefore, and Ⓡ is repeated according to the number of the cores.

According to a sixteenth aspect of the present invention, the epoxy compound having an alkoxysilyl group prepared in the second step may include a core selected from the group consisting of Formulae (A') to (N'), at least one alkoxysilyl group selected from the group consisting of Formulae S21 to S26, at least two epoxy groups selected from the group consisting of Formulae S51 to S56, and an optional substituent selected from the group consisting of Formulae S41 to S45, and when the number of the cores of Formulae (A') to (J') is equal to or greater than two, the cores of Formulae (A') to (I') may be connected via a connecting group independently selected from the group consisting of Formulae LG1 to LG7 and the cores of Formula (J') may be connected via a connecting group of LG2 according to the tenth aspect.

(A')

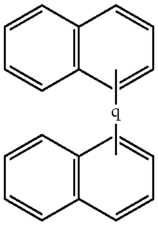

(B')

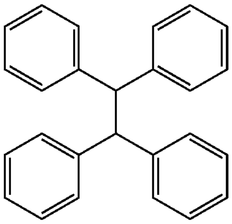

(C')

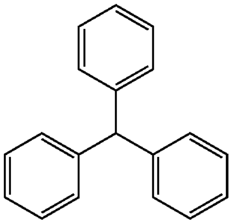

(D')

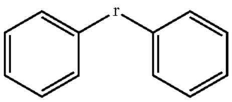

(E')

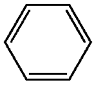

(F')

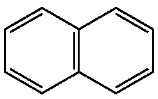

(G')

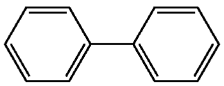

-continued (H')

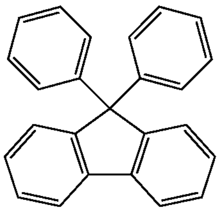

(I')

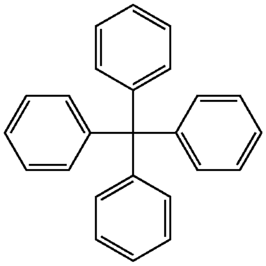

(J')

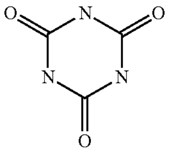

(K')

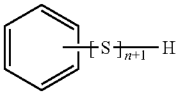

(L')

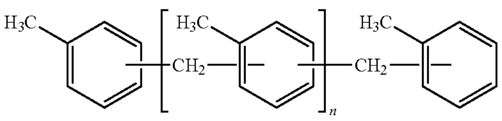

(M')

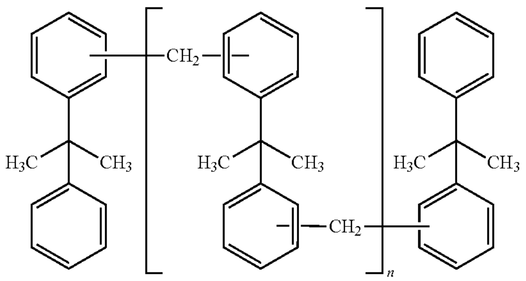

and (N')

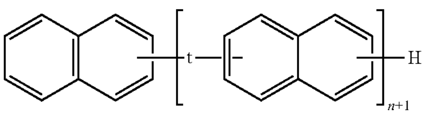

in Formula A', -q- is $—CH_2—$ or a direct linkage, in Formula D', -r- is $—C(CH_3)_2—$, $—CH_2—$, $—C(CF_3)_2—$, $—SO_2—$, —S—,

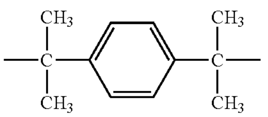

or

-continued

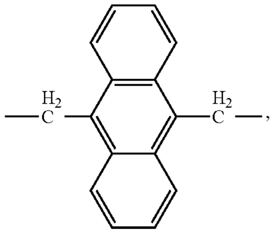

,

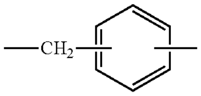

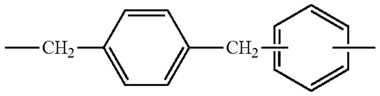

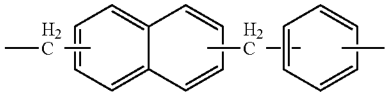

in Formula K', s is

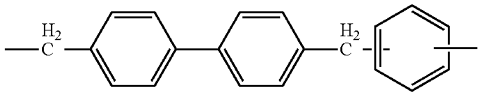

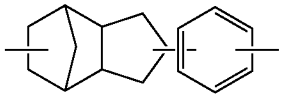

or

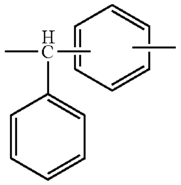

, in Formula N', t is $—CH_2—$,

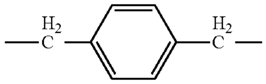

or

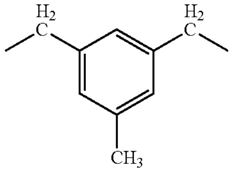

, and in Formulae K' to N', n is an integer equal to or greater than 1.

[Formula S4]

(S41)

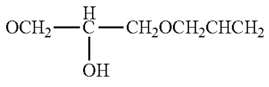

(S42)

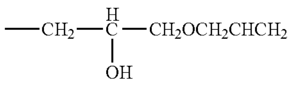

-continued (S43)

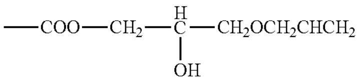

(S44)

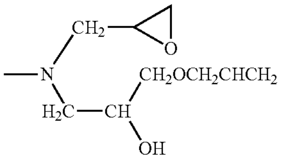

and (S45)

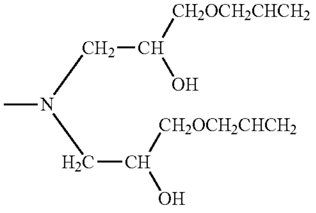

[Formula S5(2-2)]

(S51)

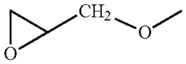

(S52)

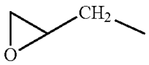

(S53)

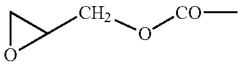

(S54)

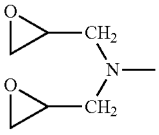

(S55)

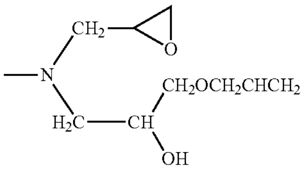

and (S56)

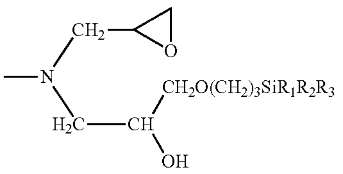

in Formula S56, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

[Formula S6(1)]

(LG1)

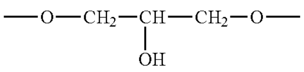

-continued (LG2)

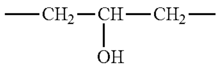

(LG3)

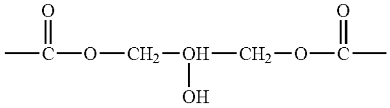

(LG4)

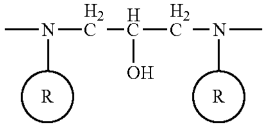

(LG5)

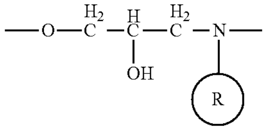

(LG6)

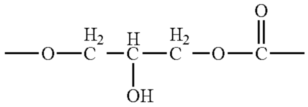

and (LG7)

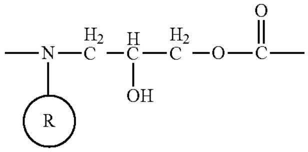

in Formulae LG4, LG5 and LG7, Ⓡ is hydrogen, a glycidyl group or

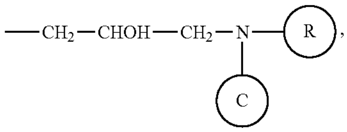

, where Ⓒ is a linking moiety to another core, and Ⓡ is as defined hereinbefore and is repeated according to the number of the cores.

According to a seventeenth aspect of the present invention, the epoxy compound having an alkoxysilyl group prepared in the third step may include a core selected from the group consisting of Formulae (A') to (N'), at least one alkoxysilyl group selected from the group consisting of a S2 substituent independently selected from the group consisting of Formulae S21 to S26, and a S3 substituent independently selected from the group consisting of Formulae S31 to S38, at least two epoxy groups selected from the group consisting of Formulae S51 to S58, and an optional substituent selected from the group consisting of Formulae S41 to S45, and when the number of the cores of Formulae (A') to (J') is equal to or greater than two, the cores of Formulae (A') to (I') may be connected via a connecting group independently selected from the group consisting of Formulae LG1 to LG14 and the cores of Formula (J') may be connected via a connecting group of LG2 and LG9 according to the eleventh aspect.

(A')

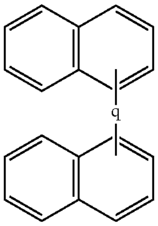

(B')

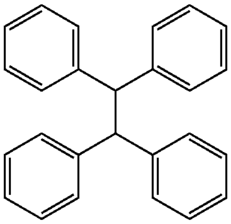

(C')

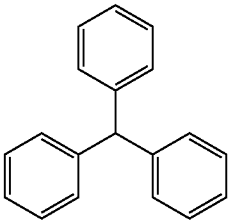

(D')

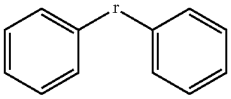

(E')

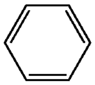

(F')

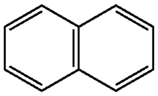

(G')

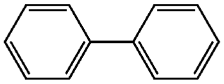

(H')

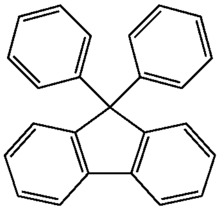

(I')

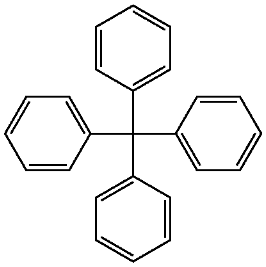

-continued
(J')
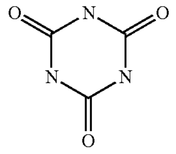
(K')
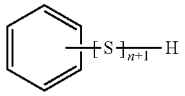
(L')
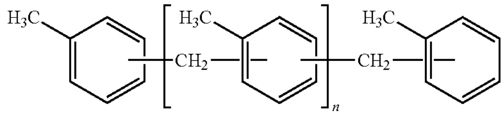
(M')
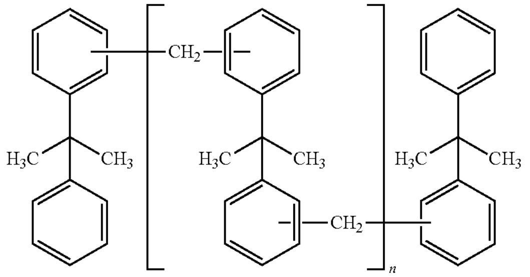
and
(N')
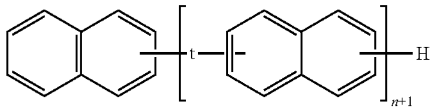
in Formula A', -q- is $-CH_2-$ or a direct linkage,
in Formula D', -r- is $-C(CH_3)_2-$, $-CH_2-$, $-C(CF_3)_2-$, $-SO_2-$, $-S-$,
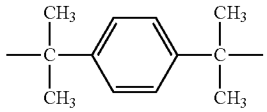
or
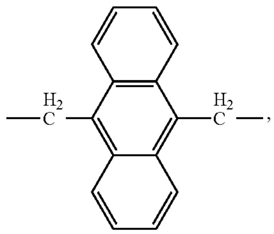
,
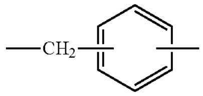
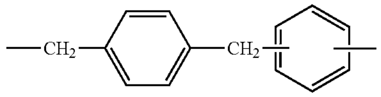
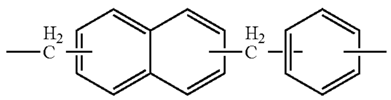
in Formula K', s is
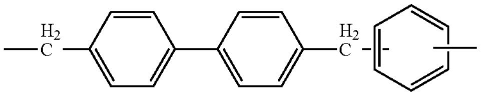
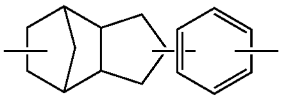
or
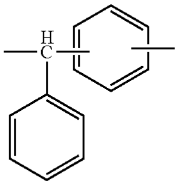
,
in Formula N', t is
$-CH_2-$,
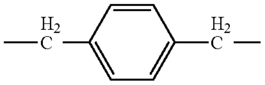
or
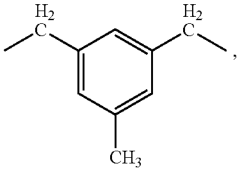
,
and
in Formulae K' to N', n is an integer equal to or greater than 1.
[Formula S4]
(S41)
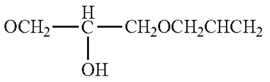
(S42)
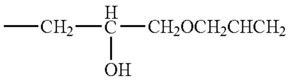
(S43)
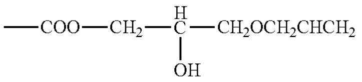
(S44)
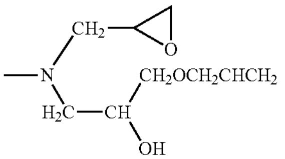
and
(S45)
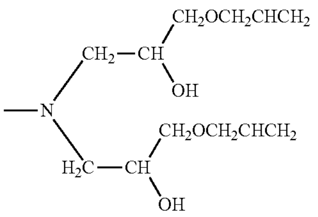

-continued
[Formula S5(3-2)]
(S51)
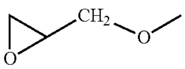
(S52)
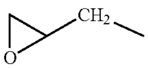
(S53)
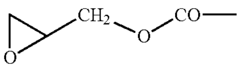
(S54)
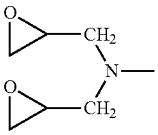
(S55)
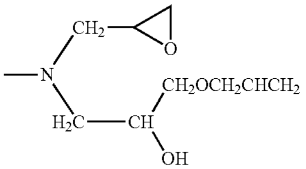
(S56)
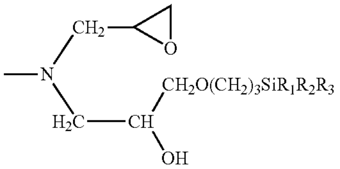
(S57)
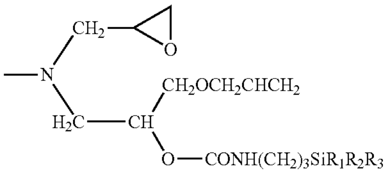
and
(S58)
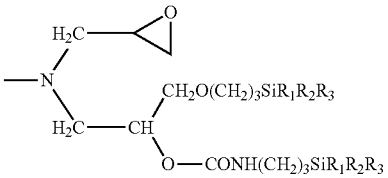
in Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.
[Formula 6(2)]
(LG1)
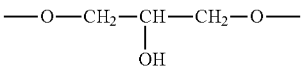
(LG2)
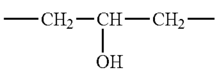
-continued
(LG3)
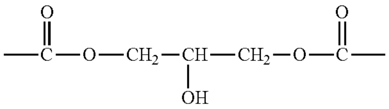
(LG4)
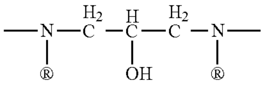
(LG5)
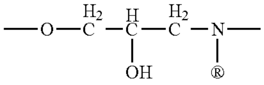
(LG6)
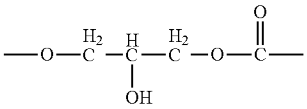
(LG7)
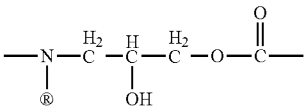
(LG8)
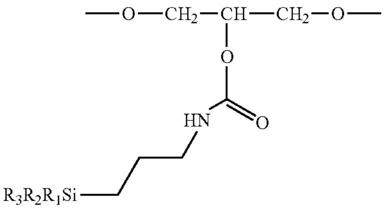
(LG9)
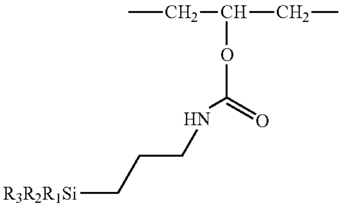
(LG10)
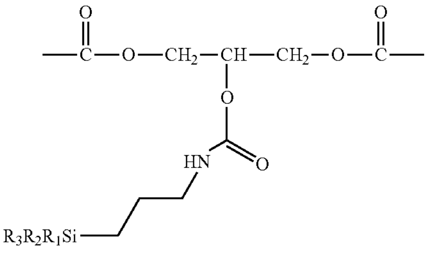
(LG11)
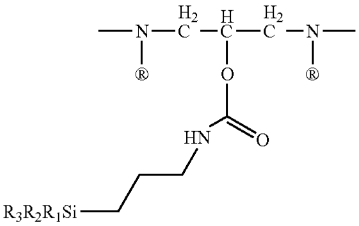

-continued (LG12)

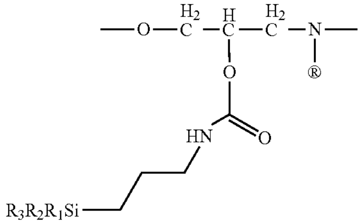

(LG13)

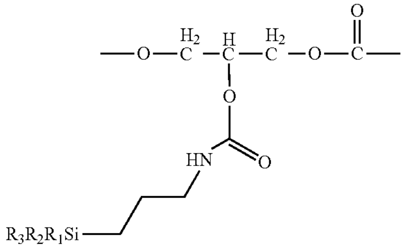

(LG14)

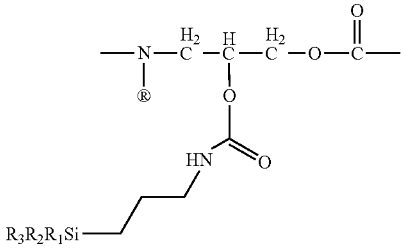

in Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen, a glycidyl group or

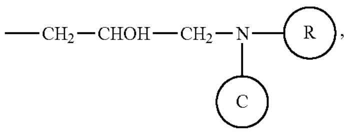

where Ⓒ is a linking moiety to another core, Ⓡ is as defined hereinbefore, and Ⓡ is repeated according to the number of the cores.

According to an eighteenth aspect of the present invention, 0.1 to 10 equivalents of the allyl alcohol may react with respect to 1 equivalent of the epoxy group of the starting material in the first step according to the eighth or tenth aspect.

According to a nineteenth aspect of the present invention, the first step may be performed at a temperature from room temperature to 120° C. for 1 to 120 hours according to the eighth or tenth aspect.

According to a twentieth aspect of the present invention, 0.1 to 5 equivalents of an alkoxysilane of the above Formula B1 may react with respect to 1 equivalent of a hydroxyl group of the intermediate in the second step according to the eighth aspect.

According to a twenty-first aspect of the present invention, 0.1 to 5 equivalents of an alkoxysilane of the above Formula B2 may react with respect to 1 equivalent of the allyl group of the intermediate in the second step according to the tenth aspect.

According to a twenty-second aspect of the present invention, the second step may be performed at a temperature from room temperature to 120° C. for 1 to 72 hours according to the eighth or tenth aspect.

According to a twenty-third aspect of the present invention, 0.1 to 5 equivalents of an alkoxysilane of the above Formula B2 may react with respect to 1 equivalent of the epoxy compound having an alkoxysilyl group obtained in the second step in the optional third step according to the ninth aspect.

According to a twenty-fourth aspect of the present invention, 0.1 to 5 equivalents of an alkoxysilane of the above Formula B1 may react with respect to 1 equivalent of a hydroxyl group of the epoxy compound having an alkoxysilyl group obtained in the second step in the optional third step according to the eleventh aspect.

According to a twenty-fifth aspect of the present invention, the optional third step may be performed at a temperature from room temperature to 120° C. for 1 to 72 hours according to the ninth or eleventh aspect.

According to a twenty-sixth aspect of the present invention, there is provided an epoxy composition including the epoxy compound having an alkoxysilyl group according to any one of the first to the sixth aspects.

According to a twenty-seventh aspect of the present invention, at least one epoxy compound selected from the group consisting of a glycidyl ether epoxy compound, a glycidyl epoxy compound, a glycidyl amine epoxy compound, a glycidyl ester epoxy compound, a rubber modified epoxy compound, an aliphatic polyglycidyl epoxy compound and an aliphatic glycidyl amine epoxy compound may be further included in the epoxy composition according to the twenty-sixth aspect.

According to a twenty-eighth aspect of the present invention, bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, may be included as a core structure in the epoxy composition according to the twenty-seventh aspect.

According to a twenty-ninth aspect of the present invention, the epoxy composition may include 10 wt % to 100 wt % of the epoxy compound having an alkoxysilyl group and 0 wt % to 90 wt % of at least one epoxy compound selected from the group consisting of the glycidyl ether epoxy compound, the glycidyl epoxy compound, the glycidyl amine epoxy compound, the glycidyl ester epoxy compound, the rubber modified epoxy compound, the aliphatic polyglycidyl epoxy compound and the aliphatic glycidyl amine epoxy compound based on the total amount of the epoxy compound in the epoxy composition according to the twenty-seventh aspect.

According to a thirtieth aspect of the present invention, the epoxy composition may include 30 wt % to 100 wt % of the epoxy compound having an alkoxysilyl group and 0 wt % to 70 wt % of at least one epoxy compound selected from the group consisting of the glycidyl ether epoxy compound, the glycidyl epoxy compound, the glycidyl amine epoxy compound, the glycidyl ester epoxy compound, the rubber modified epoxy compound, the aliphatic polyglycidyl epoxy compound and the aliphatic glycidyl amine epoxy compound based on the total amount of the epoxy compound in the epoxy composition according to the twenty-ninth aspect.

According to a thirty-first aspect of the present invention, at least one filler selected from the group consisting of inorganic particles or a fiber may be further included in the epoxy composition according to any one of the twenty-sixth to the thirtieth aspects.

According to a thirty-second aspect of the present invention, the inorganic particle may be at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane in the epoxy composition according to the thirty-first aspect.

According to a thirty-third aspect of the present invention, an amount of the inorganic particles may be 5 wt % to 95 wt % based on a total solid content of the epoxy composition in the epoxy composition according to the thirty-third aspect.

According to a thirty-fourth aspect of the present invention, an amount of the inorganic particles may be 30 wt % to 95 wt % based on a total solid content of the epoxy composition in the epoxy composition according to the thirty-third aspect.

According to a thirty-fifth aspect of the present invention, an amount of the inorganic particles may be 5 wt % to 60 wt % based on a total solid content of the epoxy composition in the epoxy composition according to the thirty-third aspect.

According to a thirty-sixth aspect of the present invention, the fiber may be at least one glass fiber selected from the group consisting of an E-glass fiber, a T-glass fiber, an S-glass fiber, an NE-glass fiber, a D-glass fiber, an H-glass fiber, quartz, and at least one organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber in the epoxy composition according to the thirty-first aspect.

According to a thirty-seventh aspect of the present invention, the fiber may be the E-glass fiber in the epoxy composition according to the thirty-sixth aspect.

According to a thirty-eighth aspect of the present invention, the fiber may be the T-glass fiber in the epoxy composition according to the thirty-sixth aspect.

According to a thirty-ninth aspect of the present invention, an amount of the fiber may be 10 wt % to 90 wt % based on a total solid content of the epoxy composition in the epoxy composition according to the thirty-first aspect.

According to a fortieth aspect of the present invention, inorganic particles may be further included in the case that a fiber is included in the epoxy composition according to the thirty-first aspect.

According to a forty-first aspect of the present invention, a curing agent may be further included in the epoxy composition according to any one of the twenty-sixth to the fortieth aspects.

According to a forty-second aspect of the present invention, a reaction catalyst for the alkoxysilyl group may be further included in the epoxy composition according to any one of the twenty-sixth to the fortieth aspects.

According to a forty-third aspect of the present invention, the reaction catalyst for the alkoxysilyl group may be at least one selected from the group consisting of at least one inorganic acid selected from the group consisting of nitric acid, sulfuric acid, hydrochloric acid, acetic acid and phosphoric acid, ammonia, KOH, $NH_4OH$, amine, a transition metal alkoxide, and a tin compound in the epoxy composition according to the forty-second aspect.

According to a forty-fourth aspect of the present invention, the reaction catalyst may be used by 0.01 phr to 10 phr based on the epoxy compound having an alkoxysilyl group in the epoxy composition according to the forty-second aspect.

According to a forty-fifth aspect of the present invention, water may be further included in the epoxy composition according to the forty-second aspect.

According to a forty-sixth aspect of the present invention, there is provided an electronic material including the epoxy composition according to any one of the twenty-sixth to the forty-fifth aspects.

According to a forty-seventh aspect of the present invention, there is provided a substrate including the epoxy composition according to any one of the twenty-sixth to the forty-fifth aspects.

According to a forty-eighth aspect of the present invention, there is provided a film including the epoxy composition according to any one of the twenty-sixth to the forty-fifth aspects.

According to a forty-ninth aspect of the present invention, there is provided a laminated including a metal layer placed on a base layer formed using the epoxy composition according to any one of the twenty-sixth to the forty-fifth aspects.

According to a fiftieth aspect of the present invention, there is provided a printed circuit board including the laminated according to the forty-ninth aspect.

According to a fifty-first aspect of the present invention, there is provided a semiconductor device including the printed circuit board according to the fiftieth aspect.

According to a fifty-second aspect of the present invention, there is provided a semiconductor packaging material including the epoxy composition according to any one of the twenty-sixth to the forty-fifth aspects.

According to a fifty-third aspect of the present invention, there is provided a semiconductor device including the semiconductor packaging material according to the fifty-second aspect.

According to a fifty-fourth aspect of the present invention, there is provided an adhesive including the epoxy composition according to any one of the twenty-sixth to the forty-fifth aspects.

According to a fifty-fifth aspect of the present invention, there is provided a paint composition including the epoxy composition according to any one of the twenty-sixth to the forty-fifth aspects.

According to a fifty-sixth aspect of the present invention, there is provided a composite material including the epoxy composition according to any one of the twenty-sixth to the forty-fifth aspects.

According to a fifty-seventh aspect of the present invention, there is provided a prepreg including the epoxy composition according to any one of the twenty-sixth to the forth-fifth aspects.

According to a fifty-eighth aspect of the present invention, there is provided a laminated including a metal layer placed on the prepreg of the fifty-seventh aspect.

According to a fifty-ninth aspect of the present invention, there is provided a cured product of the epoxy composition according to any one of the twenty-sixth to the forty-fifth aspects.

According to a sixtieth aspect of the present invention, the cured product may have a CTE of less than or equal to 60 ppm/° C. according to the fifty-ninth aspect.

According to a sixty-first aspect of the present invention, the cured product may have a glass transition temperature of 100° C. or above, or may not exhibit the glass transition temperature according to the fifty-ninth aspect.

Advantageous Effects

According to the embodiments of the present invention, due to chemical bonding formed by a chemical reaction between an alkoxysilyl group and a filler (fiber and/or inorganic particles) and between the alkoxysilyl groups in the epoxy composition, composite and/or cured product of the epoxy composition including a novel epoxy compound having an alkoxysilyl group may have improved heat resistance properties. That is, the CTE of an epoxy composite may be decreased, and a glass transition temperature may be increased or the glass transition temperature may not be exhibited (Tg-less). In addition, the cured product of the epoxy compound of the present invention may exhibit good flame retardancy.

Further, when the epoxy composition according to the present invention is applied to a metal film, good adhesive properties may be exhibited due to the chemical bonding between the functional group at the surface of the metal film and the alkoxysilyl group. In addition, due to the increase in chemical bonding efficiency of the composition including the epoxy compound having an alkoxysilyl group, a silane coupling agent used in a common epoxy composition may be unnecessary in the composition including the epoxy compound having an alkoxysilyl group. The epoxy composition including the epoxy compound may have good curing efficiency, and a composite formed through the curing thereof may exhibit good thermal expansion properties such as a low CTE and a high glass transition temperature or Tg-less.

DESCRIPTION OF DRAWINGS

The above and other aspects, features and other advantages of the present invention will be more clearly understood from the following detailed description taken in conjunction with the accompanying drawings, in which.

BEST MODE

Figure 1:
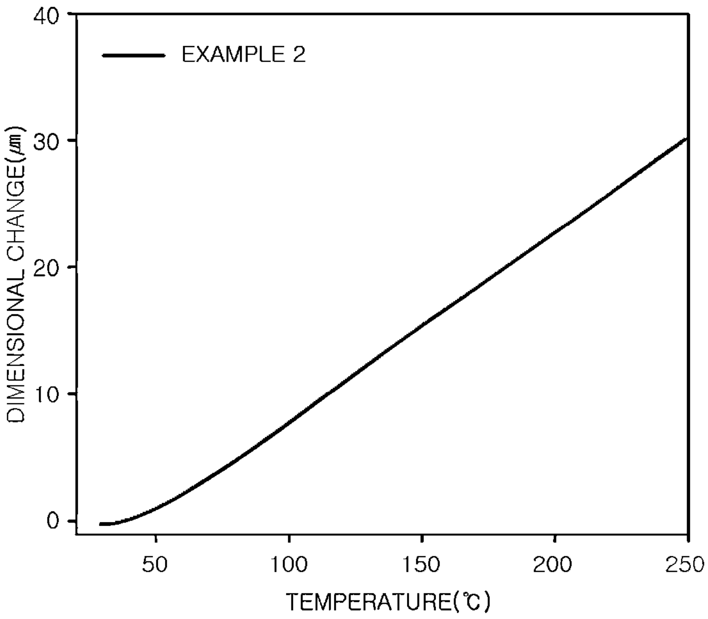
FIG. 1 is a graph illustrating dimensional change with the variation of the temperature of a composite according to Example 2.

The present invention provides a novel epoxy compound having an alkoxysilyl group, a composite obtained by curing an epoxy composition exhibiting improved heat resistance properties, a particularly low CTE and a high Tg (including Tg-less) and/or a cured product formed using the composition exhibiting good flame retardancy, a method for preparing the same, an epoxy composition including the same, a cured product made from the composition and a use of the composition.

In the present invention, "composite" refers to a cured product formed using a composition including an epoxy compound and a filler (fiber and/or inorganic particles). In the present invention, "cured product", as a general sense, refers to a cured product formed using a composition including an epoxy compound, for example, a cured product formed using a composition including an epoxy compound and a curing agent, and at least one selected from the group consisting of a filler, an optional and additional curing agent, an optional curing catalyst and other additives. In addition, the term "cured product" is also used to denote a "partially-cured product". Generally, only the cured product reinforced with inorganic particles and/or a fiber is referred to as a composite, and the meaning of the cured product is broader than that of the composite. However, the cured product reinforced with the inorganic particles and/or the fiber may be considered to have the same meaning as the composite.

When forming a composite through curing the epoxy composition including the epoxy compound having an alkoxysilyl group in accordance with the present invention, an epoxy group may react with a curing agent to conduct a crosslinking reaction, and the alkoxysilyl group may form an interfacial bonding with the surface group of the filler (fiber and/or inorganic particles) and/or between alkoxysilyl groups. Thus, the remarkably high chemical bonding efficiency in an epoxy composite system may be obtained, and as a result, a low CTE and high increasing effect of glass transition temperature or Tg-less may be achieved. Therefore, dimensional stability may be improved. In addition, separate silane coupling agents are not necessary. Further, the cured product including the epoxy compound of the present invention exhibits good flame retardancy.

In addition, when forming a composite by the thermal curing and/or the photo curing of the epoxy composition including the epoxy compound having an alkoxysilyl group of the present invention, good curing properties may be attained. Particularly, the interference of photo curing reaction due to oxygen may be prevented for an alkoxysilylated epoxy compound including $—O—CH_2—CHOHCH_2O(CH_2)_3SiR_1R_2R_3$, $—CH_2—CHOHCH_2O(CH_2)_3SiR_1R_2R_3$, or $—COO—CH_2—CHOHCH_2O(CH_2)_3SiR_1R_2R_3$ (where at least one of $R_1$ to $R_3$ is an alkoxy group having 1 to 5 carbon atoms, and the remainder thereof are alkyl groups having 1 to 10 carbon atoms), when being compared with an acryl compound, and due to the smaller curing shrinkage of the alkoxysilylated epoxy compound, good adhesion properties may be attained, and the formation of cracks may be prevented.

Further, when applying the epoxy composition of the present invention to a chemically treated metal film such as a copper film, a chemical bond may be formed with a hydroxyl group or the like on the surface of the metal produced through the metal surface treatment, thereby exhibiting good adhesion on the metal film.

1. Epoxy Compound

According to an embodiment of the present invention, an epoxy compound having at least one alkoxysilyl group and at least two epoxy groups in a core is provided. The alkoxysilyl group (1) may be independently selected from the group consisting of Formulae S11 to S16, (2) may be independently selected from the group consisting of Formulae S21 to S26, (3) may be independently selected from the group consisting of Formulae S11 to S16 and Formulae S31 to S38, or (4) may be independently selected from the group consisting of Formulae S21 to S26 and Formulae S31 to S38.

In the epoxy compound having an alkoxysilyl group according to an embodiment of the present invention, the equivalent ratio of an epoxy group:an alkoxysilyl group may be in a range from 1:10 to 10:1.

[Formula S1]

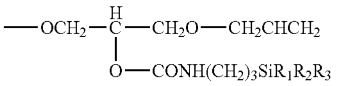

(S11)

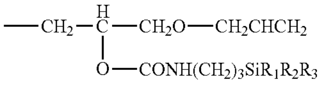

(S12)

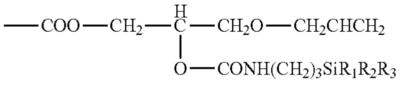

(S13)

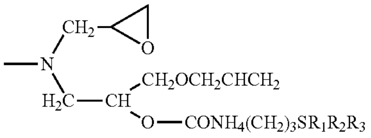

(S14)

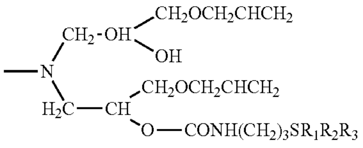

(S15)

and

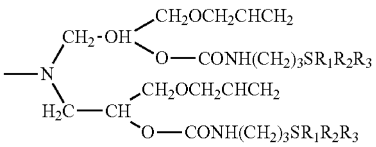

(S16)

In Formulae S11 to S16, at least one of $R_1$ to $R_3$ is an alkoxy group having 1 to 5 carbon atoms, preferably, an alkoxy group having 2 to 3 carbon atoms, and more preferably, an ethoxy group, and the remainder thereof are alkyl groups having 1 to 10 carbon atoms. The alkoxy group and the alkyl group are linear or branched.

[Formula S2]

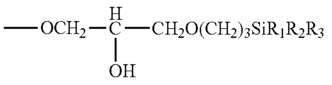

(S21)

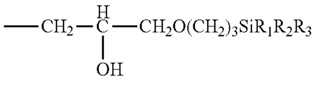

(S22)

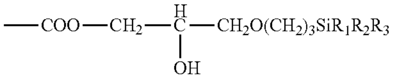

(S23)

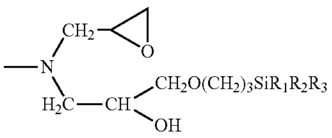

(S24)

-continued

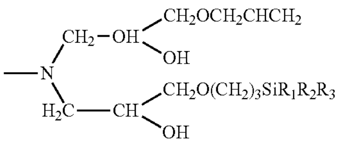

(S25)

and

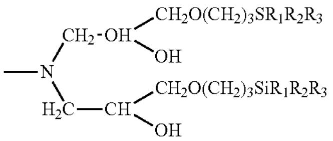

(S26)

In Formulae S21 to S26, at least one of $R_1$ to $R_3$ is an alkoxy group having 1 to 5 carbon atoms, preferably, an alkoxy group having 2 to 3 carbon atoms, and more preferably, an ethoxy group, and the remainder thereof are alkyl groups having 1 to 10 carbon atoms. The alkoxy group and the alkyl group are linear or branched.

[Formula S3]

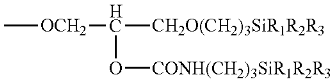

(S31)

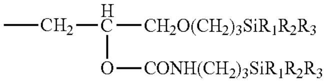

(S32)

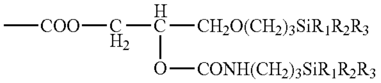

(S33)

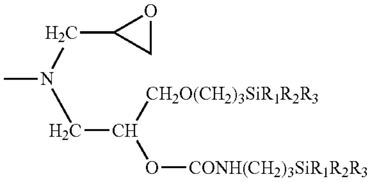

(S34)

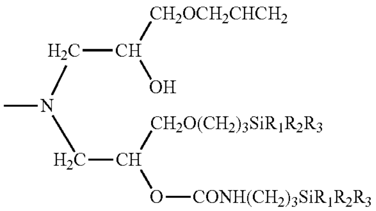

(S35)

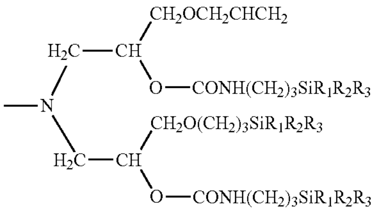

(S36)

-continued (S37)

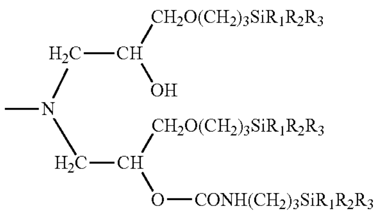

and (S38)

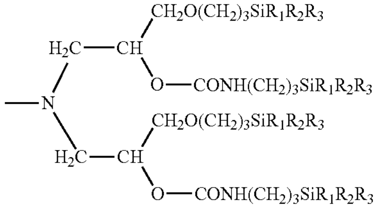

In Formulae S31 to S38, at least one of $R_1$ to $R_3$ is an alkoxy group having 1 to 5 carbon atoms, preferably, an alkoxy group having 2 to 3 carbon atoms, and more preferably, an ethoxy group, and the remainder thereof are alkyl groups having 1 to 10 carbon atoms. The alkoxy group and the alkyl group are linear or branched.

The epoxy group in the epoxy compound having an alkoxysilyl group according to an embodiment of the present invention is independently selected from Formulae S51 to S58 in the following Formula S5(3).

[Formula S5(3)]

(S51)

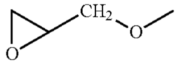

(S52)

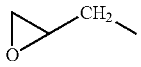

(S53)

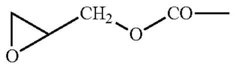

(S54)

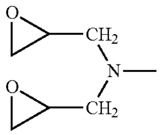

(S55)

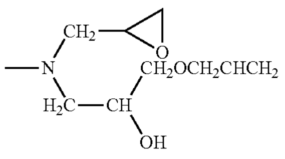

(S56)

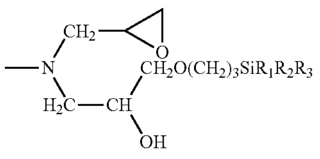

-continued (S57)

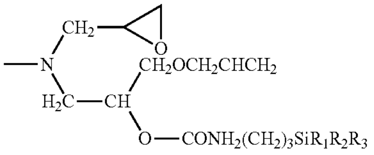

and (S58)

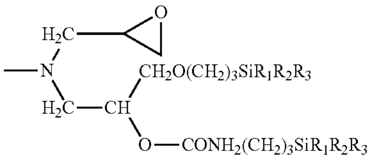

In Formulae S56 to S58, at least one of $R_1$ to $R_3$ is an alkoxy group having 1 to 5 carbon atoms, preferably, an alkoxy group having 2 to 3 carbon atoms, and more preferably, an ethoxy group, and the remainder thereof are alkyl groups having 1 to 10 carbon atoms. The alkoxy group and the alkyl group are linear or branched.

The alkoxysilylated epoxy compound may include bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as a core structure.

Further, in the alkoxysilylated epoxy compound, the core may be an aromatic core and may be one selected from the group consisting of Formulae A' to N'. In the present invention, the core is understood to include the structure of Formulae A' to J' and the structure including a repeating unit such as in Formulae K' to N'.

(A')

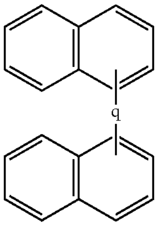

(B')

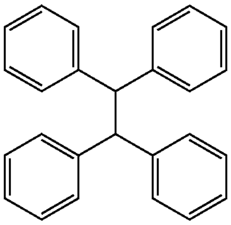

(C')

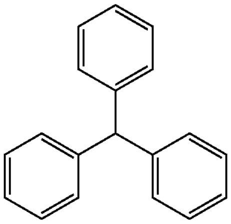

-continued
(D′)
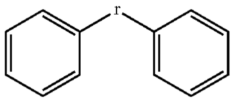
(E′)
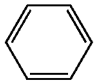
(F′)
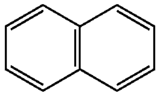
(G′)
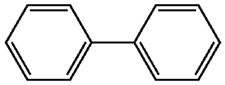
(H′)
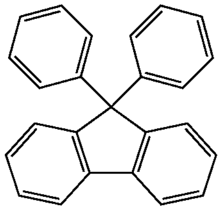
(I′)
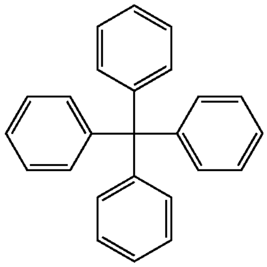
(J′)
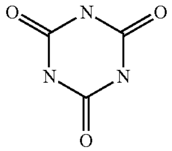
(K′)
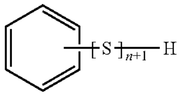
(L′)
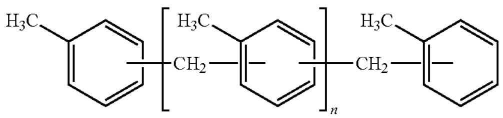
-continued
(M′)
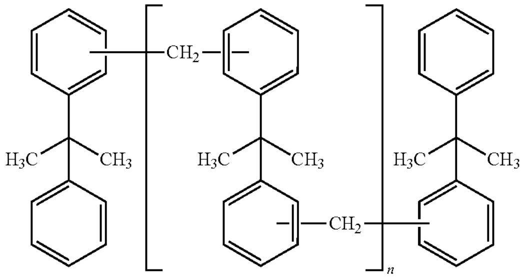
and
(N′)
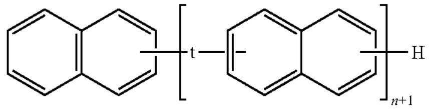
in Formula A', -q- is —$CH_2$— or a direct linkage,
in Formula D', -r- is —$C(CH_3)_2$—, —$CH_2$—, —$C(CF_3)_2$—, —$SO_2$—, —S—,
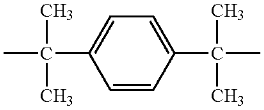
or
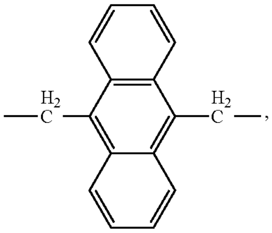
,
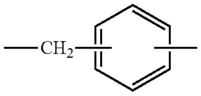
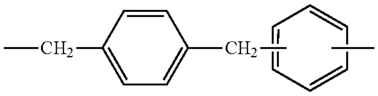
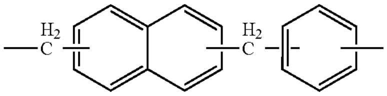
in Formula K', s is
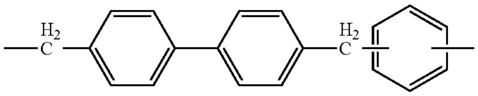
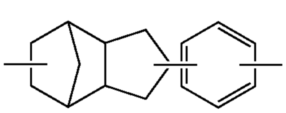
or
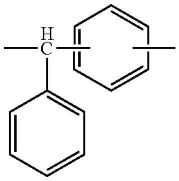
, in Formula N', t is $-CH_2-$, 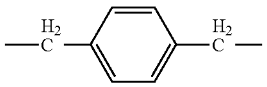 or

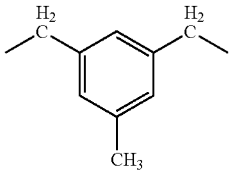, and in Formulae K' to N', n is an integer equal to or greater than 1.

Further, when the number of cores of (A') to (J') is equal to or greater than two in the alkoxysilylated epoxy compound (where the cores are the same kind, and the same will be applied for a case including at least two cores, hereinafter), the cores may be connected via a connecting group LG. From 1 to 1,000 core structures may be additionally connected, as occasion demands. Particularly, the cores of Formulae (A') to (I') may be connected via the connecting group LG independently selected from the group consisting of Formulae LG1 to LG14, and the core of Formula (J') may be connected via a connecting group independently selected from the group consisting of Formulae LG2 and LG9. Through the connecting group, from 1 to 1,000 cores may be additionally connected. For at least three cores, at least two connecting groups may be used, and in this case, each connecting group may be the same or different. When the connecting group is provided in plural, the connecting group may be independently selected from various connecting groups.

[Formula 6(2)]

(LG1)

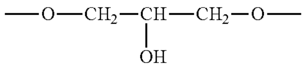

(LG2)

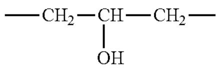

(LG3)

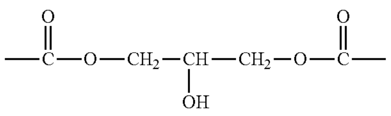

(LG4)

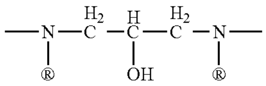

(LG5)

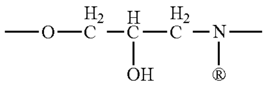

(LG6)

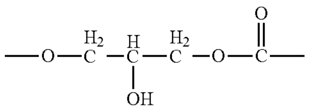

-continued (LG7)

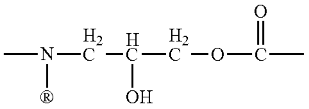

(LG8)

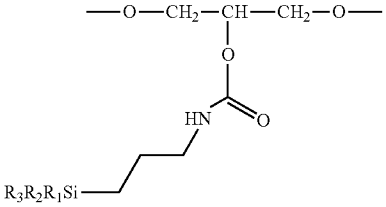

(LG9)

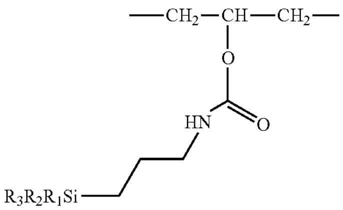

(LG10)

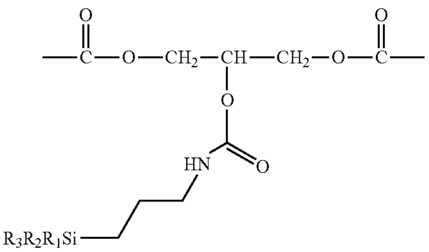

(LG11)

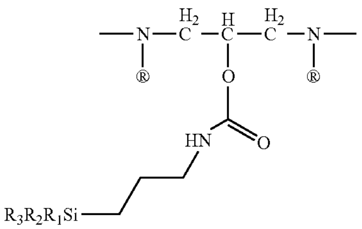

(LG12)

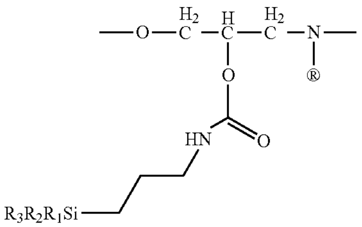

(LG13)

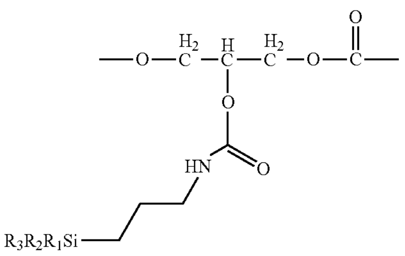

-continued (LG14)

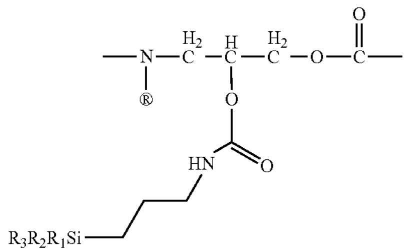

in Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen, a glycidyl group or

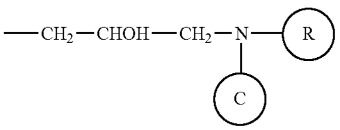

, where Ⓒ is a linking moiety to another core, Ⓡ is as defined hereinbefore, and Ⓡ is repeated according to the number of the cores.

In Formulae LG8 to LG14, at least one of $R_1$ to $R_3$ is an alkoxy group having 1 to 5 carbon atoms, preferably, an alkoxy group having 2 to 3 carbon atoms, and more preferably, an ethoxy group, and the remainder thereof are alkyl groups having 1 to 10 carbon atoms. The alkoxy group and the alkyl group are linear or branched.

Further, the epoxy compound having an alkoxysilyl group of the present invention may further include a substituent S4 selected from the group consisting of Formulae S41 to S45.

[Formula S4]

(S41)

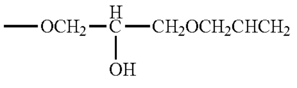

(S42)

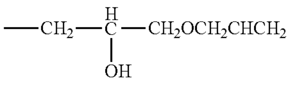

(S43)

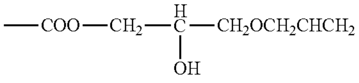

(S44)

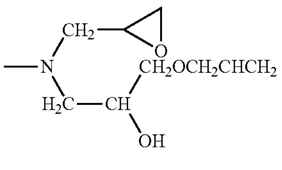

and

-continued (S45)

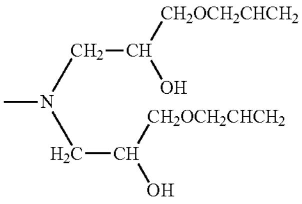

Particularly, for example, when the core is a naphthalene core of the above Formula (F'), the epoxy compound according to an embodiment of the present invention may be represented by the following Formula (FI), and when the core is a biphenyl core of the above Formula (G'), the epoxy compound according to an embodiment of the present invention may be represented by the following Formula (GI). In the epoxy compound having an alkoxysilyl group according to the present invention and any compound described in the present application, the bonding (substitution) of a substituent such as an alkoxysilyl group and an epoxy group to the core and the connection of the core via a connecting group may be clearly understood by a person skilled in the art, based on known techniques in this field. Hereinafter, the naphthalene core and the biphenyl core will be explained in particular. In addition, from the explanation, a person skilled in the art may easily understand the structure of the alkoxysilylated epoxy compound connected via a connecting group and having an epoxy group, an alkoxysilyl group, etc. according to the present invention. In addition, the epoxy compound of the present invention may include a mixture of a dimer, a trimer, etc., other than the monomer of the epoxy compound, and these features are obvious in this field.

(FI)

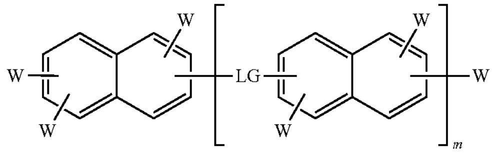

(GI)

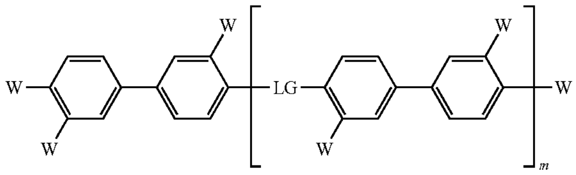

in Formulae FI and GI, at least one of a plurality of Ws may be (1) a S1 substituent independently selected from the group consisting of Formulae S11 to S16, (2) a S2 substituent independently selected from the group consisting of Formulae S21 to S26, (3) an alkoxysilyl group independently selected from the group consisting of the S1 substituent independently selected from the group consisting of Formulae S11 to S16 and a S3 substituent independently selected from the group consisting of Formulae S31 to S38, or (4) an alkoxysilyl group independently selected from the group consisting of the S2 substituent independently selected from the group consisting of Formulae S21 to S26 and the S3 substituent independently selected from the group consisting of Formulae S31 to S38, and at least two thereof are epoxy substituents independently selected from the group consisting of Formulae S51 to S54 and S56 to S58 in Formula S5(3), the remainder other than S1, S2, S3 and S5(3), may be independently selected from the group consisting of H and a S4 substituent independently selected from the group consisting of Formulae S41 to S45, LG is selected from the group consisting of Formulae LG1 to LG14, and m is an integer from 0 to 1,000.

In the epoxy compound having an alkoxysilyl group according to an embodiment of the present invention, at least one alkoxy group of $R_1$ to $R_3$ is preferably an ethoxy group in consideration of reaction stability and/or reactivity with a filler during performance of curing reaction.

In the present specification, an "alkoxy group" denotes —OR (R is an alkyl group) and may be linear or branched.

In the present specification, an "alkyl group" denotes a monovalent hydrocarbon group and may be linear or branched.

Further, when a composite obtained by curing of a composition including the epoxy compound having an alkoxysilyl group according to an embodiment of the present invention is formed, a low CTE and high glass transition temperature or Tg-less may be observed.

According to another aspect of the present invention, there is provided an epoxy compound having a hydroxyl group and an alkyl group including a core selected from the group consisting of Formulae (A') to (N'), at least one substituent selected from the group consisting of Formulae S41 to S45, and at least two epoxy groups independently selected from the group consisting of Formulae S51 to S55.

When the number of the cores of Formulae (A') to (J') is equal to or greater than two, the cores of Formulae (A') to (J') may be connected via a connecting group independently selected from the group consisting of Formulae LG1 to LG7, and the cores of Formula (J') may be connected via a connecting group of LG2. Through the connecting group, from 1 to 1,000 cores may be additionally connected.

[Formula S5(1)]

(S51)

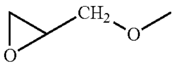

(S52)

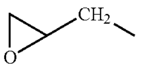

(S53)

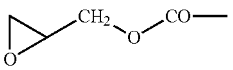

(S54)

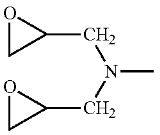 and (S55)

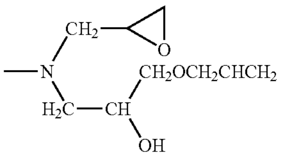

-continued

[Formula S6(1)]

(LG1)

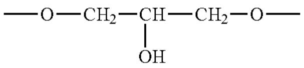

(LG2)

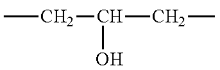

(LG3)

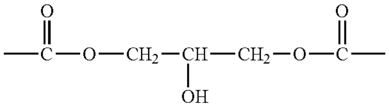

(LG4)

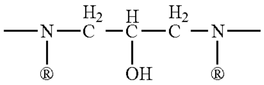

(LG5)

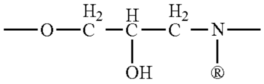

(LG6)

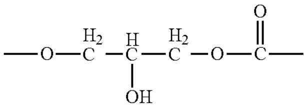 and (LG7)

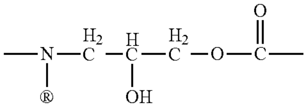

in Formulae LG4, LG5 and LG7, Ⓡ is hydrogen, a glycidyl group or

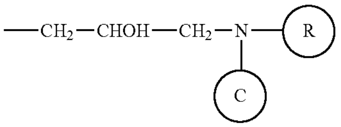, where Ⓒ is a linking moiety to another core, and Ⓡ is as defined hereinbefore and is repeated according to the number of the cores.

2. Method for Preparing Epoxy Compound

The alkoxysilylated epoxy compound according to an embodiment of the present invention may be prepared by epoxy ring-opening reaction via the reaction of an epoxy group and an allyl compound and alkoxysilylation. Accordingly, according to an embodiment of the present invention, there is provided a method for preparing an alkoxysilylated epoxy compound including epoxy ring-opening reaction through the reaction of a starting material of an epoxy compound having at least three epoxy groups and an allyl compound (first step), alkoxysilylation (second step) and an optional and additional alkoxysilylation (third step). The alkoxysilylation may include two kinds of reactions of isocyanate silylation and hydrosilylation, and the alkoxysilylated epoxy compound according to the present invention may be synthesized mainly by two methods according to the reaction order of the isocyanate silylation and the hydrosilylation.

Hereinafter, detailed description will be given considering the method for preparing an alkoxysilylated epoxy compound by the ring-opening reaction of the starting material (first step), the isocyanate silylation (second step) and the optional hydrosilylation (third step) as preparation method 1; and the method for preparing an alkoxysilylated epoxy compound by the ring-opening reaction of the starting material (first step), the hydrosilylation (second step) and the optional hydrosilylation (third step) as preparation method 2.

(1) Preparation Method 1

In the first step, an intermediate obtained by ring-opening the epoxy group of an epoxy compound through the reaction of a starting material of an epoxy compound having at least three epoxy groups with allyl alcohol ($CH_2CHCH_2OH$).

In the first step, the reaction of the starting material of the epoxy compound having at least three epoxy groups with $CH_2CHCH_2OH$ is performed in the presence of a base and an optional solvent. In this case, the reaction is performed using 0.1 to 10 equivalents of $CH_2CHCH_2OH$ per 1 equivalent of the epoxy group of the starting material.

In addition, an optional ammonium halide may be used as occasion demands to improve the solubility of the base in the reaction solvent. In the case that the ammonium halide is used, 0.05 to 5 equivalents of the ammonium halide per 1 equivalent of the epoxy group of the starting material may be used to improve the solubility of the base, thereby decreasing the reaction time of the first step.

The starting material may be any epoxy compounds commonly known as a material having at least three epoxy groups. For example, a glycidyl ether epoxy compound, a glycidyl epoxy compound, a glycidyl amine epoxy compound, or a glycidyl ester epoxy compound having at least three epoxy groups may be included. More particularly, an epoxy compound having at least three epoxy groups, and bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, an aminophenol, a cyclo aliphatic compound, or a novolac unit, as a core structure may be included.

More particularly, the epoxy compound having at least three epoxy groups as the starting material includes a kind of core selected from the group consisting of Formulae (A') to (N') and at least three epoxy groups selected from the group consisting of Formulae S51 to S54. Further, when the number of the cores of Formulae (A') to (J') is equal to or greater than two, the cores of Formulae (A') to (I') may be connected via the connecting group independently selected from the group consisting of Formulae LG1 to LG7, and the cores of Formula (J') may be connected via a connecting group of Formula LG2. Through the connecting group, from 1 to 1,000 cores may be additionally connected.

The reaction temperature and the reaction time of the first step reaction may be changed according to the kind of reactants, and the epoxy group of the starting material of the epoxy compound may be ring-opened to produce the intermediate by performing a reaction, for example, at a temperature range from room temperature (for example, 15 C.° to 25 C.°) to 120° C. for 1 to 120 hours.

The intermediate may be an epoxy compound including at least one substituent independently selected from the group consisting of Formulae S41 to S45 and at least two epoxy groups independently selected from the group consisting of Formulae S51 to S55, and particularly, an epoxy compound of a glycidyl ether type, a glycidyl type, a glycidyl amine type or a glycidyl ester type. More particularly, the intermediate may include at least one substituent independently selected from the group consisting of Formulae S41 to S45 and at least two epoxy groups independently selected from the group consisting of Formulae S51 to S55, and may be an epoxy compound having bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as the core.

More particularly, the intermediate may include a core selected from the group consisting of Formulae (A') to (N'), at least one substituent independently selected from the group consisting of Formulae S41 to S45 and at least two epoxy groups independently selected from the group consisting of Formulae S51 to S55. When the number of the cores of Formulae (A') to (J') is equal to or greater than two, the cores of Formulae (A') to (I') may be connected by a connecting group independently selected from the group consisting of Formulae LG1 to LG7, and the cores of Formula (J') may be connected by a connecting group of LG2.

The base used may include, for example, KOH, NaOH, $K_2CO_3$, $Na_2CO_3$, $KHCO_3$, $NaHCO_3$, NaH, triethylamine and diisopropylethylamine, without limitation. These bases may be used alone or as a combination of two or more thereof 0.1 to 5 equivalents of the base per 1 equivalent of the hydroxyl group of the starting material may be used in consideration of reaction efficiency.

The ammonium halide used may include, for example, tetrabutylammonium iodide ($Bu_4NI$), tetrabutylammonium bromide ($Bu_4NBr$), tetraethylammonium bromide ($Et_4NBr$), tetrabutylammonium nitrate ($Bu_4N^+NO_3^-$) and ammonium chloride ($NH_4Cl$), without limitation. These ammonium halides may be used alone or as a combination of two or more thereof 0.05 to 5 equivalents of the ammonium halide per 1 equivalent of the epoxy group of the starting material may be used in consideration of reaction efficiency. In addition, the use of the ammonium halide may be determined by a person skilled in the art.

The solvent used during the reaction of the first step may be any solvent, as occasion demands. For example, the solvent may not be used if the viscosity of the reactants at the reaction temperature is appropriate for carrying out the reaction without using an additional solvent in the first step reaction. That is, a separate solvent is not necessary in the case in which the viscosity of the reactants is sufficiently low, and the mixing and stirring of the reactants may be easily performed without solvents. This may be easily decided upon by a person skilled in the art. In the case in which a solvent is used, any organic solvents may be used, if they are able to dissolve the reactants properly, do not induce any adverse influence to the reaction, and are easily removed after the reaction. For example, acetonitrile, tetrahydrofuran (THF), methyl ethyl ketone (MEK), acetone, dimethylformamide (DMF), dimethyl sulfoxide (DMSO), methylene chloride, acetonitrile, or the like, may be used, without specific limitation. These solvents may be used alone or as a mixture of two or more thereof. The amount of the solvent may not be limited to being within a specific range, and an appropriate amount of the solvent may be used within a range needed for sufficiently dissolving the reactants and not adversely affecting the reaction. A person skilled in the art may select an appropriate amount of the solvent in consideration of the above-mentioned points.

In the second step, the intermediate obtained in the first step is isocyanate silylated through the reaction of the intermediate and an alkoxysilane of the following Formula (B1) to produce an epoxy compound having at least one alkoxysilyl group independently selected from the group consisting of Formulae S11 to S16 and at least two epoxy groups in a core. The product obtained in the second step also corresponds to an alkoxysilylated epoxy compound, a final product according to an embodiment of the present invention.

Particularly, through the reaction of the intermediate and the isocyanate alkoxysilane of the following Formula B1, the secondary alcohol (hydroxyl group) of the intermediate formed in the first step may be silylated to form an alkoxysilyl group independently selected from the group consisting of Formulae S11 to S16.

In the reaction of the second step, the reaction of the intermediate of the first step and the alkoxysilane of the following Formula B1 may be performed stoichiometrically. In addition, as described above, the alkoxysilane of Formula B1 may react with the secondary alcohol (hydroxyl group) of the intermediate. Thus, in consideration of the above-described points, the reaction between the alkoxysilane of Formula B1 and the intermediate may be conducted with 0.1 to 5 equivalents of the alkoxysilane per 1 equivalent of the alcohol group of the intermediate.

$OCN(CH_2)_3SiR_1R_2R_3$ [Formula B1]

In Formula B1, at least one of $R_1$ to $R_3$ is an alkoxy group of C1-C5, preferably, an alkoxy group of C2-C3, and more preferably, an ethoxy group, and the remainder thereof are alkyl groups of C1-C10. The alkoxy group and the alkyl group may be linear or branched.

The reaction temperature and the reaction time of the second step reaction may be different depending on the reactants and may be, for example, in a temperature range of room temperature (for example 15° C. to 25° C.) to 120° C. for 1 to 72 hours.

The reaction of the second step is conducted in the presence of a base.

The base used may include, for example, $K_2CO_3$, $Na_2CO_3$, $KHCO_3$, $NaHCO_3$, triethylamine and diisopropylethylamine, without limitation. These bases may be used alone or as a combination of two or more thereof 0.1 to 5 equivalents of the base per 1 equivalent of the hydroxyl group of the starting material may be used in consideration of reaction efficiency.

The solvents for the second step reaction may be any solvents as occasion demands. For example, the solvent may not be used if the viscosity of the reactants at the reaction temperature is appropriate for carrying out the reaction without using a additional solvent in the second step reaction. That is, a additional solvent is not necessary in the case in which the viscosity of the reactants is sufficiently low, and the mixing and stirring of the reactants may be easily performed without solvents. This may be easily decided upon by a person skilled in the art. In the case in which a solvent is used, any organic solvent may be used, if they are able to dissolve the reactants properly, do not induce any adverse influence to the reaction, and are easily removed after the reaction. For example, toluene, acetonitrile, THF, MEK, DMF, DMSO, methylene chloride, acetonitrile, or the like, may be used, without specific limitation. These solvents may be used alone or as a mixture of two or more thereof. The amount of the solvent may not be limited to being within a specific range, and an appropriate amount of the solvent may be used within a range needed for sufficiently dissolving the reactants and not adversely affecting the reaction. A person skilled in the art may select an appropriate amount of the solvent in consideration of the above-mentioned points.

As described above, the epoxy compound obtained in the second step also has an epoxy group and an alkoxysilyl group and corresponds to an epoxy compound having an alkoxysilyl group, a target product of the present invention. Particularly, the epoxy compound having an alkoxysilyl group obtained in the second step has a core selected from the group consisting of Formulae (A') to (N'), at least one alkoxysilyl group independently selected from the group consisting of Formulae S11 to S16, at least two epoxy groups selected from the group consisting of Formulae S51 to S55 and S57, and an optional substituent of the above Formula S4 selected from the group consisting of Formulae S41 to S45.

When the number of the cores of Formulae (A') to (J') is equal to or greater than two, the cores of Formulae (A') to (I') may be connected by a connecting group independently selected from the group consisting of LG1 to LG14, and the cores of the above Formula (J') may be connected by a connecting group independently selected from the group consisting of LG2 and LG9. Via the connecting group, 1 to 1,000 cores may be additionally connected.

After the second step, an optional third step of hydrosilylation may be additionally conducted as occasion demands. In the third step, the allyl group of the product of the second step is hydrosilylated through the reaction of the reaction product of the second step and the alkoxysilane of the above Formula B2 to produce an alkoxysilylated epoxy compound according to an embodiment of the present invention having at least one alkoxysilyl group independently selected from the group consisting of Formulae S11 to S16 and Formulae S31 to S38 and at least two epoxy groups.

In the reaction of the third step, the reaction product of the second step and the alkoxysilane of the following Formula B2 may react by the stoichiometrically equivalent molar ratio. In consideration of the above-points, the reaction product of the second step and the alkoxysilane of the following Formula B2 may react with 0.1 to 5 equivalents of the alkoxysilane of Formula B2 per 1 equivalent of the allyl group of the reaction product of the second step.

$HSiR_1R_2R_3$ [Formula B2]

In Formula B2, at least one of $R_1$ to $R_3$ is an alkoxy group of C1-05, preferably, an alkoxy group of C2-C3, and more preferably, an ethoxy group, and the remainder thereof are alkyl groups of C1-C10. The alkoxy group and the alkyl group are linear or branched.

The reaction temperature and the reaction time of the reaction of the third step may be different depending on the reactants, and the reaction may be completed through the reaction, for example, in a temperature range of room temperature (for example 15° C. to 25° C.) to 120° C. for 1 to 72 hours.

The reaction of the third step is conducted in the presence of a metal catalyst. As the metal catalyst, for example, a platinum catalyst of $PtO_2$ or chloroplatinic acid ($H_2PtCl_6$) may be used, without limitation. $1\times10^{-4}$ to 0.05 equivalents of the platinum catalyst per 1 equivalent of the allyl group of the reaction product of the second step may be preferable in consideration of reaction efficiency.

The solvent in the third step may be optionally used as occasion demands, and the kind, the amount and how to use of the solvent are the same as in the second step.

Particularly, the epoxy compound having an alkoxysilyl group obtained in the third step has a core selected from the group consisting of Formulae (A') to (N'), at least one alkoxysilyl group independently selected from the group consisting of Formulae S11 to S16 and Formulae S31 to S38, at least two epoxy groups selected from the group consisting of Formulae S51 to S58, and an optional substituent selected from the group consisting of Formulae S41 to S45.

When the number of the cores of Formulae (A') to (J') is equal to or greater than two, the cores of Formulae (A') to (I') may be connected by a connecting group independently selected from the group consisting of LG1 to LG14, and the cores of the above Formula (J') may be connected by a connecting group independently selected from the group consisting of LG2 and LG9. Via the connecting group, 1 to 1,000 cores may be additionally connected.

The reaction mechanism of preparation method 1 for an epoxy compound including tetraphenyl ethane aromatic core is as follows.

[Preparation Method 1-1]

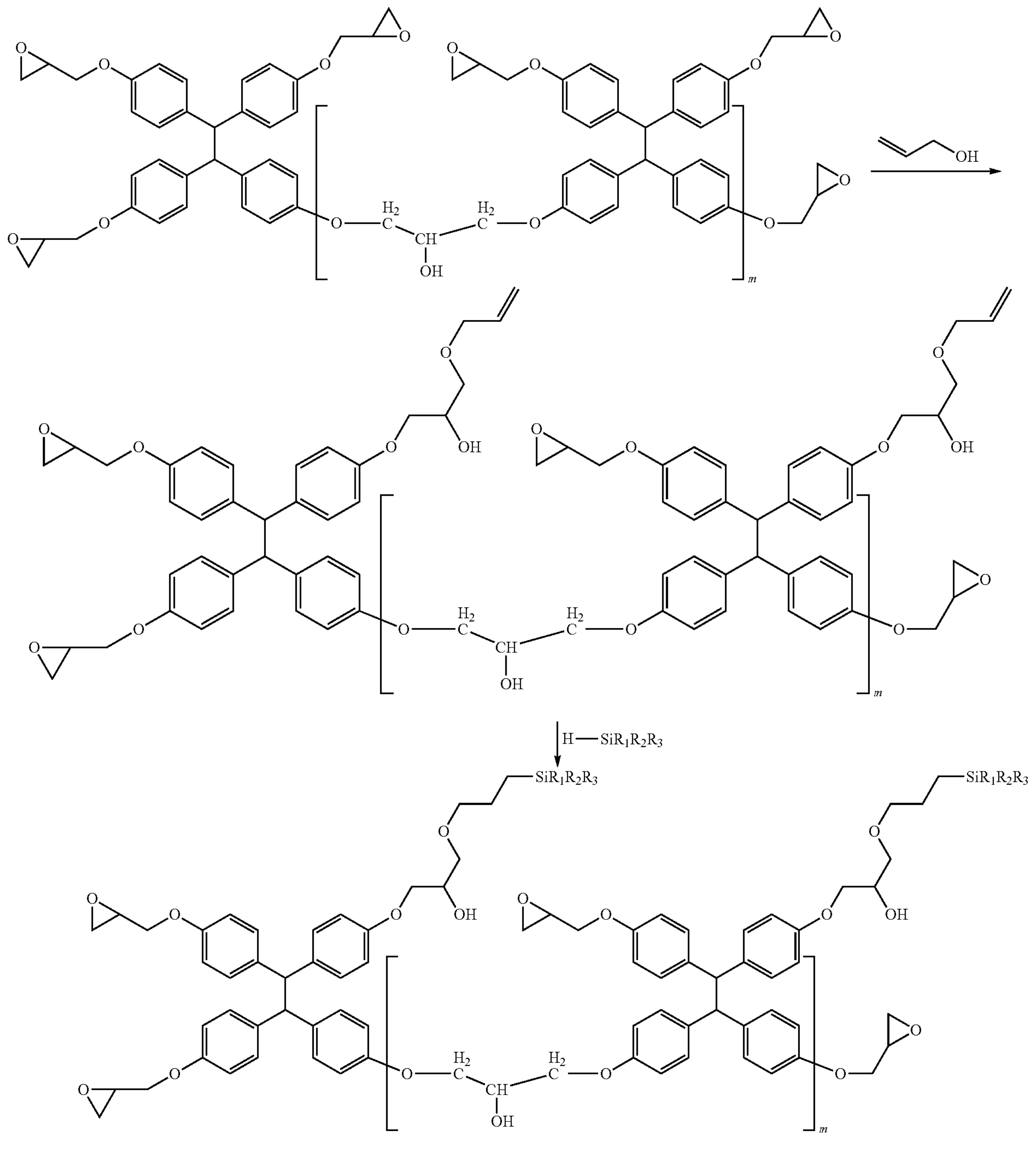

where, m is an integer from 0 to 1,000.

[Preparation Method 1-2]

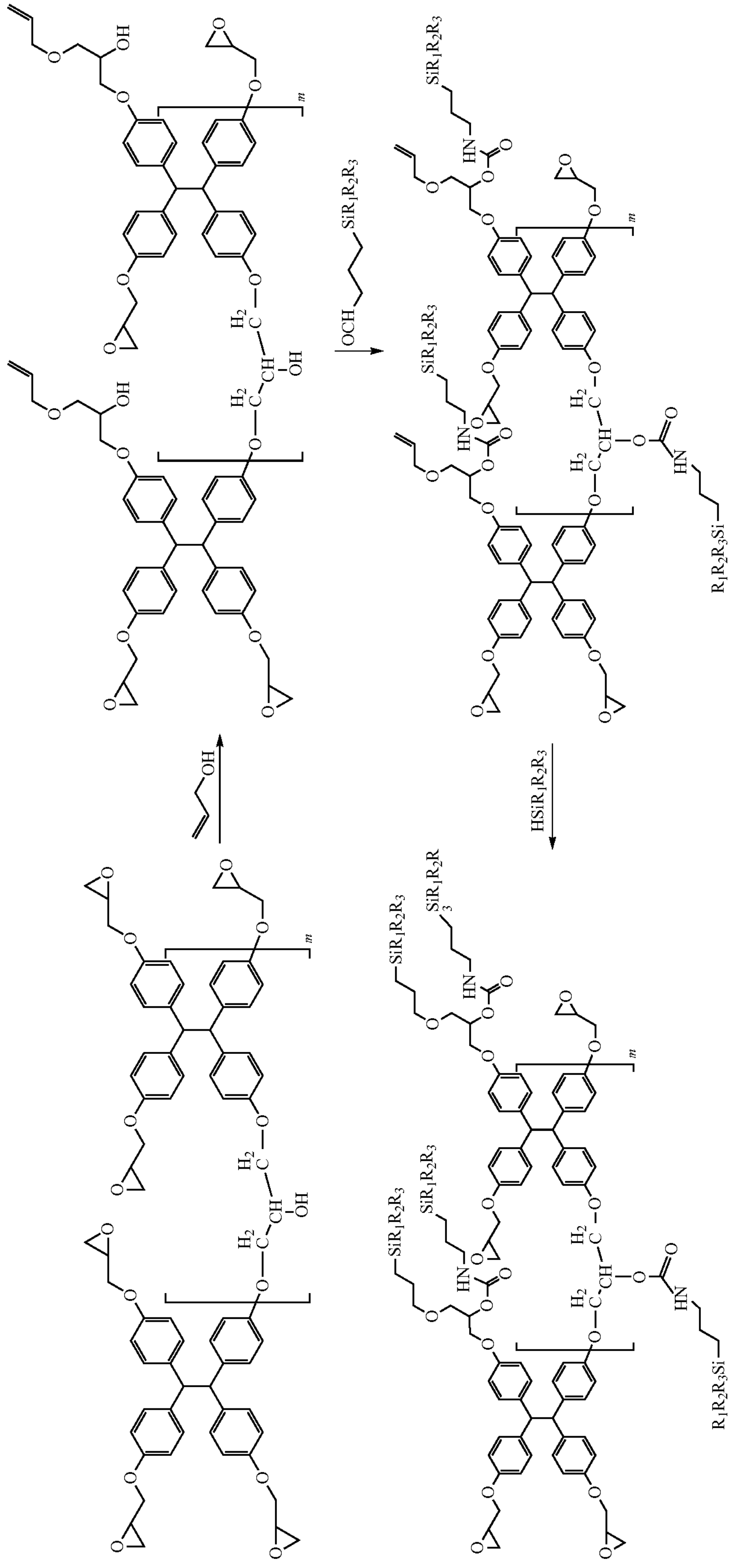
$HSiR_1R_2R_3$ where, m is an integer from 0 to 1,000.

(2) Preparation Method 2

In preparation method 2, an alkoxysilylated epoxy compound according to the present invention is prepared by a ring-opening reaction of a starting material (first step), hydrosilylation (second step) and an optional isocyanate silylation (third step).

The first step of the ring-opening reaction of the starting material is the same as in preparation method 1. Then, in the second step, the intermediate is hydrosilylated through the reaction of the intermediate obtained in the first step and the alkoxysilane of the above Formula (B2) to produce an epoxy compound having at least one alkoxysilyl group independently selected from the group consisting of Formulae S21 to S26 and at least two epoxy groups. The product obtained in the second step also corresponds to an alkoxysilylated epoxy compound, a final target material according to an embodiment of the present invention.

Particularly, through the reaction of the intermediate and the alkoxysilane of the above Formula B2, the allyl group of the intermediate is silylated to form an alkoxysilyl group independently selected from the group consisting of Formulae S21 to S26.

In the reaction of the second step, the reaction of the intermediate of the first step and the alkoxysilane of the following Formula B2 may be performed stoichiometrically. In addition, as described above, the alkoxysilane of Formula B2 may react with the allyl group of the intermediate. Thus, in consideration of the above-described points, the reaction between the alkoxysilane of Formula B1 and the intermediate may be conducted with 0.1 to 5 equivalents of the alkoxysilane per 1 equivalent of the alcohol group of the intermediate.

The reaction temperature and the reaction time of the second step reaction are different depending on the reactants and may be, for example, in a temperature range of room temperature (for example 15° C. to 25° C.) to 120° C. for 1 to 72 hours.

The reaction of the second step is conducted in the presence of a metal catalyst. As the metal catalyst, for example, a platinum catalyst of $PtO_2$ or $H_2PtCl_6$ may be used, without limitation. $1\times10^{-4}$ to 0.05 equivalents of the platinum catalyst per 1 equivalent of the allyl group of the intermediate may be preferable in consideration of reaction efficiency.

The solvent in the second step may be optionally used as occasion demands, and the kind, how to use and the amount of the solvent used are the same as in the second step of preparation method 1.

As described above, the epoxy compound obtained in the second step has an epoxy group and an alkoxysilyl group and also corresponds to an epoxy compound having an alkoxysilyl group, a target material of the present invention. Particularly, the epoxy compound having an alkoxysilyl group obtained in the second step has at least one core selected from the group consisting of Formulae (A') to (N'), at least one alkoxysilyl group independently selected from the group consisting of Formulae S21 to S26, at least two epoxy groups selected from the group consisting of Formulae S51 to S56, and an optional substituent selected from the group consisting of Formulae S41 to S45. When the number of the cores of Formulae (A') to (J') is equal to or greater than two, the cores of Formulae (A') to (I') may be connected by a connecting group independently selected from the group consisting of LG1 to LG7, and the cores of the above Formula (J') may be connected by a connecting group of LG2. Via the connecting group, 1 to 1,000 cores may be additionally connected.

After the second step, an optional third step of isocyanate silylation may be additionally conducted as occasion demands. In the third step, the hydroxyl group of the product of the second step is isocyanate silylated through the reaction of the reaction product of the second step and the alkoxysilane of the above Formula B1 to produce an alkoxysilylated epoxy compound according to an embodiment of the present invention having at least one alkoxysilyl group independently selected from the group consisting of Formulae S31 to S38 and at least two epoxy groups in a core.

In the reaction of the third step, the reaction product of the second step and the alkoxysilane of the following Formula B1 may react by the stoichiometrically equivalent molar ratio. In consideration of the above-points, the reaction product of the second step and the alkoxysilane of the following Formula B1 may react with 0.1 to 5 equivalents of the alkoxysilane of Formula B1 per 1 equivalent of the hydroxyl group of the reaction product of the second step.

The reaction temperature and the reaction time of the reaction of the third step may be changed depending on the kind of reactants, and may be, for example, a temperature range from room temperature (for example, 15 C.° to 25 C.°) to 120° C. for 1 to 120 hours.

The reaction of the third step is conducted in the presence of a base. The kind of the based used is the same as that in the second step of preparation method 1. 0.1 to 5 equivalents of the base may preferably be used with respect to 1 equivalent of the hydroxyl group of the reaction product of the second step in consideration of reaction efficiency.

In the third step, the solvent may be optionally used as occasion demands, and the kind, the amount and how to use of the solvent are the same as in the second step.

Particularly, the epoxy compound having an alkoxysilyl group obtained in the third step has a core selected from the group consisting of Formulae (A') to (N'), at least one alkoxysilyl group independently selected from the group consisting of Formulae S21 to S26 and Formulae S31 to S38, at least two epoxy groups selected from the group consisting of Formulae S51 to S58, and an optional substituent selected from the group consisting of Formulae S41 to S45.

When the number of the cores of Formulae (A') to (J') is equal to or greater than two, the cores of Formulae (A') to (I') may be connected by a connecting group independently selected from the group consisting of LG1 to LG14, and the cores of the above Formula (J') may be connected by a connecting group independently selected from the group consisting of LG2 and LG9. Via the connecting group, 1 to 1,000 cores may be additionally connected.

[Preparation Method 2-1]
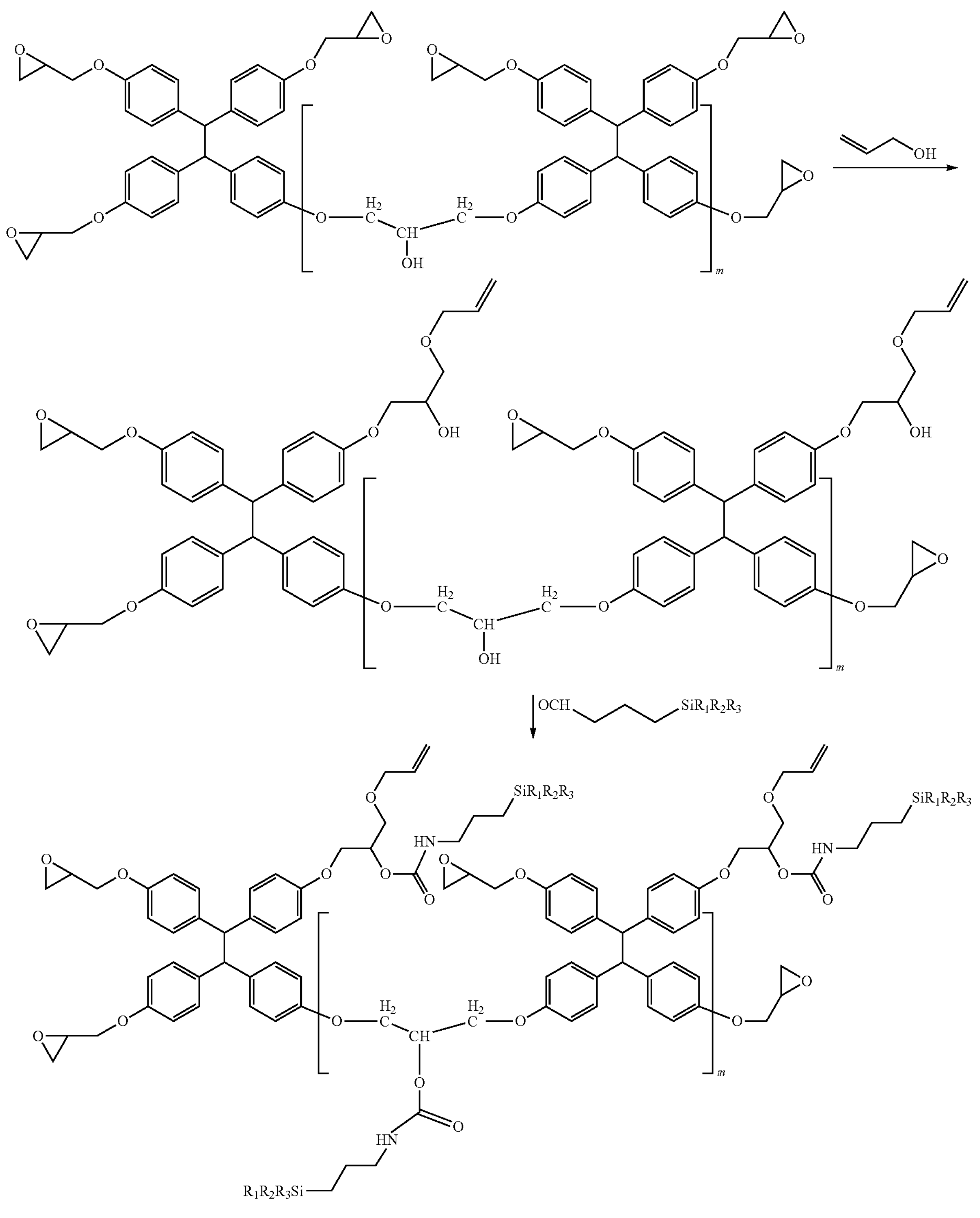
where m is an integer from 0 to 1,000.
[Preparation Method 2-2]

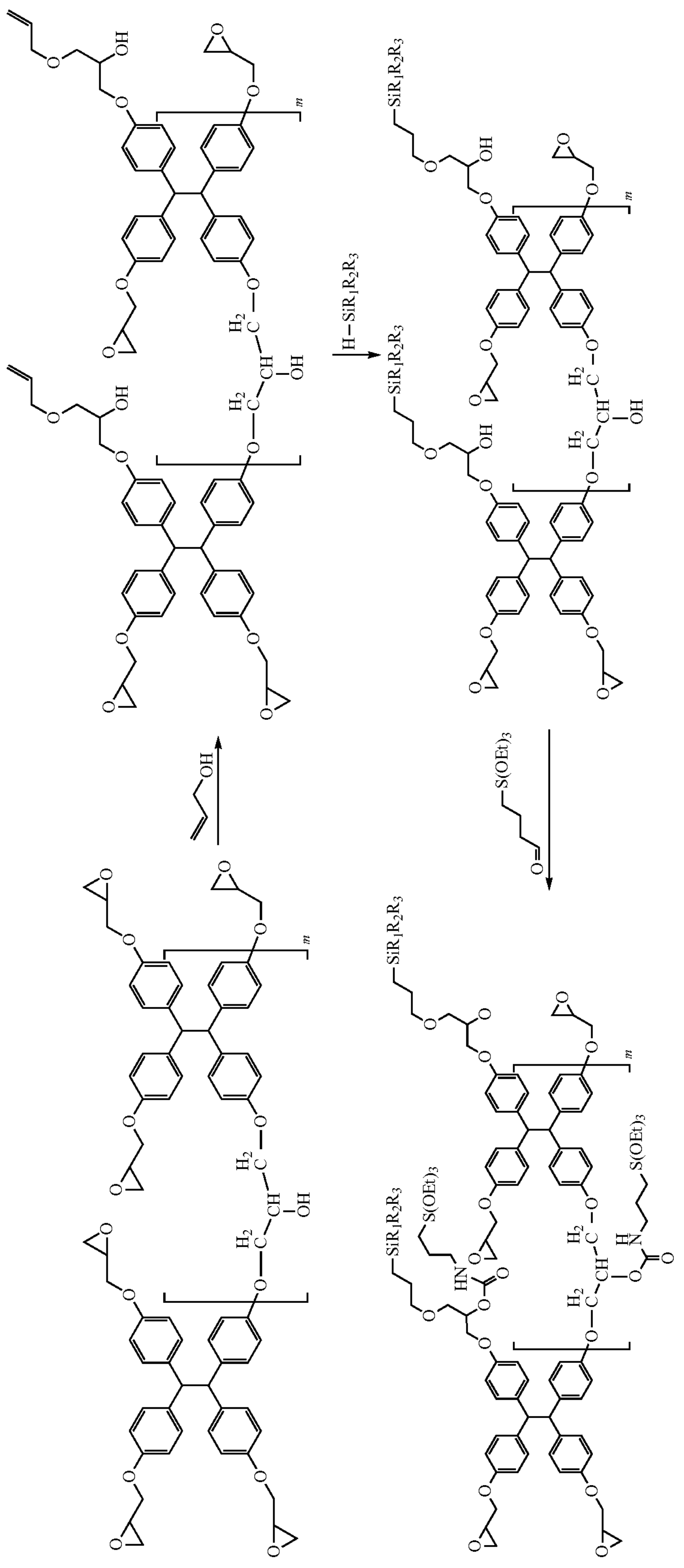
H−SiR1R2R3 where m is an integer from 0 to 1,000.

3. Epoxy Composition

According to another embodiment of the present invention, an epoxy composition including an epoxy compound having an alkoxysilyl group including at least one alkoxysilyl group independently selected from (1) a substituent of Formula S1 independently selected from the group consisting of Formulae S11 to S16, (2) a substituent of Formula S2 independently selected from the group consisting of Formulae S21 to S26, (3) the group consisting of Formulae S11 to S16 and Formulae S31 to S38, or (4) the group consisting of Formulae S21 to S26 and Formulae S31 to S38, and at least two epoxy groups. Particularly, an epoxy composition including any alkoxysilylated epoxy compound (hereinafter, 'alkoxysilylated epoxy compound') provided in any embodiments of the present invention described in the above category of 1. Epoxy compound, is provided.

Any compositions provided in the present invention may be used in various uses such as an electronic material, for example, a semiconductor substrate such as an IC substrate, a build-up film, an encapsulating material (packaging material), an electronic part such as a printed circuit board, an adhesive, a paint, a composite material, or the like, without limitation.

In addition, any compositions provided in the present invention may be a curable composition and/or a curable composition including an inorganic material.

Any epoxy compositions according to any embodiments described above or later in the present invention may include any kind and/or any mixing ratio known in the art only when including an alkoxysilylated epoxy compound provided in any embodiments of the present invention. In this case, the kind and the mixing ratio of the curing agent, the curing accelerator (catalyst), the inorganic material (filler) (for example, inorganic particles and/or a fiber), other common epoxy compounds and other additives are not limited.

Further, the epoxy composition, the cured product and/or the composite may be used with various kinds of common epoxy compounds in consideration of the controlling feature of physical properties according to the application and/or use thereof. Thus, in the epoxy compositions according to any embodiments described above or later in the present invention, the epoxy compound may include any alkoxysilylated epoxy compound provided in any embodiments of the present invention (hereinafter an 'alkoxysilylated epoxy compound of the present invention'), and any kind of epoxy compound commonly known in this art (hereinafter a 'common epoxy compound').

The common epoxy compounds may be any epoxy compounds commonly known in this art without limitation, and may be, for example, at least one epoxy compound selected from the group consisting of a glycidyl ether epoxy compound, a glycidyl epoxy compound, a glycidyl amine epoxy compound, a glycidyl ester epoxy compound, a rubber modified epoxy compound, an aliphatic polyglycidyl epoxy compound and an aliphatic glycidyl amine epoxy compound. For example, the common epoxy compound may be at least one epoxy compound selected from the group consisting of the glycidyl ether epoxy compound, the glycidyl epoxy compound, the glycidyl amine epoxy compound, the glycidyl ester epoxy compound, the rubber modified epoxy compound, the aliphatic polyglycidyl epoxy compound and the aliphatic glycidyl amine epoxy compound including bisphenol A, bisphenol F, bisphenol S, biphenyl, naphthalene, fluorene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as a core structure.

Any epoxy compositions in accordance with an embodiment of the present invention may include without limitation, based on the total amount of an epoxy compound, from 1 wt % to 100 wt % of the alkoxysilylated epoxy compound of the present invention and from 0 wt % to 99 wt % of the common epoxy compound; for example, from 10 wt % to 100 wt % of the alkoxysilylated epoxy compound of the present invention and from 0 wt % to 90 wt % of the common epoxy compound; for example, from 30 wt % to 100 wt % of the alkoxysilylated epoxy compound of the present invention and from 0 wt % to 70 wt % of the common epoxy compound; for example, from 50 wt % to 100 wt % of the alkoxysilylated epoxy compound of the present invention and from 0 wt % to 50 wt % of the common epoxy compound; for example, from 10 wt % to below 100 wt % of the alkoxysilylated epoxy compound of the present invention and from above 0 wt % to 90 wt % of the common epoxy compound; for example, from 30 wt % to below 100 wt % of the alkoxysilylated epoxy compound of the present invention and from above 0 wt % to 70 wt % of the common epoxy compound; for example, from 50 wt % to below 100 wt % of the alkoxysilylated epoxy compound of the present invention and from above 0 wt % to 50 wt % of the common epoxy compound.

Further, in accordance with an embodiment of the present invention, an epoxy composition including an alkoxysilylated epoxy compound and an inorganic material (filler) (for example, inorganic particles and/or a fiber) according to any embodiments of the present invention (hereinafter a 'composite composition') is provided. The composite composition is considered to include an epoxy composition having any kind and/or any mixing ratio commonly known in this art only when including the alkoxysilylated epoxy compound of the present invention and the filler. The kinds and the mixing ratios of the curing agent, the curing accelerator (catalyst), the inorganic material (filler) (for example, inorganic particles and/or a fiber) composing the epoxy composition, and the kinds of the common epoxy compound and other additives are not limited.

The above-described composite composition and any compositions described above or later according to the present invention may additionally include inorganic particles and/or a fiber.

Any inorganic particles known to be used to reinforce the physical properties of a common organic resin may be used. Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxane, ladder type silsesquioxane, and cage type silsesquioxane. The inorganic particles may be used alone or as a mixture of two or more thereof.

In the case that a particularly large amount of the silica is mixed, the fused silica is preferably used. The fused silica may have any shape among a cataclastic shape and a spherical shape. However, the spherical shape is preferable to increase the fill factor of the fused silica and to restrain the increase of the melt viscosity of a composite material.

The inorganic particles having a particle size of 0.5 nm to several tens of μm (for example, from 50 μm to 100 μm) may be used in consideration of the use of a composite, particularly, the dispersibility of the inorganic particles, or the like. Since the inorganic particles are dispersed in the epoxy compound, and the dispersibility is different according to the particle size, the inorganic particles having the above-described size may preferably be used. In addition, the increase of size distribution of the inorganic particles to be mixed is preferable to increase the fill factor of the inorganic particles.

In the epoxy composition in accordance with an embodiment of the present invention, the fill factor of the inorganic particles per the epoxy compound may be appropriately controlled in consideration of the CTE decrease of an epoxy composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total amount of the solid content of the epoxy compound (based on the total amount of the epoxy cured product for the epoxy cured product).

More particularly, in an exemplary embodiment, when the epoxy composition is used as a semiconductor encapsulating agent, or the like, the amount of the inorganic particles may be, for example, 30 wt % to 95 wt %, for example, 30 wt % to 90 wt %, without limitation, based on the amount of the solid content of the epoxy compound (based on the total amount of the epoxy cured product for the epoxy cured product) in consideration of the CTE value and material processability. In other exemplary embodiments, when the epoxy composition is used in a semiconductor substrate, the amount of the inorganic particles may be 5 wt % to 60 wt %, for example, 10 wt % to 50 wt % based on the total solid content of the epoxy compound (based on the total amount of the epoxy cured product for the epoxy cured product) in consideration of the CTE value and the intensity of the substrate.

Meanwhile, when the fiber is used as the inorganic material, a composite may mainly be obtained by the impregnation of the fiber within the epoxy composition. Thus, the size of the fiber may not be specifically limited. Any kind of fiber commonly used in this field may be used and dimensions thereof are not limited.

Any commonly used fibers used for improving physical properties of a common cured organic resin may be used without limitation. Particularly, a glass fiber, an organic fiber or a mixture thereof may be used. In addition, the term ‘glass fiber’ used in this application may include a glass fiber fabric, a glass fiber non woven product, or the like, as well as the glass fiber. Examples of the glass fibers may include, without limitation, an E-glass fiber, a T-glass fiber, an S-glass fiber, an NE-glass fiber, a D-glass fiber, a quartz glass fiber, or the like. For example, E- or T-glass fiber may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more.

The amount of the fiber in the epoxy composition according to the present invention, for example, in a glass fiber composite of epoxy composition, may be 10 wt % to 90 wt %, for example, 30 wt % to 70 wt %, in addition, for example, 35 wt % to 65 wt % based on the total weight of the solid content of the epoxy composition. In addition, the amount of the fiber in the cured product of the epoxy composition, for example, in a glass fiber composite, may be 10 wt % to 90 wt %, for example, 30 wt % to 70 wt %, in addition, for example, 35 wt % to 65 wt % based on the total amount of the cured product. Thus, the amount of the resin may be 10 wt % to 90 wt %, for example, 30 wt % to 70 wt %, in addition, for example, 35 wt % to 65 wt %. The amount of the fiber within the above-described range may be preferred in consideration of the increase in heat resistance and the processability. Meanwhile, in the epoxy composition, the cured product, or the like, including the fiber, solid parts excluding the fiber from the total solid content is referred to as the resin. In the epoxy composition including the fiber, the remaining amount other than the fiber is the amount of the resin.

Further, in the epoxy composition including the fiber may additionally include inorganic particles as occasion demands. In this case, the inorganic particles may be included by 1 wt % to 70 wt % based on the total amount of resin in consideration of the improvement of the physical properties and processability. In this case, the kind of the inorganic particles is not specifically limited, and any inorganic particles known in this art may be used. For example, the above-described inorganic particles may be used.

According to further another embodiment of the present invention, an alkoxysilylated epoxy composition including an epoxy compound according to any embodiments of the present invention and a curing agent is provided (hereinafter a ‘curing agent-containing composition’). Any curing agent-containing compositions may include an epoxy composition having any kind and/or any mixing ratio known in the art only when including an alkoxysilylated epoxy compound of the present invention and a curing agent. However, the kinds and the mixing ratios of the curing agent, the curing accelerator (catalyst), the inorganic material (filler) (for example, inorganic particles and/or fibers), other common epoxy compounds and other additives composing the epoxy composition are not limited.

According to further another embodiment of the present invention, an alkoxysilylated epoxy composition including an epoxy compound according to any embodiments of the present invention and a reaction catalyst for an alkoxysilyl group (hereinafter a ‘reaction catalyst’) is provided (hereinafter a ‘reaction catalyst-containing composition’). Any reaction catalyst-containing compositions may include an epoxy composition having any kind and/or any mixing ratio known in the art only when including an alkoxysilylated epoxy compound of the present invention and a reaction catalyst. However, the kinds and the mixing ratios of the curing agent, the curing accelerator (catalyst), the inorganic material (filler) (for example, inorganic particles and/or fibers), other common epoxy compounds and other additives composing the epoxy composition are not limited. In the case that the reaction catalyst for the alkoxysilyl group is included, improved processability (for example, a rapid curing rate and/or a low curing temperature) may be expected.

The curing agent-containing composition and the reaction catalyst-containing composition may also include the common epoxy compound as the epoxy compound. In this case, the kind of the common epoxy compound and the mixing ratios of the alkoxysilylated epoxy compound and the common epoxy compound are the same as described above.

When a curing agent is included in the curing agent-containing composition and the composition according to an embodiment of the present invention, any curing agents commonly known as a curing agent of an epoxy compound may be used. For example, an amine resin, a phenol resin, an anhydride compound may be used, without limitation.

More particularly, an aliphatic amine, an alicyclic amine, an aromatic amine, other amines and a modified amine may be used as the amine curing agent without limitation. In addition, an amine compound including two or more primary amine groups may be used. Particular examples of the amine curing agents may include at least one aromatic amine selected from the group consisting of 4,4'-dimethylaniline (diamino diphenyl methane, DAM or DDM), and diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl)methane, and larominc 260, other amines such as dicyanamide (DICY), or the like, and a modified amine such as a polyamide compound, an epoxide compound, or the like.

Examples of the phenol curing agent may include, without limitation, a tri-functional phenol novolac resin, a cresol novolac resin, a bisphenol A novolac resin, a xylene novolac resin, a triphenyl novolac resin, a biphenyl novolac resin, a phenol p-xylene resin, a phenol 4,4'-dimethylbiphenylene resin, a phenol dicyclopentadiene novolac resin, a dicyclopentadiene-phenol (DCPD-phenol) novolac resin, a xylok (p-xylene modified) resin, a biphenyl phenol resin, a naphthalene phenol novolac resin, a triazine compound, dihydroxy naphthalene, dihydroxy benzene, or the like.

Examples of the anhydride curing agent may include, without limitation, an aliphatic anhydride such as dodecenyl succinic anhydride (DDSA), poly azelaic poly anhydride, or the like, an alicyclic anhydride such as hexahydrophthalic anhydride (HHPA), methyl tetrahydrophthalic anhydride (MeTHPA), methylnadic anhydride (MNA), or the like, an aromatic anhydride such as trimellitic anhydride (TMA), pyromellitic acid dianhydride (PMDA), benzophenonetetracarboxylic dianhydride (BTDA), or the like, and a halogen anhydride compound such as tetrabromophthalic anhydride (TBPA), chlorendic anhydride, or the like.

In general, the degree of curing of an epoxy composite may be controlled by the extent of the reaction of the curing agent and the epoxy group. According to the range of the target degree of curing, the amount of the curing agent may be controlled based on the concentration of the epoxy group of an epoxy compound. For example, when an amine curing agent is used, the ratio of the epoxy equivalent/amine equivalent may be preferably controlled to 0.5 to 2.0, for example, 0.8 to 1.5 in an equivalent reaction of the amine curing agent and the epoxy group.

Though the mixing ratio of the curing agent has been explained with respect to the amine curing agent, a phenol curing agent, an anhydride curing agent and any curing agents for curing epoxy compounds not separately illustrated in this application but used for curing may be used by appropriately mixing a stoichiometric amount according to the chemical reaction of the epoxy functional group and the reactive functional group of the curing agent based on the concentration of the total epoxy group in the epoxy composition according to the desired range of the degree of curing. The above-described elements are commonly known in this field.

As a cationic photo curing agent (also referred to as a photo initiator), commonly known photo curing agents in this field may be used and for example, an aromatic phosphonium salt, an aromatic iodonium salt, an aromatic sulfonium salt, etc. may be illustrated without limitation. Particularly, diphenyliodonium tetrakis(pentafluorophenyl) borate, diphenyliodonium hexafluorophosphate, diphenyliodonium hexafluoroantimonate, di(4-nonylphenyl) iodonium hexafluorophosphate, triphenylsulfonium hexafluorophosphate, triphenylsulfonium hexafluoroantimonate, triphenylsulfonium tetrakis(pentafluorophenyl)borate, 4,4'-bis[diphenylsulfonio]diphenylsulfide bishexafluorophosphate, 4,4'-bis[di(β-hydroxyethoxy)phenylsulfonio] diphenylsulfide bishexafluorophosphate, etc. may be used. The photo curing agent may be used in a ratio of 0.5 to 20 parts per hundred (phr) of the epoxy compound (parts by weight on the basis of 100 parts by weight of the epoxy compound), may preferably be at least 1 phr, and may preferably be at most 15 phr.

An optional curing accelerator (catalyst) may be additionally included as occasion demands to promote the curing reaction in any epoxy compositions provided in the present invention. Any curing accelerators (catalysts) commonly used for curing an epoxy composition in this art may be used without limitation, for example, an imidazole, a tertiary amine, a quaternary ammonium, an organic acid, a phosphor compound curing accelerator may be used.

More particularly, for example, the imidazole curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine curing accelerator such as benzyldimethylamine (BDMA), tris dimethylaminomethyl phenol (DMP-30), and triethylenediamine; the quaternary ammonium curing accelerator such as tetrabutylammonium bromide, or the like; diazabicycloundecene (DBU), or an organic acid of DBU; the phosphor compound curing accelerator such as triphenyl phosphine, phosphoric acid ester, or the like, and a Lewis acid such as $BF_3$-monoethylamine ($BF_3$-MEA), or the like, may be illustrated without limitation. Latent curing accelerators, which are formed by the microcapsulation and complex salts of accelerators may also be used. These compounds may be used alone or a mixture of two or more thereof according to curing conditions.

The mixing amount of the curing accelerator may be a commonly applied mixing amount in this art without limitation. For example, 0.1 to 10 phr (parts per hundred parts of resin, parts by weight based on 100 parts by weight of the epoxy compound), for example, 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput may be expected.

When the reaction catalyst for the alkoxysilyl group is included in the curing catalyst-containing composition and a composition according to any embodiments of the present invention, the reaction catalyst for the alkoxysilyl group may be at least one selected from the group consisting of at least one inorganic acid selected from the group consisting of, for example, nitric acid, sulfuric acid, hydrochloric acid, acetic acid and phosphoric acid, ammonia, KOH, $NH_4OH$, amine, a transition metal alkoxide, a metal oxide, an organic acid salt and halide of a metal, and a tin compound (for example, dibutyltin dilaurate, tin octylate, tin(II) 2-ethylhexanoate, or the like). These compounds may be used alone or as a mixture of two or more thereof. The mixing ratio of the reaction catalyst for the alkoxysilyl group is not specifically limited; however, 0.01 phr to 10 phr of the reaction catalyst for the alkoxysilyl group may be used with respect to the epoxy compound of the present invention in consideration of reactivity.

In the composition including the reaction catalyst for the alkoxysilyl group, water may be additionally included to increase the efficiency of the reaction catalyst. The mixing ratio is not specifically limited; however, 0.01 to 20 equivalents of water may be included with respect to 1 equivalent of the alkoxysilyl group in consideration of the efficiency and reactivity as the catalyst.

In the epoxy composition, other additives such as a releasing agent, a surface treatment agent, a flame retardant, a plasticizer, bactericides, a leveling agent, a defoaming agent, a colorant, a stabilizer, a coupling agent, a viscosity controlling agent, a diluent, a rubber, a thermoplastic resin, or the like may be mixed to control the physical properties of the epoxy composition within the range of undamaging the physical properties of the epoxy composition as occasion demands.

For example, when a thin film is formed using any compositions of the present invention, and when forming a thin layer using a composition having insufficient flexibility, the thin layer thus formed may be brittle, and cracks may be easily generated. This phenomenon may be exhibited when, for example, the composition of the present invention includes a large amount of inorganic particles. Thus, to improve the processability as the thin film by imparting solubility to the composition, the rubber and/or the thermoplastic resin may be added to the epoxy composition of the present invention. As the thermoplastic resin and a rubber-modified epoxy resin, commonly known resins in this field may be used. As rubber particles, any rubbers known in this field may be used only if the rubber particles are not dissolved in a solvent used in the composition and maintains a dispersed state in the composition. The kind of the rubber may include, for example, an acrylonitrile butadiene rubber, a butadiene rubber, an acryl rubber, core-shell type rubber particles, a cross-linked acrylonitrile butadiene rubber, cross-linked styrene butadiene rubber particles, acryl rubber particles, or the like, without limitation. These materials may be used alone, or at least two thereof may be used at the same time. When a rubber having a particle shape is used, the mean particle diameter may preferably be from 0.005 to 1 μm, and more preferably may be from 0.2 to 0.6 μm in consideration of the improvement of physical properties. The rubber particles may be mixed in an amount ratio, for example, of 0.5 to 10 wt % based on the solid content of the epoxy composition in consideration of physical properties.

As the thermoplastic resin, a phenoxy resin, a polyvinyl acetal resin, a polyimide resin, a polyamideimide resin, a polyether sulfone resin, a polysulfone resin, or the like may be used, without limitation. These materials may be used alone or at least two thereof may be used at the same time. The thermoplastic resin may be mixed in a ratio of, for example, from 0.5 to 60 wt %, and preferably from 3 to 50 wt % based on the solid content of the epoxy composition in consideration of physical properties.

As described above, the term "epoxy composition" used in the present application is understood to include an epoxy compound of the present invention and other constituents composing the epoxy composition, for example, an optional curing agent, a curing accelerator (catalyst), an inorganic material (filler) (for example, inorganic particles and/or a fiber), other common epoxy compounds, a solvent and other additives mixed as occasion demands in this field. In general, the solvent may be optionally used to control the amount and/or the viscosity of the solid content of the epoxy composition in consideration of the processability of the epoxy composition, and the like. Meanwhile, the "total solid content of the epoxy composition" used in the present invention refers to the total amount of a solid component other than a liquid component such as solvents composing the epoxy composition.

The epoxy composition provided in accordance with an exemplary embodiment of the present invention may be used as an electronic material. The electronic material may include, for example, a substrate for semiconductor, a film, a prepreg, a laminated obtained by placing a metal layer on a base layer formed using the composition of the present invention, a substrate, an encapsulating material (a packaging material), a build-up film (substrate), a printed circuit board, or the like. In addition, the epoxy composition may be used in various applications such as an adhesive, a paint and a composite material. In accordance with other exemplary embodiments of the present invention, an electronic material including or manufactured using a composition including the alkoxysilylated epoxy compound of the present invention is provided. Further, a semiconductor apparatus including or manufactured by essentially using or using the electronic material, is provided. Particularly, the semiconductor apparatus may be a semiconductor apparatus including a printed circuit board (for example, for installing a semiconductor device) including or manufactured by essentially using or using the composition including the alkoxysilylated epoxy compound of the present invention and/or may be a semiconductor apparatus including a semiconductor packaging material. In addition, a curing agent, an adhesive, a paint or a composite material including or manufactured by essentially using or using any epoxy compositions provided in any embodiments of the present invention, may be provided.

In accordance with other exemplary embodiments of the present invention, a cured product including or manufactured by essentially using or using the epoxy composition provided in accordance with an exemplary embodiment of the present invention may be provided. In the case that applying the epoxy composition provided in an exemplary embodiment of the present invention is practically used, for example, when the epoxy composition is applied as the electronic material, or the like, a cured product formed from the epoxy composition may be used. In this art, the cured product formed from the composition including the epoxy compound and the filler of the inorganic component may be commonly referred to as a composite.

The alkoxysilylated epoxy compound provided in above-described exemplary embodiments of the present invention may show good heat resistance in the composite and/or good flame retardancy in the cured product.

Particularly, the composite may exhibit a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are better as the CTE value is smaller, and the lower value of the CTE is not particularly delimited.

For example, a composite including any alkoxysilylated epoxy compounds in accordance with exemplary embodiments of the present invention as the epoxy compound, and a glass fiber, for example, an E-glass fiber and/or a T-glass fiber as the inorganic material, and having the resin content (the resin content may or may not include inorganic particles) of 30 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite including any alkoxysilylated epoxy compounds in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product including an inorganic material) according to the present invention may be higher than 100° C., for example, 130° C. or higher, in addition, for example, 250° C. or higher. Otherwise, the composite may be Tg-less. The physical properties of the composite are good when the Tg value is large, and the upper value of the Tg is not particularly delimited.

Meanwhile, the cured product formed using the alkoxysilylated epoxy compound (a cured product excluding an inorganic material) according to the present invention may have a CTE of 50 ppm/° C. to 150 ppm/° C.

In the present application, the values delimited by the range include the lower limit, the upper limit, any sub ranges in the range, and all numerals included in the range, unless otherwise specifically stated. For example, C1 to C10 is understood to include all of C1, C2, C3, C4, C5, C6, C7, C8, C9 and C10. In addition, in the case when the lower limit or the upper limit of the numerical range is not defined, it would be found that the smaller or the larger value may provide the better properties. In addition, in the case when the limit is not defined, any values may be included. For example, CTE of 4 ppm/° C. or less is understood to include every values in the range such as the CTE of 4, 3.5, 3, 2.7, 2, 1.4, 1, 0.5 ppm/° C., or the like.

Hereinafter, the present invention will be described in detail referring to preferred embodiments. However, the following embodiments are for illustration, and the present invention is not limited thereto.

Synthetic Example 1. Synthesis of Binaphthalene Epoxy Having Alkoxysilyl Group (Structure A-1) (Method 1)

(1) First Step

To a two-necked flask, 10 g of bis(2,7-bis(oxiran-2-ylmethoxy)naphthalene-1-yl)methane (DIC Co, EXA-4700, Formula A-epoxy) was added, and 22.5 ml of THF and acetonitrile were respectively added to dissolve an epoxy specimen. Then, 0.93 g of NaOH, 1.13 g of $Et_4NBr$ and 26.09 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate A-0 having the ratio of epoxy group:allyl group of 1:1. NMR data are as follows.

$^1H$ NMR (400 MHz, $CDCl_3$): δ=2.70-2.88 (m, 4H), 3.26-3.37 (m, 2H), 3.69-4.17 (m, 18H), 4.90 (s, 2H), 5.20-5.28 (m, 4H), 5.86-5.98 (m, 2H), 6.88-7.18 (m, 4H), 7.42-7.62 (m, 6H).

(2) Second Step

To a two-necked flask, 10 g of Intermediate A-0 synthesized in the first step and acetonitrile were added and stirred. Then, 9.41 g of 3-(triethoxysilyl)propyl isocyanate and 4.92 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin A-1, in which the ratio of epoxy group:alkoxysilyl group was 1:1, was produced. NMR data are as follows.

$^1H$ NMR (400 MHz, $CDCl_3$): δ=0.61 (t, J=4 Hz, 4H), 1.06-1.28 (m, 18H), 1.42-1.72 (m, 4H), 2.71-2.88 (m, 4H), 3.15 (t, J=8 Hz, 4H), 3.26-3.37 (m, 2H), 3.69-3.83 (m, 30H), 4.90 (s, 2H), 5.13-5.29 (m, 6H), 5.86-5.98 (m, 2H), 6.88-7.18 (m, 4H), 7.42-7.62 (m, 6H).

The synthetic scheme of the above Synthetic Example 1 is as follows.

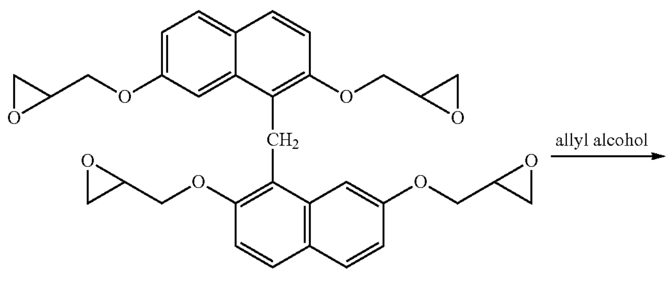

A-epoxy

-continued

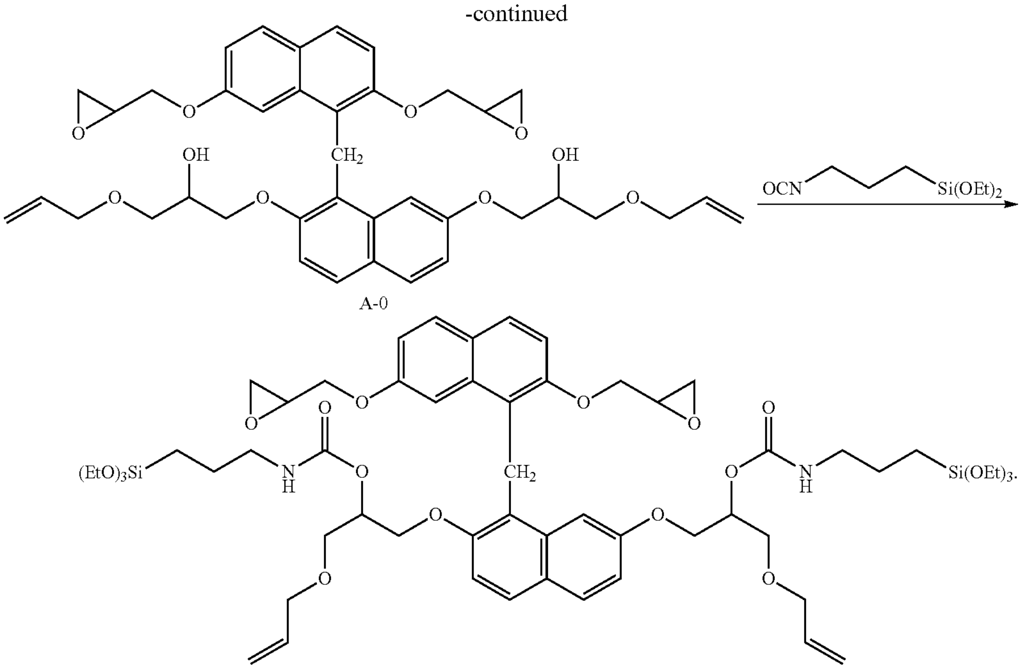

A-0

A-1

The main reaction of the above Synthetic Example 1 is illustrated in the synthetic scheme of the above Synthetic Example 1. However, the produced compound may have the ratio of epoxy group:allyl group of 1:1, together with 4:0, 3:1, 1:3 and 0:4 according to circumstances. The above-described ratio of epoxy group:allyl group in the synthetic example means the average ratio of epoxy group:allyl group for the whole mixed epoxy compound having different ratios of epoxy group:allyl group. In addition, in the synthetic scheme, the substitution is performed at a specific position of the core for convenience of illustration; however, substitution may be conducted at any position in the core in practical reaction. The present invention is understood to include all cases described above. These points are applied to the following synthetic examples, similarly. In addition, the reaction between an allyl group and a glycidyl ether functional group is illustrated in the above synthetic scheme; however, the allyl group may react with a glycidyl group.

Synthetic Example 2. Synthesis of Binaphthalene Epoxy Having Alkoxysilyl Group (Structure A-2) (Method 2)

To a flask, 10 g of Intermediate A-0 obtained in the first step of the above Synthetic Example 1, 135 mg of $PtO_2$, 5.37 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy A-2 having an alkoxysilyl group, of which ratio of epoxy group:alkoxysilyl group was 1:1. NMR data are as follows.

$^1$H NMR (400 MHz, $CDCl_3$): δ=0.60 (t, J=4 Hz, 4H), 1.22 (t, J=8 Hz 18H), 1.56-1.61 (m, 4H), 2.70-2.88 (m, 4H), 3.24-4.17 (m, 32H), 4.92 (s, 2H), 6.88-7.18 (m, 4H), 7.42-7.62 (m, 6H).

The synthetic reaction of the above Synthetic Example 2 is as follows.

Synthetic Example 3. Synthesis of Tetraphenylethane Epoxy Having Alkoxysilyl Group (Structure B-1(1)) (Method 1)

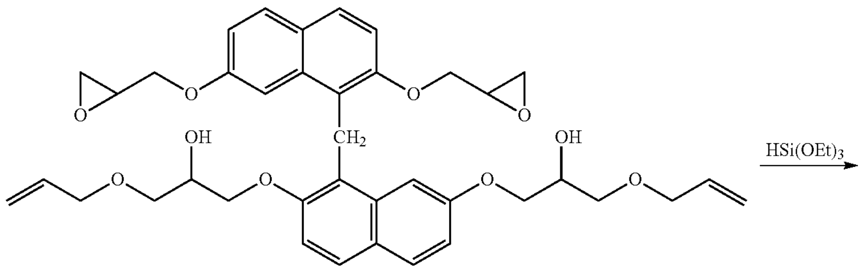

A-0

-continued

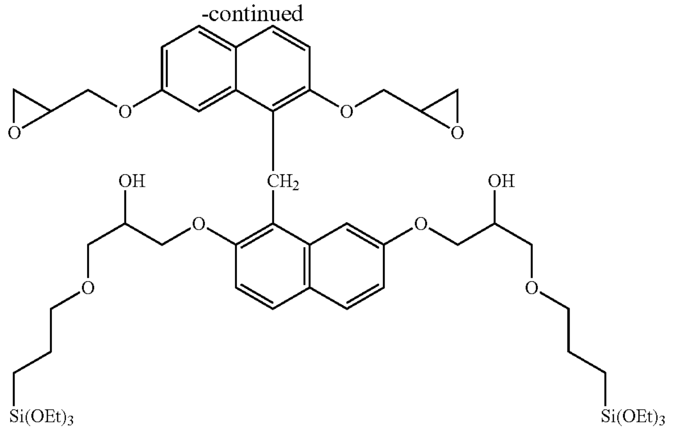

A-2

(1) First Step

To a two-necked flask, 10 g of tetra-glycidyl ether of tetraphenylethane (Nippon Kayaku, GTR 1800, Formula B-epoxy) was added, and 20 ml of THF and acetonitrile were respectively added to dissolve an epoxy specimen. Then, 0.84 g of NaOH, 1.01 g of $Et_4NBr$ and 23.32 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate B-0(1) having the ratio of epoxy group:allyl group of 1:1. NMR data are as follows.

$^1$H NMR (400 MHz, $CDCl_3$): δ=2.68 (dd, J=4.8 Hz, 2.8 Hz, 2H), 2.84 (t, J=4.8 Hz, 2H), 3.22-3.27 (m, 2H), 3.80-3.84 (m, 4H), 3.87-3.91 (m, 4H), 4.00-4.01 (m, 4H), 4.05-4.13 (m, 6H), 4.47 (s, 2H), 5.20 (m, 4H), 5.87 (m, 2H), 6.65 (d, J=8.4 Hz, 8H), 7.00 (d, J=8.0 Hz, 8H).

(2) Second Step

To a two-necked flask, 10 g of Intermediate B-0(1) synthesized in the first step and acetonitrile were added and stirred. Then, 8.57 g of 3-(triethoxysilyl)propyl isocyanate and 4.48 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin B-1(1), in which the ratio of epoxy group:alkoxysilyl group was 1:1, was produced. NMR data are as follows.

$^1$H NMR (400 MHz, $CDCl_3$): δ=0.61 (t, J=8 Hz, 4H), 1.22 (t, J=8 Hz, 18H), 1.60 (t, J=8 Hz, 4H), 2.70 (dd, J=4.8 Hz, 2.8 Hz, 2H), 2.86 (t, J=4.8 Hz, 2H), 3.15 (t, J=8 Hz, 4H), 3.50-3.60 (m, 4H), 3.78-3.91 (m, 20H), 3.97-4.13 (m, 8H), 4.55 (s, 2H), 5.13-5.26 (m, 6H), 5.85 (m, 2H), 6.67 (d, J=8.8 Hz, 8H), 7.00 (d, J=8.4 Hz, 8H).

The synthetic scheme of the above Synthetic Example 3 is as follows.

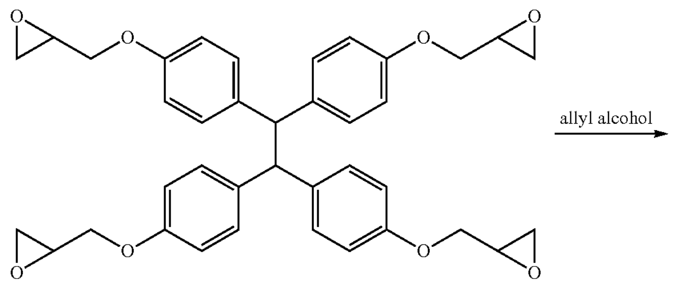

B-epoxy

-continued

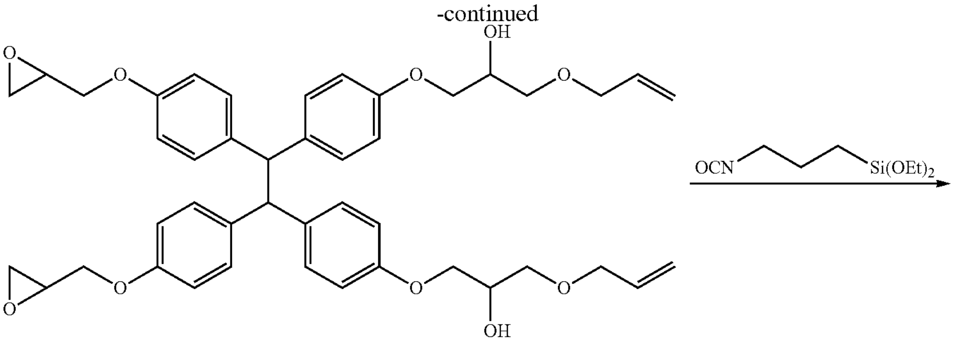

B-0(1)

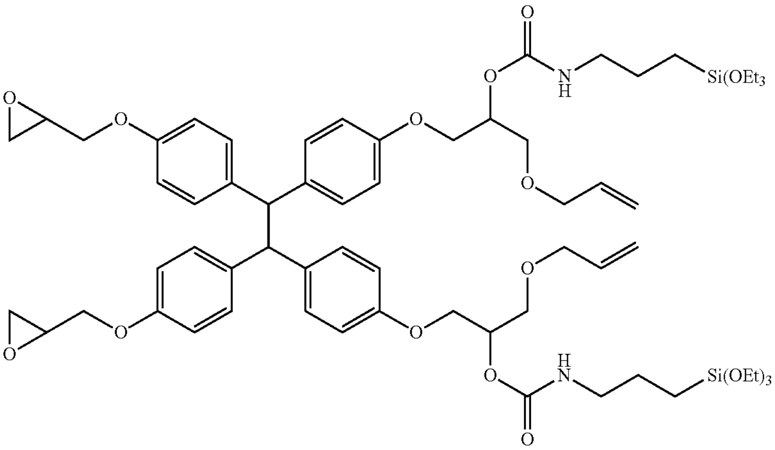

B-1(1)

Synthetic Examples 4 and 5: Synthesis of Tetraphenylethane Epoxy Having Alkoxysilyl Group (Method 1)

The compounds of Formulae B-1(2) and B-1(3) were synthesized by conducting the same first step and second step of the above Synthetic Example 3 except for changing the contents as described in the following Tables B1 and B2. The ratios of epoxy group:alkoxysilyl group of Formula B-1 synthesized in Example 4 and Example 5 were 2:1 and 3:1.

TABLE B1

Amounts of reactants used in the first step for synthesizing Compound B-1

| Synthetic Example (1/2 step) | B-epoxy | Allyl alcohol | NaOH | $Et_4NBr$ | Time | [epoxy group]:[alkenyl group] of Compound B-1 |
|---|---|---|---|---|---|---|
| 4 (B-1(2)) | 10 g | 23.32 g | 0.84 g | 1.01 g | 3 hr | 2:1 |
| 5 (B-1(3)) | 10 g | 23.32 g | 0.84 g | 1.01 g | 1 hr 30 min | 3:1 |

TABLE B2

Amounts of reactants used in the second step for synthesizing Compound B-1

| Synthetic Example (2/2 step) | Intermediate (B-0) | 3-(triethoxysilyl)propyl isocyanate | diisopropylethylamine | Time/Temperature | [epoxy group]:[alkenyl group] of Compound B-1 |
|---|---|---|---|---|---|
| 4 (B-1(2)) | 10 g | 12.06 g | 6.30 g | 30 hr/65° C. | 2:1 |
| 5 (B-1(3)) | 10 g | 13.95 g | 7.29 g | 30 hr/65° C. | 3:1 |

B-1(2) First Step NMR (Epoxy:Allyl 2:1)

$^1H$ NMR (400 MHz, $CDCl_3$): δ=2.68 (dd, J=4.8 Hz, 2.8 Hz, 2.67H), 2.84 (t, J=4.8 Hz, 2.67H), 3.22-3.27 (m, 2.67H), 3.80-3.84 (m, 2.67, 1.33H), 3.87-3.91 (m, 2.66H), 4.00-4.01 (m, 2.67, 1.33H), 4.05-4.13 (m, 2.67, 1.33H), 4.47 (s, 2H), 5.20 (m, 2.66H), 5.87 (m, 1.33H), 6.65 (d, J=8.4 Hz, 8H), 7.00 (d, J=8.0 Hz, 8H).

B-1(2) Second Step NMR (Epoxy:Alkoxysilyl=2:1)

$^1H$ NMR (400 MHz, $CDCl_3$): δ=0.61 (t, J=8 Hz, 4H), 1.22 (t, J=8 Hz, 18H), 1.60 (t, J=8 Hz, 4H), 2.70 (dd, J=4.8 Hz, 2.8 Hz, 2H), 2.86 (t, J=4.8 Hz, 2H), 3.15 (t, J=8 Hz, 4H), 3.50-3.60 (m, 4H), 3.77-3.91 (m, 20H), 3.97-4.13 (m, 8H), 4.55 (s, 2H), 5.13-5.26 (m, 6H), 5.85 (m, 2H), 6.67 (d, J=8.8 Hz, 8H), 7.00 (d, J=8.4 Hz, 8H).

B-1(3) First Step NMR (Epoxy:Allyl 3:1)

$^1H$ NMR (400 MHz, $CDCl_3$): δ=2.68 (dd, J=4.8 Hz, 2.8 Hz, 3H), 2.84 (t, J=4.8 Hz, 3H), 3.22-3.27 (m, 3H), 3.80-3.84 (m, 4H), 3.87-3.91 (m, 2H), 4.00-4.01 (m, 4H), 4.05-4.13 (m, 3H), 4.47 (s, 2H), 5.20 (m, 2H), 5.87 (m, 1H), 6.65 (d, J=8.4 Hz, 8H), 7.00 (d, J=8.0 Hz, 8H).

B-1(3) Second Step NMR (Epoxy:Alkoxysilyl=3:1)

$^1H$ NMR (400 MHz, $CDCl_3$): δ=0.61 (t, J=8 Hz, 2H), 1.22 (t, J=8 Hz, 9H), 1.60 (t, J=8 Hz, 2H), 2.68 (dd, J=4.8 Hz, 2.8 Hz, 3H), 2.84 (t, J=4.8 Hz, 3H), 3.15 (t, J=8 Hz, 2H), 3.22-3.27 (m, 3H), 3.78-3.84 (m, 10H), 3.87-3.91 (m, 2H), 4.00-4.13 (m, 7H), 4.47 (s, 2H), 5.13-5.26 (m, 3H), 5.87 (m, 1H), 6.65 (d, J=8.4 Hz, 8H), 7.00 (d, J=8.0 Hz, 8H).

Synthetic Example 6. Synthesis of Tetraphenylethane Epoxy Having Alkoxysilyl Group (Structure B-2) (Method 2)

To a two-necked flask, 10 g of Intermediate B-0(1) obtained in the first step of the above Synthetic Example 3, 123 mg of $PtO_2$, 4.89 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce the final target material of Epoxy B-2 having an alkoxysilyl group, in which the ratio of epoxy group:alkoxysilyl group was 1:1. NMR data are as follows.

$^1H$ NMR (400 MHz, $CDCl_3$): δ=0.60 (t, J=4 Hz, 4H), 1.21 (t, J=8 Hz 18H), 1.57-1.61 (m, 4H), 2.65 (dd, J=4.8 Hz, 2.8 Hz, 2H), 2.82 (t, J=4.8 Hz, 2H), 3.24-3.28 (m, 4H 2H), 3.51-3.55 (m, 2H), 3.71-3.74 (m, 2H), 3.80 (q, J=8 Hz, 12H), 3.82-3.88 (m, 2H), 3.96-4.01 (m, 4H), 4.04-4.08 (m, 4H), 4.53 (s, 2H), 6.64 (d, J=8.4 Hz, 8H), 7.00 (d, J=8.0 Hz, 8H).

The synthetic scheme of the above Synthetic Example 6 is as follows.

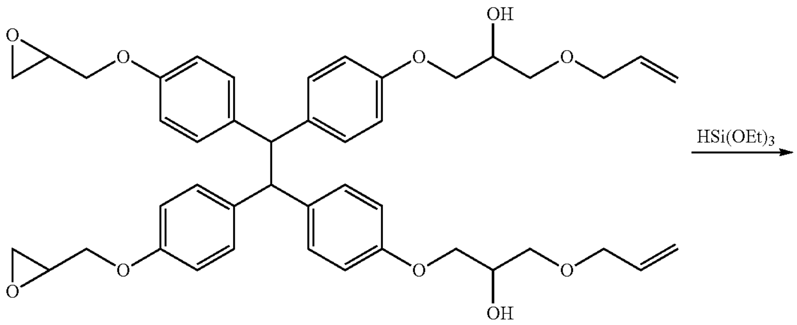

B-0(1)

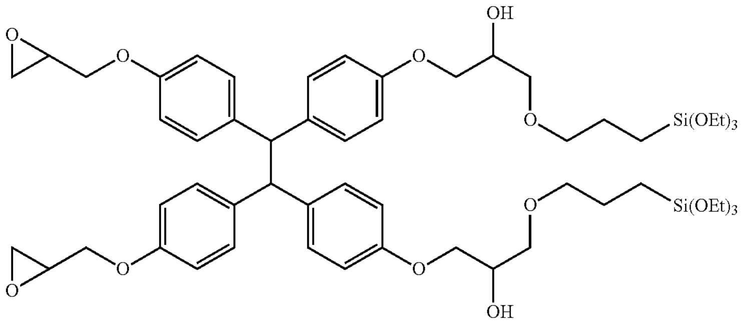

B-2

Synthetic Example 7. Synthesis of Tetraphenylethane Epoxy Having Alkoxysilyl Group (Structure B-3) (Method 3)

To a two-necked flask, 10 g of Epoxy B-1(1) having an alkoxysilyl group obtained in the above Synthetic Example 3, 74 mg of $PtO_2$, 2.93 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce the final target material of Epoxy B-3 having an alkoxysilyl group, in which the ratio of epoxy group:alkoxysilyl group was 1:2. NMR data are as follows.

$^1$H NMR (400 MHz, $CDCl_3$): δ=0.61 (t, J=8 Hz, 8H), 1.22 (t, J=8 Hz, 36H), 1.60 (t, J=8 Hz, 8H), 2.70 (dd, J=4.8 Hz, 2.8 Hz, 2H), 2.86 (t, J=4.8 Hz, 2H), 3.15 (t, J=8 Hz, 8H), 3.50-3.60 (m, 4H), 3.81-3.91 (m, 4H), 3.78-3.83 (m, 28H), 3.97-4.13 (m, 4H), 4.55 (s, 2H), 5.13-5.15 (m, 2H), 6.67 (d, J=8.8 Hz, 8H), 7.00 (d, J=8.4 Hz, 8H).

The synthetic scheme of the above Synthetic Example 7 is as follows.

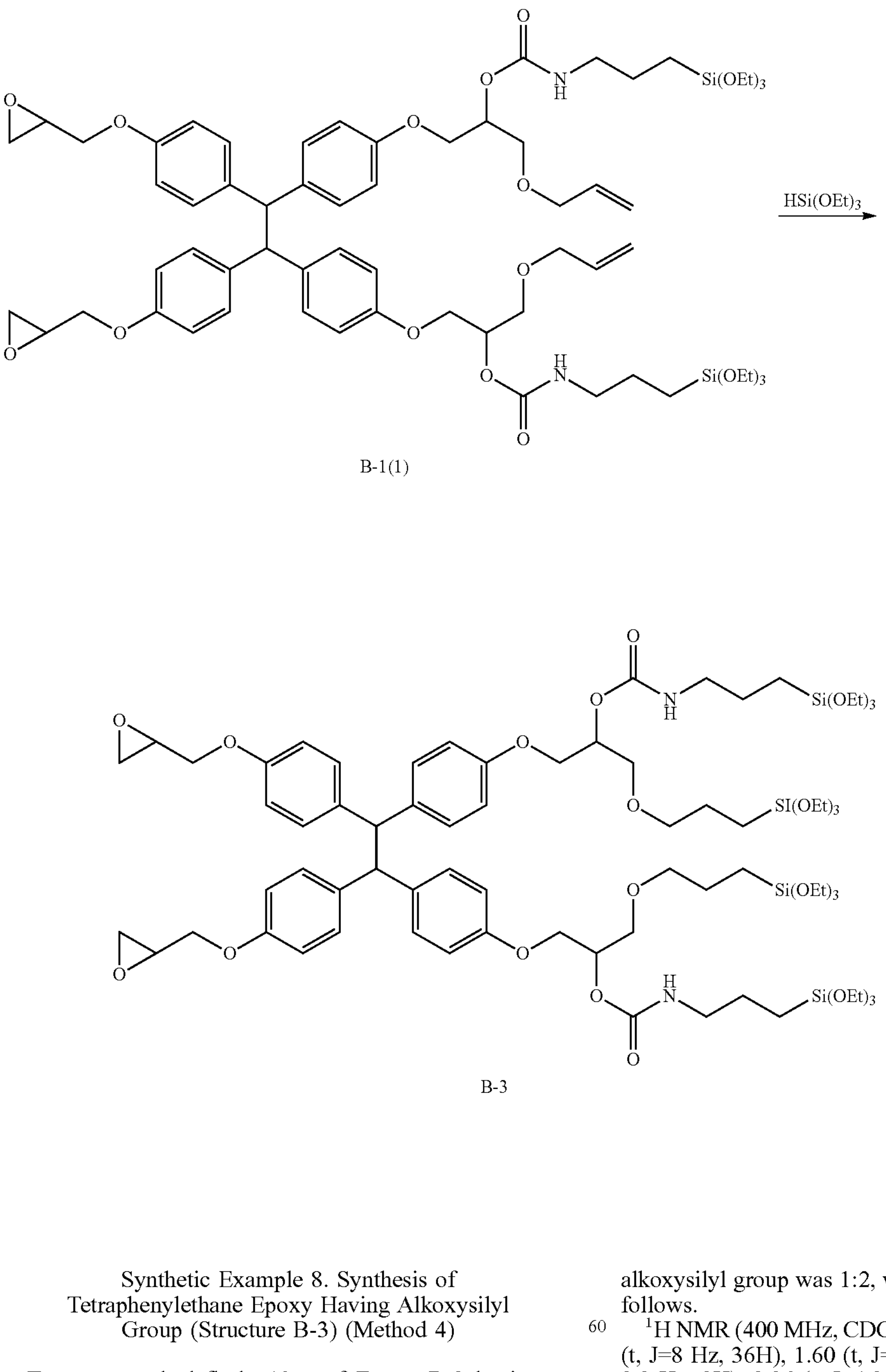

B-1(1)

B-3

Synthetic Example 8. Synthesis of Tetraphenylethane Epoxy Having Alkoxysilyl Group (Structure B-3) (Method 4)

To a two-necked flask, 10 g of Epoxy B-2 having an alkoxysilyl group synthesized in the Synthetic Example 6 and acetonitrile were added and stirred. Then, 5.13 g of 3-(triethoxysilyl)propyl isocyanate and 2.68 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin B-3, in which the ratio of epoxy group: alkoxysilyl group was 1:2, was produced. NMR data are as follows.

$^1$H NMR (400 MHz, $CDCl_3$): δ=0.61 (t, J=8 Hz, 8H), 1.22 (t, J=8 Hz, 36H), 1.60 (t, J=8 Hz, 8H), 2.70 (dd, J=4.8 Hz, 2.8 Hz, 2H), 2.86 (t, J=4.8 Hz, 2H), 3.15 (t, J=8 Hz, 8H), 3.50-3.60 (m, 4H), 3.81-3.91 (m, 4H), 3.78-3.83 (m, 28H), 3.97-4.13 (m, 4H), 4.55 (s, 2H), 5.13-5.15 (m, 2H), 6.67 (d, J=8.8 Hz, 8H), 7.00 (d, J=8.4 Hz, 8H).

The synthetic scheme of the above Synthetic Example 8 is as follows.

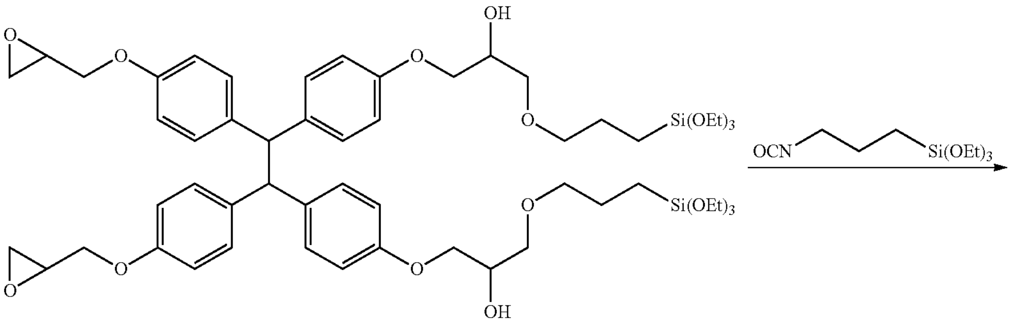

B-2

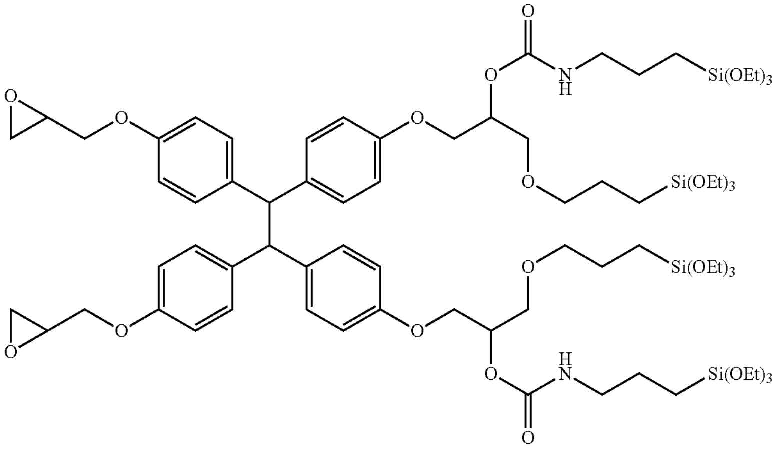

B-3

Synthetic Example 9. Synthesis of Triphenylmethane Epoxy Having Alkoxysilyl Group (Structure C-1

(1) First Step

To a two-necked flask, 10 g of triglycidyl ether of triphenylmethane (Aldrich, Formula C-epoxy) was added, and 20 ml of THF and acetonitrile were respectively added to dissolve an epoxy specimen. Then, 0.85 g of NaOH, 1.03 g of $Et_4NBr$ and 23.65 g of allyl alcohol were added thereto, followed by stirring at room temperature for 3 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate C-0 having the ratio of epoxy group: allyl group of 1:1. NMR data are as follows.

$^1H$ NMR (400 MHz, $CDCl_3$): δ=2.72-2.75 (m, 2H), 2.88-2.90 (m, 2H), 3.31-3.36 (m, 2H), 3.94 (dd, 2H, J=11.9 Hz, 5.6 Hz), 3.80-4.14 (m, 7H), 4.17 (dd, 2H, J=12.0 Hz, 3.6 Hz), 5.20-5.28 (m, 2H), 5.41 (s, 1H), 5.86-5.98 (m, 1H), 6.73 (d, 2H, J=8.8 Hz), 6.82 (d, 4H, J=8.8 Hz), 6.95 (d, 2H, J=8.8 Hz), 6.99 (d, 4H, J=8.8 Hz).

(2) Second Step

To a two-necked flask, 10 g of Intermediate C-0 synthesized in the first step and acetonitrile were added and stirred. Then, 6.11 g of 3-(triethoxysilyl)propyl isocyanate and 3.19 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin C-1, in which the ratio of epoxy group:alkoxysilyl group was 2:1, was produced. NMR data are as follows.

$^1H$ NMR (400 MHz, $CDCl_3$): δ=0.61 (1, J=8 Hz, 2H), 1.22 (t, J=8 Hz, 9H), 1.60 (t, J=8 Hz, 2H), 2.72-2.75 (m, 2H), 2.88-2.90 (m, 2H), 3.15 (t, J=8 Hz, 2H), 3.31-3.36 (m, 2H), 3.78-4.14 (m, 15H), 4.17 (dd, 2H, J=12.0 Hz, 3.6 Hz), 5.13-5.28 (m, 3H), 5.41 (s, 1H), 5.86-5.98 (m, 1H), 6.73 (d, 2H, J=8.8 Hz), 6.82 (d, 4H, J=8.8 Hz), 6.95 (d, 2H, J=8.8 Hz), 6.99 (d, 4H, J=8.8 Hz).

The synthetic scheme of the above Synthetic Example 9 is as follows.

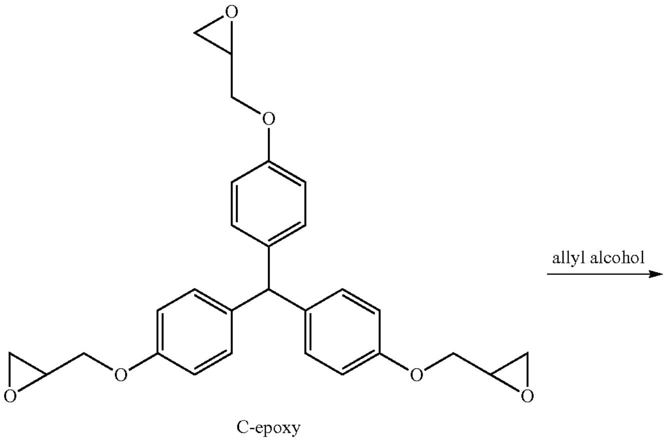

C-epoxy

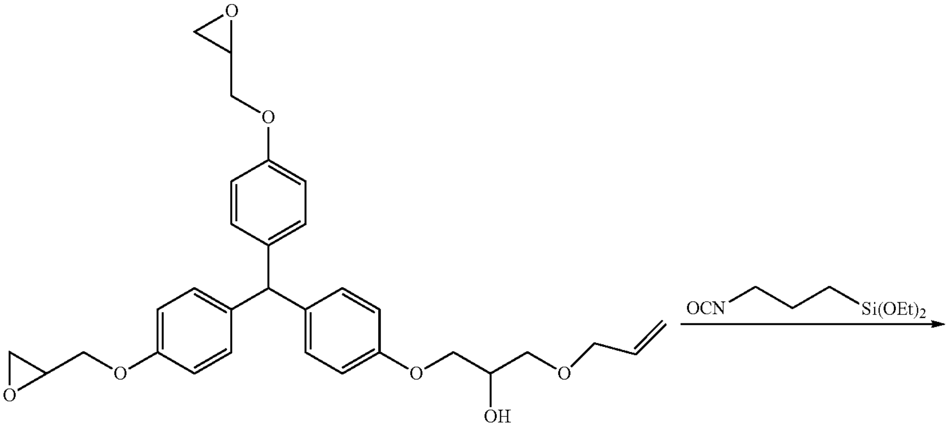

C-0

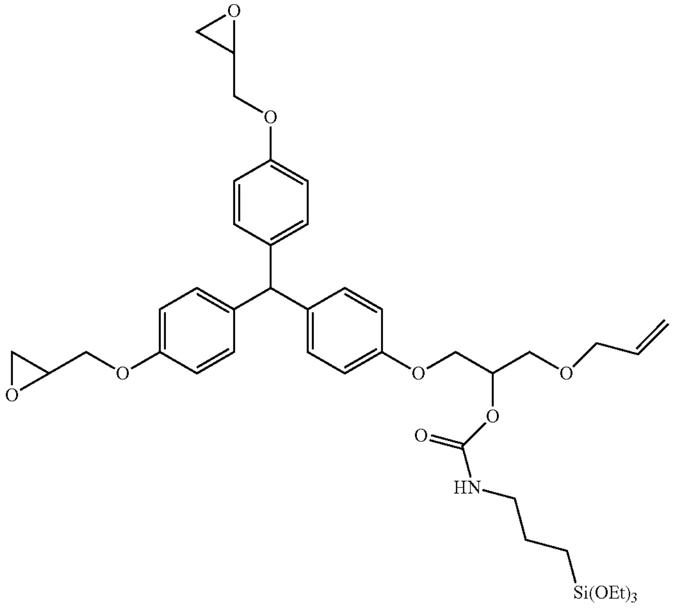

C-1

Synthetic Example 10. Synthesis of Triphenylmethane Epoxy Having Alkoxysilyl Group (Structure C-2) (Method 2)

To a flask, 10 g of Intermediate C-0 obtained in the first step of the above Synthetic Example 9, 88 mg of $PtO_2$, 3.48 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy C-2 having an alkoxysilyl group, in which the ratio of epoxy group:alkoxysilyl group was 2:1. NMR data are as follows.

$^1$H NMR (400 MHz, $CDCl_3$): δ=0.60 (t, J=4 Hz, 2H), 1.23 (t, J=8 Hz 9H), 1.55-1.61 (m, 2H), 2.72-2.75 (m, 2H), 2.88-2.90 (m, 2H), 3.24-3.28 (m, 2H), 3.31-3.36 (m, 2H), 3.80-4.17 (m, 15H), 5.41 (s, 1H), 6.73 (d, 2H, J=8.8 Hz), 6.82 (d, 4H, J=8.8 Hz), 6.95 (d, 2H, J=8.8 Hz), 6.99 (d, 4H, J=8.8 Hz).

The synthetic scheme of the above Synthetic Example 10 is as follows.

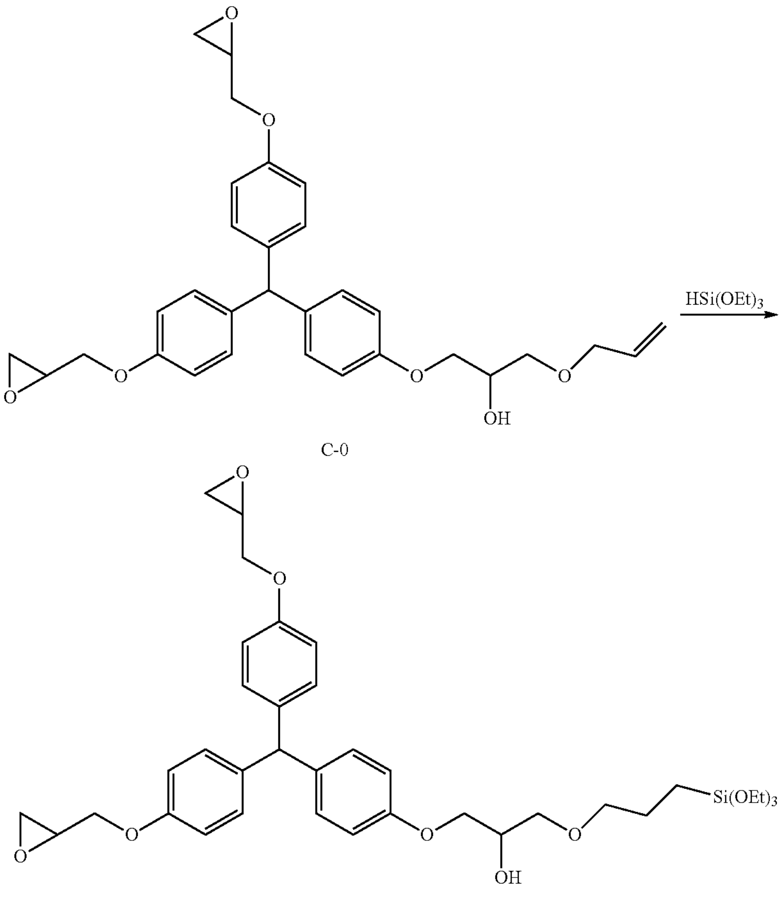

C-0

C-2

Synthetic Example 11. Synthesis of Bisphenol Epoxy Having Alkoxysilyl Group (Structure D-1) (Method 1)

(1) First Step

To a two-necked flask, 10 g of tetraglycidyl-4,4'-diaminodiphenylmethane (Aldrich, Formula D-epoxy) was added, and 29.6 ml of THF and acetonitrile were respectively added to dissolve an epoxy specimen. Then, 1.23 g of NaOH, 1.49 g of $Et_4NBr$ and 34.37 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate D-0 having the ratio of epoxy group: allyl group of 1:1. NMR data are as follows.

$^1$H NMR (400 MHz, $CDCl_3$): δ=2.58-2.60 (m, 2H), 2.78-2.81 (m, 2H), 3.16-3.20 (m, 2H), 3.490-3.49 (m, 2H), 3.73-4.14 (m, 18H), 5.21-5.28 (m, 4H), 5.84-5.97 (m, 2H), 6.74-6.77 (m, 4H), 7.08-7.12 (m, 4H).

(2) Second Step

To a two-necked flask, 10 g of Intermediate D-0 synthesized in the first step and acetonitrile were added and stirred. Then, 11.76 g of 3-(triethoxysilyl)propyl isocyanate and 6.14 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin D-1, in which the ratio of epoxy group:alkoxysilyl group was 1:1, was produced. NMR data are as follows.

$^1$H NMR (400 MHz, $CDCl_3$): δ=0.61 (t, J=8 Hz, 4H), 1.25 (t, J=8 Hz, 18H), 1.62 (t, J=8 Hz, 4H), 2.58-2.60 (m, 2H), 2.78-2.81 (m, 2H), 3.15-3.20 (m, 6H), 3.49-3.40 (m, 2H), 3.78-4.14 (m, 30H), 5.13-5.29 (m, 6H), 5.84-5.97 (m, 2H), 6.74-6.77 (m, 4H), 7.08-7.12 (m, 4H).

The synthetic scheme of the above Synthetic Example 11 is as follows.

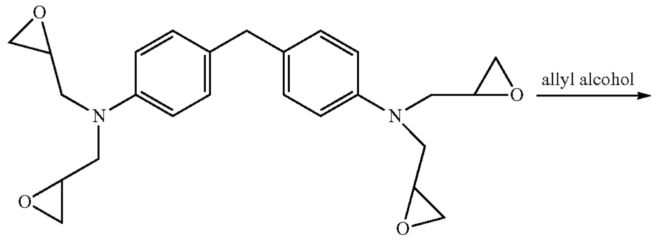

D-epoxy

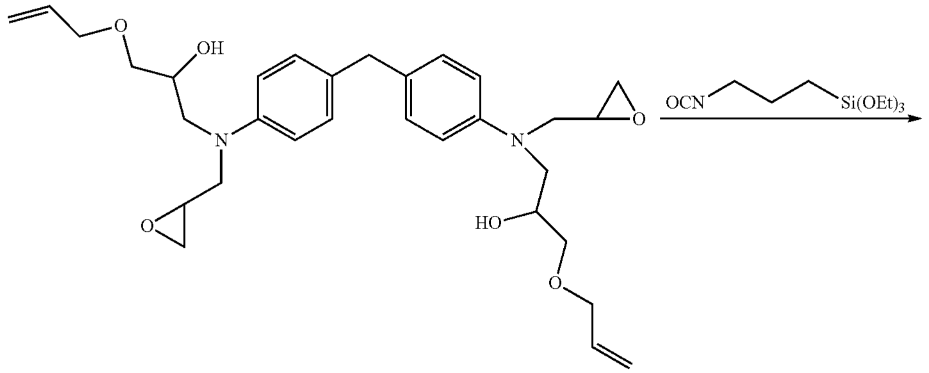

D-0

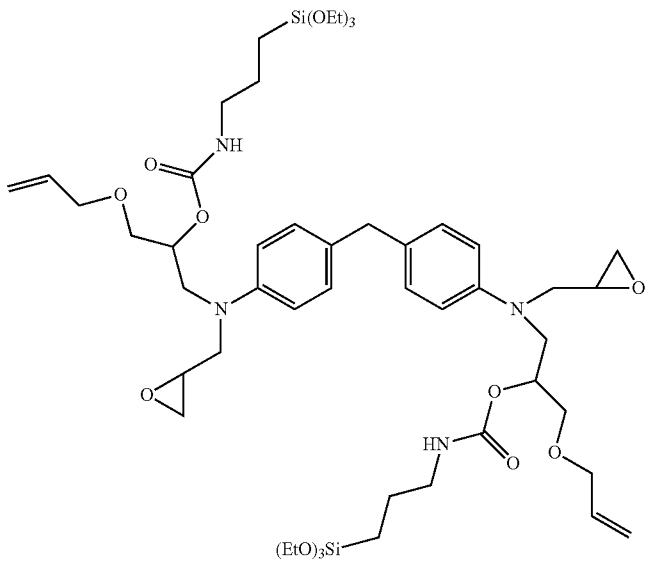

D-1

Synthetic Example 12. Synthesis of Bisphenol Epoxy Having Alkoxysilyl Group (Structure D-2) (Method 2)

To a flask, 10 g of Intermediate D-0 obtained in the first step of the above Synthetic Example 11, 189 mg of $PtO_2$, 6.71 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy D-2 having an alkoxysilyl group, of which ratio of epoxy group:alkoxysilyl group was 1:1. NMR data are as follows.

$^1$H NMR (400 MHz, $CDCl_3$): δ=0.60 (t, J=4 Hz, 4H), 1.21 (t, J=8 Hz 18H), 1.57-1.63 (m, 4H), 2.58-2.60 (m, 2H), 2.78-2.81 (m, 2H), 3.16-3.28 (m, 6H), 3.40-3.49 (m, 2H), 3.73-4.14 (m, 26H), 6.74-6.77 (m, 4H), 7.08-7.13 (m, 4H).

The synthetic scheme of the above Synthetic Example 12 is as follows.

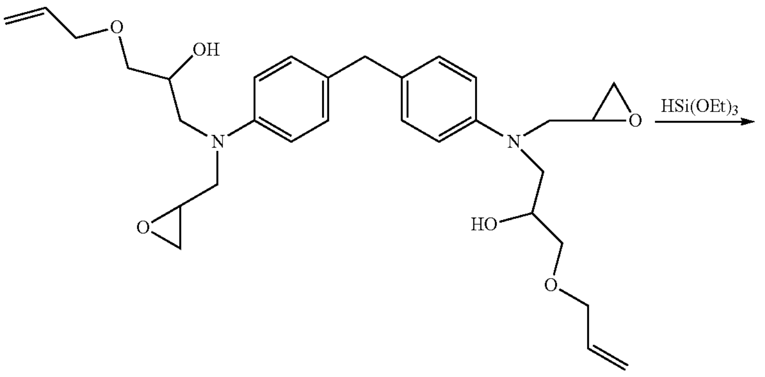

D-0

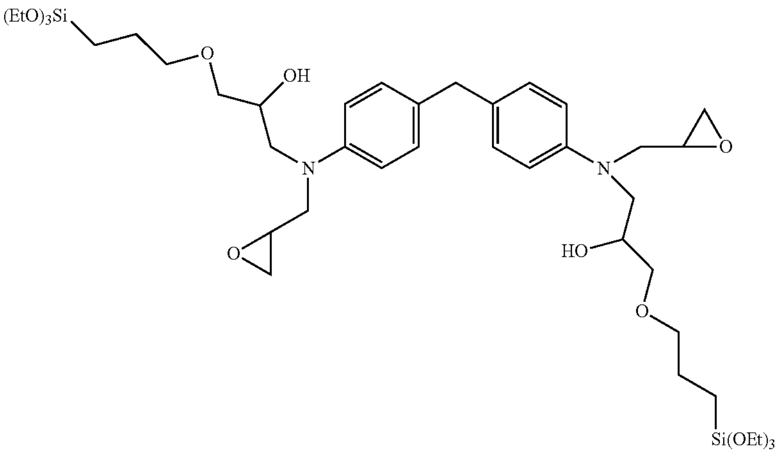

D-2

Synthetic Example 13. Synthesis of Aminophenol Epoxy Having Alkoxysilyl Group (Structure E-1) (Method 1)

(1) First Step

To a two-necked flask, 10 g of N,N-diglycidyl-4-glycidyloxyaniline (Ciba Geigy, MY-0510, Formula E-epoxy) was added, and 34 ml of THF and acetonitrile were respectively added to dissolve an epoxy specimen. Then, 1.41 g of NaOH, 1.71 g of $Et_4NBr$ and 39.27 g of allyl alcohol were added thereto, followed by stirring at room temperature for 3 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate E-0 having the ratio of epoxy group:allyl group of 2:1. NMR data are as follows.

$^1H$ NMR (400 MHz, $CDCl_3$): δ=2.58-2.60 (m, 1.3H), 2.73-2.90 (m, 2H), 3.16-3.20 (m, 0.7H), 3.31-3.35 (m, 1.3H), 3.40-3.49 (m, 2H), 3.76-4.14 (m, 9H), 4.16-4.20 (m, 0.7H), 5.20-5.28 (m, 2H), 5.86-5.98 (m, 1H), 6.62-6.69 (m, 2H), 6.80-6.83 (m, 2H).

(2) Second Step

To a two-necked flask, 10 g of Intermediate E-0 synthesized in the first step and acetonitrile were added and stirred. Then, 9.44 g of 3-(triethoxysilyl)propyl isocyanate and 4.93 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin E-1, in which the ratio of epoxy group:alkoxysilyl group was 2:1, was produced. NMR data are as follows.

$^1H$ NMR (400 MHz, $CDCl_3$): δ=0.61 (t, J=8 Hz, 2H), 1.22 (t, J=8 Hz, 9H), 1.60 (t, J=8 Hz, 2H), 2.58-2.60 (m, 1.3H), 2.73-2.90 (m, 2H), 3.15-3.21 (m, 2.7H), 3.31-3.35 (m, 1.3H), 3.40-4.20 (m, 17.7H), 5.13-5.28 (m, 3H), 5.86-5.98 (m, 1H), 6.62-6.69 (m, 2H), 6.80-6.83 (m, 2H).

The synthetic scheme of the above Synthetic Example 13 is as follows.

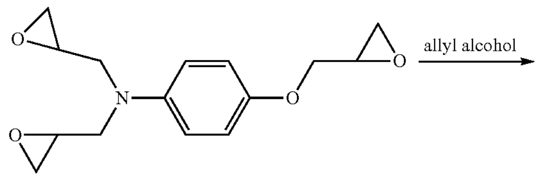

E-epoxy

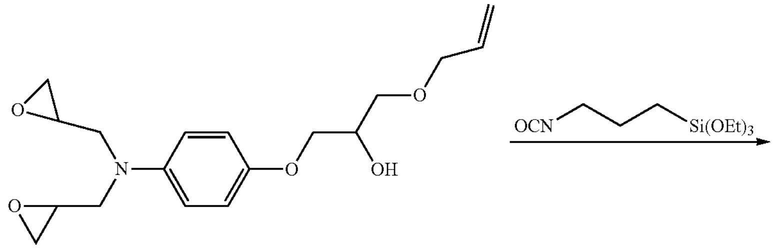

E-0

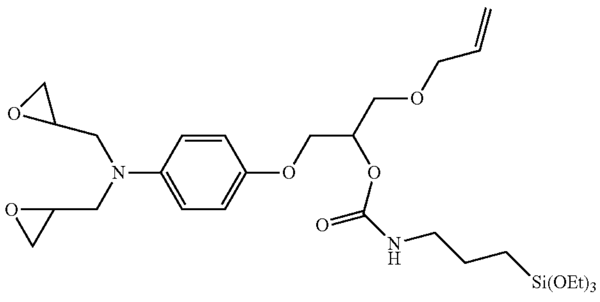

E-1

Synthetic Example 14. Synthesis of Aminophenol Epoxy Having Alkoxysilyl Group (Structure E-2) (Method 2)

To a flask, 10 g of Intermediate E-0 obtained in the first step of the above Synthetic Example 13, 135 mg of $PtO_2$, 5.39 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy E-2 having an alkoxysilyl group, of which ratio of epoxy group:alkoxysilyl group was 2:1. NMR data are as follows.

$^1H$ NMR (400 MHz, $CDCl_3$): δ=0.61 (t, J=4 Hz, 2H), 1.21 (t, J=8 Hz 9H), 1.56-1.61 (m, 2H), 2.58-2.61 (m, 1.3H), 2.74-2.90 (m, 2H), 3.16-3.28 (m, 2.7H), 3.31-3.49 (m, 3.3H), 3.80 (q, J=8 Hz, 6H), 3.76-4.20 (m, 7.7H), 6.62-6.69 (m, 2H), 6.80-6.83 (m, 2H).

The synthetic scheme of the above Synthetic Example 14 is as follows.

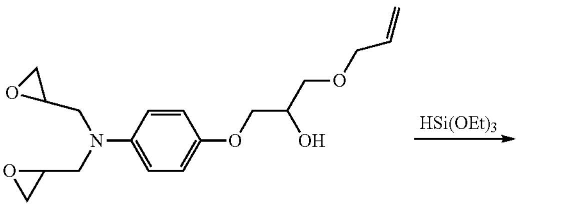

E-0

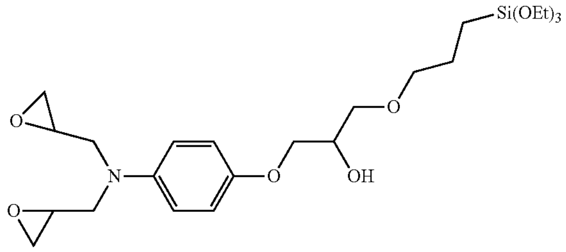

E-2

Synthetic Example 15. Synthesis of Naphthalene Epoxy Having Alkoxysilyl Group (Structure F-1) (Method 1)

(1) First Step

To a two-necked flask, 10 g of 1,5-diglycidyloxy-2,6-diglycidylnaphthalene (not commercially available, but synthesizable by a synthetic method disclosed in Korean Registered Patent No. 10-1252063 of Korea Institute of Industrial Technology, and the method is described in the following Reference Example, F-epoxy) was added, and 33 ml of THF and acetonitrile were respectively added to dissolve an epoxy specimen. Then, 1.35 g of NaOH, 1.64 g of $Et_4NBr$ and 37.77 g of allyl alcohol were added thereto, followed by stirring at room temperature for 3 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate F-0 having the ratio of epoxy group: allyl group of 1:1. NMR data are as follows.

$^1H$ NMR (400 MHz, $CDCl_3$): δ=2.52-2.57 (m, 1H), 2.61-2.66 (m, 2H) 2.73-2.81 (m, 3H), 2.90-2.93 (m, 2H), 3.16-3.18 (m, 1H), 3.35-3.37 (m, 1H), 3.80-4.13 (m, 13H), 4.22-4.25 (m, 1H), 5.20-5.27 (m, 4H), 5.87-6.00 (m, 2H), 7.28 (d, J=8.5 Hz, 2H), 7.75 (d, J=8.5 Hz, 2H).

(2) Second Step

To a two-necked flask, 10 g of Intermediate F-0 synthesized in the first step and acetonitrile were added and stirred. Then, 12.65 g of 3-(triethoxysilyl)propyl isocyanate and 6.61 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin F-1, in which the ratio of epoxy group:alkoxysilyl group was 1:1, was produced. NMR data are as follows.

$^1H$ NMR (400 MHz, $CDCl_3$): δ=0.60 (t, J=8 Hz, 4H), 1.25 (t, J=8 Hz, 18H), 1.65 (t, J=8 Hz, 4H), 2.52-2.57 (m, 1H), 2.61-2.66 (m, 2H) 2.73-2.81 (m, 3H), 2.90-2.93 (m, 2H), 3.16-3.20 (m, 5H), 3.35-3.37 (m, 1H), 3.76-4.13 (m, 25H), 4.22-4.25 (m, 1H), 5.12-5.28 (m, 6H), 5.87-6.00 (m, 2H), 7.28 (d, J=8.5 Hz, 2H), 7.75 (d, J=8.5 Hz, 2H).

The synthetic scheme of the above Synthetic Example 15 is as follows.

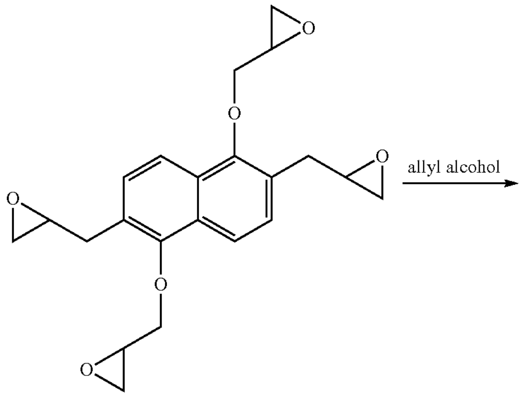

F-epoxy

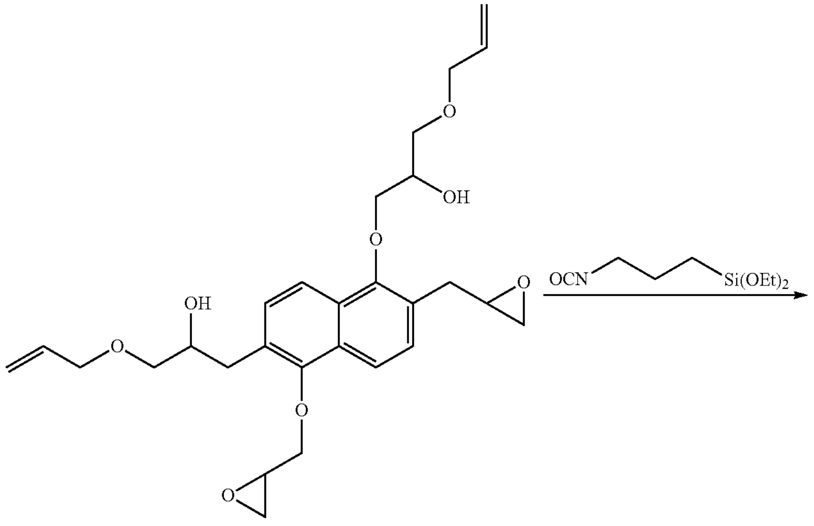

F-0

-continued

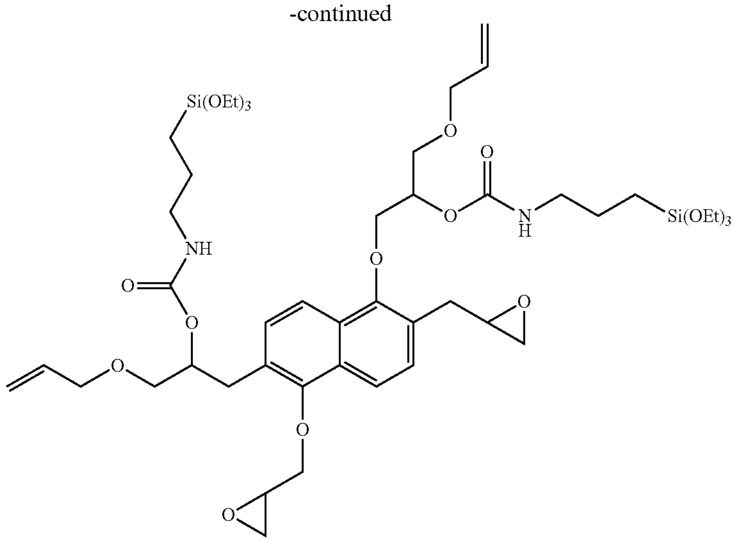

F-1

Synthetic Example 16. Synthesis of Naphthalene Epoxy Having Alkoxysilyl Group (Structure F-2) (Method 2)

To a flask, 10 g of Intermediate F-0 obtained in the first step of the above Synthetic Example 15, 181 mg of $PtO_2$, 7.22 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy F-2 having an alkoxysilyl group, of which ratio of epoxy group:alkoxysilyl group was 1:1. NMR data are as follows.

$^1H$ NMR (400 MHz, $CDCl_3$): δ=0.60 (t, J=4 Hz, 4H), 1.21 (t, J=8 Hz 18H), 1.57-1.61 (m, 4H), 2.52-2.57 (m, 1H), 2.61-2.66 (m, 2H) 2.73-2.81 (m, 3H), 2.90-2.93 (m, 2H), 3.16-3.18 (m, 1H), 3.24-3.28 (m, 4H), 3.35-3.37 (m, 1H), 3.78-4.13 (m, 21H), 4.22-4.25 (m, 1H), 7.28 (d, J=8.5 Hz, 2H), 7.75 (d, J=8.5 Hz, 2H).

The synthetic scheme of the above Synthetic Example 16 is as follows.

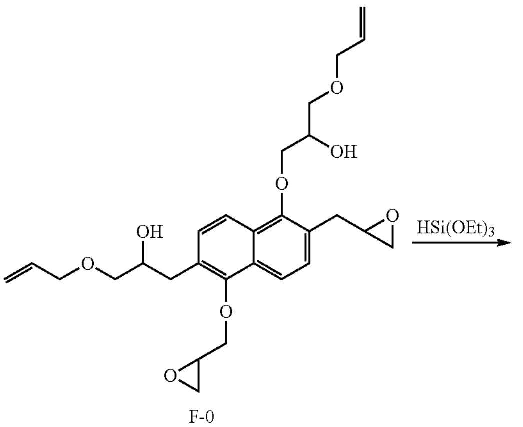

F-0

-continued

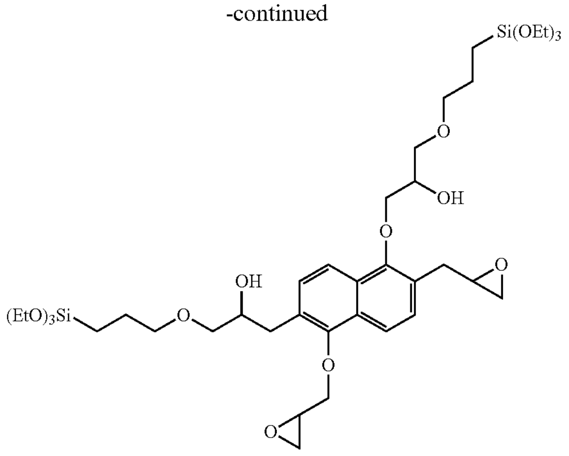

F-2

Synthetic Example 17. Synthesis of Biphenyl Epoxy Having Alkoxysilyl Group (Structure G) (Method 1)

(1) First Step

To a two-necked flask, 10 g of 3,3'-diglycidyl-4,4'-diglycidyloxy biphenyl (not commercially available, but synthesizable by a synthetic method disclosed in Korean Registered Patent No. 10-1252063 of Korea Institute of Industrial Technology, and the method is described in the following Reference Example 2, G-epoxy) was added, and 31 ml of THF and acetonitrile were respectively added to dissolve an epoxy specimen. Then, 1.27 g of NaOH, 1.54 g of $Et_4NBr$ and 35.37 g of allyl alcohol were added thereto, followed by stirring at room temperature for 3 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate G-0 having the ratio of epoxy group:allyl group of 1:1. NMR data are as follows.

$^1$H NMR (400 MHz, $CDCl_3$): δ=2.53-2.57 (m, 1H), 2.61-2.65 (m, 2H), 2.73-2.81 (m, 3H), 2.88-2.92 (m, 2H), 3.16-3.18 (m, 1H), 3.35-3.37 (m, 1H), 3.80-4.04 (m, 13H), 4.22-4.25 (m, 1H), 5.20-5.26 (m, 4H), 5.86-5.99 (m, 2H), 6.73-6.75 (m, 2H), 7.03-7.05 (m, 4H).

(2) Second Step

To a two-necked flask, 10 g of Intermediate G-0 synthesized in the first step and acetonitrile were added and stirred. Then, 12.02 g of 3-(triethoxysilyl)propyl isocyanate and 6.28 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin G-1, in which the ratio of epoxy group:alkoxysilyl group was 1:1, was produced. NMR data are as follows.

$^1$H NMR (400 MHz, $CDCl_3$): δ=0.62 (t, J=8 Hz, 4H), 1.24 (t, J=8 Hz, 18H), 1.62 (t, J=8 Hz, 4H), 2.53-2.57 (m, 1H), 2.61-2.65 (m, 2H), 2.73-2.81 (m, 3H), 2.88-2.92 (m, 2H), 3.15-3.18 (m, 5H), 3.35-3.37 (m, 1H), 3.78-4.04 (m, 25H), 4.22-4.25 (m, 1H), 5.12-5.27 (m, 6H), 5.86-5.99 (m, 2H), 6.73-6.75 (m, 2H), 7.03-7.05 (m, 4H).

The synthetic scheme of the above Synthetic Example 17 is as follows.

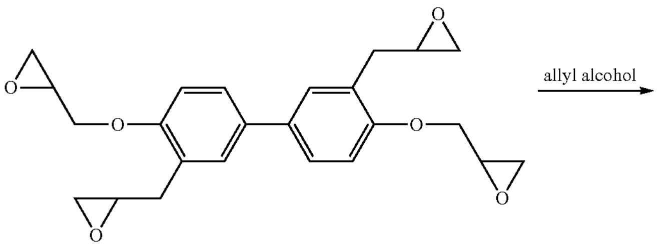

G-epoxy

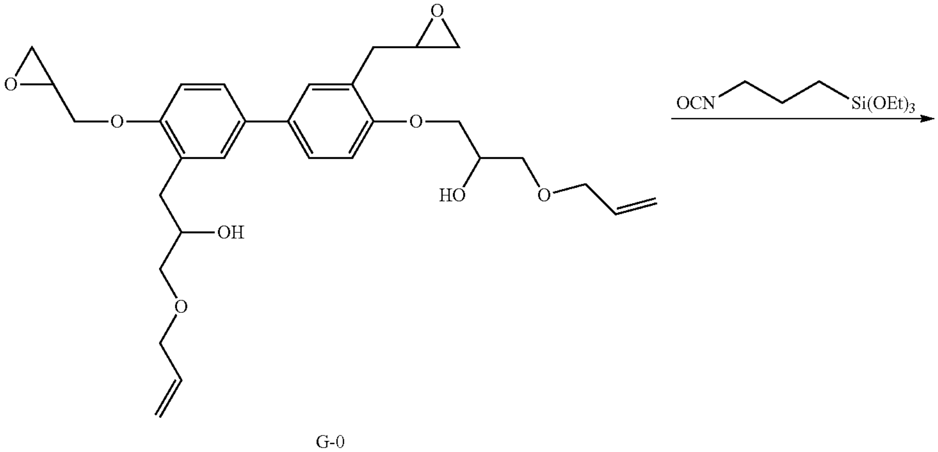

G-0

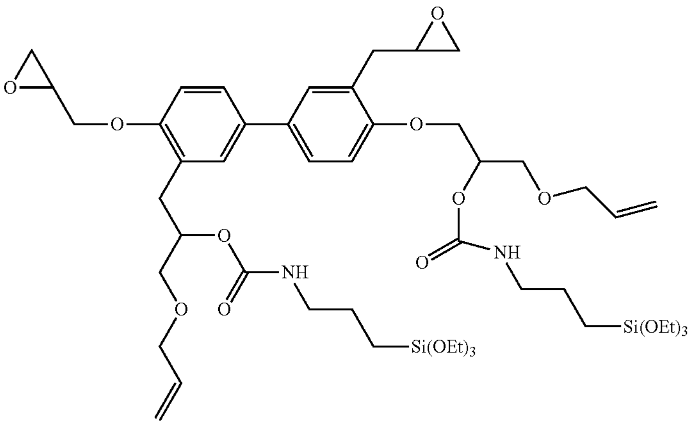

G-1

Synthetic Example 18. Synthesis of Biphenyl Epoxy Having Alkoxysilyl Group (Structure G-2) (Method 2)

To a flask, 10 g of Intermediate G-0 obtained in the first step of the above Synthetic Example 17, 172 mg of $PtO_2$, 6.86 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy G-2 having an alkoxysilyl group, of which ratio of epoxy group:alkoxysilyl group was 1:1. NMR data are as follows.

$^1$H NMR (400 MHz, $CDCl_3$): δ=0.60 (t, J=4 Hz, 4H), 1.23 (t, J=8 Hz 18H), 1.57-1.62 (m, 4H), 2.53-2.57 (m, 1H), 2.61-2.65 (m, 2H), 2.73-2.81 (m, 3H), 2.88-2.92 (m, 2H), 3.16-3.18 (m, 1H), 3.24-3.28 (m, 4H), 3.35-3.37 (m, 1H), 3.80-4.04 (m, 21H), 4.22-4.25 (m, 1H), 6.73-6.75 (m, 2H), 7.03-7.05 (m, 4H).

The synthetic scheme of the above Synthetic Example 18 is as follows.

Synthetic Example 19. Synthesis of Fluorene Epoxy Having Alkoxysilyl Group (Structure H-1) (Method 1)

(1) First Step

To a two-necked flask, 10 g of 9,9-di(3-glycidyl-4-diglycidyloxyphenyl)fluorene (not commercially available, but synthesizable by a synthetic method disclosed in Korean Registered Patent No. 10-1252063 of Korea Institute of Industrial Technology, and the method is described in the following Reference Example 3, H-epoxy) was added, and 21 ml of THF and acetonitrile were respectively added to dissolve an epoxy specimen. Then, 0.90 g of NaOH, 1.10 g of $Et_4NBr$ and 25.27 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate H-0 having the ratio of epoxy group: allyl group of 1:1. NMR data are as follows.

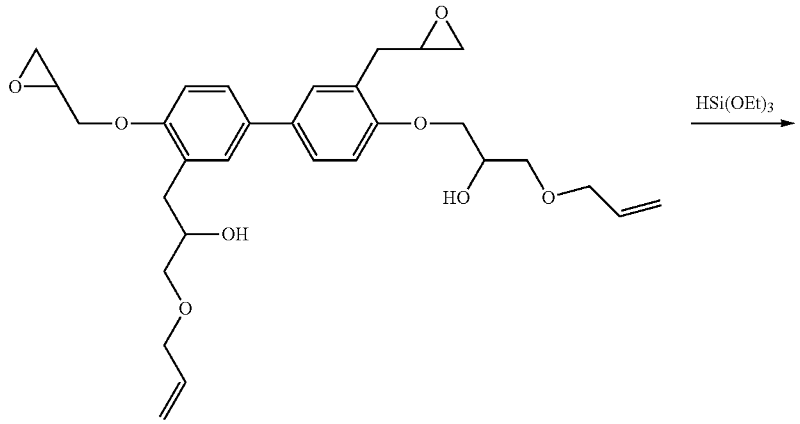

G-0

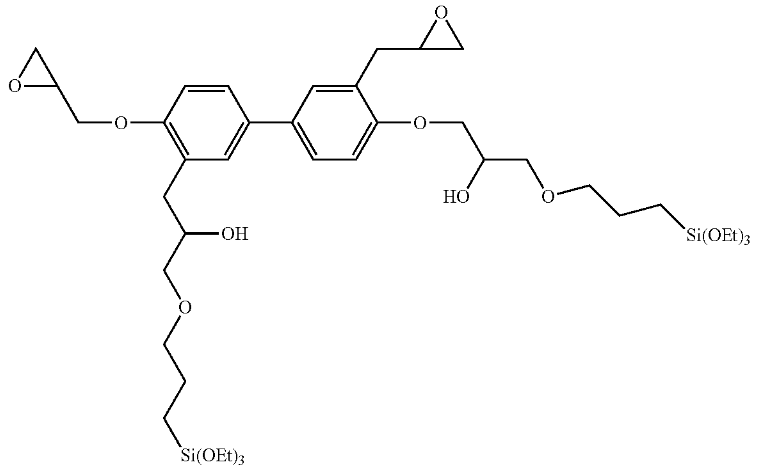

G-2

$^1$H NMR (400 MHz, $CDCl_3$): δ=2.53-2.56 (m, 1H), 2.59-2.66 (m, 2H), 2.72-2.81 (m, 3H), 2.89-2.93 (m, 2H), 3.16-3.18 (m, 1H), 3.35-3.37 (m, 1H), 3.79-4.15 (m, 13H), 4.22-4.25 (m, 1H), 5.20-5.28 (m, 4H), 5.86-5.98 (m, 2H), 6.73-6.75 (m, 2H), 7.03-7.05 (m, 4H), 7.22-7.36 (m, 6H), 7.74 (d, J=7.2 Hz, 2H).

(2) Second Step

To a two-necked flask, 10 g of Intermediate H-0 synthesized in the first step and acetonitrile were added and stirred. Then, 9.17 g of 3-(triethoxysilyl)propyl isocyanate and 4.79 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin H-1, in which the ratio of epoxy group:alkoxysilyl group was 1:1, was produced.

$^1$H NMR (400 MHz, $CDCl_3$): δ=0.62 (t, J=8 Hz, 4H), 1.23 (t, J=8 Hz, 18H), 1.61 (t, J=8 Hz, 4H), 2.52-2.56 (m, 1H), 2.60-2.66 (m, 2H), 2.72-2.81 (m, 3H), 2.89-2.93 (m, 2H), 3.15-3.20 (m, 5H), 3.35-3.37 (m, 1H), 3.78-4.15 (m, 25H), 4.22-4.25 (m, 1H), 5.13-5.28 (m, 6H), 5.86-5.98 (m, 2H), 6.73-6.75 (m, 2H), 7.03-7.05 (m, 4H), 7.22-7.36 (m, 6H), 7.74 (d, J=7.2 Hz, 2H).

The synthetic scheme of the above Synthetic Example 19 is as follows.

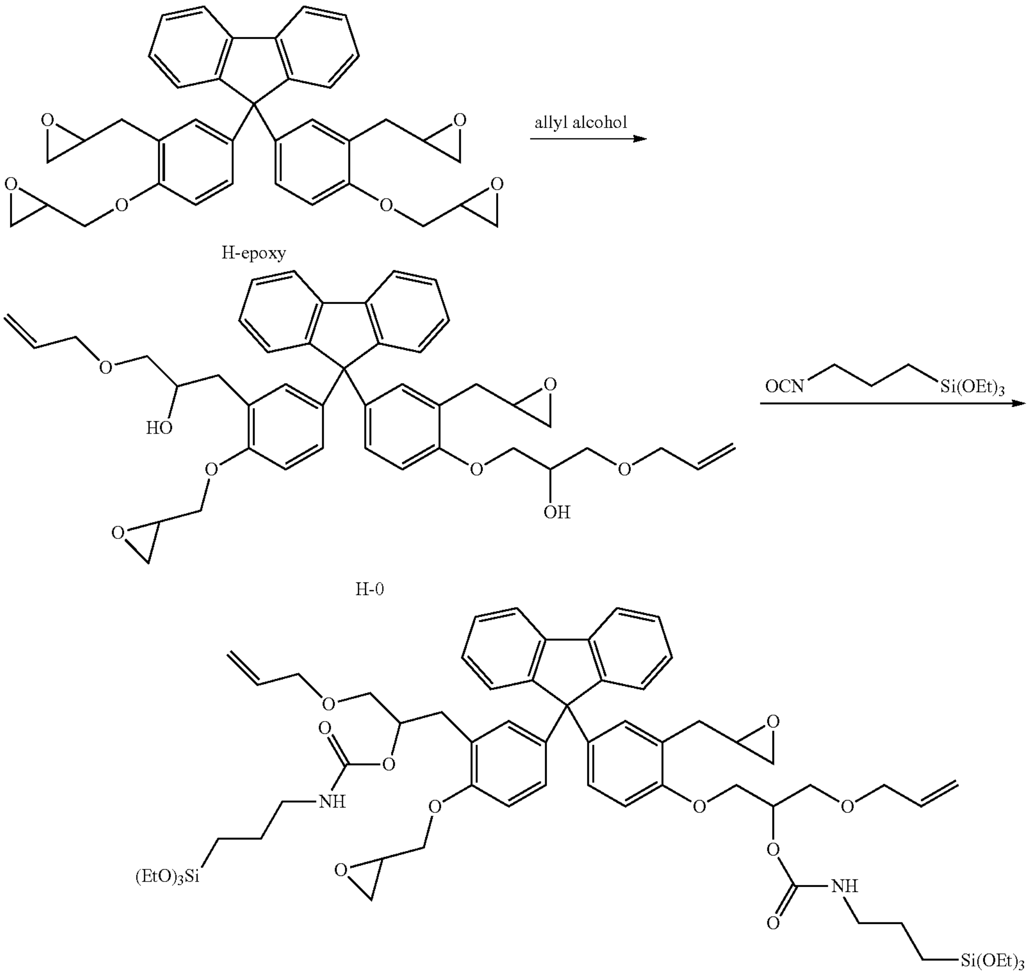

H-epoxy

H-0

H-1

Synthetic Example 20. Synthesis of Fluorene Epoxy Having Alkoxysilyl Group (Structure H-2) (Method 2)

To a flask, 10 g of Intermediate H-0 obtained in the first step of the above Synthetic Example 19, 131 mg of $PtO_2$, 5.23 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy H-2 having an alkoxysilyl group, of which ratio of epoxy group:alkoxysilyl group is 1:1. NMR data are as follows.

$^1$H NMR (400 MHz, $CDCl_3$): δ=0.60 (t, J=4 Hz, 4H), 1.22 (t, J=8 Hz 18H), 1.55-1.61 (m, 4H), 2.53-2.66 (m, 3H), 2.72-2.81 (m, 3H), 2.89-2.93 (m, 2H), 3.16-3.18 (m, 1H), 3.24-3.28 (m, 4H), 3.35-3.37 (m, 1H), 3.79-4.25 (m, 22H), 6.73-6.75 (m, 2H), 7.03-7.05 (m, 4H), 7.22-7.36 (m, 6H), 7.74 (d, J=7.2 Hz, 2H).

The synthetic scheme of the above Synthetic Example 20 is as follows.

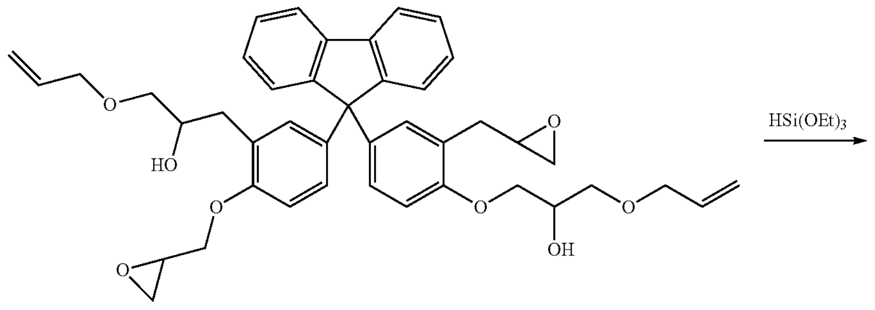

H-0

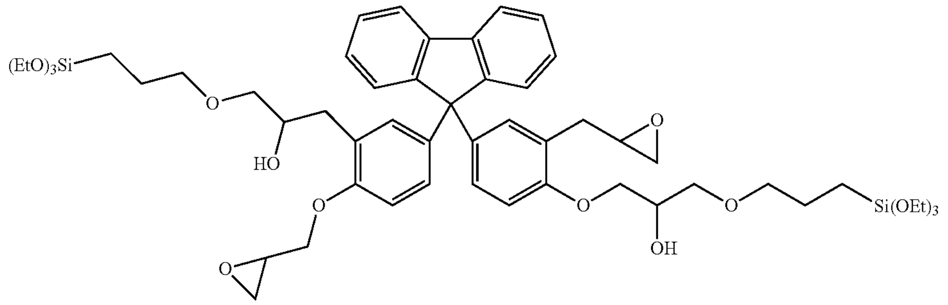

H-2

Synthetic Example 21. Synthesis of Tetraphenylmethane Epoxy Having Alkoxysilyl Group (Structure I-1) (Method 1) (Expected Example 1)

(1) First Step

To a two-necked flask, 10 g of 3,3'-diglycidyl-4,4'-diglycidyloxytetraphenylmethane (I-epoxy) is added, and 22 ml of THF and acetonitrile are, respectively added thereto to dissolve an epoxy specimen. Then, 0.90 g of NaOH, 1.09 g of $Et_4NBr$ and 25.18 g of allyl alcohol are added thereto, followed by stirring at room temperature for 6 hours. 10 ml of a saturated $NH_4Cl$ solution is added thereto to terminate the reaction. Thereafter, solvents are partially removed using a rotary evaporator, and the residue is worked-up using 150 ml of ethyl acetate and 50 ml of tap water three times. An organic layer is separated, residual $H_2O$ is removed with $MgSO_4$, and the organic layer is completely dried using a rotary evaporator and a vacuum pump to produce Intermediate I-0 having the ratio of epoxy group:allyl group of 1:1.

(2) Second Step

To a two-necked flask, 10 g of Intermediate I-0 synthesized in the first step and acetonitrile are added and stirred. Then, 9.14 g of 3-(triethoxysilyl)propyl isocyanate and 4.78 g of diisopropylethylamine are added thereto, followed by performing a reaction at 65° C. for 30 hours. After completing the reaction, the reaction mixture is cooled to room temperature and worked-up using 100 ml of ethyl acetate and 40 ml of a saturated $NH_4Cl$ solution. An organic layer is separated, and $MgSO_4$ was added thereto to remove residual $H_2O$. Solvents are removed using a rotary evaporator and separated using a hexane slurry. After removing a supernatant hexane layer and completely drying using a vacuum pump, Epoxy resin I-1, in which the ratio of epoxy group:alkoxysilyl group is 1:1, is produced.

The synthetic scheme of the above Synthetic Example 21 is as follows.

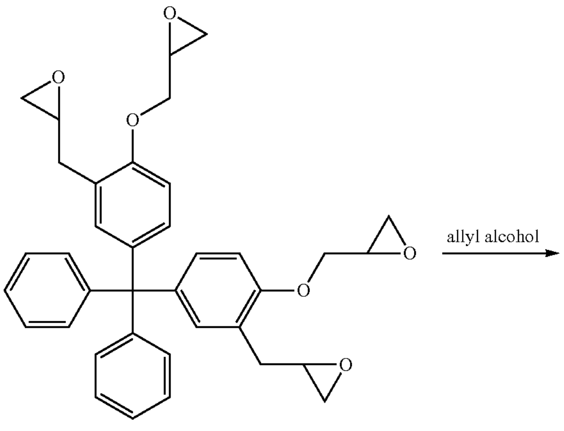

I-epoxy

-continued

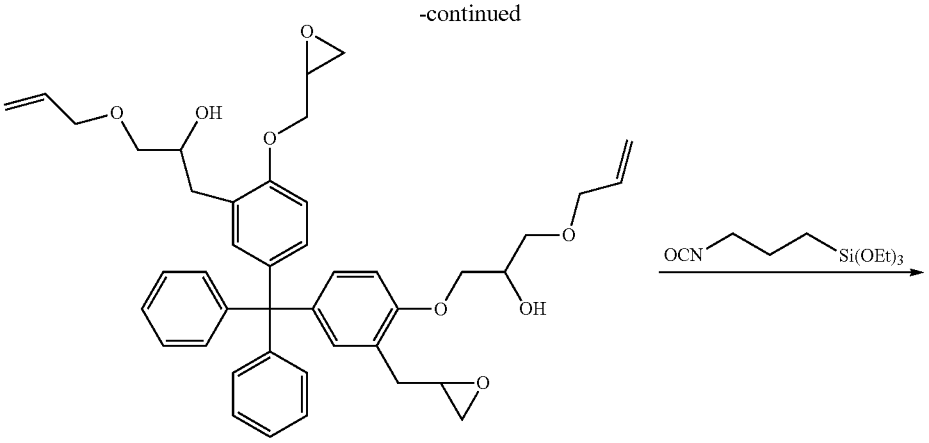

I-0

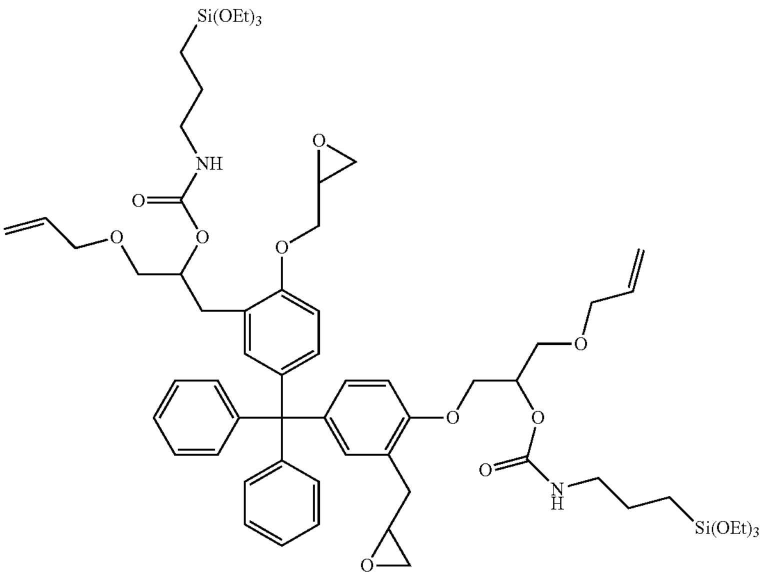

I-1

Synthetic Example 22. Synthesis of Tetraphenylmethane Epoxy Having Alkoxysilyl Group (Structure I-2) (Method 2) (Expected Example 2)

To a flask, 10 g of Intermediate I-0 obtained in the first step of the above Synthetic Example 21, 131 mg of $PtO_2$, 5.22 g of triethoxysilane and 150 ml of toluene are added and stirred at room temperature for 5 minutes. The temperature is elevated to 80° C., and the reaction mixture is heated and stirred for 24 hours. After completing the reaction, the temperature is decreased to room temperature, and inorganic materials are removed using a celite filter. Through evaporation, toluene is removed, and using a vacuum pump, the product is completely dried to produce Epoxy 1-2 having an alkoxysilyl group, of which ratio of epoxy group:alkoxysilyl group is 1:1.

The synthetic scheme of the above Synthetic Example 22 is as follows.

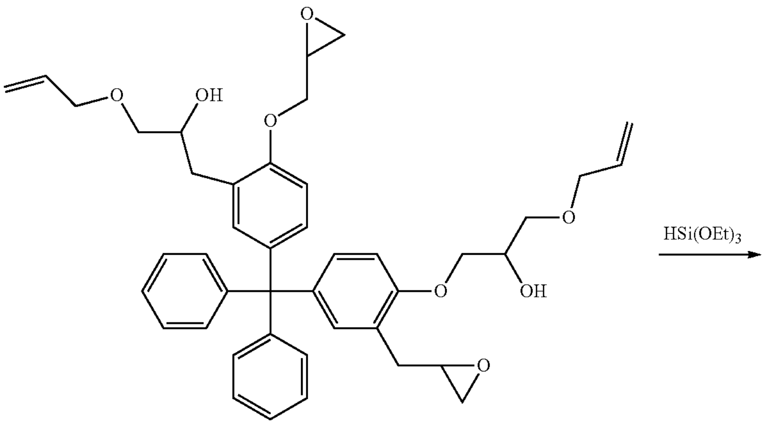

I-0

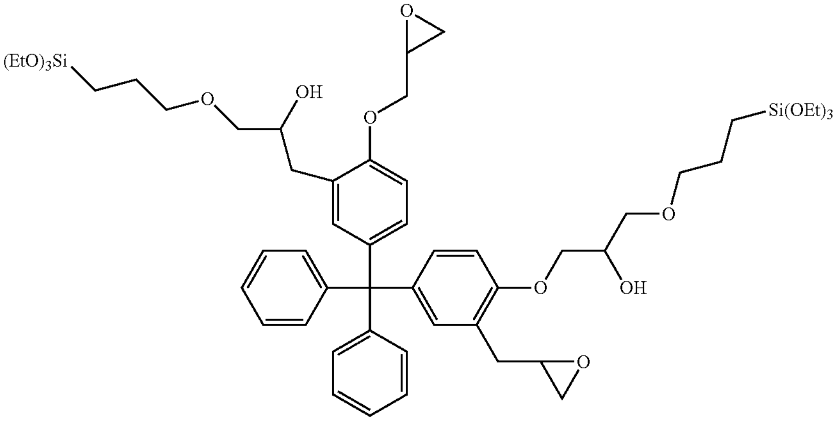

I-2

Synthetic Example 23. Synthesis of Isoisocyanurate Epoxy Having Alkoxysilyl Group (Structure J-1) (Method 1)

(1) First Step

To a two-necked flask, 10 g of tris(2,3-epoxypropyl) isocyanurate (Aldrich, Formula J-epoxy) was added, and 31.5 ml of THF and acetonitrile were respectively added to dissolve an epoxy specimen. Then, 1.31 g of NaOH, 1.59 g of $Et_4NBr$ and 36.63 g of allyl alcohol were added thereto, followed by stirring at room temperature for 3 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate J-0 having the ratio of epoxy group: allyl group of 2:1. NMR data are as follows.

$^1H$ NMR (400 MHz, $CDCl_3$): δ=2.61-2.64 (m, 2H), 2.71-2.75 (m, 2H), 3.13-3.20 (m, 2H), 3.75-4.14 (m, 11H), 5.19-5.27 (m, 2H), 5.86-5.97 (m, 1H).

(2) Second Step

To a two-necked flask, 10 g of Intermediate J-0 synthesized in the first step and acetonitrile were added and stirred. Then, 8.91 g of 3-(triethoxysilyl)propyl isocyanate and 4.66 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin J-1, in which the ratio of epoxy group:alkoxysilyl group was 2:1, was produced. NMR data are as follows.

$^1H$ NMR (400 MHz, $CDC_{13}$): δ=0.63 (t, J=8 Hz, 2H), 1.26 (t, J=8 Hz, 9H), 1.63 (t, J=8 Hz, 2H), 2.60-2.64 (m, 2H), 2.71-2.75 (m, 2H), 3.13-3.20 (m, 4H), 3.75-4.14 (m, 17H), 5.13-5.29 (m, 3H), 5.86-5.97 (m, 1H).

The synthetic scheme of the Synthetic Example 23 is as follows.

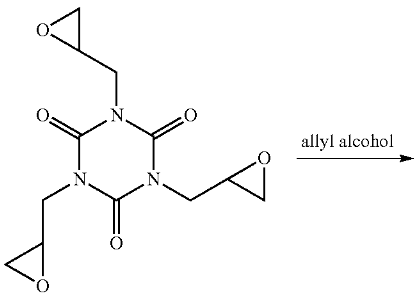

J-epoxy

-continued

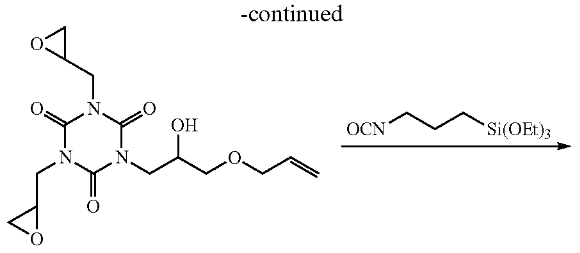

J-0

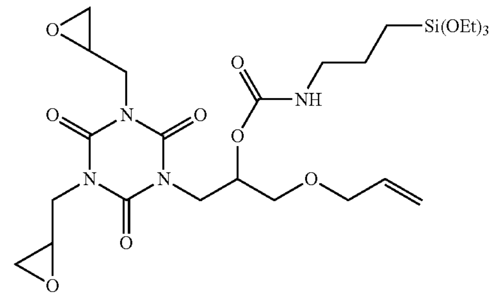

J-1

Synthetic Example 24. Synthesis of Isocyanurate Epoxy Having Alkoxysilyl Group (Structure J-2) (Method 2)

To a flask, 10 g of Intermediate J-0 obtained in the first step of the above Synthetic Example 23, 128 mg of $PtO_2$, 5.09 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy J-2 having an alkoxysilyl group, of which ratio of epoxy group:alkoxysilyl group is 2:1. NMR data are as follows.

$^1H$ NMR (400 MHz, $CDCl_3$): δ=0.59 (t, J=4 Hz, 2H), 1.23 (t, J=8 Hz, 9H), 1.57-1.61 (m, 2H), 2.61-2.64 (m, 2H), 2.71-2.75 (m, 2H), 3.13-3.28 (m, 4H), 3.75-4.14 (m, 15H).

The synthetic scheme of the above Synthetic Example 24 is as follows.

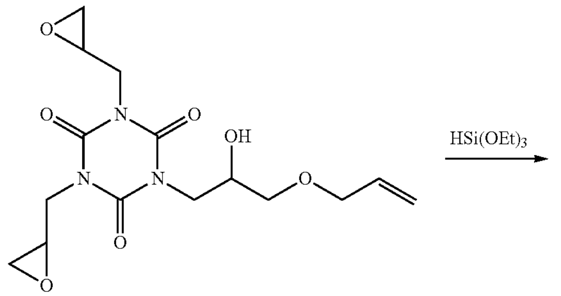

J-0

-continued

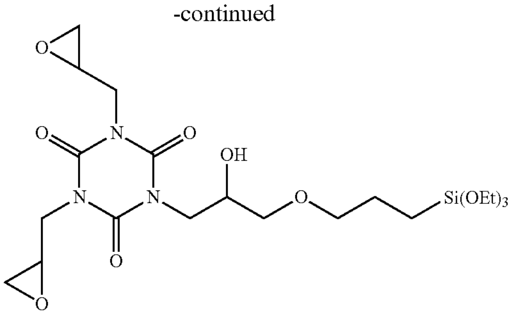

J-2

Synthetic Example 25. Synthesis of Phenolnovolac Epoxy Having Alkoxysilyl Group (Structure K-1) (Method 1)

(1) First Step

To a two-necked flask, 10 g of phenolnovolac epoxy (Kukdo Chemical Co., YDPN, K-epoxy) was added, and 19 ml of THF and acetonitrile were respectively added to dissolve an epoxy specimen. Then, 0.79 g of NaOH, 0.96 g of $Et_4NBr$ and 22.00 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate K-0 having the ratio of epoxy group: allyl group of 1:1. NMR data are as follows.

$^1H$ NMR (400 MHz, $CDCl_3$): δ=2.60-2.73 (m, 6.89H), 3.29-3.32 (m, 3.51H), 3.78-4.17 (m, 35.59H), 4.47-4.49 (m, 7.61H), 5.20-5.41 (m, 6.91H), 6.00-6.04 (m, 3.66H), 6.70-7.14 (m, 21.68H).

(2) Second Step

To a two-necked flask, 10 g of Intermediate K-0 synthesized in the first step and acetonitrile were added and stirred. Then, 8.16 g of 3-(triethoxysilyl)propyl isocyanate and 4.26 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin K-1, in which the ratio of epoxy group:alkoxysilyl group was 1:1, was produced. NMR data are as follows.

$^1H$ NMR (400 MHz, $CDCl_3$): δ=0.61 (1, J=8 Hz, 7.33), 1.22 (t, J=8 Hz, 32.94H), 1.60 (t, J=8 Hz, 7.71H), 2.60-2.73 (m, 6.89H), 3.15-3.32 (m, 10.87H), 3.78-4.18 (m, 57.74H), 4.47-4.49 (m, 7.61H), 5.13-5.41 (m, 10.62H), 6.00-6.04 (m, 3.66H), 6.70-7.14 (m, 21.68H).

The synthetic scheme of the above Synthetic Example 25 is as follows.

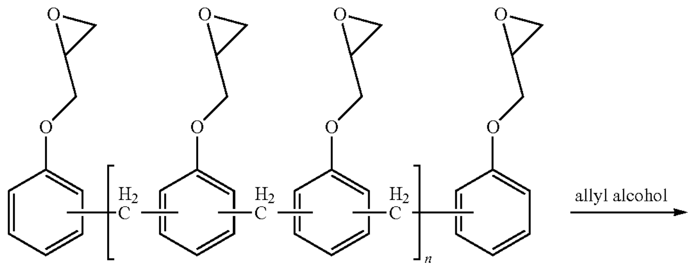

K-epoxy

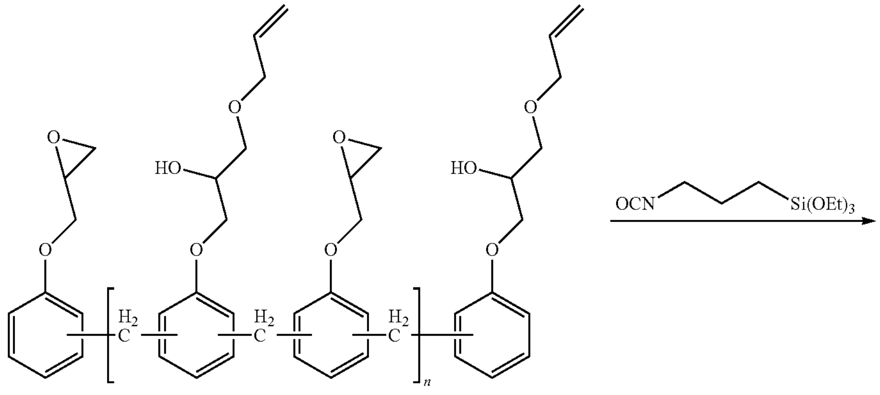

K-0

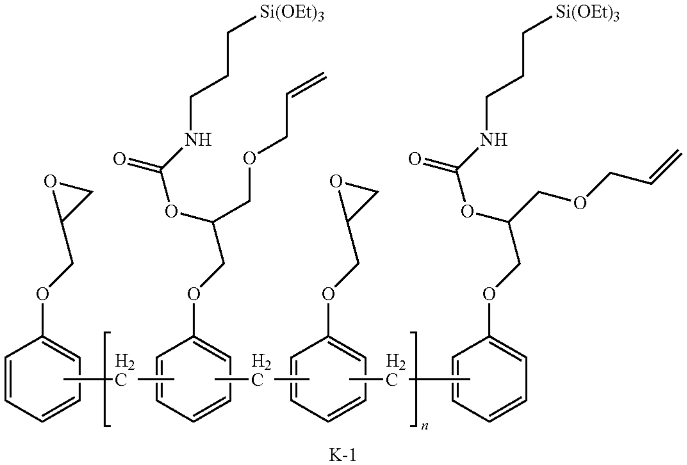

K-1

For the K-0 structure of the above synthetic scheme, the reaction site of the allyl alcohol of the novolac epoxy is considered to not having an alternating structure but having a randomly distributed structure of an epoxy functional group and the allyl group along a main chain. Based on the same reason, the concentration of the epoxy group and the alkoxysilyl group in the K-1 structure is 1:1, however the position of the epoxy group and the alkoxysilyl group does not have the alternating structure but the random structure. The alternating structure shown in the above scheme is illustrated for convenience to adjust the ratio of the epoxy group and a modified functional group and is different from the structure of a real compound. Hereinafter, a core structure is applied to the synthetic scheme and the structure of the novolac epoxy of K' to N'.

Synthetic Example 26. Synthesis of Phenolnovolac Epoxy Having Alkoxysilyl Group (Structure K-2) (Method 2)

To a two-necked flask, 10 g of Intermediate K-0 obtained in the first step of the above Synthetic Example 25, 117 mg of $PtO_2$, 4.66 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce the final target material of Epoxy K-2 having an alkoxysilyl group, of which ratio of epoxy group:alkoxysilyl group was 1:1. NMR data are as follows.

$^1$H NMR (400 MHz, $CDCl_3$): δ=0.62 (t, J=4 Hz, 7.41H), 1.22 (t, J=8 Hz 33.91H), 1.55-1.61 (m, 7.33H), 2.60-2.73 (m, 6.89H), 3.24-3.32 (m, 11.01H), 3.78-4.17 (m, 58.58H), 6.70-7.14 (m, 21.68H).

The synthetic scheme of the above Synthetic Example 26 is as follows.

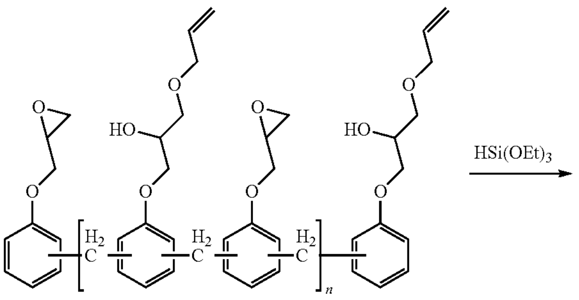

K-0

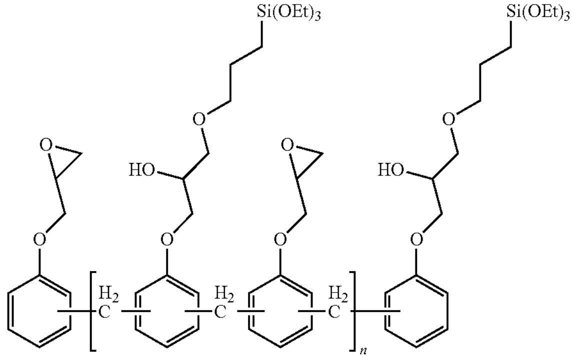

K-2

Synthetic Example 27. Synthesis of Cresol Novolac Epoxy Having Alkoxysilyl Group (Structure L-1(1)) (Method 1)

(1) First Step

To a two-necked flask, 10 g of o-cresol novolac epoxy (NIPPON KAYAKU CO., EOCN-1020, Structure L-epoxy) was added, and 22 ml of THF and acetonitrile were respectively added to dissolve an epoxy specimen. Then, 0.91 g of NaOH, 1.10 g of $Et_4NBr$ and 25.39 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate L-0(1) having the ratio of epoxy group:allyl group of 1:1. NMR data are as follows.

$^1$H NMR (400 MHz, $CDCl_3$): δ=2.19-2.32 (m, 3.28H), 2.64-2.91 (m, 1.21H), 3.20-3.36 (m, 0.72H), 3.62-4.13 (m, 12.15H), 5.20-5.28 (m, 1.33H), 5.86-5.98 (m, 0.62H), 6.71-7.04 (m, 3.00H).

(2) Second Step

To a two-necked flask, 10 g of Intermediate L-0(1) synthesized in the first step and acetonitrile were added and stirred. Then, 9.97 g of 3-(triethoxysilyl)propyl isocyanate and 5.21 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin L-1(1), in which the ratio of epoxy group:alkoxysilyl group was 1:1, was produced. NMR data are as follows.

$^1$H NMR (400 MHz, $CDCl_3$): δ=0.63 (t, J=8 Hz, 1.25H), 1.26 (t, J=8 Hz, 5.58H), 1.62 (t, J=8 Hz, 1.25H), 2.17-2.32 (m, 3.28H), 2.64-2.91 (m, 1.21H), 3.15-3.36 (m, 1.97H), 3.62-4.13 (m, 16.57H), 5.13-5.30 (m, 1.95H), 5.86-5.98 (m, 0.62H), 6.71-7.04 (m, 3.00H).

The synthetic scheme of the above Synthetic Example 27 is as follows.

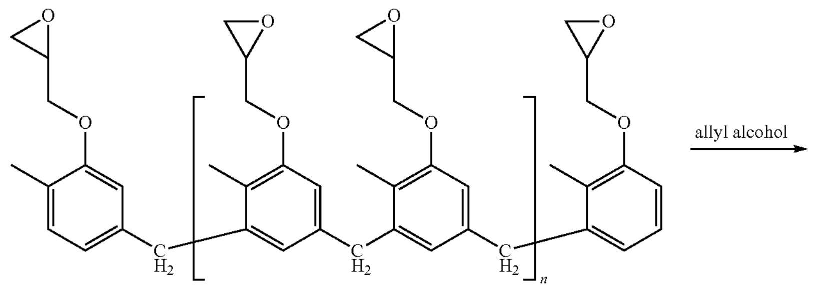

L-epoxy

-continued

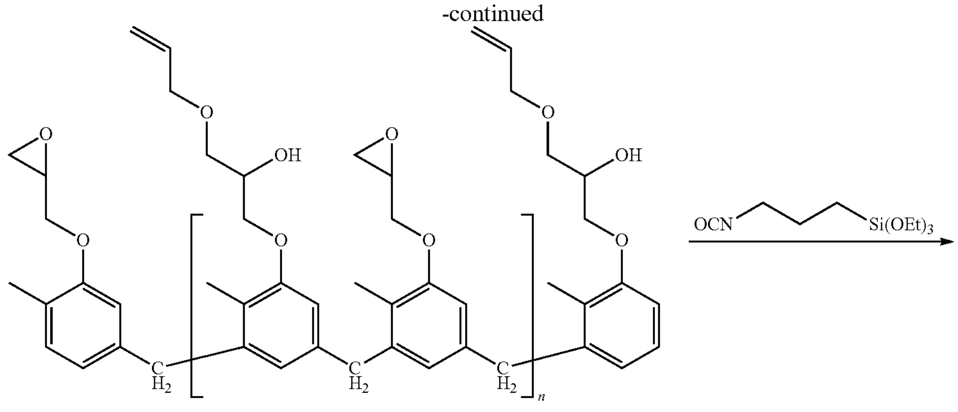

L-0(1)

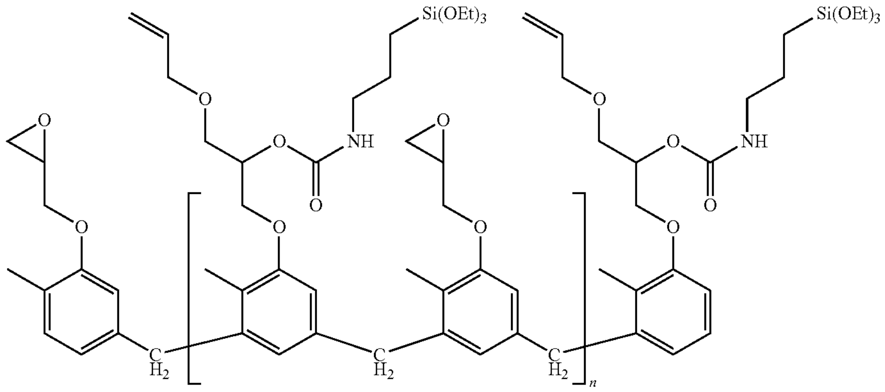

L-1(1)

Synthetic Examples 28 and 29: Synthesis of Cresol Novolac Epoxy Having Alkoxysilyl Group (Method 1)

The compound of Formula L-1 was synthesized by conducting the same first and second steps of the above Synthetic Example 27 except for changing the details as described in the following Tables L1 and L2. The ratios of epoxy group:alkoxysilyl group of Formula L-1 synthesized in Example 28 and Example 29 were 2:1 and 3:1, respectively.

TABLE L1

Amounts of reactants used in the first step for synthesizing Compound L-1

| Synthetic Example (1/2 step) | L-epoxy | Allyl alcohol | NaOH | $Et_4NBr$ | Time | Temperature | [epoxy group]:[alkenyl group] of Compound L-1 |
|---|---|---|---|---|---|---|---|
| 28 (L-1(2)) | 10 g | 25.38 g | 0.91 g | 1.10 g | 3 hr | 28° C. | 2:1 |
| 29 (L-1(3)) | 10 g | 25.38 g | 0.91 g | 1.10 g | 1 hr 30 min | 28° C. | 3:1 |

TABLE L2

| Amounts of reactants used in the second step for synthesizing Compound L-1 | | | | | |
|---|---|---|---|---|---|
| Synthetic Example (1/2 step) | L-0 | 3-(triethoxysilyl)propyl isocyanate | diisopropylamine | Time/Temperature | [epoxy group]:[alkenyl group] of Compound L-1 |
| 28 L-1(2) | 10 g | 13.00 g | 6.79 g | 30 hr/65° C. | 2:1 |
| 29 L-1(3) | 10 g | 15.08 g | 7.88 g | 30 hr/65° C. | 3:1 |

L-1(2) First Step NMR (Epoxy:Allyl=2:1)

$^1$H NMR (400 MHz, $CDCl_3$): δ=2.19-2.32 (m, 3.28H), 2.64-2.91 (m, 1.79H), 3.20-3.36 (m, 0.90H), 3.62-4.13 (m, 10.01H), 5.20-5.28 (m, 0.95H), 5.86-5.98 (m, 0.45H), 6.71-7.04 (m, 3.00H).

L-1(2) Second Step NMR (Epoxy:Alkoxysilyl=2:1)

$^1$H NMR (400 MHz, $CDCl_3$): δ=0.61 (t, J=8 Hz, 1.00H), 1.22 (t, J=8 Hz, 4.21H), 1.60 (t, J=8 Hz, 0.92H), 2.19-2.32 (m, 3.28H), 2.64-2.91 (m, 1.79H), 3.15 (t, J=8 Hz, 0.98H), 3.20-3.36 (m, 0.90H), 3.78-3.83 (m, 2.70H), 3.62-4.13 (m, 10.01H), 5.12-5.28 (m, 1.42H), 5.86-5.98 (m, 0.45H), 6.71-7.04 (m, 3.00H).

L-1(3) First Step NMR (Epoxy:Allyl 3:1)

$^1$H NMR (400 MHz, $CDCl_3$): δ=2.19-2.32 (m, 3.28H), 2.64-2.91 (m, 2.11H), 3.20-3.36 (m, 1.12H), 3.62-4.13 (m, 9.6H), 5.20-5.28 (m, 0.73H), 5.86-5.98 (m, 0.35H), 6.71-7.04 (m, 3.00H).

L-1(3) Second Step NMR (Epoxy:Alkoxysilyl 3:1)

$^1$H NMR (400 MHz, $CDCl_3$): δ=0.61 (t, J=8 Hz, 0.71H), 1.22 (t, J=8 Hz, 3.89H), 1.60 (t, J=8 Hz, 0.73H), 2.19-2.32 (m, 3.28H), 2.64-2.91 (m, 2.11H), 3.15 (t, J=8 Hz, 0.70H), 3.20-3.36 (m, 1.12H), 3.78-3.83 (m, 2.21H), 3.62-4.13 (m, 9.6H), 5.13-5.28 (m, 1.14H), 5.86-5.98 (m, 0.35H), 6.71-7.04 (m, 3.00H).

Synthetic Example 30. Synthesis of Cresol Novolac Epoxy Having Alkoxysilyl Group (Structure L-2) (Method 2)

To a two-necked flask, 10 g of Intermediate L-0 synthesized in the first step of the above Synthetic Example 25, 143 mg of $PtO_2$, 5.69 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy L-2 having an alkoxysilyl group, of which ratio of epoxy group:alkoxysilyl group was 1:1. NMR data are as follows.

$^1$H NMR (400 MHz, $CDCl_3$): δ=0.60 (t, J=4 Hz, 1.35H), 1.21 (t, J=8 Hz 6.39H), 1.57-1.61 (m, 1.36H), 2.19-2.32 (m, 3.28H), 2.64-2.91 (m, 1.21H), 3.20-3.36 (m, 2.16H), 3.62-4.13 (m, 13.94H), 6.71-7.04 (m, 3.00H).

The synthetic scheme of the above Synthetic Example 30 is as follows.

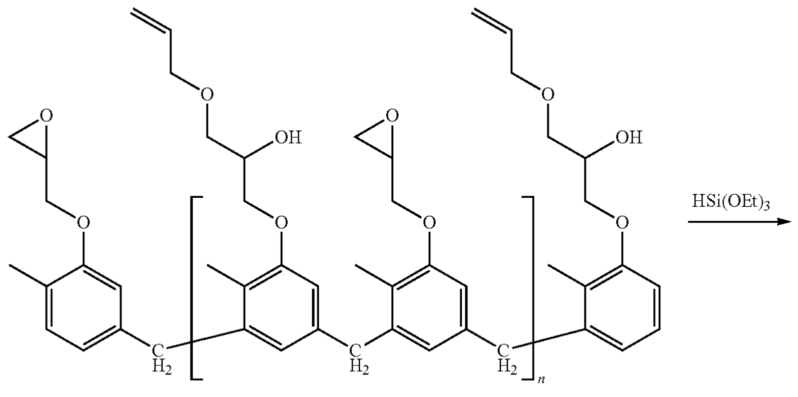

L-0(1)

-continued

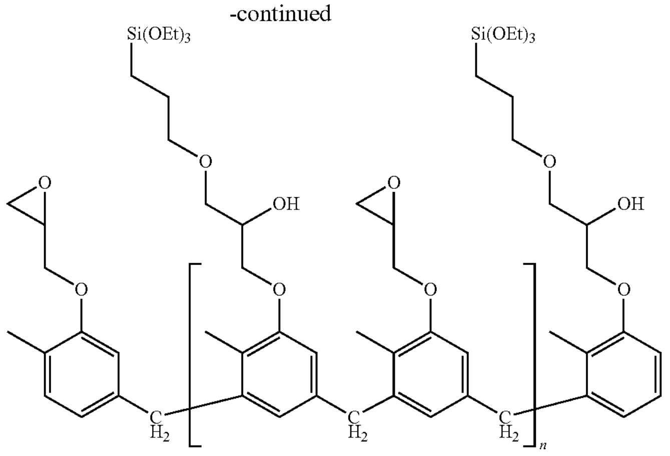

L-2

Synthetic Example 31. Synthesis of Cresol Novolac Epoxy Having Alkoxysilyl Group (Structure L-3) (Method 3)

10 g of Epoxy L-1(1) having an alkoxysilyl group obtained in the above Synthetic Example 25, 80 mg of $PtO_2$, 3.20 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce the final target material of Epoxy L-3 having an alkoxysilyl group, of which ratio of epoxy group:alkoxysilyl group was 1:2. NMR data are as follows.

$^1H$ NMR (400 MHz, $CDCl_3$): δ=0.63 (t, J=8 Hz, 2.62H), 1.26 (t, J=8 Hz, 11.97H), 1.60-1.63 (m, 2.62H), 2.17-2.32 (m, 3.28H), 2.64-2.91 (m, 2.58H), 3.15-3.36 (m, 1.97H), 3.62-4.13 (m, 18.72H), 6.71-7.04 (m, 3.00H).

The synthetic scheme of the above Synthetic Example 31 is as follows.

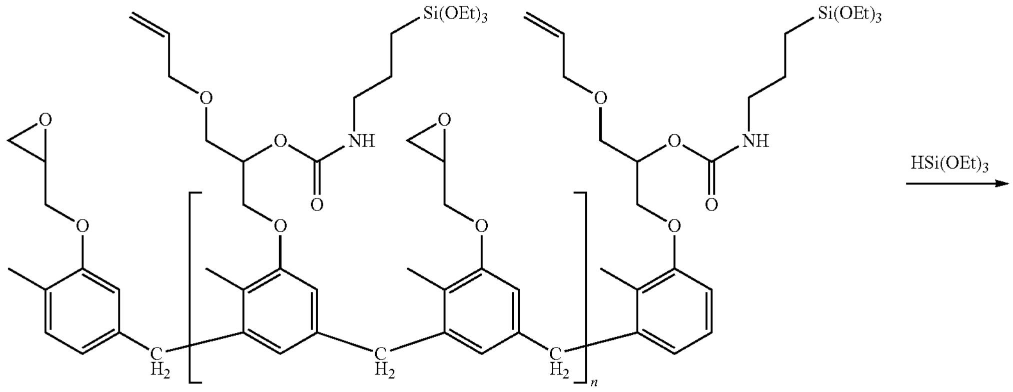

L-1(1)

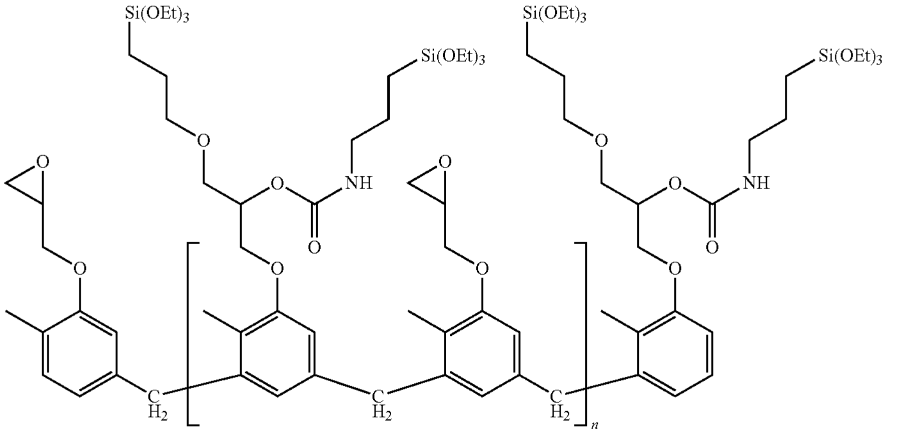

L-3

Synthetic Example 32. Synthesis of Cresol Novolac Epoxy Having Alkoxysilyl Group (Structure L-3) (Method 4)

10 g of Intermediate L-2 synthesized in the Synthetic Example 30 and acetonitrile were added and stirred. Then, 6.57 g of 3-(triethoxysilyl)propyl isocyanate and 3.43 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin L-3, in which the ratio of epoxy group:alkoxysilyl group was 1:2, was produced. NMR data are as follows.

$^1$H NMR (400 MHz, $CDCl_3$): δ=0.63 (t, J=8 Hz, 2.62H), 1.26 (t, J=8 Hz, 11.97H), 1.60-1.63 (m, 2.62H), 2.17-2.32 (m, 3.28H), 2.64-2.91 (m, 2.58H), 3.15-3.36 (m, 1.97H), 3.62-4.13 (m, 18.72H), 6.71-7.04 (m, 3.00H).

The synthetic scheme of the above Synthetic Example 32 is as follows.

Synthetic Example 33. Synthesis of Bisphenol Novolac Epoxy Having Alkoxysilyl Group (Structure M-1) (Method 1)

(1) First Step

To a two-necked flask, 10 g of bisphenol A novolac epoxy (DIC, LF, Structure M-epoxy) was added, and 18 ml of THF and acetonitrile were respectively added to dissolve an epoxy specimen. Then, 0.74 g of NaOH, 0.90 g of $Et_4NBr$ and 20.63 g of allyl alcohol were added thereto, followed by stirring at room temperature for 6 hours. 10 ml of a saturated $NH_4Cl$ solution was added thereto to terminate the reaction. Thereafter, solvents were partially removed using a rotary evaporator, and the residue was worked-up using 150 ml of ethyl acetate and 50 ml of tap water three times. An organic layer was separated, residual $H_2O$ was removed with $MgSO_4$, and the organic layer was completely dried using a rotary evaporator and a vacuum pump to produce Intermediate M-0 having the ratio of epoxy group:allyl group of 1:1.

$^1$H NMR (400 MHz, $CDCl_3$): δ=1.62 (m, 31.92H), 2.58-2.77 (m, 10.99H), 3.28-3.33 (m, 4.67H), 3.67-4.18 (m, 49.42H), 4.47-4.51 (m, 11.90H), 5.22-5.44 (m, 10.74H), 6.06-6.15 (m, 5.12H), 6.65-6.72 (m, 20.21H), 7.26-7.31 (m, 12.68H).

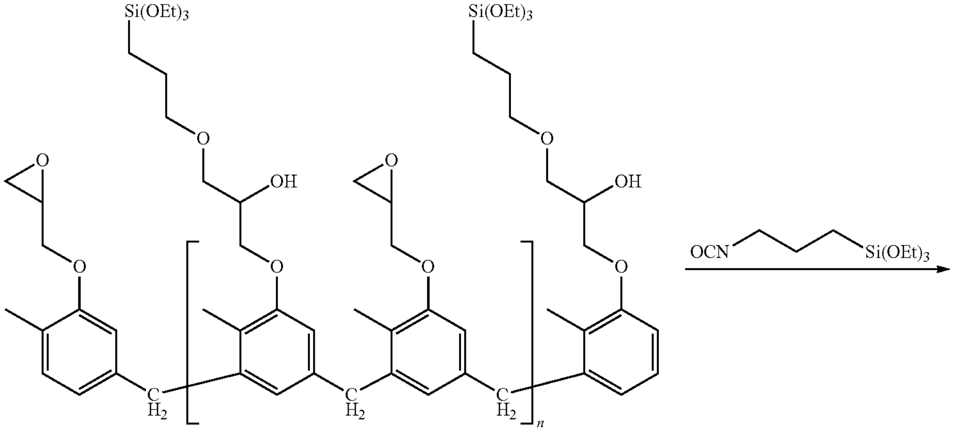

L-2

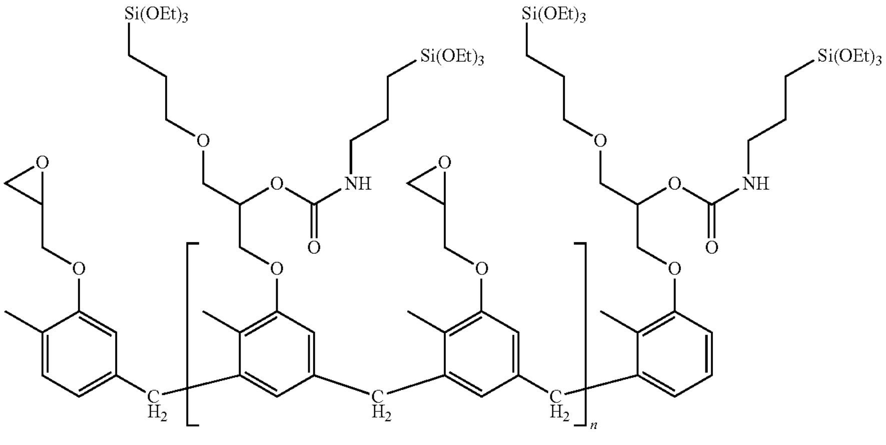

L-3

(2) Second Step

To a two-necked flask, 10 g of Intermediate M-0 synthesized in the first step and acetonitrile were added and stirred. Then, 7.72 g of 3-(triethoxysilyl)propyl isocyanate and 4.03 g of diisopropylethylamine were added thereto, followed by performing a reaction at 65° C. for 30 hours. After completing the reaction, the reaction mixture was cooled to room temperature and worked-up using 100 ml of ethyl acetate and 40 ml of a saturated $NH_4Cl$ solution. An organic layer was separated, and $MgSO_4$ was added thereto to remove residual $H_2O$. Solvents were removed using a rotary evaporator and separated using a hexane slurry. After removing a supernatant hexane layer and completely drying using a vacuum pump, Epoxy resin M-1, in which the ratio of epoxy group:alkoxysilyl group was 1:1, was produced. NMR data are as follows.

$^1H$ NMR (400 MHz, $CDCl_3$): δ=0.60 (t, J=8 Hz, 10.62H), 1.22 (t, J=8 Hz, 47.08H), 1.60-1.63 (m, 43.54H), 2.58-2.77 (m, 10.99H), 3.15 (t, J=8 Hz, 10.82H), 3.28-3.33 (m, 4.67H), 3.67-4.18 (m, 80.13H), 4.47-4.51 (m, 11.90H), 5.13-5.42 (m, 15.88H), 6.06-6.15 (m, 5.12H), 6.65-6.72 (m, 20.21H), 7.26-7.31 (m, 12.68H).

The synthetic scheme of the above Synthetic Example 33 is as follows.

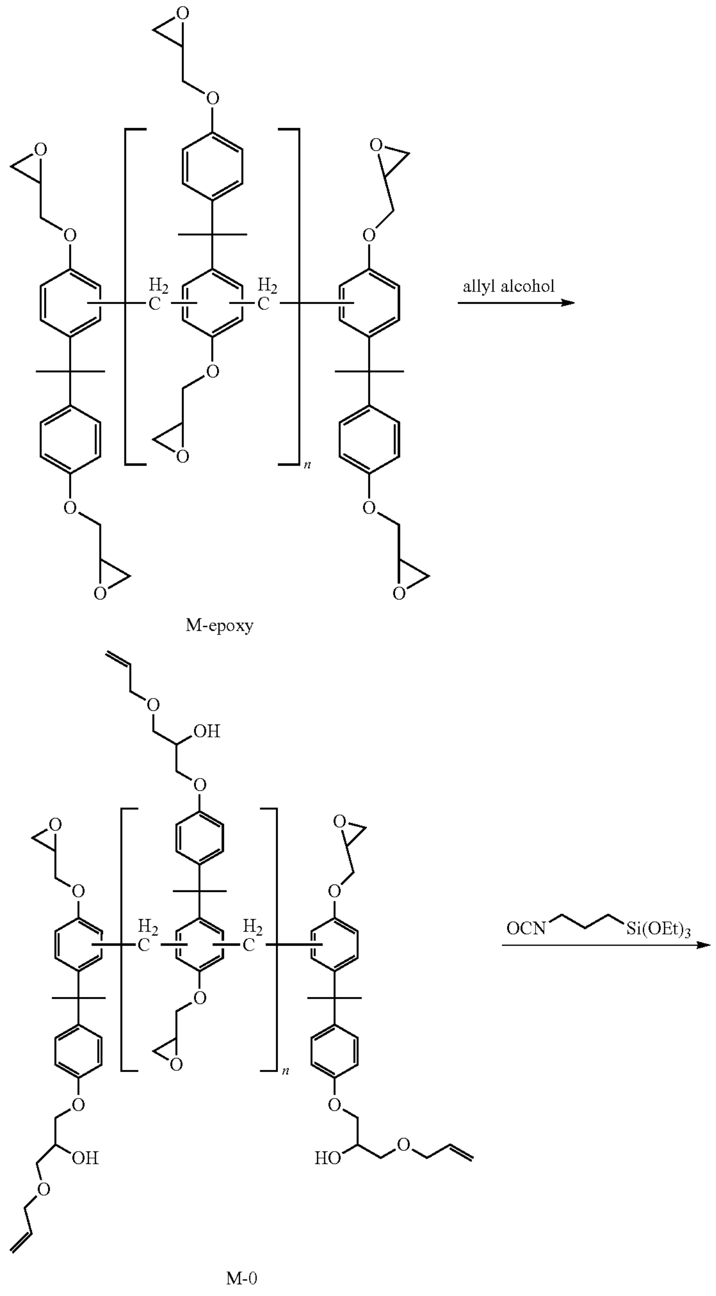

-continued

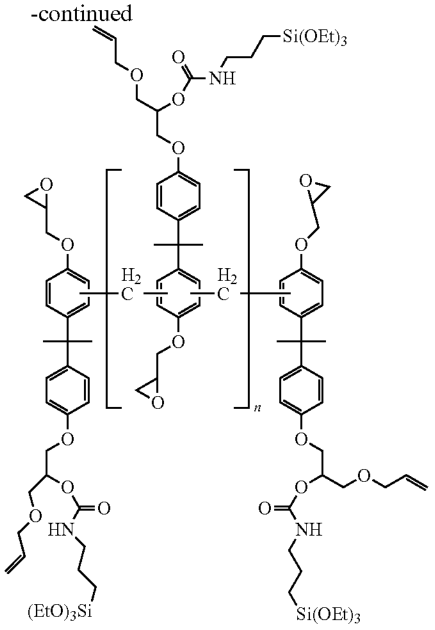

M-1

Synthetic Example 34. Synthesis of Bisphenyl Novolac Epoxy Having Alkoxysilyl Group (Structure M-2) (Method 2)

To a flask, 10 g of Intermediate M-0 obtained in the first step of the above Synthetic Example 33, 111 mg of $PtO_2$, 4.41 g of triethoxysilane and 150 ml of toluene were added and stirred at room temperature for 5 minutes. The temperature was elevated to 80° C., and the reaction mixture was heated and stirred for 24 hours. After completing the reaction, the temperature was decreased to room temperature, and inorganic materials were removed using a celite filter. Through evaporation, toluene was removed, and using a vacuum pump, the product was completely dried to produce Epoxy M-2 having an alkoxysilyl group, of which ratio of epoxy group:alkoxysilyl group was 1:1. NMR data are as follows.

$^1$H NMR (400 MHz, $CDCl_3$): δ=0.62 (t, J=4 Hz, 10.66H), 1.23 (t, J=8 Hz 47.05H), 1.55-1.63 (m, 42.46H), 2.58-2.76 (m, 10.99H), 3.24-3.33 (m, 15.67H), 3.67-4.18 (m, 71.78H), 4.46-4.51 (m, 11.90H), 6.66-6.72 (m, 20.21H), 7.25-7.31 (m, 12.68H).

The synthetic scheme of the above Synthetic Example 34 is as follows.

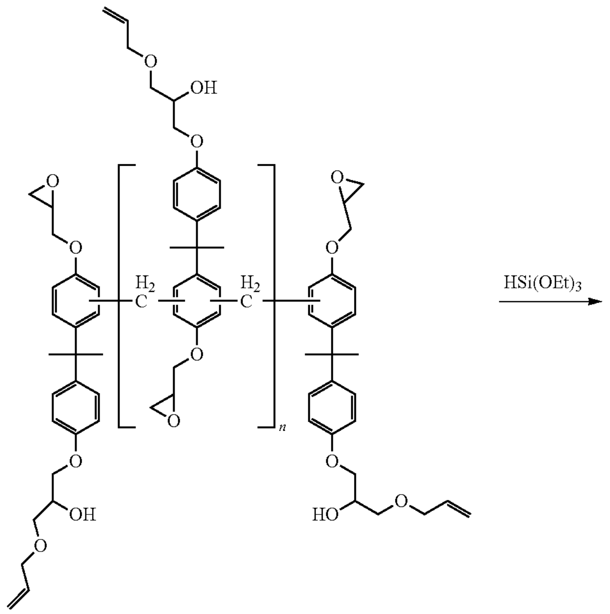

M-0

-continued

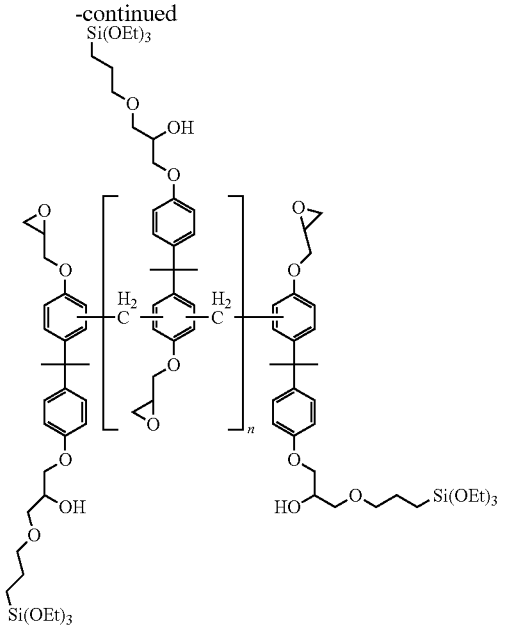

M-2

Synthetic Example 35. Synthesis of Naphthalene Novolac Epoxy Having Alkoxysilyl Group (Structure N-1) (Method 1) (Expected Example 3)

(1) First Step

To a two-necked flask, 10 g of naphthalene novolac epoxy (Structure N-epoxy) is added, and 16 ml of THF and acetonitrile are, respectively added thereto to dissolve an epoxy specimen. Then, 0.66 g of NaOH, 0.80 g of $Et_4NBr$ and 18.52 g of allyl alcohol are added thereto, followed by stirring at room temperature for 6 hours. 10 ml of a saturated $NH_4Cl$ solution is added thereto to terminate the reaction. Thereafter, solvents are partially removed using a rotary evaporator, and the residue is worked-up using 150 ml of ethyl acetate and 50 ml of tap water three times. An organic layer is separated, residual $H_2O$ is removed with $MgSO_4$, and the organic layer is completely dried using a rotary evaporator and a vacuum pump to produce Intermediate N-0 having the ratio of epoxy group:allyl group of 1:1.

(2) Second Step

To a two-necked flask, 10 g of Intermediate N-0 synthesized in the first step and acetonitrile are added and stirred. Then, 7.03 g of 3-(triethoxysilyl)propyl isocyanate and 3.68 g of diisopropylethylamine are added thereto, followed by performing a reaction at 65° C. for 30 hours. After completing the reaction, the reaction mixture is cooled to room temperature and worked-up using 100 ml of ethyl acetate and 40 ml of a saturated $NH_4Cl$ solution. An organic layer is separated, and $MgSO_4$ is added thereto to remove residual $H_2O$. Solvents are removed using a rotary evaporator and separated using a hexane slurry. After removing a supernatant hexane layer and completely drying using a vacuum pump, Epoxy resin N-1, in which the ratio of epoxy group: alkoxysilyl group is 1:1, is produced.

The synthetic scheme of the above Synthetic Example 35 is as follows.

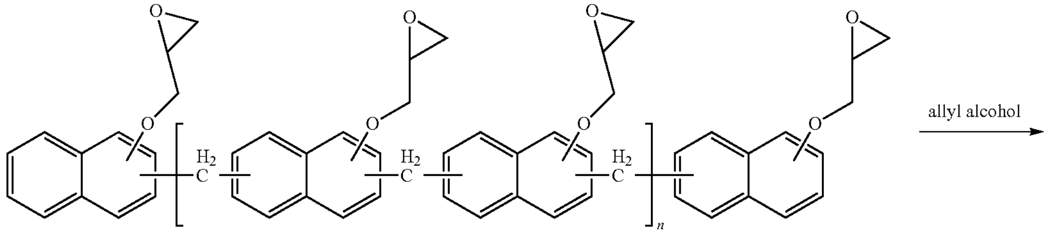

N-epoxy

-continued

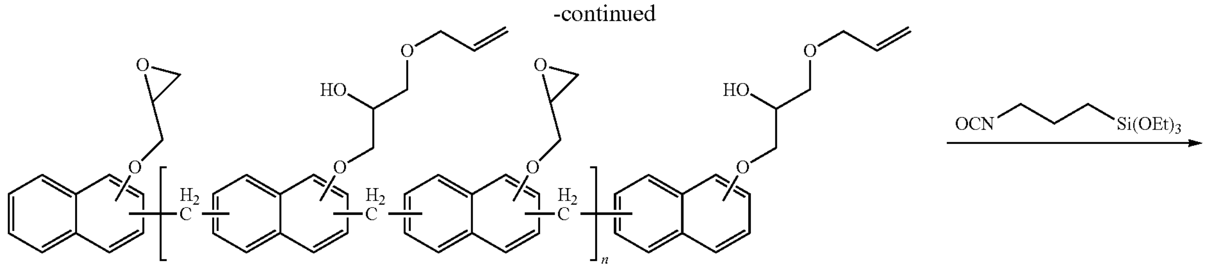

N-0

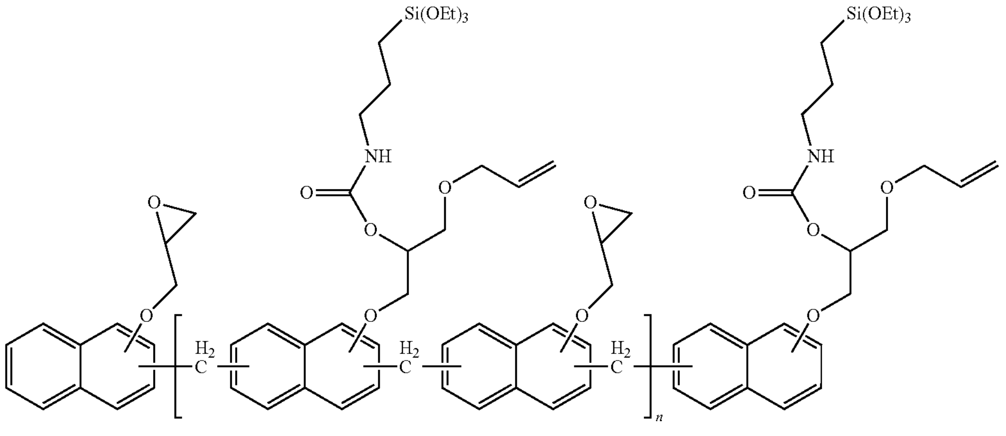

N-1

Synthetic Example 36. Synthesis of Naphthalene Novolac Epoxy Having Alkoxysilyl Group (Structure N-2) (Method 2) (Expected Example 4)

To a flask, 10 g of Intermediate N-0 obtained in the first step of the above Expected Example 3, 101 mg of $PtO_2$, 4.01 g of triethoxysilane and 150 ml of toluene are added and stirred at room temperature for 5 minutes. The temperature is elevated to 80° C., and the reaction mixture is heated and stirred for 24 hours. After completing the reaction, the temperature is decreased to room temperature, and inorganic materials are removed using a celite filter. Through evaporation, toluene is removed, and using a vacuum pump, the product is completely dried to produce Epoxy N-2 having an alkoxysilyl group, of which ratio of epoxy group:alkoxysilyl group is 1:1.

The synthetic scheme of the above Synthetic Example 36 is as follows.

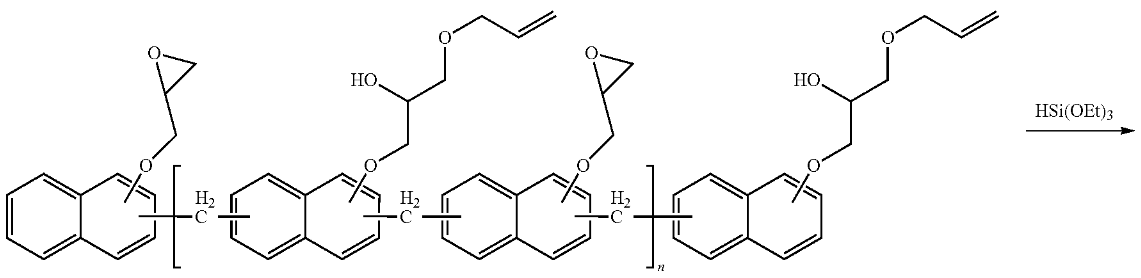

N-0

-continued

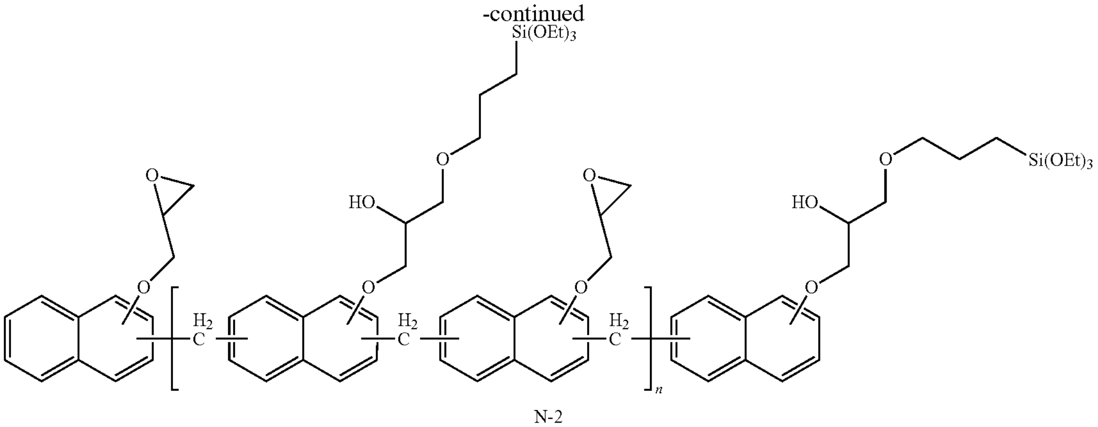

N-2

Reference Example 1. Synthesis of Starting Material of Synthetic Example 15

(1) First Step: Synthesis of 1,5-bis(allyloxy)naphthalene

To a 1,000 ml, two-necked flask equipped with a refluxing condenser, 20.0 g of 1,5-dihydroxynaphthalene (Sigma Aldrich), 27.0 ml of allyl bromide (Sigma Aldrich), 103.61 g of $K_2CO_3$ and 500 ml of acetone were added, followed by mixing at room temperature. A homogeneously mixed solution was refluxed with the refluxing temperature of 80° C. overnight. After completing the reaction, reaction mixture was cooled to room temperature, filtered with celite and evaporated to obtain a crude product. A target component in the crude product was extracted with ethyl acetate, washed three times with water, and dried with $MgSO_4$. $MgSO_4$ was removed by filtering, and solvents were removed using an evaporator to produce 1,5-bis(allyloxy)naphthalene as Intermediate 11. NMR data are as follows.

$^1$H NMR (400 MHz, $CDCl_3$): δ=4.70 (dt, J=5.2 Hz, 1.6 Hz, 4H), 5.32-5.34 (m, 2H), 5.49-5.54 (m, 2H), 6.12-6.21 (m, 2H), 6.84 (d, J=8.0 Hz, 2H), 7.35 (dd, J=7.6, 0.8 Hz, 2H), 7.89 (d, J=8.8 Hz, 2H).

(2) Second Step: Synthesis of 2,6-diallylnaphthalene-1,5-diol

To a 1,000 ml, two-necked flask equipped with a refluxing condenser, 20.0 g of Intermediate 11 obtained in the first step and 100 ml of 1,2-dichlorobenzene (Sigma Aldrich) were added, followed by mixing well at room temperature. A homogeneous solution was refluxed with the refluxing temperature of 190° C. for 8 hours. After completing the reaction, the reaction mixture was cooled to room temperature, and solvents were removed by a vacuum oven to produce 2,6-diallylnaphthalene-1,5-diol as Intermediate 12. NMR data of Intermediate 12 thus obtained are as follows.

$^1$H NMR (400 MHz, $CDCl_3$): δ=3.57 (dt, J=6.4 Hz, 1.6 Hz, 4H), 5.21-5.27 (m, 4H), 5.50 (s, 2H), 6.02-6.12 (m, 2H), 7.21 (d, J=8.4 Hz, 2H), 7.70 (d, J=8.4 Hz, 2H).

(3) Third Step: Synthesis of 2,2'-(2,6-diallylnaphthalene-1,5-diyl)bis(oxy)bis(methylene)dioxirane To a 1,000 ml, two-necked flask equipped with a refluxing condenser, 20.0 g of Intermediate 12 obtained in the second step, 65.07 ml of epichlorohydrin (Sigma Aldrich), 74.15 g of $K_2CO_3$ and 300 ml of acetonitrile were added, followed by mixing at room temperature. Then, the temperature was elevated, and a reaction was performed at 80° C. overnight. After completing the reaction, the reaction mixture cooled to room temperature was filtered with celite, and an organic solution was evaporated to produce Intermediate 13. NMR data of Intermediate 13 are as follows.

$^1$H NMR (400 MHz, $CDCl_3$): δ=2.77 (dd, J=2.6 Hz, 2H), 2.93 (dd, J=4.4 Hz, 2H), 3.44-3.48 (m, 2H), 3.61 (d, J=6.4 Hz, 4H), 3.91 (dd, J=6.0 Hz, 2H), 4.24 (dd, J=2.8 Hz, 2H), 5.07-5.12 (m, 4H), 5.98-6.08 (m, 2H), 7.34 (d, J=8.4 Hz, 2H), 7.88 (d, J=8.4 Hz, 2H).

(4) Fourth Step: Synthesis of 2,2'-(1,5-bis(oxiran-2-ylmethoxy)naphthalene-2,6-diyl)bis(methylene)dioxirane To a 500 ml flask, 10.0 g of 2,2'-(2,6-diallylnaphthalene-1,5-diyl)bis(oxy)bis(methylene)dioxirane, 19.08 g of 77 mol % 3-chloroperoxybenzoic acid and 200 ml of methylene chloride were added and stirred at room temperature for 2 days. Then, the reactant was worked-up with an aqueous sodium thiosulfate solution and extracted with ethyl acetate. Thereafter, the reactant was washed with a 1 N sodium hydroxide aqueous solution and brine, dried with MgSO4, and filtered using a filter. Solvents were removed, and the residue was separated by a column to produce 2,2'-(1,5-bis(oxiran-2-ylmethoxy)naphthalene-2,6-diyl)bis(methylene)dioxirane. NMR data of the product are as follows.

$^1$H NMR (400 MHz, $CDCl_3$): δ=2.53-2.57 (m, 2H), 2.73-2.81 (m, 6H), 2.89-2.92 (m, 4H), 3.16-3.18 (m, 2H), 3.35-3.37 (m, 2H), 3.90-3.97 (m, 2H), 4.22-4.25 (m, 2H), 7.28 (d, J=8.5 Hz, 2H), 7.75 (d, J=8.5 Hz, 2H).

The synthetic mechanism of Reference Example 1 is as follows.

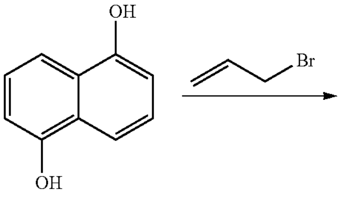

-continued

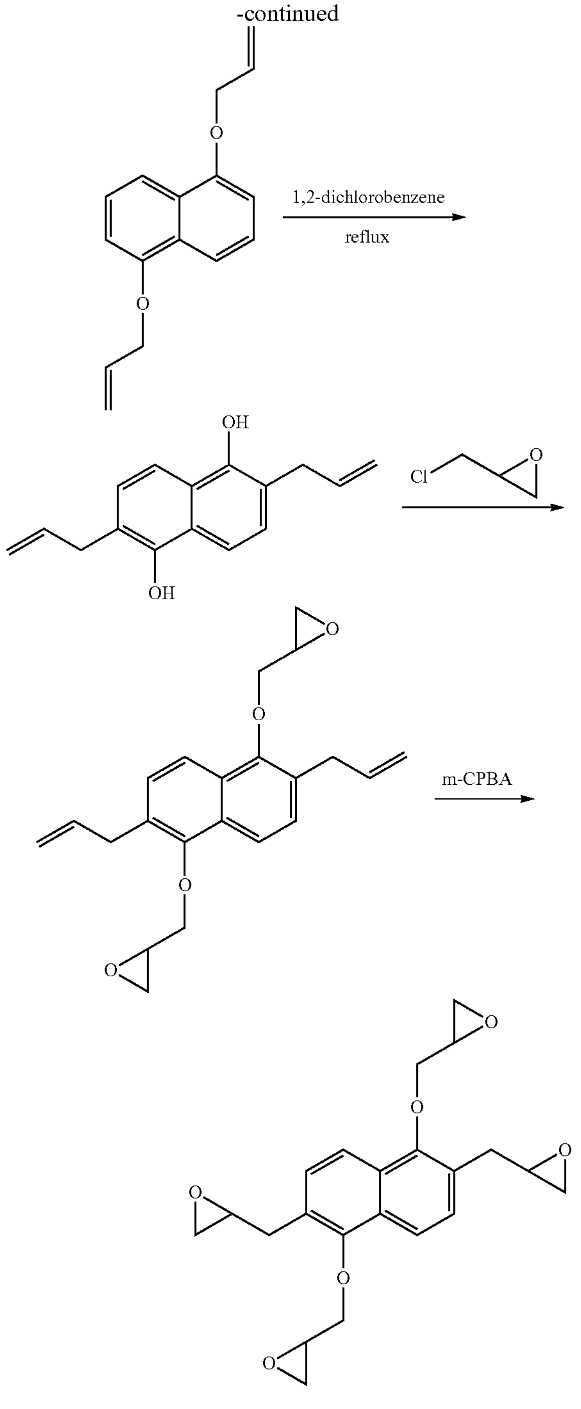

Reference Example 2. Synthesis of Starting Material of Synthetic Example 17

(1) First Step: Synthesis of 4,4'-bis(allylyloxy)biphenyl

To a 1,000 ml, two-necked flask equipped with a refluxing condenser, 10.0 g of biphenyl-4,4'-diol (Sigma Aldrich), 11.61 ml of allyl bromide (Sigma Aldrich), 44.56 g of $K_2CO_3$ and 500 ml of acetone were added and mixed at room temperature. A homogeneously well mixed solution was refluxed with the refluxing temperature of 80° C. overnight. After completing the reaction, the reaction mixture was cooled to room temperature, filtered with celite and evaporated to obtain a crude product. A target component was extracted with ethyl acetate from the crude product, washed three times with water, and dried with $MgSO_4$. $MgSO_4$ was removed by filtering, and solvents were removed using an evaporator to produce 4,4'-bis(allylyloxy)biphenyl as Intermediate 21. NMR data are as follows.

$^1$H NMR (400 MHz, $CDCl_3$): δ=4.56 (dt, J=5.2 Hz, 1.6 Hz, 4H), 5.30-5.33 (m, 2H), 5.41-5.44 (m, 2H), 6.03-6.12 (m, 2H), 6.96 (td, J=3.0, 2.2, 8.8 Hz, 4H), 7.46 (td, J=3.0, 2.2, 8.8 Hz, 4H).

(2) Second Step: Synthesis of 3,3'-diallylbiphenyl-4,4'-diol

To a 1,000 ml, two-necked flask equipped with a refluxing condenser, 10.0 g of Intermediate 21 obtained in the first step and 100 ml of 1,2-dichlorobenzene (Sigma Aldrich) were added and well mixed at room temperature. A homogeneous solution was refluxed with the refluxing temperature of 190° C. for 72 hours. After completing the reaction, the reaction mixture was cooled to room temperature, and solvents were removed by a vacuum oven to produce 3,3'-diallylbiphenyl-4,4'-diol as Intermediate 22. NMR data are as follows.

$^1$H NMR (400 MHz, $CDCl_3$): δ=3.35 (d, J=6.4 Hz, 4H), 5.14-5.25 (m, 6H), 6.00-6.10 (m, 2H), 6.84 (dd, J=2.0 Hz, 7.2 Hz, 2H), 7.29 (dd, J=10.6 Hz, 4H).

(3) Third Step: Synthesis of 2,2'-(3,3'-diallylbiphenyl-4,4'-diyl)bis(oxy)bis(methylene)dioxirane To a 1,000 ml, two-necked flask equipped with a refluxing condenser, 10.0 g of Intermediate 22 obtained in the second step, 30.38 ml of epichlorohydrin (Sigma Aldrich), 35.13 g of $K_2CO_3$ and 300 ml of acetonitrile were added and mixed at room temperature. Then, the temperature was elevated, and a reaction was performed at 80° C. overnight. After completing the reaction, the reaction mixture was cooled to room temperature and filtered with celite, and organic solution was evaporated to produce Intermediate 23. NMR data are as follows.

$^1$H NMR (400 MHz, $CDCl_3$): δ=2.75 (dd, J=2.6 Hz, 2H), 2.87 (dd, J=4.2 Hz, 2H), 3.11-3.35 (m, 6H), 3.96 (dd, J=5.4 Hz, 2H), 4.25 (dd, J=3.2 Hz, 2H), 5.03-5.13 (m, 4H), 5.93-6.03 (m, 2H), 6.81 (d, J=7.2 Hz, 2H), 7.34-7.42 (m, 4H).

(4) Fourth Step: Synthesis of 2,2'-(4,4'-bis(oxirane-2-ylmethoxy)biphenyl-3,3'-diyl)bis(methylene)dioxirane To a 500 ml flask, 10.0 g of 2,2'-(3,3'-diallylbiphenyl-4,4'-diyl)bis(oxy)bis(methylene)dioxirane, 17.77 g of 77 mol % 3-chloroperoxybenzoic acid and 200 ml of methylene chloride were added and stirred at room temperature for 2 days. Then, the reactant was worked-up with an aqueous sodium thiosulfate solution and extracted with ethyl acetate. Thereafter, the reactant was washed with a 1 N sodium hydroxide aqueous solution and brine, dried with $MgSO_4$, and filtered using a filter. Solvents were removed, and the residue was separated by a column to produce 2,2'-(4,4'-bis(oxiran-2-ylmethoxy)biphenyl-3,3'-diyl)bis(methylene)dioxirane. NMR data of the final product are as follows.

$^1$H NMR (400 MHz, $CDCl_3$): δ=2.53-2.57 (m, 2H), 2.73-2.81 (m, 6H), 2.89-2.92 (m, 4H), 3.16-3.18 (m, 2H), 3.35-3.37 (m, 2H), 3.90-3.97 (m, 2H), 4.22-4.25 (m, 2H), 6.73-6.75 (m, 2H), 7.03-7.05 (m, 4H).

The synthetic mechanism of Reference Example 2 is as follows.

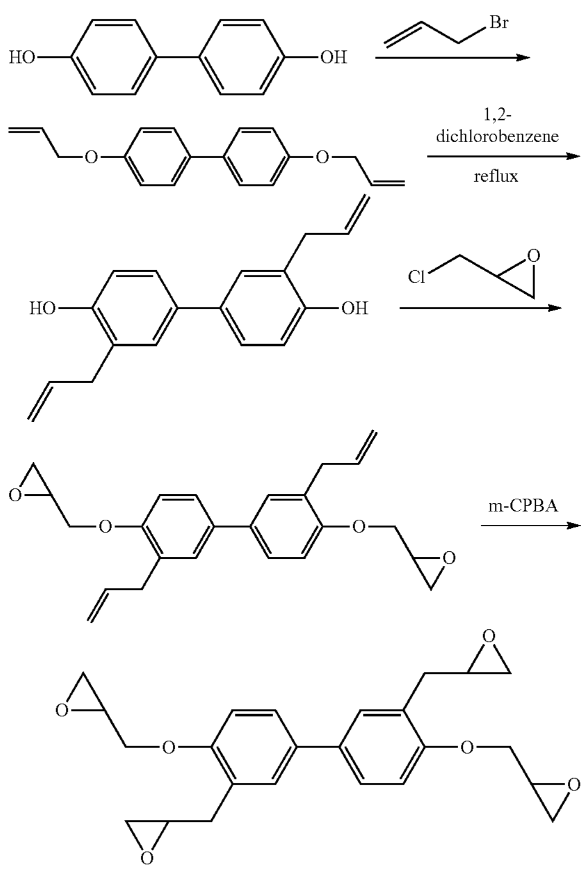

Reference Example 3. Synthesis of Starting Material of Synthetic Example 19

(1) First Step: Synthesis of 9,9-bis(4-allyloxy)phenyl-9H-fluorene

To a 1,000 ml, two-necked flask equipped with a refluxing condenser, 10.0 g of 4,4'-(9H-fluorene-9,9-diyl)diphenol (Sigma Aldrich), 6.17 ml of allyl bromide (Sigma Aldrich), 23.68 g of $K_2CO_3$ and 500 ml of acetone were added and mixed at room temperature. A homogeneously well mixed solution was refluxed with the refluxing temperature of 80° C. overnight. After completing the reaction, the reaction mixture was cooled to room temperature, filtered with celite and evaporated to obtain a crude product. A target component was extracted with ethyl acetate from the crude product, washed three times with water and dried with $MgSO_4$. $MgSO_4$ was removed by filtering, and solvents were removed using an evaporator to produce 9,9-bis(4-allyloxy)phenyl)-9H-fluorene as Intermediate 31. NMR data are as follows.

$^1$H NMR (400 MHz, $CDCl_3$): δ=4.46 (td, J=1.4, 2.4 Hz, 4H), 5.25 (qd, J=1.6, 1.2, 10.4 Hz, 2H), 5.35-5.38 (m, 2H), 5.97-6.06 (m, 2H), 6.75 (td, J=3.2, 2.0, 8.8 Hz, 4H), 7.10 (td, J=3.2, 2.0, 8.8 Hz, 4H), 7.23-7.39 (m, 6H), 7.70-7.79 (m, 2H).

(2) Second Step: Synthesis of 4,4'-(9H-fluorene-9,9-diyl)bis(2-allylphenol)

To a 1,000 ml, two-necked flask equipped with a refluxing condenser, 10.0 g of Intermediate 31 obtained in the first step and 100 ml of 1,2-dichlorobenzene (Sigma Aldrich) were added and well mixed at room temperature. A homogeneous solution was refluxed with the refluxing temperature of 190° C. for 96 hours. After completing the reaction, the reaction mixture was cooled to room temperature, and solvents were removed by a vacuum oven to produce 4,4'-(9H-fluorene-diyl)bis(2-allylphenol) as Intermediate 32. NMR data are as follows.

$^1$H NMR (400 MHz, $CDCl_3$): δ=3.28 (d, J=6.0 Hz, 4H), 5.04-5.09 (m, 4H), 5.21 (s, 2H), 5.87-5.97 (m, 2H), 6.62 (d, J=8.4 Hz, 2H), 6.88 (dd, J=2.4, 6.0 Hz, 2H), 6.96 (d, J=2.4 Hz, 2H), 7.22-7.36 (m, 6H), 7.74 (d, J=7.2 Hz, 2H).

(3) Third Step: Synthesis of 2,2'-(4,4'-(9H-fluorene-9,9-diyl)bis(2-allyl-4,1-phenylene)bis(oxy)bis(methylene)dioxirane To a 1,000 ml, two-necked flask equipped with a refluxing condenser, 10.0 g of Intermediate 32 obtained in the second step, 18.16 ml of epichlorohydrin (Sigma Aldrich), 21.00 g of $K_2CO_3$ and 300 ml of acetonitrile were added and mixed at room temperature. Then, the temperature was elevated, and a reaction was performed at 80° C. overnight. After completing the reaction, the reaction mixture was cooled to room temperature and filtered with celite, and organic solution was evaporated to produce Intermediate 33. NMR data are as follows.

$^1$H NMR (400 MHz, $CDCl_3$): δ=2.75 (dd, J=2.6 Hz, 2H), 2.87 (dd, J=4.2 Hz, 2H), 3.11-3.35 (m, 6H), 3.96 (dd, J=5.4 Hz, 2H), 4.12 (dd, J=3.2 Hz, 2H), 4.97-5.03 (m, 4H), 5.93-6.03 (m, 2H), 6.69 (d, J=8.4 Hz, 2H), 6.80-6.83 (m, 2H), 7.05 (s, 2H), 7.22-7.36 (m, 6H), 7.74 (d, J=7.2 Hz, 2H).

(4) Fourth Step: Synthesis of 2,2'-(5,5'-(9H-fluorene-9,9-diyl)bis(2-(oxiran-2-ylmethoxy)-5,1-phenylene))bis(methylene)-dioxirane To a 500 ml flask, 10.0 g of 2,2'-(4,4'-(9H-fluorene-9,9-diyl)bis(2-allyl-4,1-phenylene))bis(oxy)bis(methylene)dioxirane, 12.39 g of 77 mol % 3-chloroperoxybenzoic acid and 200 ml of methylene chloride were added and stirred at room temperature for 2 days. Then, the reactant was worked-up with an aqueous sodium thiosulfate solution and extracted with ethyl acetate. Thereafter, the reactant was washed with a 1 N sodium hydroxide aqueous solution and brine, dried with $MgSO_4$, and filtered using a filter. Solvents were removed, and the residue was separated by a column to produce 2,2'-(5,5'-(9H-fluorene-9,9-diyl)bis(2-(oxiran-2-ylmethoxy)-5,1-phenylene))bis(methylene)-dioxirane. NMR data of the final product are as follows.

$^1$H NMR (400 MHz, $CDCl_3$): δ=2.53-2.57 (m, 2H), 2.73-2.81 (m, 6H), 2.89-2.92 (m, 4H), 3.16-3.18 (m, 2H), 3.35-3.37 (m, 2H), 3.90-3.97 (m, 2H), 4.22-4.25 (m, 2H), 6.73-6.75 (m, 2H), 7.03-7.05 (m, 4H), 7.22-7.36 (m, 6H), 7.74 (d, J=7.2 Hz, 2H).

The synthetic mechanism of Reference Example 3 is as follows.

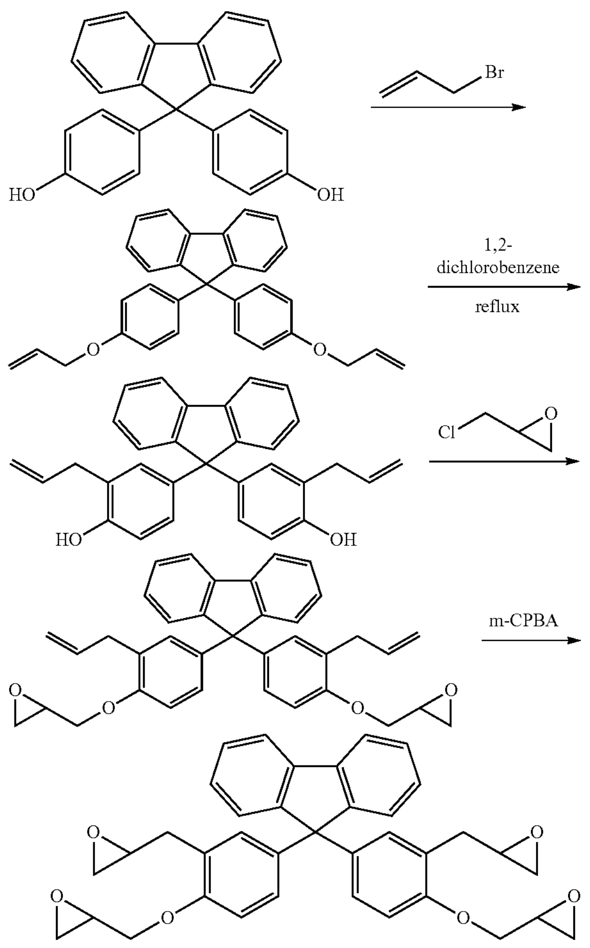

Evaluation of Physical Properties: Manufacturing of Cured Product and Evaluation of Heat Resistance 1. Manufacturing of Epoxy Composite (1) Manufacturing of Epoxy Glass Fiber Composite (Cured Product)

An epoxy compound, a curing agent, a curing catalyst and a reaction catalyst were dissolved in methyl ethyl ketone according to the formulation illustrated in Table 1 so that a solid content was 40 wt % and mixed to obtain a homogeneous solution. A glass fiber (a glass fiber texture of Nittobo Co, E-glass 2116 or T-glass 2116) was impregnated with the mixture thus obtained to manufacture a glass fiber composite including an epoxy compound. Then, the composite was placed in a vacuum oven heated to 100° C. to remove solvents, and was cured in a preheated hot press at 120° C. for 2 hours, at 180° C. for 2 hours and >200° C. for 2 hours to manufacture a glass fiber composite film (4 mm×16 mm×0.1 mm) While manufacturing the composite film, the amount of the resin of the composite film was controlled according to the pressure of a press and the viscosity of the resin. The amount of resin in the composite film is illustrated in the following Table 1.

In addition, when a composition for a glass fiber composite includes silica, an epoxy compound, and a silica slurry (70 wt % of solid content, 2-methoxyethanol solvent, 1 μm of silica average size) were dissolved in methyl ethyl ketone according to the formulation illustrated in the following Table 1 so that a solid content was 40 wt %. The mixture thus obtained was mixed in a rate of 1,500 rpm for 1 hour, and a curing agent was added, followed by further mixing for 50 minutes. Finally, a curing catalyst and a reaction catalyst were added and mixed for 10 minutes further to obtain an epoxy mixture. A glass fiber composite was manufactured by immersing a glass fiber (glass fiber fabric by Nittobo Co., E-glass 2116) with the epoxy mixture. Then, the same curing process was performed under the same conditions as described above to manufacture a composite film.

(2) Manufacturing of Epoxy Filler Composite (Cured Product)

Epoxy compound except for the curing agent, the curing catalyst and the reaction catalyst, a silica slurry (70 wt % of solid content, 2-methoxyethanol solvent, 1 μm of silica average size) and an optional thermoplastic polymer were dissolved in methyl ethyl ketone according to the formulation illustrated in the following Table 2 so that a solid content was 40 wt %. The mixture thus obtained was mixed in a rate of 1,500 rpm for 1 hour, and the curing agent was added, followed by further mixing for 50 minutes. Finally, the curing catalyst and the reaction catalyst were added and mixed for 10 minutes further to obtain an epoxy mixture. Then, the mixture was placed in a vacuum oven heated to 100° C. to remove solvents, and was cured in a hot press preheated to 120° C., at 120° C. for 2 hours, at 180° C. for 2 hours and at >200° C. for 2 hours to manufacture an epoxy filler (inorganic particles) composite (5 mm×5 mm×3 mm).

2. Evaluation of Heat Resistant Physical Properties

The dimensional changes with the temperature of the cured products according to the examples and comparative examples illustrated in the following Tables 1 and 2 were evaluated using a Thermo-mechanical analyzer and are illustrated in the following Tables 1 and 2. The specimens of the epoxy glass fiber composite films were manufactured to have a size of 4 mm×16 mm×0.1 mm, and the specimens of the filler composites were manufactured to have a size of 5 mm×5 mm×3 mm.

TABLE 1

| Epoxy glass fiber composite | | | | | | |
|---|---|---|---|---|---|---|
| | | Epoxy compound (No. of synthetic example) | Example 1 | Example 2 | Example 3 | Example 4 |
| Epoxy formulation (g) | Epoxy | Synthetic Example 1 | 5.00 | 5.00 | 5.00 | 5.00 |
| | | Synthetic Example 2 | | | | |
| | | Synthetic Example 3 | | | | |
| | | Synthetic Example 4 | | | | |
| | | Synthetic Example 5 | | | | |
| | | Synthetic Example 6 | | | | |
| | | Synthetic Example 7/8 | | | | |
| | | Synthetic Example 9 | | | | |
| | | Synthetic Example 10 | | | | |

TABLE 1-continued

Epoxy glass fiber composite

| | | | | | | |
|---|---|---|---|---|---|---|
| | | Synthetic Example 11 | | | | |
| | | Synthetic Example 12 | | | | |
| | | Synthetic Example 13 | | | | |
| | | Synthetic Example 14 | | | | |
| | | Synthetic Example 15 | | | | |
| | | Synthetic Example 16 | | | | |
| | | Synthetic Example 17 | | | | |
| | | Synthetic Example 18 | | | | |
| | | Synthetic Example 23 | | | | |
| | | Synthetic Example 24 | | | | |
| | | EXA 4700(1) | | | | |
| | | GTR 1800(2) | | | | |
| | | TMTE(3) | | | | |
| | | AP(4) | | | | |
| | | DGEBA(5) | | | | |
| | | polydis(6) | | 0.88 | | 0.88 |
| | | EOCN(7) | | | | |
| | HF-1M(8) | | 0.92 | 1.08 | 1.00 | 1.08 |
| | TPP(9) | | 0.03 | 0.03 | 0.03 | 0.03 |
| | Tin-OC(10) | | | | | |
| | Silica | | | 7.02 | | 7.02 |
| | Glass fiber type | | E | E | T | T |
| | Resin amount (wt %) | | 40% | 51% | 32 | 48% |
| Heat resistance | CTE (ppm/° C.) | $\alpha_1$ (T < Tg) | 8.5 | 8.7 | 1.18 | 3.50 |
| | Tg (° C.) | | TgL | TgL | TgL | TgL |

| | Epoxy compound (No. of synthetic example) | | Example 5 | Example 6 | Example 7 | Example 8 | Example 9 | Example 10 | Example 11 |
|---|---|---|---|---|---|---|---|---|---|
| Epoxy formulation (g) | Epoxy | Synthetic Example 1 | | | | | | | |
| | | Synthetic Example 2 | 5.00 | | | | | | |
| | | Synthetic Example 3 | | 5.00 | 5.00 | 4.50 | 4.50 | 5.00 | 5.00 |
| | | Synthetic Example 4 | | | | | | | |
| | | Synthetic Example 5 | | | | | | | |
| | | Synthetic Example 6 | | | | | | | |
| | | Synthetic Example 7/8 | | | | | | | |
| | | Synthetic Example 9 | | | | | | | |
| | | Synthetic Example 10 | | | | | | | |
| | | Synthetic Example 11 | | | | | | | |
| | | Synthetic Example 12 | | | | | | | |
| | | Synthetic Example 13 | | | | | | | |
| | | Synthetic Example 14 | | | | | | | |
| | | Synthetic Example 15 | | | | | | | |
| | | Synthetic Example 16 | | | | | | | |
| | | Synthetic Example 17 | | | | | | | |
| | | Synthetic Example 18 | | | | | | | |
| | | Synthetic Example 23 | | | | | | | |
| | | Synthetic Example 24 | | | | | | | |
| | | EXA 4700(1) | | | | | | | |
| | | GTR 1800(2) | | | | | | | |
| | | TMTE(3) | | | | | | | |
| | | AP(4) | | | | | | | |
| | | DGEBA(5) | | | | 0.50 | 0.50 | | |
| | | polydis(6) | | | | | | | |
| | | EOCN(7) | | | | | | | |
| | HF-1M(8) | | 1.07 | 0.87 | 0.87 | 1.06 | 1.06 | 0.87 | 0.87 |
| | TPP(9) | | 0.03 | 0.03 | 0.03 | 0.03 | 0.03 | 0.03 | 0.03 |
| | Tin-OC(10) | | | | | | | 0.25 | |
| | Silica | | | | 1.48 | | 1.52 | | 1.48 |
| | Glass fiber type | | E | E | E | E | E | E | T |
| | Resin amount (wt %) | | 40% | 41% | 43% | 44% | 45% | 43% | 43% |
| Heat resistance | CTE (ppm/° C.) | $\alpha_1$ (T < Tg) | 8.3 | 7.6 | 7.3 | 8.8 | 8.9 | 7.5 | 4.0 |
| | Tg (° C.) | | TgL | TgL | TgL | TgL | TgL | TgL | TgL |

| | Epoxy compound (No. of synthetic example) | | Example 12 | Example 13 | Example 14 | Example 15 | Example 16 | Example 17 | Example 18 | Example 19 |
|---|---|---|---|---|---|---|---|---|---|---|
| Epoxy formulation (g) | Epoxy | Synthetic Example 1 | | | | | | | | |
| | | Synthetic Example 2 | | | | | | | | |
| | | Synthetic Example 3 | | | | | | | | |
| | | Synthetic Example 4 | 5.00 | | | | | | | |
| | | Synthetic Example 5 | | 5.00 | | | | | | |
| | | Synthetic Example 6 | | | 5.00 | | | | | |
| | | Synthetic Example 7/8 | | | | 5.00 | | | | |
| | | Synthetic Example 9 | | | | | 5.00 | | | |
| | | Synthetic Example 10 | | | | | | 5.00 | | |

TABLE 1-continued

| Epoxy glass fiber composite | | | | | | | | | | |
|---|---|---|---|---|---|---|---|---|---|---|
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |
| | | Synthetic Example 16 | | | | | | | | |
| | | Synthetic Example 17 | | | | | | | | |
| | | Synthetic Example 18 | | | | | | | | |
| | | Synthetic Example 23 | | | | | | | 5.00 | |
| | | Synthetic Example 24 | | | | | | | | 5.00 |
| | | EXA 4700(1) | | | | | | | | |
| | | GTR 1800(2) | | | | | | | | |
| | | TMTE(3) | | | | | | | | |
| | | AP(4) | | | | | | | | |
| | | DGEBA(5) | | | | | | | | |
| | | polydis(6) | | | | | | | | |
| | | EOCN(7) | | | | | | | | |
| | HF-1M(8) | | 1.39 | 1.73 | 1.00 | 0.69 | 1.40 | 1.57 | 1.78 | 2.06 |
| | TPP(9) | | 0.02 | 0.02 | 0.03 | 0.05 | 0.04 | 0.04 | 0.04 | 0.04 |
| | Tin-OC(10) | | | | | | | | | |
| | Silica | | | | | | | | | |
| | Glass fiber type | | E | E | E | E | E | E | E | E |
| | Resin amount (wt %) | | 43% | 40% | 42% | 40% | 41% | 40% | 42% | 43% |
| Heat resistance | CTE (ppm/° C.) | $\alpha_1$ (T < Tg) | 8.4 | 8.9 | 7.3 | 7.0 | 7.2 | 7.1 | 7.5 | 7.3 |
| | Tg (° C.) | | TgL | TgL | TgL | TgL | TgL | TgL | TgL | TgL |

| | | Epoxy compound (No. of synthetic example) | Example 20 | Example 21 | Example 22 | Example 23 | Example 24 | Example 25 | Example 26 | Example 27 |
|---|---|---|---|---|---|---|---|---|---|---|
| Epoxy formulation (g) | Epoxy | Synthetic Example 11 | 5.00 | | | | | | | |
| | | Synthetic Example 12 | | 5.00 | | | | | | |
| | | Synthetic Example 13 | | | 5.00 | | | | | |
| | | Synthetic Example 14 | | | | 5.00 | | | | |
| | | Synthetic Example 15 | | | | | 5.00 | | | |
| | | Synthetic Example 16 | | | | | | 5.00 | | |
| | | Synthetic Example 17 | | | | | | | 5.00 | |
| | | Synthetic Example 18 | | | | | | | | 5.00 |
| | | Synthetic Example 19 | | | | | | | | |
| | | Synthetic Example 20 | | | | | | | | |
| | | Synthetic Example 25 | | | | | | | | |
| | | Synthetic Example 26 | | | | | | | | |
| | | Synthetic Example 27 | | | | | | | | |
| | | Synthetic Example 28 | | | | | | | | |
| | | Synthetic Example 29 | | | | | | | | |
| | | Synthetic Example 30 | | | | | | | | |
| | | Synthetic Example 31/32 | | | | | | | | |
| | | Synthetic Example 33 | | | | | | | | |
| | | Synthetic Example 34 | | | | | | | | |
| | | EXA 4700(1) | | | | | | | | |
| | | GTR 1800(2) | | | | | | | | |
| | | TMTE(3) | | | | | | | | |
| | | AP(4) | | | | | | | | |
| | | DGEBA(5) | | | | | | | | |
| | | polydis(6) | | | | | | | | |
| | | EOCN(7) | | | | | | | | |
| | HF-1M(8) | | 1.04 | 1.23 | 1.84 | 2.14 | 1.08 | 1.29 | 1.05 | 1.25 |
| | TPP(9) | | 0.05 | 0.05 | 0.04 | 0.04 | 0.04 | 0.04 | 0.05 | 0.05 |
| | Tin-OC(10) | | | | | | | | | |
| | Silica | | | | | | | | | |
| | Glass fiber type | | E | E | E | E | E | E | E | E |
| | Resin amount (wt %) | | 40% | 41% | 43% | 40% | 42% | 42% | 41% | 43% |
| Heat resistance | CTE (ppm/° C.) | $\alpha_1$ (T < Tg) | 8.0 | 7.6 | 7.0 | 6.5 | 6.7 | 6.4 | 6.5 | 6.3 |
| | Tg (° C.) | | TgL | TgL | TgL | TgL | TgL | TgL | TgL | TgL |

| | | Epoxy compound (No. of synthetic example) | Example 28 | Example 29 | Example 30 | Example 31 | Example 32 | Example 33 |
|---|---|---|---|---|---|---|---|---|
| Epoxy formulation (g) | Epoxy | Synthetic Example 19 | 5.00 | | | | | |
| | | Synthetic Example 20 | | 5.00 | | | | |
| | | Synthetic Example 25 | | | 5.00 | | | |
| | | Synthetic Example 26 | | | | 5.00 | | |
| | | Synthetic Example 27 | | | | | 5.00 | 5.00 |
| | | Synthetic Example 28 | | | | | | |
| | | Synthetic Example 29 | | | | | | |
| | | Synthetic Example 30 | | | | | | |
| | | Synthetic Example 31/32 | | | | | | |

TABLE 1-continued

Epoxy glass fiber composite

| | | | | | | | | |
|---|---|---|---|---|---|---|---|---|
| | | Synthetic Example 33 | | | | | | |
| | | Synthetic Example 34 | | | | | | |
| | | EXA 4700(1) | | | | | | |
| | | GTR 1800(2) | | | | | | |
| | | TMTE(3) | | | | | | |
| | | AP(4) | | | | | | |
| | | DGEBA(5) | | | | | | |
| | | polydis(6) | | | | | | |
| | | EOCN(7) | | | | | | |
| | HF-1M(8) | | 0.90 | 1.05 | 0.84 | 0.97 | 0.95 | 0.95 |
| | TPP(9) | | 0.03 | 0.03 | 0.03 | 0.03 | 0.03 | 0.03 |
| | Tin-OC(10) | | | | | | | |
| | Silica | | | | | | | 1.50 |
| | Glass fiber type | | E | E | E | E | E | E |
| | Resin amount (wt %) | | 45% | 44% | 41% | 40% | 42% | 43% |
| Heat resistance | CTE (ppm/° C.) | $\alpha_1$ (T < Tg) | 8.4 | 8.0 | 7.5 | 7.3 | 7.8 | 7.7 |
| | Tg (° C.) | | TgL | TgL | TgL | TgL | TgL | TgL |

| | Epoxy compound (No. of synthetic example) | | Example 34 | Example 35 | Example 36 | Example 37 | Example 38 | Example 39 | Example 40 | Example 41 |
|---|---|---|---|---|---|---|---|---|---|---|
| Epoxy formulation (g) | Epoxy | Synthetic Example 19 | | | | | | | | |
| | | Synthetic Example 20 | | | | | | | | |
| | | Synthetic Example 25 | | | | | | | | |
| | | Synthetic Example 26 | | | | | | | | |
| | | Synthetic Example 27 | 4.50 | 4.50 | 5.00 | 5.00 | | | | |
| | | Synthetic Example 28 | | | | | 5.00 | | | |
| | | Synthetic Example 29 | | | | | | 5.00 | | |
| | | Synthetic Example 30 | | | | | | | 5.00 | |
| | | Synthetic Example 31/32 | | | | | | | | 5.00 |
| | | Synthetic Example 33 | | | | | | | | |
| | | Synthetic Example 34 | | | | | | | | |
| | | EXA 4700(1) | | | | | | | | |
| | | GTR 1800(2) | | | | | | | | |
| | | TMTE(3) | | | | | | | | |
| | | AP(4) | | | | | | | | |
| | | DGEBA(5) | 0.50 | 0.50 | | | | | | |
| | | polydis(6) | | | | | | | | |
| | | EOCN(7) | | | | | | | | |
| | HF-1M(8) | | 1.14 | 1.14 | 0.95 | 0.95 | 1.46 | 1.83 | 1.11 | 0.72 |
| | TPP(9) | | 0.03 | 0.03 | 0.03 | 0.03 | 0.03 | 0.03 | 0.03 | 0.05 |
| | Tin-OC(10) | | | | 0.15 | | | | | |
| | Silica | | | 1.54 | | 1.50 | | | | |
| | Glass fiber type | | E | E | E | T | E | E | E | E |
| | Resin amount (wt %) | | 43% | 44% | 44% | 42% | 43% | 43% | 42% | 41% |
| Heat resistance | CTE (ppm/° C.) | $\alpha_1$ (T < Tg) | 8.1 | 8.0 | 8.6 | 4.2 | 8.7 | 8.9 | 7.7 | 7.1 |
| | Tg (° C.) | | TgL | TgL | TgL | TgL | TgL | TgL | TgL | TgL |

| | Epoxy compound (No. of synthetic example) | | Example 42 | Example 43 | Com. Example 1 | Com. Example 2 | Com. Example 3 | Com. Example 4 | Com. Example 5 | Com. Example 6 |
|---|---|---|---|---|---|---|---|---|---|---|
| Epoxy formulation (g) | Epoxy | Synthetic Example 19 | | | | | | | | |
| | | Synthetic Example 20 | | | | | | | | |
| | | Synthetic Example 25 | | | | | | | | |
| | | Synthetic Example 26 | | | | | | | | |
| | | Synthetic Example 27 | | | | | | | | |
| | | Synthetic Example 28 | | | | | | | | |
| | | Synthetic Example 29 | | | | | | | | |
| | | Synthetic Example 30 | | | | | | | | |
| | | Synthetic Example 31/32 | | | | | | | | |
| | | Synthetic Example 33 | 5.00 | | | | | | | |
| | | Synthetic Example 34 | | 5.00 | | | | | | |
| | | EXA 4700(1) | | | 5.00 | | | | | |
| | | GTR 1800(2) | | | | 3.00 | | | | |
| | | TMTE(3) | | | | | 5.00 | | | |
| | | AP(4) | | | | | | 5.00 | | |
| | | DGEBA(5) | | | | 2.0 | | | 5.00 | |
| | | polydis(6) | | | | | | | | |
| | | EOCN(7) | | | | | | | | 5.00 |
| | HF-1M(8) | | 0.81 | 0.93 | 3.302 | 3.0 | 3.48 | 5.30 | 2.84 | 2.34 |
| | TPP(9) | | 0.03 | 0.03 | 0.05 | 0.025 | 0.05 | 0.05 | 0.05 | 0.03 |
| | Tin-OC(10) | | | | | | | | | |
| | Silica | | | | | | | | | |
| | Glass fiber type | | E | E | E | E | E | E | E | E |
| | Resin amount (wt %) | | 43% | 42% | 47% | 37% | 43% | 41% | 40% | 40% |

TABLE 1-continued

| | | | | | | | | | | |
|---|---|---|---|---|---|---|---|---|---|---|
| Epoxy glass fiber composite | | | | | | | | | | |
| Heat resistance | CTE (ppm/° C.) | $\alpha_1$ (T < Tg) | 8.0 | 7.7 | 16.6 | 13.0 | 15.8 | 17.0 | 12.8 | 15 |
| | Tg (° C.) | | TgL | TgL | 200 | 200 | 170 | 160 | 150 | 150 |

TABLE 2

| Epoxy filler composite | | | | | | | | | | | | | | |
|---|---|---|---|---|---|---|---|---|---|---|---|---|---|---|
| | Epoxy compound (No. of synthetic example) | | Exam. 44 | Exam. 45 | Exam. 46 | Exam. 47 | Exam. 48 | Exam. 49 | Exam. 50 | Exam. 51 | Exam. 52 | Exam. 53 | Exam. 54 | Exam. 55 |
| Epoxy formulation (g) | Epoxy | Synthetic Exam. 1 | 5.0 | | | | | | | | | | | |
| | | Synthetic Exam. 2 | | 5.0 | | | | | | | | | | |
| | | Synthetic Exam. 3 | | | 5.0 | 4.5 | | | | | | | | |
| | | Synthetic Exam. 4 | | | | | 5.0 | 4.5 | | | | | | |
| | | Synthetic Exam. 5 | | | | | | | 5.0 | 4.5 | | | | |
| | | Synthetic Exam. 6 | | | | | | | | | 5.0 | 4.5 | | |
| | | Synthetic Exam. 7/8 | | | | | | | | | | | 5.0 | 4.5 |
| | | Synthetic Exam. 9 | | | | | | | | | | | | |
| | | Synthetic Exam. 10 | | | | | | | | | | | | |
| | | Synthetic Exam. 11 | | | | | | | | | | | | |
| | | Synthetic Exam. 12 | | | | | | | | | | | | |
| | | Synthetic Exam. 13 | | | | | | | | | | | | |
| | | Synthetic Exam. 14 | | | | | | | | | | | | |
| | | Synthetic Exam. 15 | | | | | | | | | | | | |
| | | Synthetic Exam. 16 | | | | | | | | | | | | |
| | | Synthetic Exam. 17 | | | | | | | | | | | | |
| | | Synthetic Exam. 18 | | | | | | | | | | | | |
| | | Synthetic Exam. 23 | | | | | | | | | | | | |
| | | Synthetic Exam. 24 | | | | | | | | | | | | |
| | | YX-4000H(11) | | | | 0.5 | | 0.5 | | 0.5 | | 0.5 | | 0.5 |
| | | DGEBA(5) | | | | | | | | | | | | |
| | | EOCN(7) | | | | | | | | | | | | |
| | | polydis(6) | 0.6 | 0.6 | 0.6 | 0.6 | 0.6 | 0.6 | 0.6 | 0.6 | 0.6 | 0.6 | 0.6 | 0.6 |
| | HR5(12) | | 1.2 | 1.2 | 1.2 | 1.2 | 1.2 | 1.2 | 1.2 | 1.2 | 1.2 | 1.2 | 1.2 | 1.2 |
| | HF-1M(8) | | 1.08 | 1.23 | 1.03 | 1.22 | 1.55 | 1.69 | 1.89 | 2.00 | 1.17 | 1.35 | 0.84 | 1.06 |
| | TPP(9) | | 0.04 | 0.03 | 0.03 | 0.03 | 0.03 | 0.03 | 0.03 | 0.03 | 0.04 | 0.03 | 0.06 | 0.04 |
| | Silica | | 31.88 | 32.44 | 31.64 | 32.40 | 33.71 | 34.26 | 35.09 | 35.50 | 32.22 | 32.89 | 31.02 | 31.79 |
| | Filler amount (wt %) | | 80 | 80 | 80 | 80 | 80 | 80 | 80 | 80 | 80 | 80 | 80 | 80 |
| Heat resistance | CTE (ppm/° C.) | $\alpha_1$ (T < Tg) | 8.5 | 7.3 | 9.29 | 8.52 | 8.87 | 7.99 | 8.79 | 8.64 | 6.98 | 6.45 | 8.87 | 7.61 |
| | Tg (° C.) | | TgL | TgL | TgL | TgL | TgL | TgL | TgL | TgL | TgL | TgL | TgL | TgL |
| | Epoxy compound (No. of synthetic example) | | Exam. 56 | Exam. 57 | Exam. 58 | Exam. 59 | Exam. 60 | Exam. 61 | Exam. 62 | Exam. 63 | Exam. 64 | Exam. 65 | Exam. 66 | Exam. 67 |
| Epoxy formulation (g) | Epoxy | Synthetic Exam. 1 | | | | | | | | | | | | |
| | | Synthetic Exam. 2 | | | | | | | | | | | | |
| | | Synthetic Exam. 3 | | | | | | | | | | | | |
| | | Synthetic Exam. 4 | | | | | | | | | | | | |
| | | Synthetic Exam. 5 | | | | | | | | | | | | |
| | | Synthetic Exam. 6 | | | | | | | | | | | | |
| | | Synthetic Exam. 7/8 | | | | | | | | | | | | |
| | | Synthetic Exam. 9 | 5.0 | | | | | | | | | | | |
| | | Synthetic Exam. 10 | | 5.0 | | | | | | | | | | |
| | | Synthetic Exam. 11 | | | | | 5.0 | | | | | | | |
| | | Synthetic Exam. 12 | | | | | | 5.0 | | | | | | |
| | | Synthetic Exam. 13 | | | | | | | 5.0 | | | | | |
| | | Synthetic Exam. 14 | | | | | | | | 5.0 | | | | |
| | | Synthetic Exam. 15 | | | | | | | | | 5.0 | | | |
| | | Synthetic Exam. 16 | | | | | | | | | | 5.0 | | |
| | | Synthetic Exam. 17 | | | | | | | | | | | 5.0 | |
| | | Synthetic Exam. 18 | | | | | | | | | | | | 5.0 |
| | | Synthetic Exam. 23 | | | 5.0 | | | | | | | | | |
| | | Synthetic Exam. 24 | | | | 5.0 | | | | | | | | |
| | | YX-4000H(11) | | | | | | | | | | | | |
| | | DGEBA(5) | | | | | | | | | | | | |
| | | EOCN(7) | | | | | | | | | | | | |
| | | polydis(6) | 0.6 | 0.6 | 0.6 | 0.6 | 0.6 | 0.6 | 0.6 | 0.6 | 0.6 | 0.6 | 0.6 | 0.6 |
| | HR5(12) | | 1.2 | 1.2 | 1.2 | 1.2 | 1.2 | 1.2 | 1.2 | 1.2 | 1.2 | 1.2 | 1.2 | 1.2 |
| | HF-1M(8) | | 1.56 | 1.73 | 1.94 | 2.22 | 1.20 | 1.40 | 2.00 | 2.31 | 1.24 | 1.46 | 1.21 | 1.42 |
| | TPP(9) | | 0.04 | 0.04 | 0.04 | 0.04 | 0.06 | 0.06 | 0.04 | 0.04 | 0.04 | 0.04 | 0.06 | 0.06 |
| | Silica | | 33.80 | 34.48 | 35.32 | 36.45 | 32.42 | 33.22 | 35.56 | 36.78 | 32.51 | 33.38 | 32.47 | 33.29 |

TABLE 2-continued

| Epoxy filler composite | | | | | | | | | | | | | | |
|---|---|---|---|---|---|---|---|---|---|---|---|---|---|---|
| | Filler amount (wt %) | | 80 | 80 | 80 | 80 | 80 | 80 | 80 | 80 | 80 | 80 | 80 | 80 |
| Heat resistance | CTE (ppm/° C.) | $\alpha_1$ (T < Tg) | 8.77 | 8.25 | 8.64 | 8.08 | 8.70 | 7.54 | 9.03 | 8.11 | 8.22 | 7.29 | 8.18 | 7.55 |
| | Tg (° C.) | | TgL | TgL | TgL | TgL | TgL | TgL | TgL | TgL | TgL | TgL | TgL | TgL |

| | | Epoxy compound (No. of synthetic example) | Exam. 68 | Exam. 69 | Exam. 70 | Exam. 71 | Exam. 72 | Exam. 73 | Exam. 74 | Exam. 75 | Exam. 76 | Exam. 77 |
|---|---|---|---|---|---|---|---|---|---|---|---|---|
| Epoxy formulation (g) | Epoxy | Synthetic Exam. 19 | 5.0 | | | | | | | | | |
| | | Synthetic Exam. 20 | | 5.0 | | | | | | | | |
| | | Synthetic Exam. 25 | | | 5.0 | | | | | | | |
| | | Synthetic Exam. 26 | | | | 5.0 | | | | | | |
| | | Synthetic Exam. 27 | | | | | 5.0 | 4.5 | | | | |
| | | Synthetic Exam. 28 | | | | | | | 5.0 | 4.5 | | |
| | | Synthetic Exam. 29 | | | | | | | | | 5.0 | 4.5 |
| | | Synthetic Exam. 30 | | | | | | | | | | |
| | | Synthetic Exam. 31/32 | | | | | | | | | | |
| | | Synthetic Exam. 33 | | | | | | | | | | |
| | | Synthetic Exam. 34 | | | | | | | | | | |
| | | YX-4000H(11) | | | | | | 0.5 | | 0.5 | | 0.5 |
| | | DGEBA(5) | | | | | | | | | | |
| | | EOCN(7) | | | | | | | | | | |
| | | polydis(6) | 0.6 | 0.6 | 0.6 | 0.6 | 0.6 | 0.6 | 0.6 | 0.6 | 0.6 | 0.6 |
| | HR5(12) | | 1.2 | 1.2 | 1.2 | 1.2 | 1.2 | 1.2 | 1.2 | 1.2 | 1.2 | 1.2 |
| | HF-1M(8) | | 1.07 | 1.21 | 1.01 | 1.13 | 1.11 | 1.29 | 1.62 | 1.75 | 1.99 | |
| | TPP(9) | | 0.03 | 0.03 | 0.04 | 0.04 | 0.03 | 0.03 | 0.03 | 0.03 | 0.03 | 0.03 |
| | Silica | | 31.89 | 32.37 | 31.58 | 32.09 | 31.96 | 32.69 | 34.00 | 34.52 | 35.49 | 35.86 |
| | Filler amount (wt %) | | 80 | 80 | 80 | 80 | 80 | 80 | 80 | 80 | 80 | 80 |
| Heat resistance | CTE (ppm/° C.) | $\alpha_1$ (T < Tg) | 9.88 | 9.27 | 7.65 | 7.24 | 8.28 | 8.11 | 8.51 | 8.43 | 9.28 | 10.51 |
| | Tg (° C.) | | TgL | TgL | TgL | TgL | TgL | TgL | TgL | TgL | TgL | TgL |

| | | Epoxy compound (No. of synthetic example) | Exam. 78 | Exam. 79 | Exam. 80 | Exam. 81 | Exam. 82 | Exam. 83 | Com. Exam. 7 | Com. Exam. 8 |
|---|---|---|---|---|---|---|---|---|---|---|
| Epoxy formulation (g) | Epoxy | Synthetic Exam. 19 | | | | | | | | |
| | | Synthetic Exam. 20 | | | | | | | | |
| | | Synthetic Exam. 25 | | | | | | | | |
| | | Synthetic Exam. 26 | | | | | | | | |
| | | Synthetic Exam. 27 | | | | | | | | |
| | | Synthetic Exam. 28 | | | | | | | | |
| | | Synthetic Exam. 29 | | | | | | | | |
| | | Synthetic Exam. 30 | 5.0 | 4.5 | | | | | | |
| | | Synthetic Exam. 31/32 | | | 5.0 | 4.5 | | | | |
| | | Synthetic Exam. 33 | | | | | 5.0 | | | |
| | | Synthetic Exam. 34 | | | | | | 5.0 | | |
| | | YX-4000H(11) | | 0.5 | | 0.5 | | | | |
| | | DGEBA(5) | | | | | | | 5.0 | |
| | | EOCN(7) | | | | | | | | 5.0 |
| | | polydis(6) | 0.6 | 0.6 | 0.6 | 0.6 | 0.6 | 0.6 | 0.6 | 0.6 |
| | HR5(12) | | 1.2 | 1.2 | 1.2 | 1.2 | 1.2 | 1.2 | 1.2 | |
| | HF-1M(8) | | 1.28 | 1.44 | 0.89 | 1.09 | 0.98 | 1.10 | 2.84 | 2.73 |
| | TPP(9) | | 0.03 | 0.03 | 0.04 | 0.04 | 0.03 | 0.03 | 0.05 | 0.03 |
| | Silica | | 32.61 | 33.28 | 31.10 | 31.92 | 31.42 | 31.90 | 31.56 | 31.04 |
| | Filler amount (wt %) | | 80 | 80 | 80 | 80 | 80 | 80 | 80 | 80 |

TABLE 2-continued

| | | | | | | | | | | |
|---|---|---|---|---|---|---|---|---|---|---|
| Epoxy filler composite | | | | | | | | | | |
| Heat resistance | CTE (ppm/° C.) | $\alpha_1$ (T < Tg) | 6.5 | 6.3 | 7.8 | 7.2 | 8.8 | 8.2 | 14 | 13 |
| | Tg (° C.) | | TgL | TgL | TgL | TgL | TgL | TgL | 110 | 140 |

Note:
The compounds in Tables 1 and 2 are as follows.

(1) EXA-4700: Binaphthalene epoxy (DIC Co. in Japan)

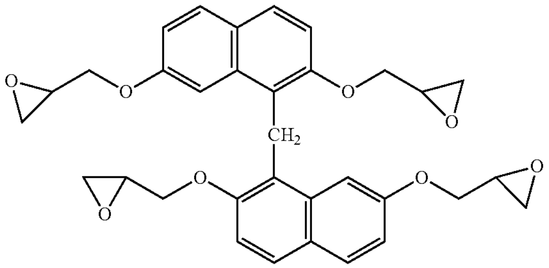 [SMILES: c1cc2ccc(OCC3CO3)c(Cc3c(OCC4CO4)ccc4ccc(OCC5CO5)cc34)c2cc1OCC1CO1]

(2) GTR 1800: Binaphthalene epoxy (Nippon Kayaku)

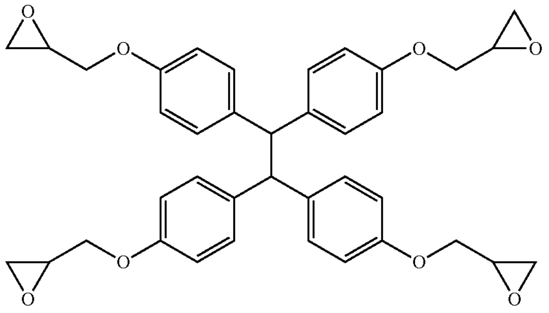 [SMILES: c1cc(C(c2ccc(OCC3CO3)cc2)C(c2ccc(OCC3CO3)cc2)c2ccc(OCC3CO3)cc2)ccc1OCC1CO1]

(3) TMTE: Triphenylmethane epoxy (Aldrich Co.)

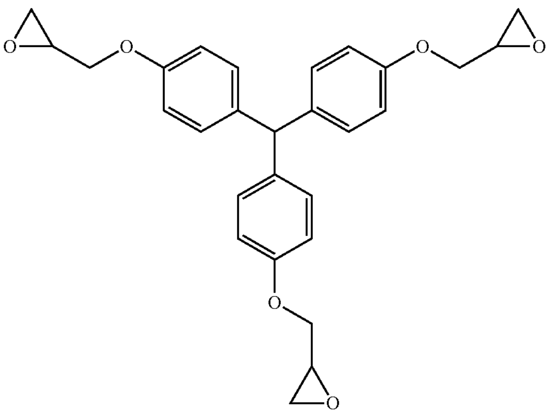 [SMILES: c1cc(C(c2ccc(OCC3CO3)cc2)c2ccc(OCC3CO3)cc2)ccc1OCC1CO1]

(4) AP: Aminophenol epoxy (Ciba Geigy, MY-0510)

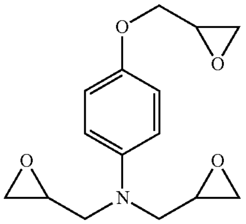 [SMILES: c1cc(N(CC2CO2)CC2CO2)ccc1OCC1CO1]

(5) DGEBA: Diglycidyl ether of bisphenol A (Aldrich Co.)

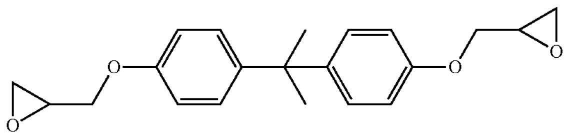 [SMILES: CC(C)(c1ccc(OCC2CO2)cc1)c1ccc(OCC2CO2)cc1]

(6) POLYDIS® 3615: Rubber modified DGEBA epoxy resin (Strruktol Co.)

(7) EOCN: Epoxy resin of ortho-cresol novolac (Nippon Kayaku Co.)

(8) HF-1M: Phenol novolac curing agent (Meiwa Plastic Industries)

(9) TPP: Triphenylphosphine (Aldrich Co.)

(10) Tin-OC: Tin(II)-ethylhexanoate (Aldrich Co.)

(11) YX-4000H: Biphenyl epoxy (Yuka Shell Epoxy Co.)

(12) HRS™: Thermoplastic polymer (Sekisui)

*TgL: Tg-less and not exhibiting glass transition

Figure 2:
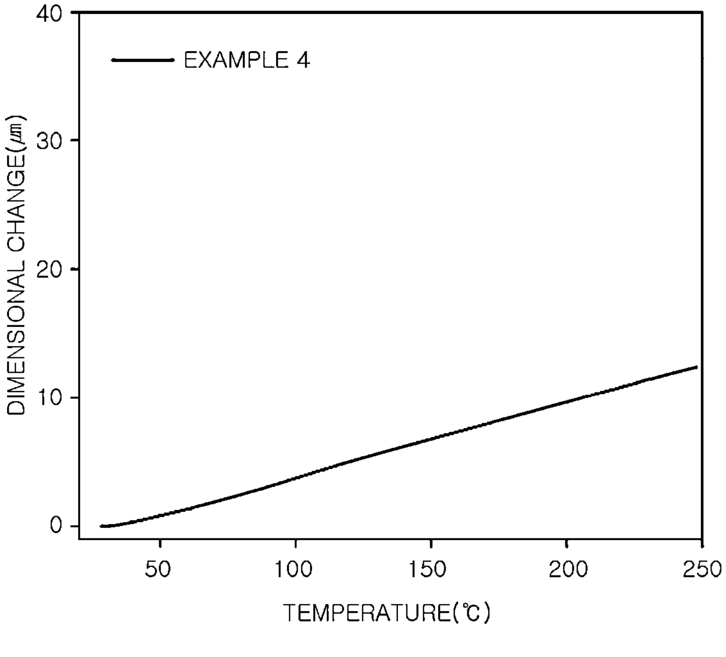
FIG. 2 is a graph illustrating dimensional change with the variation of the temperature of a composite according to Example 4.

As shown in the above Table 1, the glass fiber composite of the novolac epoxy compound modified with the alkoxysilyl group by the present invention has greatly improved heat resistance and exhibits a low CTE and high glass transition temperature or Tg-less. Particularly, the glass fiber composites according to Examples 1 to 43 have the CTE from 1.18 to 8.9 ppm/° C., smaller than the CTE values from 12.8 to 17.0 ppm/° C. of the epoxy resin composites without the alkoxysilyl group (Comparative Examples 1 to 6), and exhibit Tg-less. In addition, the CTE value of the inorganic particles (filler) of Examples 44 to 83 is 6.45 to 10.51 ppm/° C., and very good CTE and Tg-less may be attained. Particularly, as shown in FIGS. 1 and 2, the epoxy composite having an alkoxysilyl group of Examples 2 to 4 exhibited Tg-less transition.

The good CTE and glass transition temperature properties of the epoxy compound having an alkoxysilyl group, observed through the present invention are considered to be obtained due to the effective formation of the interfacial bond of the alkoxysilyl group with the glass fiber and/or the inorganic particles (filler).

3. Evaluation of Flame Retardancy

Figure 3:
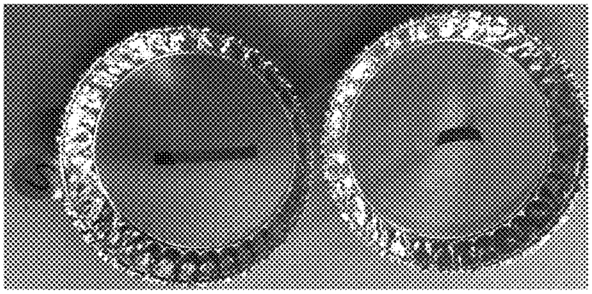
FIG. 3 is a photographic image illustrating the combustion state of the strips of the composites according to Example 1 and Comparative Example 1.

Strips of the composites according to Example 1 and Comparative Example 1 in the above Table 1 were ignited, and photographic images of the burned strips are illustrated in FIG. 3. As illustrated in FIG. 3, the strip of the composite of the epoxy compound according to Example 1 of the present invention was extinguished spontaneously within 1 to 2 seconds (left photographic image in FIG. 3). However, the strip of the composite not including an alkoxysilyl group according to Comparative Example 1 was completely burned (right photographic image in FIG. 3, unburned part in the photographic images corresponding portion held with tweezers). Thus, it would be known that the alkoxysilylated epoxy compound according to the present invention has good flame retardancy.

While the present invention has been shown and described in connection with the exemplary embodiments, it will be apparent to those skilled in the art that modifications and variations can be made without departing from the scope of the present invention as defined by the appended claims.

The invention claimed is:

1. An epoxy compound having an alkoxysilyl group, comprising:

at least one alkoxysilyl group (1) independently selected from the group consisting of Formulae S11 to S16, (2) independently selected from the group consisting of Formulae S21 to S26, (3) independently selected from the group consisting of Formulae S11 to S16 and Formulae S31 to S38 or (4) independently selected from the group consisting of Formulae S21 to S26 and Formulae S31 to S38; and at least two epoxy groups independently selected from the group consisting of Formulae S51 to S58 attached to a core, wherein the core is one selected from the group consisting of Formulae A' to N':

(A')

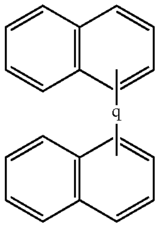

(B')

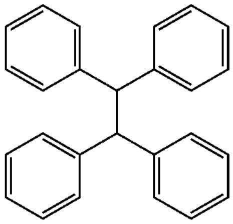

(C')

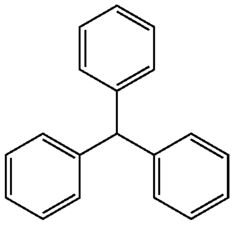

(D')

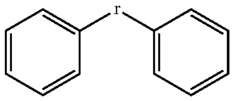

-continued (E')

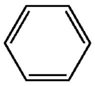

(F')

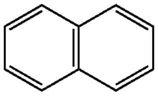

(G')

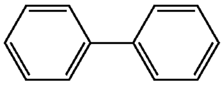

(H')

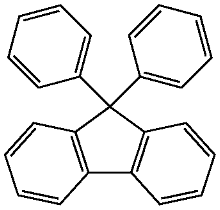

(I')

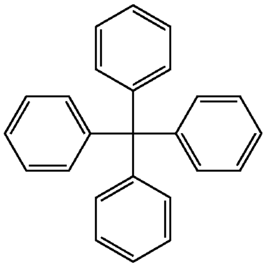

(J')

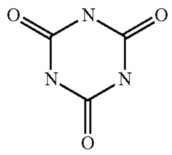

(K')

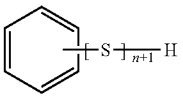

(L')

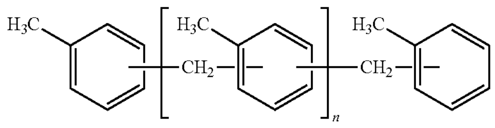

(M')

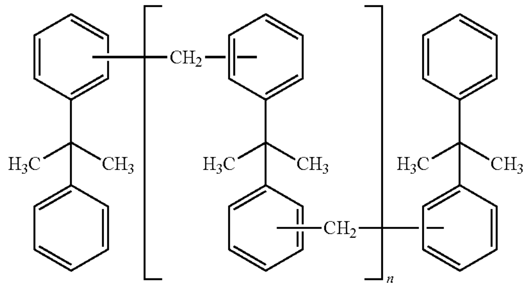

and

-continued (N')

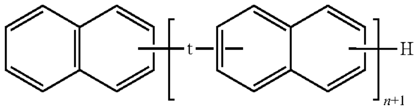

in Formula A', -q- is $—CH_2—$ or a direct linkage, in Formula D', -r- is $—C(CH_3)_2—$, $—CH_2—$, $—C(CF_3)_2—$, $—SO_2—$, $—S—$,

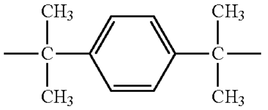 or

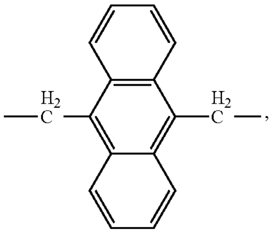, 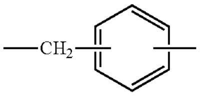

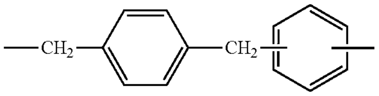

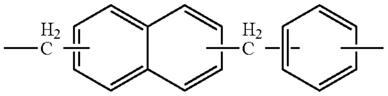

in Formula K', s is

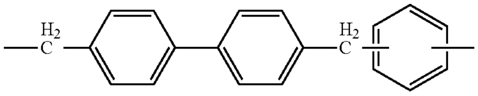

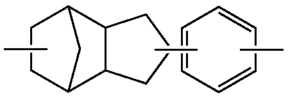 or 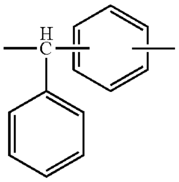, in Formula N', t is $—CH_2—$, 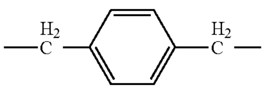 or

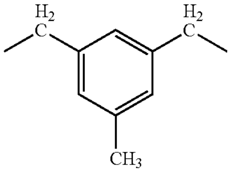, and in Formulae K' to N', n is an integer equal to or greater than 1, (S11)

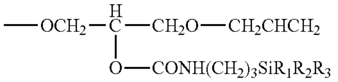

(S12)

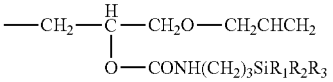

(S13)

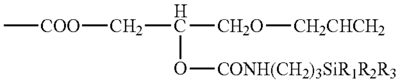

(S14)

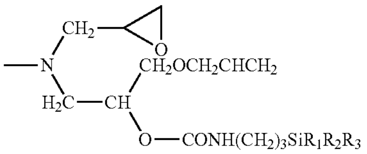

(S15)

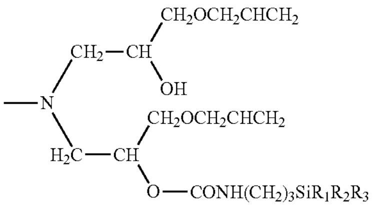

and (S16)

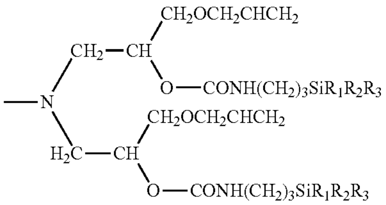

for each Si atom in each formula of Formulae S11 to S16, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched;

(S21)

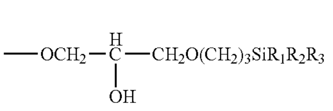

(S22)

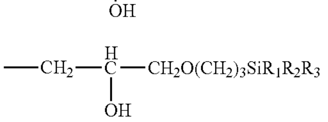

(S23)

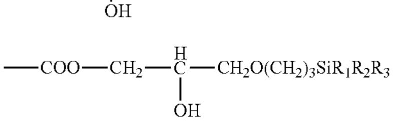

(S24)

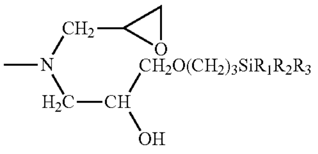

-continued (S25)

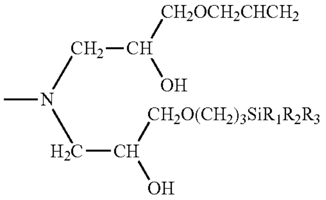

and (S26)

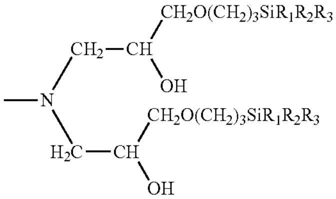

for each Si atom in each formula of Formulae S21 to S26, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched;

(S31)

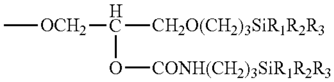

(S32)

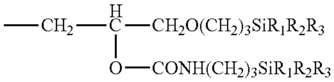

(S33)

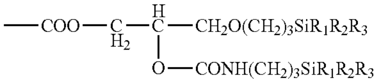

(S34)

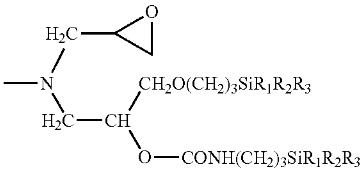

(S35)

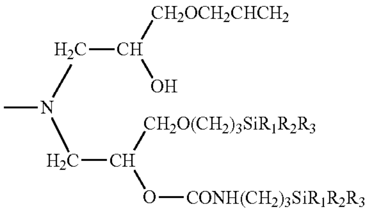

(S36)

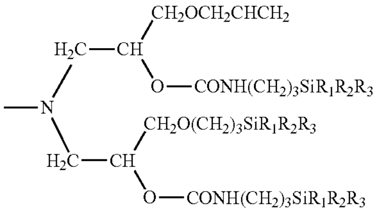

-continued (S37)

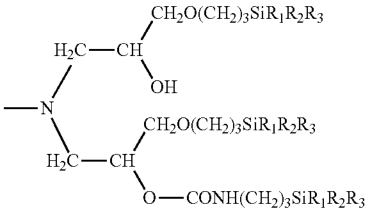

and (S38)

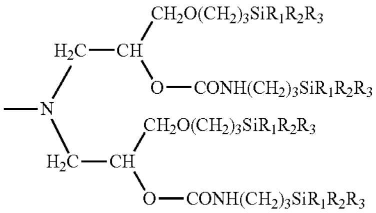

for each Si atom in each formula of Formulae S31 to S38, at least one of R1 to R3 is an alkoxy group having 1 to 5 carbon atoms, the remainder thereof are alkyl groups having 1 to 10 carbon atoms, and the alkoxy group and the alkyl group are linear or branched;

(S51)

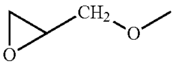

(S52)

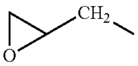

(S53)

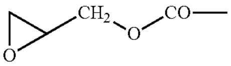

(S54)

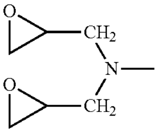

(S55)

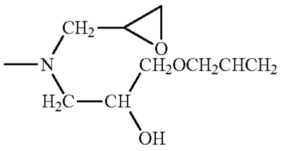

(S56)

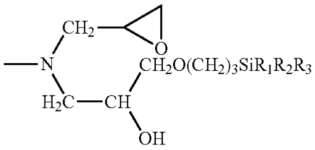

(S57)

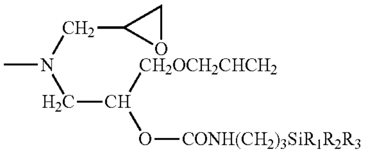

and

-continued (S58)

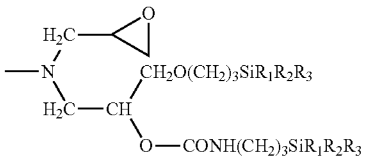

for each Si atom in each formula of Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

2. The epoxy compound having an alkoxysilyl group of claim 1, further comprising a second core selected from selected from a group consisting of Formulae A' to I', and the second core is connected to the core by a connecting group independently selected from the group consisting of Formulae LG1 to LG14:

(LG1)

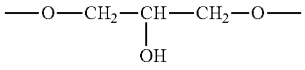

(LG2)

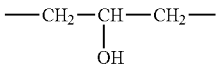

(LG3)

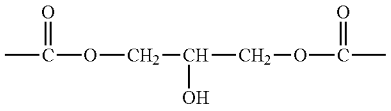

(LG4)

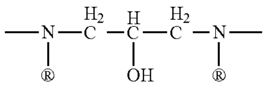

(LG5)

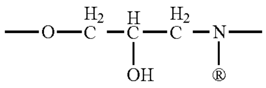

(LG6)

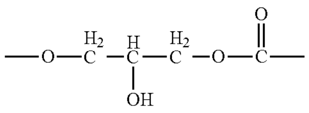

(LG7)

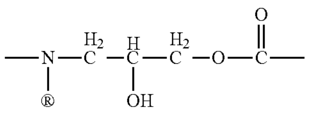

(LG8)

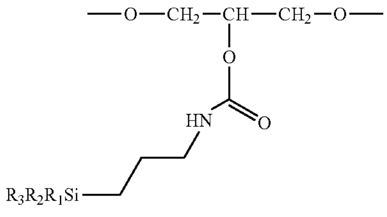

-continued (LG9)

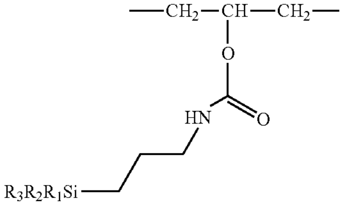

(LG10)

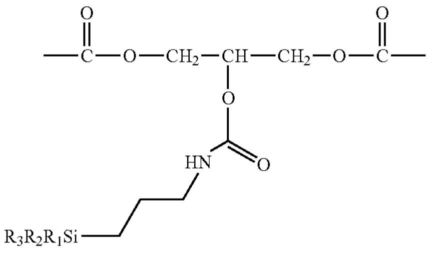

(LG11)

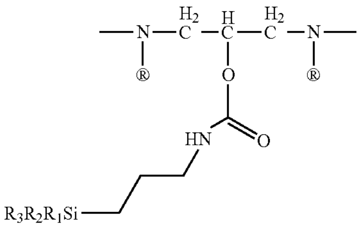

(LG12)

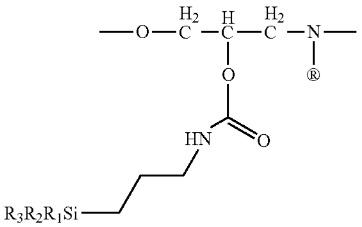

(LG13)

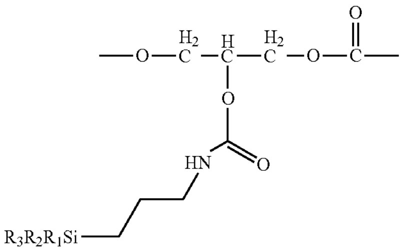

(LG14)

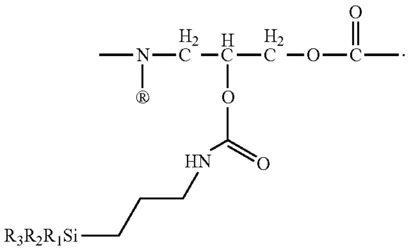

in each formula of Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen or a glycidyl group.

3. The epoxy compound having an alkoxysilyl group according to claim 1, wherein the epoxy compound having an alkoxysilyl group further comprises a substituent selected from the group consisting of Formulae S41 to S45:

(S41)

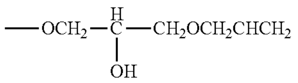

(S42)

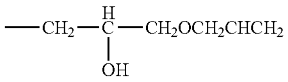

(S43)

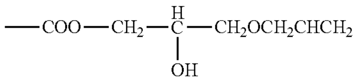

(S44)

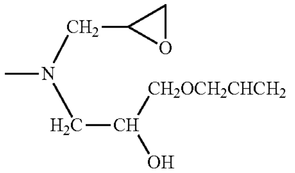

and (S45)

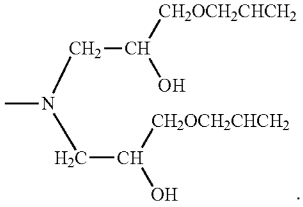

4. An epoxy composition comprising the epoxy compound having an alkoxysilyl group according to claim 1.

5. A cured product of the epoxy composition according to claim 4.

6. The cured product of claim 5, wherein the cured product has a glass transition temperature of 100° C. or above, or does not exhibit the glass transition temperature.

7. The epoxy compound having an alkoxysilyl group of claim 1, further comprising a second core of Formula J', wherein the second core is connected to the core via a connecting group independently selected from the group consisting of Formulae LG2 and LG9:

(LG2)

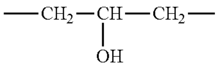

(LG9)

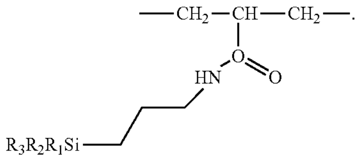

in Formula LG9, at least one of R1 to R3 is an alkoxy group having 1 to 5 carbon atoms, the remainder thereof are alkyl groups having 1 to 10 carbon atoms, and the alkoxy group and the alkyl group are linear or branched.

8. A method for preparing an epoxy compound having an alkoxysilyl group, comprising:

a first step of preparing an intermediate by reacting a starting material of an epoxy compound having at least three epoxy groups and allyl alcohol in the presence of a base and an optional solvent, wherein the starting material of the epoxy compound having at least three epoxy groups includes a core selected from the group consisting of Formulae (A') to (N') and at least three epoxy groups selected from the group consisting of Formulae S51 to S54; and a second step of reacting the intermediate and a compound of the following Formula B1 in the presence of a base and an optional solvent to prepare an epoxy compound including at least one alkoxysilyl group independently selected from the group consisting of Formulae S11 to S16 and at least two epoxy groups selected from the group consisting of Formulae S51 to S55 and S57 attached to the core, wherein the core is selected from the group consisting of Formulae (A') to (N'):

(A')

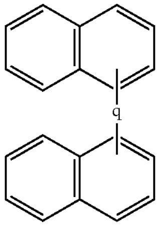

(B')

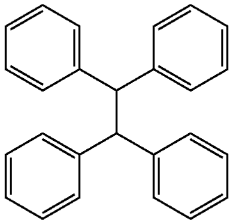

(C')

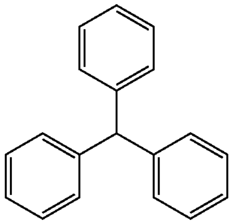

(D')

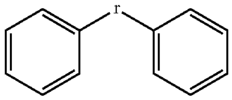

(E')

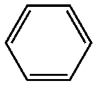

(F')

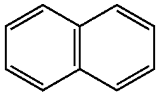

(G')

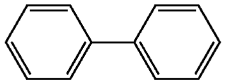

-continued
(H')
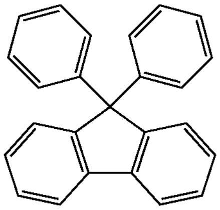
(I')
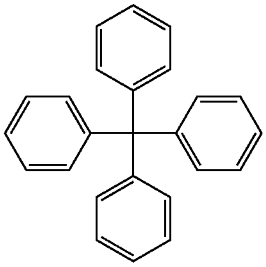
(J')
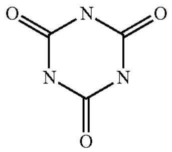
(K')
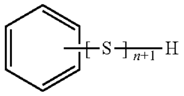
(L')
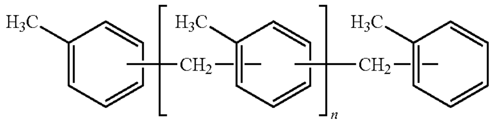
(M')
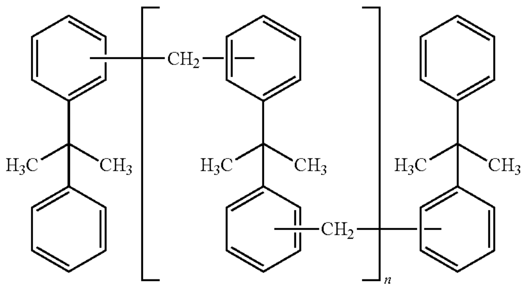
and
(N')
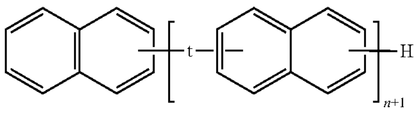
in Formula A', -q- is $-CH_2-$ or a direct linkage,
in Formula D', -r- is $-C(CH_3)_2-$, $-CH_2-$, $-C(CF_3)_2-$, $-SO_2-$, $-S-$,
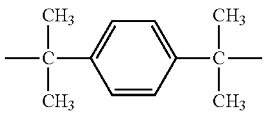
or
-continued
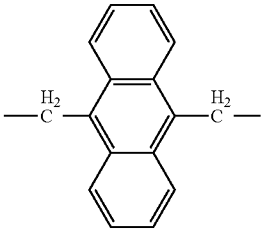
,
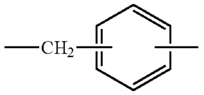
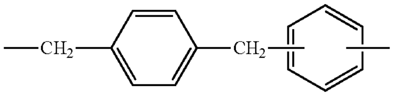
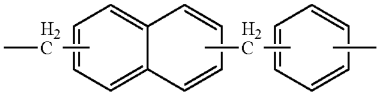
in Formula K', s is
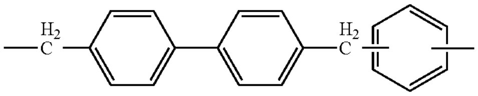
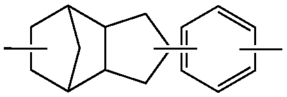
or
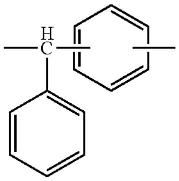
,
$-CH_2-$ ,
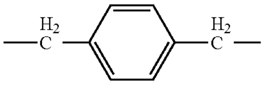
or
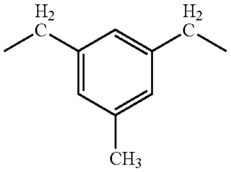
,
in Formula N', t is, and
in Formulae K' to N', n is an integer equal to or greater than 1,
(S51)
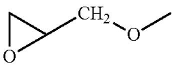
(S52)
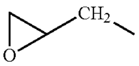
(S53)
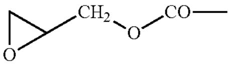
and
(S54)
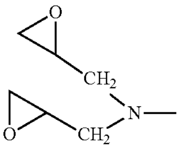
$OCN(CH_2)_3SiR_1R_2R_3$ [Formula B1]

in Formula B1, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S11)

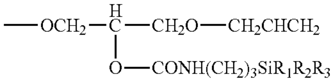

(S12)

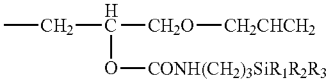

(S13)

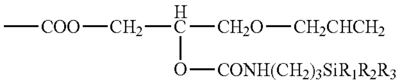

(S14)

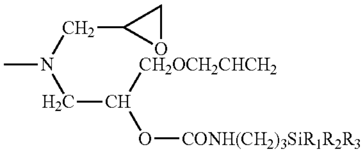

(S15)

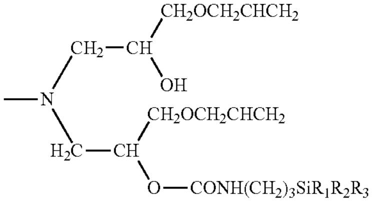

and (S16)

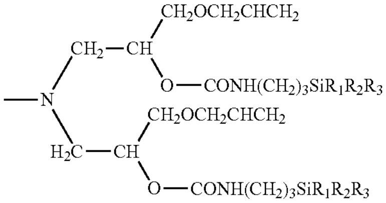

in each formula of Formulae S11 to S16, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S51)

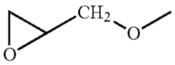

(S52)

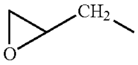

(S53)

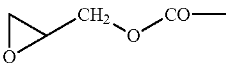

(S54)

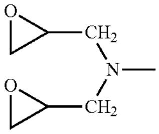

-continued (S55)

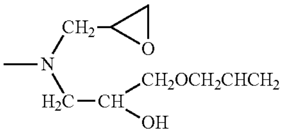

and (S57)

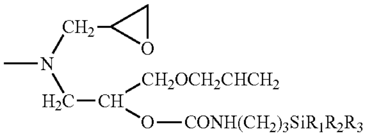

in Formula S57, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

9. The method for preparing an epoxy compound having an alkoxysilyl group of claim 8, further comprising:

a third step of reacting the epoxy compound prepared in the second step and a compound of the following Formula B2 in the presence of a metal catalyst and an optional solvent to prepare an epoxy compound having at least one alkoxysilyl group independently selected from the group consisting of Formulae S11 to S16 and Formulae S31 to S38 and at least two epoxy groups selected from the group consisting of Formulae S51 to S58 to the core:

$HSiR_1R_2R_3$ [Formula B2]

in Formula B2, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S31)

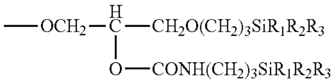

(S32)

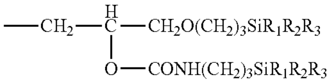

(S33)

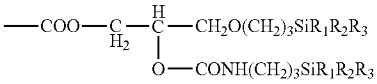

(S34)

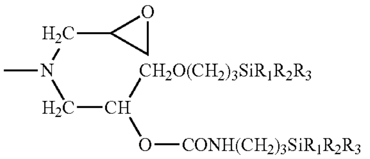

(S35)

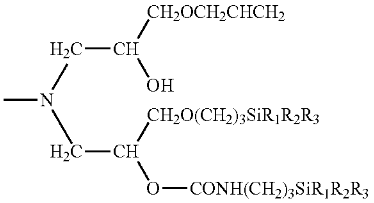

-continued (S36)

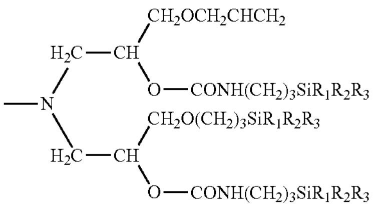

(S37)

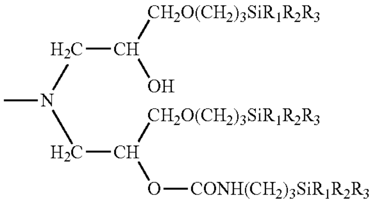

and (S38)

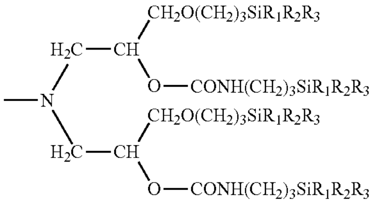

for each Si atom in each formula of Formulae S31 to S38, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S51)

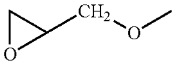

(S52)

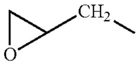

(S53)

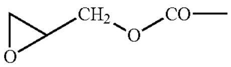

(S54)

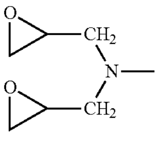

(S55)

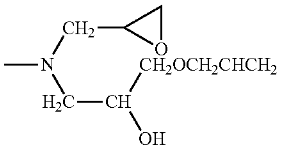

(S56)

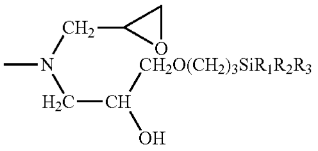

-continued (S57)

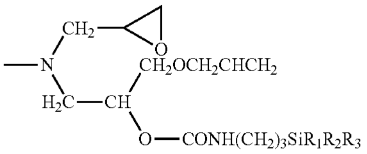

and (S58)

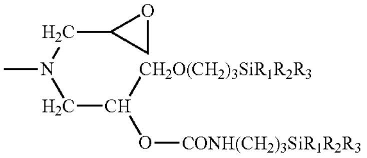

for each Si atom in each formula of Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

10. The method for preparing an epoxy compound having an alkoxysilyl group of claim 9, wherein the epoxy compound having an alkoxysilyl group prepared in the third step includes a second core of Formulae (A') to (J'), wherein, when the second core has Formulae (A') to (I'), the second core is connected to the core via a connecting group independently selected from the group consisting of Formulae LG1 to LG14, and wherein, when the second core has Formula (J'), the second core is connected to the core via a connecting group of LG2 and LG9:

(LG1)

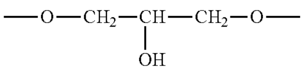

(LG2)

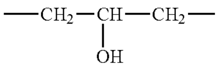

(LG3)

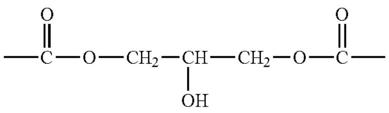

(LG4)

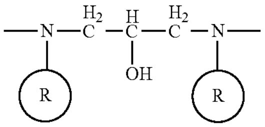

(LG5)

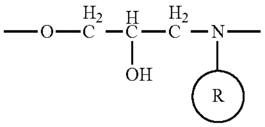

(LG6)

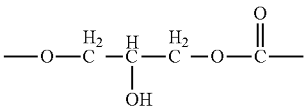

-continued (LG7)

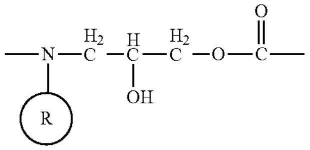

(LG8)

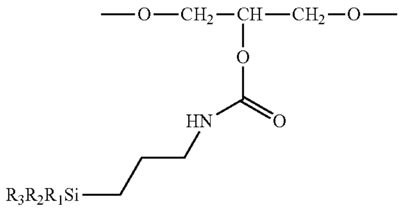

(LG9)

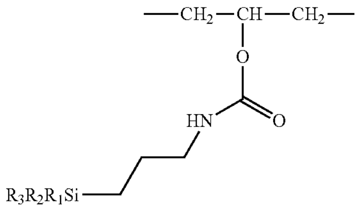

(LG10)

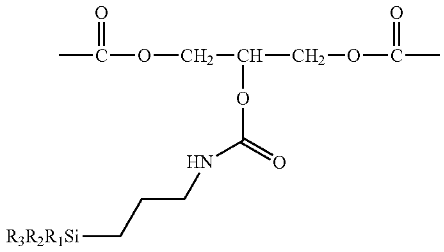

(LG11)

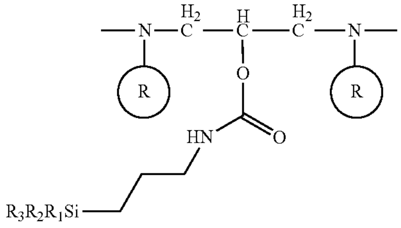

(LG12)

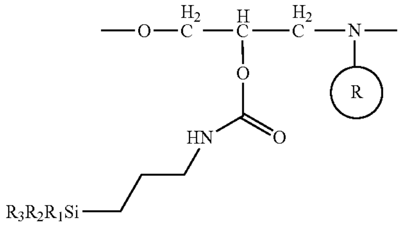

(LG13)

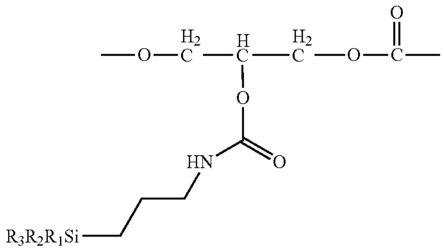

-continued (LG14)

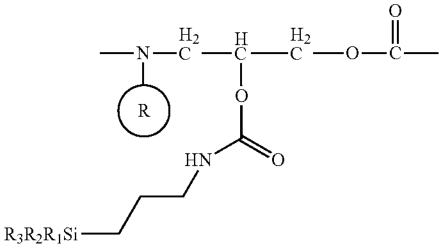

in each formula of Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen or a glycidyl group.

11. The method for preparing an epoxy compound having an alkoxysilyl group of claim 8, wherein the intermediate includes a second core of Formulae (A') to (J'), wherein, when the second core is a core of Formulae (A') to (I'), the second core is connected to the core via a connecting group independently selected from the group consisting of Formulae LG1 to LG7, and wherein, when the second core is a core of Formula (J'), the second core is connected to the core via a connecting group of LG2:

(LG1)

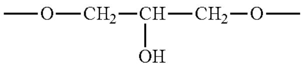

(LG2)

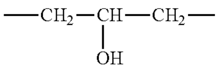

(LG3)

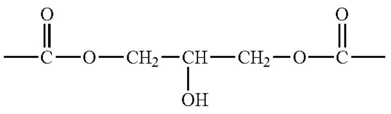

(LG4)

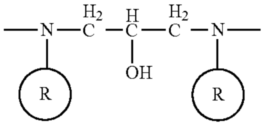

(LG5)

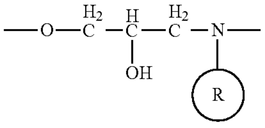

(LG6)

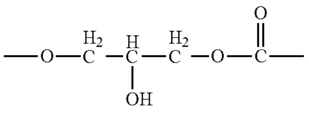

and (LG7)

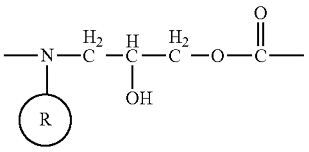

in Formulae LG4, LG5 and LG7, Ⓡ is hydrogen or a glycidyl group.

12. The method for preparing an epoxy compound having an alkoxysilyl group of claim 8, wherein the epoxy compound having an alkoxysilyl group prepared in the second step includes a second core of Formulae (A') to (J'), wherein, when the second core is a core of Formulae (A') to (I'), the second core is connected to the core via a connecting group independently selected from the group consisting of Formulae LG1 to LG14, and wherein, when the second core is a core of Formula (J'), the second core is connected to the core via a connecting group of LG2 and LG9:

(LG1)

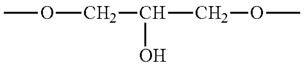

(LG2)

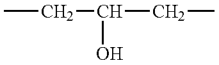

(LG3)

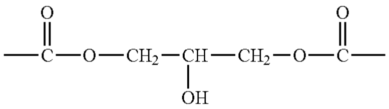

(LG4)

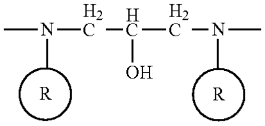

(LG5)

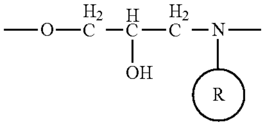

(LG6)

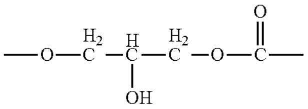

(LG7)

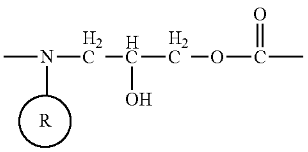

(LG8)

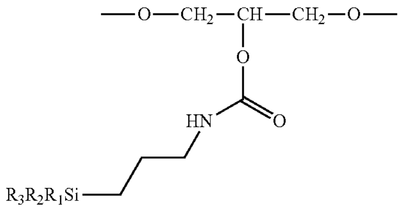

(LG9)

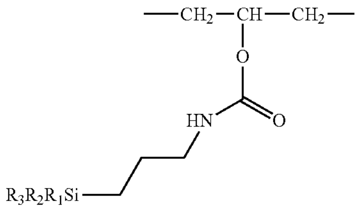

-continued (LG10)

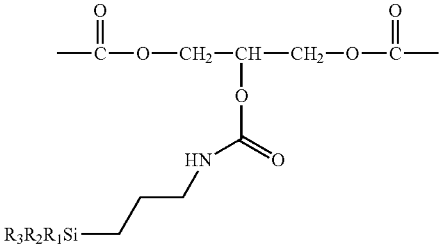

(LG11)

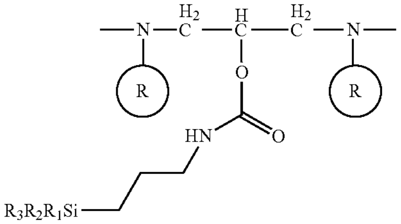

(LG12)

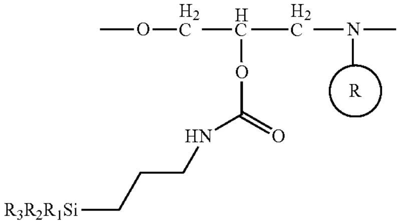

(LG13)

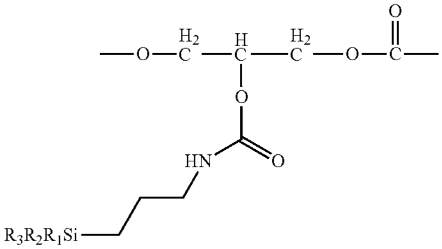

(LG14)

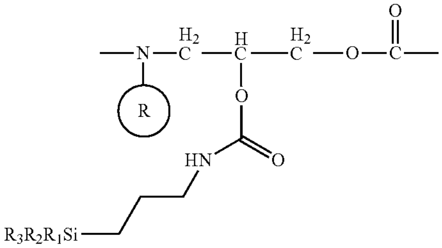

in each formula of Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen or a glycidyl group.

13. A method for preparing an epoxy compound having an alkoxysilyl group, comprising:

a first step of preparing an intermediate by reacting a starting material of an epoxy compound having at least three epoxy groups and allyl alcohol in the presence of a base and an optional solvent, wherein the starting material of the epoxy compound having at least three epoxy groups includes a core selected from the group consisting of Formulae (A') to (N') and at least three epoxy groups selected from the group consisting of Formulae S51 to S54; and a second step of reacting the intermediate and a compound of the following Formula B2 in the presence of a metal catalyst and an optional solvent to prepare an epoxy compound including at least one alkoxysilyl group independently selected from the group consisting of Formulae S21 to S26 and at least two epoxy groups selected from the group consisting of Formulae S51 to S56 attached to the core, wherein the core is selected from the group consisting of Formulae (A') to (N'):

(A')

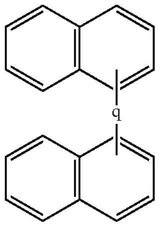

(B')

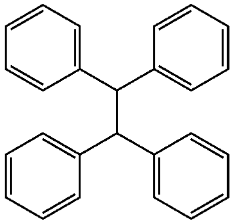

(C')

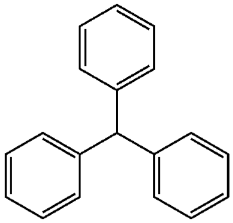

(D')

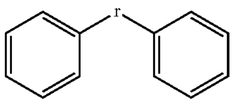

(E')

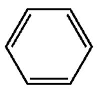

(F')

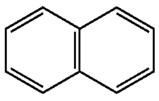

(G')

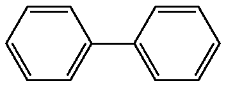

-continued (H')

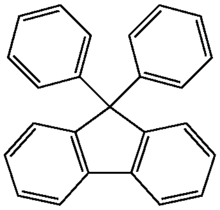

(I')

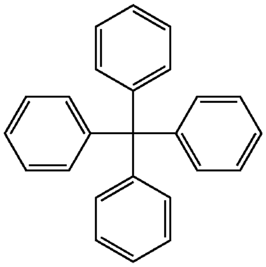

(J')

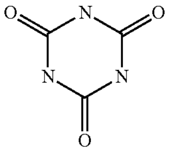

(K')

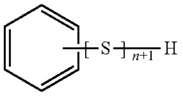

(L')

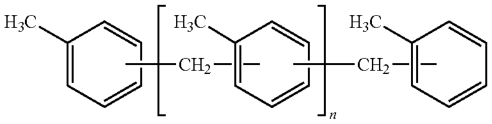

(M')

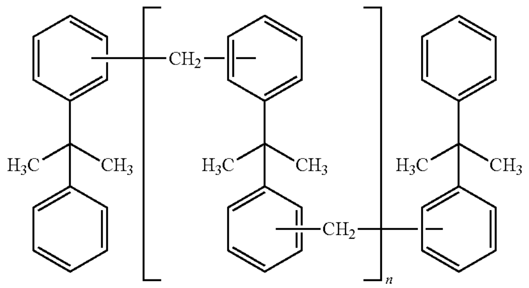

and (N')

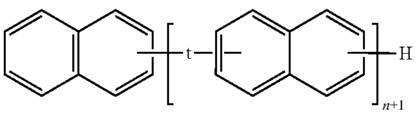

in Formula A', -q- is —$CH_2$— or a direct linkage, in Formula D', -r- is —$C(CH_3)_2$—, —$CH_2$—, —$C(CF_3)_2$—, —$SO_2$—, —S—,

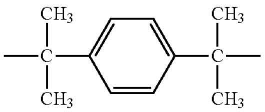

or

-continued

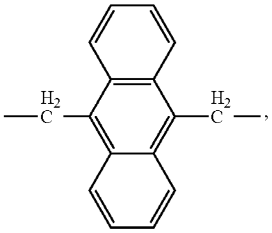

,

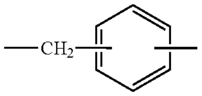

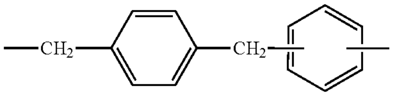

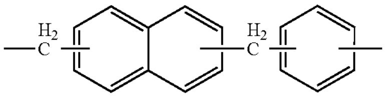

in Formula K', s is

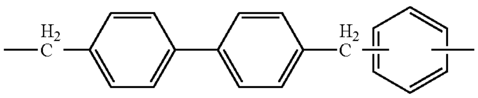

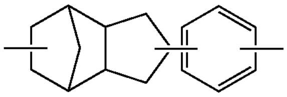

or

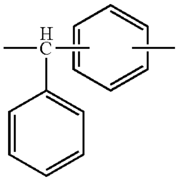

, in Formula N', t is

—$CH_2$— ,

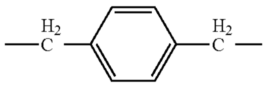

or

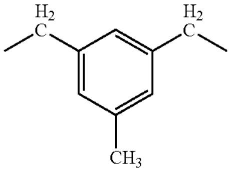

, and in Formulae K' to N', n is an integer equal to or greater than 1, (S51)

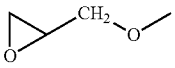

(S52)

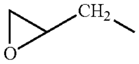

(S53)

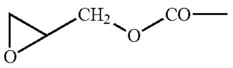

and

-continued (S54)

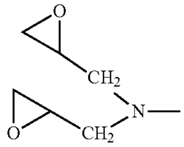

$HSiR_1R_2R_3$ [Formula B2]

in Formula B2, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S21)

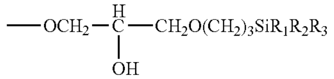

(S22)

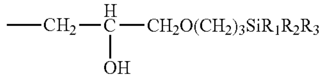

(S23)

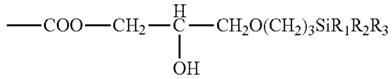

(S24)

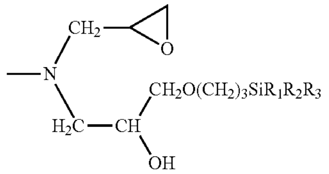

(S25)

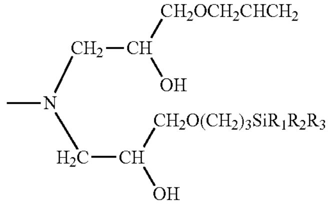

and (S26)

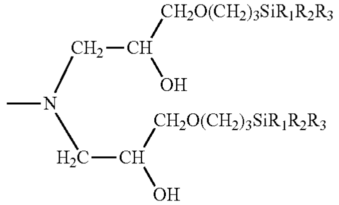

for each Si atom in each formula of Formulae S21 to S26, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S51)

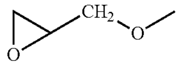

-continued (S52)

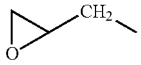

(S53)

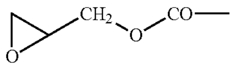

(S54)

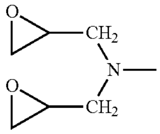

(S55)

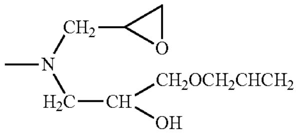

and (S56)

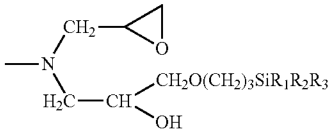

in Formula S56, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

14. The method for preparing an epoxy compound having an alkoxysilyl group of claim 13, further comprising:

a third step of reacting the epoxy compound prepared in the second step and a compound of the following Formula B1 in the presence of a base and an optional solvent to prepare an epoxy compound having at least one alkoxysilyl group independently selected from the group consisting of Formulae S21 to S26 and Formulae S31 to S38, at least two epoxy groups selected from the group consisting of Formulae S51 to S58, attached to the core:

$OCN(CH_2)_3SiR_1R_2R_3$ [Formula B1]

in Formula B1, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S31)

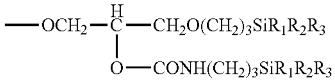

(S32)

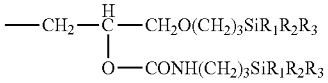

(S33)

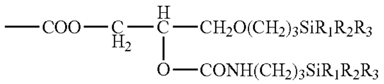

-continued (S34)

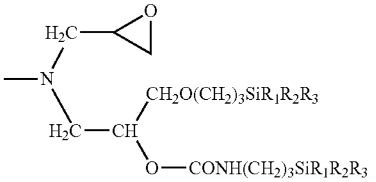

(S35)

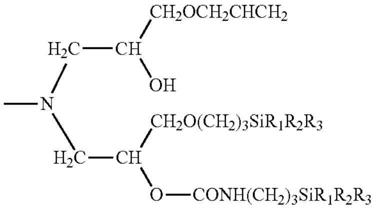

(S36)

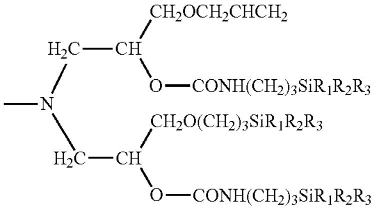

(S37)

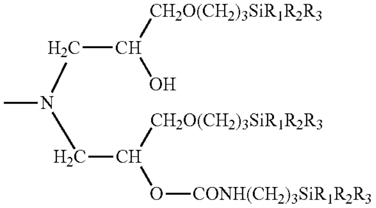

and (S38)

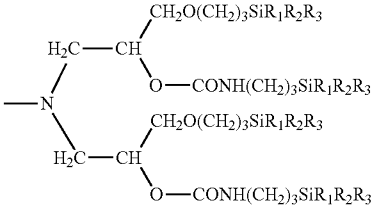

for each Si atom in each formula of Formulae S31 to S38, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, (S51)

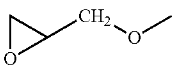

(S52)

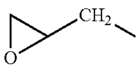

(S53)

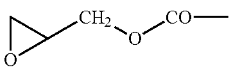

-continued (S54)

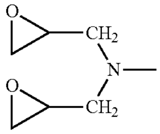

(S55)

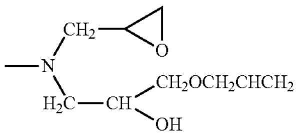

(S56)

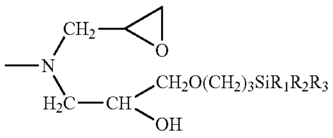

(S57)

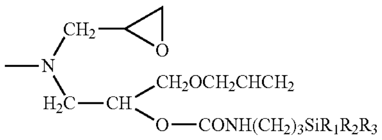

and (S58)

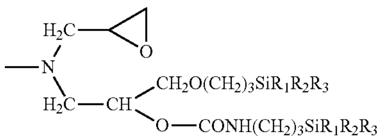

for each Si atom in each formula of Formulae S56 to S58, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched.

15. The method for preparing an epoxy compound having an alkoxysilyl group of claim 14, wherein the epoxy compound having an alkoxysilyl group prepared in the third step includes a second core, wherein, when the second core has Formulae (A') to (I') the second core is connected to the core via a connecting group independently selected from the group consisting of Formulae LG1 to LG14, and wherein, when the second core has Formula (J'), the second core is connected to the core via a connecting group of LG2 and LG9:

(LG1)

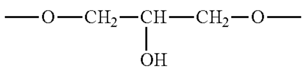

(LG2)

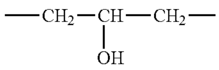

(LG3)

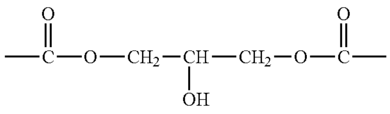

-continued (LG4)

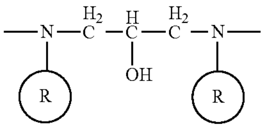

(LG5)

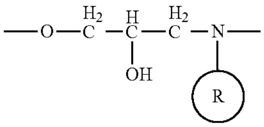

(LG6)

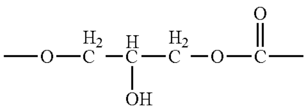

(LG7)

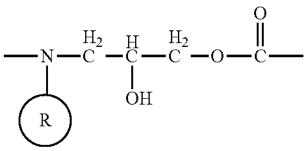

(LG8)

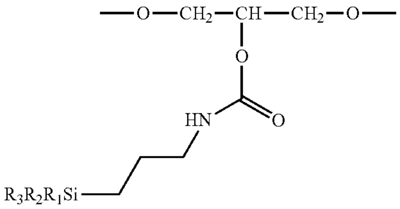

(LG9)

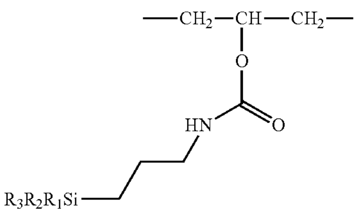

(LG10)

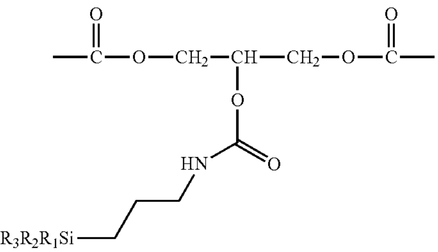

(LG11)

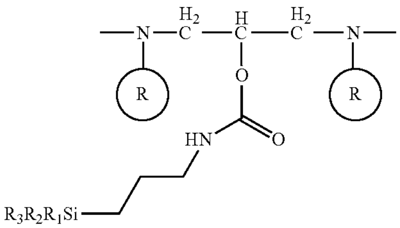

-continued (LG12)

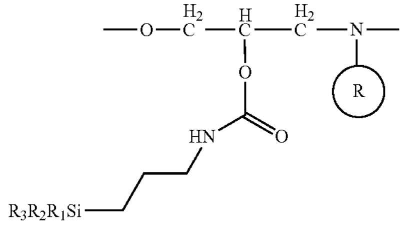

(LG13)

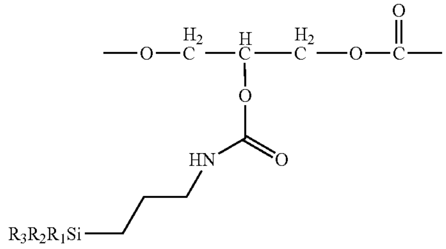

(LG14)

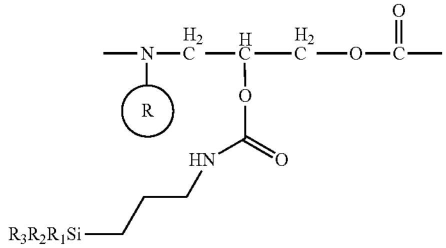

in each formula of Formulae LG8 to LG14, at least one of $R_1$ to $R_3$ is an alkoxy group having 1 to 5 carbon atoms, the remainder thereof are alkyl groups having 1 to 10 carbon atoms, and the alkoxy group and the alkyl group are linear or branched, and in Formulae LG4, LG5, LG7, LG11, LG12 and LG14, Ⓡ is hydrogen or a glycidyl group.

16. The method for preparing an epoxy compound having an alkoxysilyl group of claim 13, wherein the epoxy compound having an alkoxysilyl group prepared in the second step includes a second core of Formulae (A') to (J'), wherein, when the second core has Formulae (A') to (I'), the second core is connected to the core via a connecting group independently selected from the group consisting of Formulae LG1 to LG7, and wherein, when the second core has Formula (J'), the second core is connected to the core via a connecting group of LG2:

(LG1)

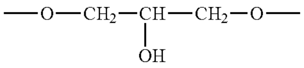

(LG2)

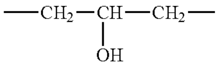

(LG3)

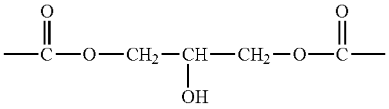

(LG4)

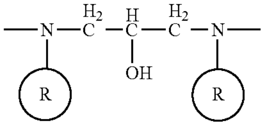

(LG5)

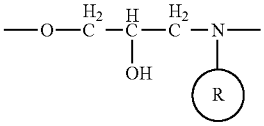

(LG6)

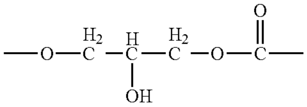

and (LG7)

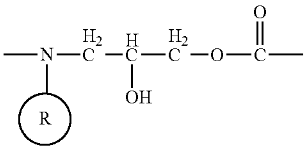

in Formulae LG4, LG5 and LG7, Ⓡ is hydrogen or a glycidyl group.

* * * * *